(12) United States Patent
Fraser, Jr. et al.

(10) Patent No.: US 7,105,343 B1
(45) Date of Patent: Sep. 12, 2006

(54) METHODS AND COMPOSITIONS FOR TRANSPOSITION USING MINIMAL SEGMENTS OF THE EUKARYOTIC TRANSFORMATION VECTOR PIGGYBAC

(75) Inventors: Malcolm J. Fraser, Jr., Granger, IN (US); Xu Li, Notre Dame, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 57 days.

(21) Appl. No.: 10/826,523

(22) Filed: Apr. 19, 2004

Related U.S. Application Data

(63) Continuation-in-part of application No. 10/001,189, filed on Oct. 30, 2001, now Pat. No. 6,962,810.

(60) Provisional application No. 60/244,984, filed on Nov. 1, 2000, provisional application No. 60/244,667, filed on Oct. 31, 2000, provisional application No. 60/562,324, filed on Apr. 15, 2004.

(51) Int. Cl.
*C12N 15/00* (2006.01)
*C12N 15/64* (2006.01)
*C12P 19/34* (2006.01)
*C07H 21/04* (2006.01)

(52) U.S. Cl. ............... 435/320.1; 435/91.41; 435/91.52; 536/23.1

(58) Field of Classification Search ............ 435/320.1, 435/91.1; 536/23.1, 24.1, 24.2
See application file for complete search history.

(56) References Cited

U.S. PATENT DOCUMENTS

| 6,218,185 | B1 | 4/2001 | Shirk et al. |
| 6,551,825 | B1 | 4/2003 | Shirk et al. |
| 6,773,914 | B1 * | 8/2004 | Handler .................... 435/320.1 |

OTHER PUBLICATIONS

Carey et al. Transposon mutagenesis of baculoviruses: analysis of Trichoplusia ni transposon IFP2 insertions within the FP-locus of nuclear polyhedrosis viruses. Virology. Sep. 1989;172(1):156-69.*
Elick et al. PCR analysis of insertion site specificity, transcription, and structural uniformity of the Lepidopteran transposable element IFP2 in the TN-368 cell genome. Genetica. 97(2):127-39, Mar. 1996.*
Elick et al. Excision of the piggyBac transposable element in vitro is a precise event that is enhanced by the expression of its encoded transposase. Genetica. 98(1):33-41, Jul. 1996.*
Fraser et al. Assay for movement of Lepidopteran transposon IFP2 in insect cells using a baculovirus genome as a target DNA. Virology. 211(2):397-407, Aug. 1995.*
Fraser et al. Precise excision of TTAA-specific lepidopteran transposons piggyBac (IFP2) and tagalong (TFP3) from the baculovirus genome in cell lines from two species of Lepidoptera. Insect Mol Biol. 5(2):141-51, May 1996.*
Li et al. The minimum internal and external sequence requirements for transposition of the eukaryotic transformation vector piggyBac. Mol Genet Genomics. 266(2):190-8, Oct. 2001.*
Becker HA, Kunze R (1997) Maize Activator transposase has a bipartite DNA binding domain that recognizes subterminal sequences and the terminal inverted repeats, Mol. Gen. Genet., 254(3): pp. 219-230.
Beeman RW, Stauth DM (1997) Rapid cloning of insect transposon insertion junctions using 'universal' PCR, Insect Mol. Biol., 6(1): pp. 83-88.
Berghammer AJ, Klingler M, Wimmer EA (1999) A universal marker for transgenic insects, Nature, 402: pp. 370-371.
Elick TA, Lobo N, Fraser MJ Jr (1997) Analysis of the *cis*-acting DNA elements required for *piggyBac* transposable element excision, Mol. Gen. Genet., 255(6): pp. 605-610.
Fraser MJ Jr, Smith GB and Summers MD (1983) Acquisition of host cell DNA sequences by baculoviruses: Relationship between host DNA insertions and FP mutants of *Autographa californica* and *Galleria mellonella* nuclear polyhedrosis viruses, J. Virol., 47: pp. 287-300.
Fraser MJ Jr, Brusca JS, Smith GE, Summers MD (1985) Transposon-mediated mutagenesis of a baculovirus, Virology, 145(2): pp. 356-361.
Geier and Modrich (1979) Recognition Sequences of the *dam* Methylase of *Escherichia coli* K12 and Mode of Cleavage of *Dpn* I Endonuclease, The Journal of Biological Chemistry, 254(4): pp. 1408-1413.
Gierl A, Lutticke S, Saedler H (1988) *TnpA* product encoded by the transposable element *En-1* of *Zea mays* is a DNA binding protein, Embo J., 7(13): pp. 4045-4053.
Goryshin IY, Kil YV, Reznikoff WS (1994) DNA length, binding, and twisting constraints on IS5O transposition, Proc. Nat. Acad. USA, 91: pp. 10834-10838.
Grossman GL, Rafferty CS, Fraser MJ Jr, Benedict MQ (2000) The *piggyBac* element is capable of precise excision and transposition in cells and embryos of the mosquito, *Anopheles gambiae*, Insect Biochem. Mol. Biol. 30(10): pp. 909-914.
Grossman GL, Rafferty CS, Clayton JR, Stevens TK, Mukabayire O, Benedict M (2001) Germline transformation of the malaria vector, *Anopheles gambiae*, with the *piggyBac* transposable element, Insect Mol. Biol., 10(6): pp. 597-604.
Grossniklaus U, Pearson RK, Gehring WJ (1992) The *Drosophila* sloppy paired lucus encodes two proteins involved in segmentation that show homology to mammalian transcription factors, Genes Dev., 6(6): pp. 1030-1051.
Handler AM, McCombs SD, Fraser MJ Jr, Saul SH (1998) The Lepidopteran transposon vector, *piggyBac*, mediates germ-line transformation in the Mediterranean fruit fly, Proc. Natl. Acad. Sci. USA, 95(13): pp. 7520-7525.

(Continued)

*Primary Examiner*—Terry McKelvey
*Assistant Examiner*—Jennifer Dunston
(74) *Attorney, Agent, or Firm*—Jagtiani & Guttag

(57) ABSTRACT

The present invention provides efficient transfer of genes into host cells or embryos to transform the cells or embryos by transposition vectors using the minimal amount of nucleotide sequences in the transposon piggyBac required for gene transfer. The transformed cells or embryos may also be developed into transgenic organisms.

9 Claims, 166 Drawing Sheets

OTHER PUBLICATIONS

Handler AM, Harrell RA 2nd (1999) Germline transformation of *Drosophila melanogaster* with the *piggyBac* transposon vector, Insect Mol. Biol., 8(4): pp. 449-457.

Handler AM, McCombs SD (2000) The *piggyBac* transposon mediates germ-line transformation in the Oriental fruit fly and closely related elements exist in its genome, Insect Mol. Biol., 9(6): pp. 605-612.

Handler AM, Harrell RA 2nd (2001) Polyubiquitin-regulated DsRed marker for transgenic insects, Biotechniques, 31(4): pp. 824-828.

Handler AM, Harrell RA 2nd (2001) Transformation of the Caribbean fruit fly, *Anastrepha suspensa*, with a *piggyBac* vector marked with polyubiquitin-regulated GFP, Insect Biochem. Mol. Biol., 31(2): pp. 199-205.

Handler AM (2002) Use of the *piggyBac* transposon for germ-like transformation of insects, Insect Biochem. Mol. Biol., 32(10): pp. 1211-1220.

Hediger M, Niessen M, Wimmer EA, Dubendorfer A, Bopp D (2001) Genetic transformation of the housefly *Musca domestica* wtih the *Lepidopteran* derived transposon *piggyback*, Insect Mol. Biol.,10 (2): pp. 113-119.

Heinrich JC, Li X, Henry RA, Haack N, Stringfellow L, Heath AC, Scott MJ (2002) Germ-line transformation of the Australian sheep blowfly *Lucilia cuprina*, Insect Mol. Biol., 11(1): pp. 1-10.

Hirt B (1967) Selective extraction of polyoma DNA from infected mouse cell cultures, J. Mol. Biol., 26: pp. 365-369.

Horn C, Wimmer EA (2000) A versatile vector set for animal transgenesis, Dev. Genes Evol., 210(12): pp. 630-637.

Ivics Z, Hackett PB, Plasterk RH, Izsvak Z (1997) Molecular reconstruction of *Sleeping Beauty*, a *Tc1*-like transposon from fish, and its transposition in human cells, Cell, 91(4): pp. 501-510.

Jarvis et al. (1990) Use of early baculovirus promoters for continuous expression and efficient processing of foreign gene products in stably transformed lepidopteran cells, Biotechnology (NY) 10: 950-5. (Abstract).

Jasinskiene N, Coates CJ, James AA (2000) Structure of *hermes* integration in the germline of the yellow fever mosquito, *Aedes aegypti*, Insect Mol. Biol., 9(1): pp. 11-8.

Kaufman PD, Doll RF, Rio DC (1989) *Drosophila* P element transposase recognizes internal P element DNA sequences, Cell, 59(2): pp. 359-371.

Kokoza V, Ahmed A, Wimmer EA, Raikhel AS (2001) Efficient transformation of the yellow fever mosquito *Aedes aegypti* using the PiggyBac transposable element vector (pBac[3xP3-EGFP afm], Insect Biochem. Mol. Biol., 31(12): pp. 1137-1143.

Kunze R, Starlinger P (1989) The putative transposase of transposable element Ac from *Zea mays* L. interacts with subterminal sequences of Ac, Embo J., 8(11): pp. 3177-3185.

Li X, Heinrich JC, Scott MJ (2001) *piggyBac*-mediated transposition in *Drosophila melanogaster*. an evaluation of the use of constitutive promoters to control transposase gene expression, Insect Mol. Biol., 10(5): pp. 447-455.

Liu D, Mack A, Wang R, Galli M, Belk J. Ketpura NI, Crawford NM (2000) Functional dissection of the *cis*-acting sequences of the Arabidopsis transposable element *Tag1* reveals dissimilar subterminal sequence and minimal spacing requirements for transposition, Genetics, 157(2): pp. 817-830.

Lobo N, Li X, Fraser MJ Jr (1999) Transposition of the *piggyBac* element in embryos of *Drosophila melanogaster*, *Aedes aegypti* and *Trichoplusia ni*, Mol. Gen. Genet., 261(4-5): pp. 803-810.

Lobo N, Li X, Hua-Van A, Fraser MJ Jr (2001) Mobility of the *piggyBac* transposon in embryos of the vectors of Dengue fever (*Aedes albopictus*) and La Crosse encephalitis (*Ae. triseriatus*), Mol. Genet. Gen., 265(1): pp. 66-71.

Lobo NF, Hua-Van A, Li X, Nolen BM, Fraser MJ Jr (2002) Germ line transformation of the yellow fever mosquito, *Aedes aegypti*, mediated by transpositional Insertion of a *piggyBac* vector, Insect Mol. Biol., 11(2): pp. 133-139.

Lohe AR, Hartl DL (2001) Effficient mobilization of *mariner in vivo* requires multiple internal sequences, Genetics, 160(2): pp. 519-526.

Lozovsky ER, Nurminsky D, Wimmer EA, Hartl DL (2002) Unexpected stability of *mariner* transgenes in *Drosophila*, Genetics, 160(2): pp. 527-535.

Mandrioli, et al. "Stable transformation of a *Mamestra brassicae* (*Lepidoptera*) cell line with the *Lepidopteran*-derived transposon *piggyback*" Insect Biochem. Mol. Bio., vol. 33(1), pp. 1-5, 2002.

Mullins, et al. "cis-acting DNA sequence requirements for P-element transposition" Genes Dev., vol. 3(5), pp. 729-738, 1989.

Nolan, et al. "*piggyback*-mediated germline transformation of the malaria mosquito *Anopheles stephensi* using the red fluorescent protein dsRED as a selectable marker" J. Biol. Chem., 277(11), pp. 8759-8762, 2002.

Ochman, et al. "Genetic applications of an inverse polymerase chain reaction" Genetics, vol. 120(3), pp. 621-623, 1988.

Peloquin, et al: "Germ-line transformation of pink bollworm (*Lepidoptera:gelechiidae*) mediated by the *piggyback* transposable element" Insect Mol. Biol., vol. 9(3), pp. 323-333, 2000.

Perera, et al. "Germ-line transformation of the South American malaria vector, *Anopheles albimanus*, with a *piggyback*/EGFP transposon vector in routine and highly efficient" Insect Mol. Biol., vol. 11(4), pp. 291-297, 2002.

Pfaffle, et al. "Studies on rates of nucleosome formation with DNA under stress" The Journal of Biological Chemistry, vol. 265(28), pp. 16821-16829, 1990.

Rio, et al. "Identification and purification of a *Drosophila* protein that binds to the terminal 31-base-pair inverted repeats of P transposable element" Proc. Natl. Acad. Sci. USA, vol. 85, pp. 8929-8933, 1988.

Rubin, et al. "Genetic transformation of *Drosophila* with transposable element vectors" Science, vol. 218(4570), pp. 348-353, 1982.

Rubin, et al. "Vectors for P element-mediated gene transfer in *Drosophila*" Nucleic Acids Res., vol. 11(18), pp. 6341-6351, 1983.

Sarkar A, et al. "Transposition of the *Hermes* element in embryos of the vector mosquito, *Aedes aegypti*," Insect Biochem. Mol. Biol., 27(5): pp. 359-363, 1997.

Sarkar A, et al. "The Hermes element from *Musca domestica* can transpose in four families of cyclorrhaphan flies" Genetica., 99(1): pp. 15-29, 1997.

Sarkar A, et al. "Molecular evolutionary analysis of the widespread *piggyBac* transposon family and related "domesticated" sequences", Mol. Genet. Genomics, 270(2): pp. 173-180, 2003.

Sekar V. "A rapid screening procedure for the identification of recombinant bacterial clones" BioTechniques, 5: pp. 11-13, 1987.

Sumitani, et al. "Germline transformation of the sawfly, *Athalia rosae* (*Hymenoptera: symphyta*), mediated by a *piggyBac*-derived vector" Insect Biochem. Mol. Biol., 33(4): pp. 449-458, 2003.

Tamura T, et al. "Germline transformation of the silkworm *Bombyx mori* L. using a *piggyBac* transposon-derived vector" Nat. Biotechnol. 18(1): pp. 81-84, 2000.

Thibault ST, et al. "Precise excision and transposition of *piggyBac* in pink bollworm embryos" Insect Mol. Biol., 8(1): pp. 119-123, 1999.

Thomas JL, et al. "3xP3-EGFP marker facilitates screening for transgenic silkworm *Bombyx mori* L. from the embryonic stage onwards" Insect Biochem. Mol. Biol., 32(3): pp. 247-253, 2002.

Thummel, CS, et al. "New pCaSpeR P element vectors" Dros. Info. Service, 71: pp. 150-150, 1992.

Tosi LR; et al. "cis and trans factors affecting Mos 1 *mariner* evolution and transposition in vitro, and its potential for functional genomics" Nucleic Acids Res., 28(3): pp. 784-790, 2000.

Trentmann SM, et al. "The transposable element En/Spm-encoded TNPA protein contains a DNA binding and a dimerization domain" Mol. Gen. Genet., 238(1-2): pp. 201-208, 1993.

Wang HH, et al. "TTAA serves as the target site for TFP3 Lepidopteran insertions in both nuclear polyhedrosis virus and *Trichoplusia ni* genomes" Insect Mol. Biol., 1: pp. 109-116. 1993.

Zayed H, et al. "The DNA-bending protein HMGB1 is a cellular cofactor of Sleeping Beauty transposition" Nucleic Acids Res. 31(9): pp. 2313-2322, 2003.

* cited by examiner

| PLASMIDS | INSERTION SEQUENCE | IPTA FREQUENCY |
|---|---|---|
| pIAO-P/L-TTAA | TTAA | 0 |
| pIAO-P/L-TTAA2 | TTAATTAA | 0 |
| pIAO-P/L | TTAATCTAGAGGATCCTCTAGAGATTAA (XbaI/BamHI/XbaI)--(SEQ ID NO:35)-- | $5.4 \times 10^{-3}$ |
| pIAO-P/L-18 bp | TTAATCTAGACGTACGCGGAGCTTAA--(SEQ ID NO:36)-- | $1.0 \times 10^{-6}$ |
| pIAO-P/L-22 bp | TTAATCTAGCTAGTACTAGAACTAGATTAA--(SEQ ID NO:37)-- | $3.6 \times 10^{-6}$ |
| pIAO-P/L-40 bp | TTAATCTAGTTCTAGACGTACGCGGCCACTAGTACTAGTAGCTAGATTAA--(SEQ ID NO:38)-- | $2.5 \times 10^{-5}$ |
| pIAO-P/L-55 bp | TTAATCTAGTTCTAGACTGCGCGTCTCTAGACGTACGCGGCGCACTA-GTACTAGCTAGATTAA--(SEQ ID NO:39)-- | $1.2 \times 10^{-4}$ |
| pIAO-P/L-73 bp | 63bp of Lambda PvuII fragment between XbaI sites of pIAO-P/L | $1.3 \times 10^{-4}$ |
| pIAO-P/L-212 bp | 63 bp + 141 bp of Lambda PvuII fragment between XbaI sites of pIAO-P/L | $3.1 \times 10^{-4}$ |
| pIAO-P/L-354 bp | 43 bp of Lambda PvuII fragment between XbaI sites of pIAO-P/L | $2.9 \times 10^{-4}$ |
| pIAO-P/L-589 bp | 579 bp of Lambda PvuII fragment between XbaI sites of pIAO-P/L | $3.2 \times 10^{-4}$ |
| pIAO-P/L-2.2 kb | 2.2 kb of Lambda HindIII fragment between XbaI sites of pIAO-P/L | $3.4 \times 10^{-4}$ |

FIG. 2(A)

```
Sequence Range: 1 to 7670

100  AACGCGCGGGGAGAGGCGGTTTGCGTATTGGGCGCTCTTCCGCTTCCTCGCTCACTGACTCGCTGCGCTCGGTCGTTCGGCTGCGGCGAGCGGTATCAGC
200  TCACTCAAAGGCGGTAATACGGTTATCCACAGAATCAGGGGATAACGCAGGAAAGAACATGTGAGCAAAAGGCCAGCAAAAGGCCAGGAACCGTAAAAAG
     >ori
     |——
300  GCCGCGTTGCTGGCGTTTTTCCATAGGCTCCGCCCCCCTGACGAGCATCACAAAAATCGACGCTCAAGTCAGAGGTGGCGAAACCCGACAGGACTATAAA
400  GATACCAGGCGTTTCCCCCTGGAAGCTCCCTCGTGCGCTCTCCTGTTCCGACCCTGCCGCTTACCGGATACCTGTCCGCCTTTCTCCCTTCGGGAAGCGT
500  GGCGCTTTCTCAATGCTCACGCTGTAGGTATCTCAGTTCGGTGTAGGTCGTTCGCTCCAAGCTGGGCTGTGTGCACGAACCCCCCGTTCAGCCCGACCGC
600  TGCGCCTTATCCGGTAACTATCGTCTTGAGTCCAACCCGGTAAGACAGGATTAGCAGAGCGAGGT
700  ATGTAGGCGGTGCTACAGAGTTCTTGAAGTGGTGGCCTAACTACGGCTACACTAGAAGGACAGTATTTGGTATCTGCGCTCTGCTGAAGCCAGTTACCTT
800  CGGAAAAAGAGTTGGTAGCTCTTGATCCGGCAAACAAACCACCGCTGGTAGCGGTGGTTTTTTTGTTTGCAAGCAGCAGATTACGCGCAGAAAAAAAGGA
900  TCTCAAGAAGATCCTTTGATCTTTTCTACGGGGTCTGACGCTCAGTGGAACGAAAACTCACGTTAAGGGATTTTGGTCATGAGATTATCAAAAGGATCT
1000 TCACCTAGATCCTTTAAATTAAAAATGAAGTTTTAAATCAATCTAAAGTATATATGAGTAAACTTGGTCTGACAGTTACCAATGCTTAATCAGTGAGGC
     <W  H  K  I  L  S  A
     <———— AMP RESIST
```

```
1800
TCGATGTAACCCACTCTGTGCACCCAACTGATCTTTCAGCATCTTTCACTTCACCAGCGTTTCTGGGTGAGCAAAAACAGGAAGCAAAATGCCGCAAAAA
 E  I  Y  G  V  R  A  G  L  Q  D  E  A  D  K  V  K  V  L  T  E  P  H  A  F  V  P  L  C  F  A  A  F  F
                                            AMP RESIST

1900
AGGGAATAAGGGCGACACGGAAAATGTTGAATACTCATATCTCTTCCTTTTTCAATATATTATTGAAGCATTTATCAGGGTTATTGTCTCATGAGCGGATACAT
 P  I  L  A  V  R  F  H  Q  I  S  M  --(SEQ ID NO:58)--
         AMP RESIST

2000
ATTTGAATGTATTTAGAAAAATAAACAAATAGGGGGTTCCGCGCACATTTCCCGAAAAGTGCCACCTGAGCTCTAAGAAACCATTATTATCATGACATTA

2100
ACCTATAAAAAATAGGCGTATCACGGGGCCCTGAGGTGAACCAATTGTCACACGTAATATTACGACAACTACCGTGCACAGGCTTTGATAACTCCTTCACG
 R  Y  F  Y  A  Y  *  P  A  R  L  H  V  L  Q  *  V  Y  Y  *  S  L  *  R  A  C  A  K  I  V  G  E  R
                                                        ORF1 N-TERM [SPLIT]

2200
TAGTATTCACCGAGTGGTACTCCGTTGGTCTGTGTCCTCTTCCCAAATAAGGCATTCCATTTATCATATACTTGTACCACTGTCACACATCATGAGGA
 L  I  *  R  T  T  S  R  Q  D  T  N  R  K  G  F  L  A  N  W  K  D  Y  V  E  Y  W  Q  *  V  D  H  P
                                                ORF1 N-TERM [SPLIT]

2300
TTTTTATTCCATACTTACTTGGCTTGTTGGGATATACATCCTAAAACGGACACCGTCCTAAAACCAAGTAACTGTTCATCTATGTCAAATGAGCCCC
 N  K  N  W  V  *  K  A  Q  K  P  Y  V  D  *  V  S  V  T  R  *  F  W  T  V  T  *  R  H  D  F  S  G  R
                                        ORF1 N-TERM [SPLIT]

2400
TGGAGTGTAATTTGTATGCACTGATGGATAAAGAGATCCCATATTTTCTAACAGGAGTAAATACATCGTTTTCTCGAAGTGTGGGCCGTATACTTTTG
 S  H  L  K  T  H  V  S  P  Y  L  S  G  M  N  K  *  C  S  Y  I  C  R  K  R  S  T  H  A  T  Y  K  Q
                                        ORF1 N-TERM [SPLIT]
```

FIG. 2(C1) CONT.

```
2500
TCATCCATTCTAAGACATCGTATCAAAAATCCAAACGATCCACAGACTCATTACAGAGACTACACATTGACAAAGATCGATCCAAAGAGTCATCTG
 * S M T D F F G F R D V S E N C L R V C Q C L D I W L P * R
     ORF1 N-TERM [SPLIT]

2600
TGGACATGTGGTTATCTTTTCTCACTGCTGTCATTACCAGAATACCAAAGAAGCATAGATTCATCTTCATTCCTGTCACGAAATGTAGCACCTGTCAT
 H V H P * R K E S S D N G S Y W L F C L N * R * E H * S I Y C R D Y
      ORF1 N-TERM [SPLIT]

2700
AGATTCCCGACGTTCAATGATATCTCAGCATTTGTCCATTTACAATTGGCGAAATTATCTCATCAGTAAAAAATAGTTTGAAGCATAAAGTGGGTCA
 I G S T E I I D * C K D M K C N A F N D * * Y F I T Q L M F T P *
       ORF1 N-TERM [SPLIT]

2800
TATATATTGCGGCACATACGCGTCGGACCTCTTTGAGATCTGACAATGTTCAGTGCAGAGACTCGGCTACCGCTCGTCGTGGACTTTGAAGTAAATTCAGAT
 I Y Q P V Y A D S R K S I Q C H E T C L S P * R E H V K F N --(SEQ ID NO:59)--
        ORF1 N-TERM [SPLIT]

2900
ATAAAGACGCTGAAAATCATTTGATTTTCGCTCTAACATACCACCCTAAAGATTATAAATTAATGAATTATAAAATACGTACAACAATTGTCTGTAAA

3000
TCAACAACGCACAGAATCTAGCGCTTAATAAATGTACTAATAACAATGTATCGTGTTTTAATACGCCGGACCAGTGAACAGAGGTGCGTCTGGTGCAAAC

3100
TCCTTTACTTTGAACACCAGGGAAACTTCAAGGAGAGAATTCCTCCTCTTCAGCAGAGTCGGTACCGGTCACCCGGGATCCCCCCTGCCCGGTTATTATT

3200
ATTTTTGACACCAGACCAACTGGTAAGTGGTAGCGACCGGCGCTCAGCTGAATTCCGCGATCTGACGGGCTCCAGAGTCGTCGCCACCAATCCCCAT
 K Q C W V L Q Y H Y R G A S L Q F E A S V S P S W S D D G G I G M
                                LACZ
```

*FIG. 2(C1) CONT.*

```
3300
ATGGAAACCGTCGATATTCAGCCATGTGCCTTCTTCCGGTCGTGCTGTTCCATCAGTTGCTGTGACTGTAGGGCTGATGTTG
<H F G D I N L W T G E E A H L L H R H S T E M L Q Q Q S Y R S I N
         LACZ

3400
AACTGGAAGTCGCGCCGCGCCACTGGTGTGGGCCATAATTCAATTCGCGCGCAGACCGTTTGCGCTCGGAAGAGTACGGGGTATACATGT
<F Q F F D G R W Q H P G Y N L E R T G C R L G N E S P F V Y P T Y M D
         LACZ

3500
CTGACAATGGCAGATCCCAGGCGGTCAAAAACAGGCGGCGTCAGTAAGGCGGTCGGATAGTTTTCTTGCGGCCCTAATCCGAGCCAGTTTACCCGCTCTGCTAC
<S L P L D W R D F C A A T L R D P Y N E Q P G L G L W N V R E A V
         LACZ

3600
CTGCGCCAGCTGGCCAGTTCAGGCCCAATCCGCGCCGGATGCGGTGTATCGTCGCCACTTCAACATCAACGGTAATCGCCATTTGACCACTACCATCAATC
<Q A L Q C N L G I R A P H P T D S A V E V D V T I A M Q G S G D I
         LACZ

3700
CGGTAGGTTTCCGGCTGATAAATAAGGTTTTCCCCTGATGCTGCCATGCGTCGAGCGTCGTAATCAGCACCGCAAGTGTATCGCCGTGCACT
<R Y T K R S I F L T K G Q H Q W A H A T T I L V A D A L T D A T C Q
         LACZ

3800
GCAACAACGCTGCTTCGGCCTGGTAATGCGGCCTTCGACCCCAGCCGTTCGATCAATGCGGGTCGCTTCACTTACGCCAATGTCTGTT
<L A A E A Q Y H G A A K W R E V W A N P D I R T A E S V G I D N
         LACZ

3900
ATCCAGCGGGGTGCACGGGTGAACTGATGCGGCCAGCGGCGTCAGCAGTTGTTTTTATCGCCAATCCACATCTGAAAGAAAGCCTGACTCTGTGAAAATT
<D L P A R T F Q D R L P T L L Q K K D G I W M Q S L F G S Q R N F
         LACZ
```

FIG. 2(C1) CONT.

```
4000
TGCCAACGCTTATTACCCAGCTCGATGCAAAAATCCATTTCGCTGGTGTCAGATGCGGGATGGCGTGGGACGCGGGGCGGAGCGTCACACTGAGGTTTT
 <Q  V  W  R  K  N  G  L  E  I  C  F  D  M  E  S  T  I  H  P  I  A  H  S  A  A  P  L  T  V  S  L  N  E
                                              LACZ

4100
CCGGCCAGACGCCACTGCTGCCAGGCGCTGATGCGCCGGTTCTGACCATGCGGTTGCGCTTCGGTTGCCGGTACTGTGAGCCAGAGTGCCGGC
 A  L  R  W  Q  Q  W  A  S  I  H  G  A  E  S  W  A  T  A  N  P  Q  V  V  R  V  T  L  W  L  Q  G  A
                                              LACZ

4200
GCTCTCCGGCTGCCGGTAGTTCAGGCAGTTCAATCAACTGTTTACCTTGTGGAGCGACATCCAGAGGCACTTCACCGCTTGCCAGCGGCTTACCATCCAGC
 S  E  P  Q  P  L  E  P  L  E  I  L  Q  K  G  Q  P  A  V  D  L  P  V  E  G  S  A  L  P  K  G  D  L
                                              LACZ

4300
GCCACCATCCAGTGCAGGAGCTCGTTATCGACGAACAGTATTCGCTGCTGTCACTTCGATGGTTTGCCCGATAAACGAACTGGAAAAACTGCT
 A  V  M  W  H  L  L  E  N  D  S  H  R  F  L  Y  E  S  T  V  E  I  T  Q  S  L  R  F  Q  F  F  Q  Q
                                              LACZ

4400
GCTGGTGTTTGCTTCCGTCAGCGCTGGATGCGGGTCGCAAAGACCGTTCATACAGAACCGTTCGCGATCGTTCGGCTATCGCCAAAATC
 H  K  A  E  T  L  A  P  H  P  T  R  D  A  F  V  L  G  N  M  C  F  Q  R  D  N  P  T  D  G  F  D
                                              LACZ

4500
ACGCCCGTAAGCCGACCACCAGGGTTGCCGTTTTCATCATATTTAATCAGCAGCGACTGATCCACCAGTCCCAGAGACGAAGCCCCTGTAAACGGGATACTGA
 G  Y  A  S  W  P  N  G  N  E  D  Y  K  I  L  S  Q  D  V  W  D  W  V  F  G  G  Q  L  R  P  Y  Q
                                              LACZ

4600
CGAAACGCCTGCCAGTATTTAGCGAAACTGTTACCGCCAAGACTGCCGTTGGGCGTATTCGAAAGGATCAGGCTATTCGAAGCTACCAGGTCCTCCAGTAGCCGGAAA
 R  F  A  Q  W  Y  K  A  F  G  G  L  S  N  G  M  A  H  A  Y  E  C  L  I  L  P  R  T  E  G  P  L  S  L
                                              LACZ
```

*FIG. 2(C1) CONT.*

```
4700
GCCATTTTTGATGGACCATTCGGCACAGCCGGGAAGGGCTGGTCTTCATCCACGCGGGCGTACATCGGGCAAATAATATCGTGGTGGCCGTGTGGTGTCGGC
<W  K  K  I  S  W  K  P  V  A  P  F  P  Q  D  E  D  V  R  A  Y  M  P  C  I  D  T  A  T  T  D  A
                                                    LACZ
4800
TCCGGCCCCGCCTTCATACTGCACCGGGCGGGAAGGATCGACAGATTGATCGTGATTAGCGCGTGCCTGATTCATTCCCCAGC
<G  G  G  E  Y  Q  V  P  R  S  P  D  V  S  K  I  W  R  Y  L  A  D  H  N  A  G  H  G  S  E  N  G  L
                                                    LACZ
4900
GACCAGATGATCACACTCGGGTGATTACGATGCGCTGCCACCATTCGCGTTACGCGTTCGCTCATCGCCGGTAGCCAGCCGGGATCATCGGTCAGACGAT
<S  W  I  I  V  S  P  H  N  R  D  R  Q  V  M  R  T  V  R  E  S  M  A  P  L  W  R  P  D  D  T  L  R  N
                                                    LACZ
5000
TCATTGGCACCATGCCGTGGGTTTCAATATTGGCTTCATCCACCACATACAGGCCGTAGCCGTGCCACAGCGTGTACCACAGCGGATGGTTCGGATAATG
<M  P  V  M  G  H  T  E  I  N  A  E  D  V  V  Y  L  G  Y  R  D  C  L  T  Y  W  L  P  H  N  P  Y  H
                                                    LACZ
5100
CGAACAGCAGCGCACGGCCGTTAAAGTGTTCTGCTTCATCAGCAGGATATCCTGCACCATCGTCTGCTCATCCATGACCTGACCATGCAGAGGATGATGCTCG
<S  C  R  V  A  N  F  N  N  Q  K  M  L  L  I  D  Q  V  M  T  Q  E  D  M  V  Q  G  H  L  P  H  H  E
                                                    LACZ
5200
TGAGCGGTTAACGCCTCGAATCAGCAACGGCTTGCCGTTCAGCAGGCAGACCATTTCAATCCGCGGAAACCGACATCGCAGGCTTCTGCTT
<H  R  N  V  G  R  I  L  L  P  K  G  N  L  L  L  L  G  N  E  I  R  V  E  R  F  G  V  D  C  A  E  A  E
                                                    LACZ
5300
CAATCAGCGTGCCGTCGGCGTGCAGTTCAAGCCACCGGACGATAGAGATTCGGGATTCGGGCGTTCCACAGTTTCGACGTTTCGACGTAG
<I  L  T  G  D  A  T  H  L  E  V  V  A  R  Y  L  N  P  I  E  A  S  W  L  K  P  N  E  V  N  L  R  L
                                                    LACZ
```

FIG. 2(C1) CONT.

```
5400
TGTGACGCGATCGGCATAACCACCACGCTCATCGATAAATTTCACCGCCGAAAGGCGGTGCCGCTGGCCACCTGGCGTTTCACCCCTGCCATAAAGAAACT
 T  V  T  R  D  A  Y  G  G  R  E  D  I  I  E  G  G  F  P  A  T  G  S  A  V  Q  T  E  G  Q  W  L  S  V
                                          LACZ

5500
GTTACCCGGTAGGTAGTCACGCAACTCGCCCGCCAACATCTGAACTTCAGCGCTACACGGCGGCTGAAATCATCATTAAAGCGAGTGGCAACATGGAAAT
 V  T  V  R  L  Y  D  R  L  E  G  C  M  Q  V  E  A  E  L  V  A  R  S  F  D  D  N  F  R  T  A  V  H  F  D
                                          LACZ

5600
CGCTGATTTGTGTAGTCGGTTTATGCAGCAACGAGACGTCAGGGAAAATGCCGCTCATCCGCCACATATCCTGATCTTCCAGATAACTGCCGTCACTCCA
 S  I  Q  T  T  P  K  H  L  L  S  V  D  R  F  I  G  S  M  R  W  M  D  Q  D  E  L  Y  S  G  D  S  W
                                          LACZ

5700
ACGCAGCAGCACCATCACCGCGAGGCGGTTTCTCCGGGCGTAAAAATGCGCTCAGTTCAAATTCAGACGGCCAAACGACTGTCCTGCCGTAACGACCCAG
 R  L  V  M  V  A  L  R  N  E  G  A  R  L  F  A  S  L  D  F  E  S  P  L  R  S  D  Q  G  Y  G  V  W
                                          LACZ

5800
CGCCCGTTGCACCACAGATGAAACGCCGAGTTAACGCCATCAACAAAAATAATTCGCGTCTGGCCTTCCTGTAGCCAGTTTCATCAACATTAAATGTGAGCG
 R  G  N  C  W  L  H  F  A  S  N  V  G  D  E  F  I  R  T  Q  G  E  Q  L  W  S  E  D  V  N  F  T  L  S
                                          LACZ

5900
AGTAACAACCCGTCGGATTCTCCGTGGGAACAAACGGCGATTGACCGTAATGGGATAGGTTACGTTGGTGTAGATGGGCGCATCGTAACCGTGCATCTG
 Y  C  G  T  P  N  E  T  P  V  F  P  P  N  V  T  I  P  Y  T  V  N  T  Y  I  P  A  D  Y  G  H  M  Q
                                          LACZ
```

*FIG. 2(C1) CONT.*

```
6000
     CCAGTTTGAGGGGACGACGACGGGATCCGTTTTTTATTACAAAACTGTTACGAAAACAGTAAAATACTTATTTATTCGGACCAACAATGTTTATTCTTA
   <V  L  L  T  *  E  *
   <  ORF1 N-TERM [S
   <              W  N  S  P  V  V  V  P  D  T  K  K  N  C  F  Q  *  S  F  L  L  I  S  I  *  E  S  W  C  --(SEQ ID NO:60)--
                                                              LACZ

6100
     CCTCTAATAGTCCTCTGTGGCTGCAAGGTCAAGATTCTGTTAGAAGCCAATGAAGAACCTGGTTGTTCAATAACATTTGTTCGTCTAATATTCACTACGCT
   <R  *  Y  D  E  T  A  L  D  L  N  Q  *  F  G  I  E  F  R  T  *  Y  C  K  T  R  R  I  N  *  *  A
   <                                       ORF1 N-TERM [SPLIT]
   <              Q  R  Q  S  S  V  S  *  T  G  *  R  Y  V  S  R  R  Y  R  E  P  R  R  *  K  R  S  R  R  I  N  *  Q  *  F  G
                                              ORF1 N-TERM [SPLIT]

6200
     TGACGTTGGCTGACACTTCATGTACCTCATCTATAAACGCTTCTCTGTATCGCTCTTCACTTACGTGATCTGATATTTCACTGTCAGAATC
   <                                          ORF1 N-TERM [SPLIT]
   <              C  *  R  R  A  S  C  L  P  Y  A  *  R  R  F  F  M  G  X  --(SEQ ID NO:61)--

6300
     CTCACCAACAAGCTCGTCATCGCCTTGCAGAAGAGCAGAGAGGATATGCTCATCGTCTAAAGAACATCCCATTTTATTATATATTAGTCACGATATCTAT
   <*  W  C  A  R  *  R  R  A  S  C  L  P  Y  A  *  R  R  F  F  M  G  X  --(SEQ ID NO:61)--
   <                     ORF1 N-TERM [SPLIT]

6400
     ACAAGAAAATATATATATATAAGTTATCACGTAAGTAGAACATGAAATAACAATATTAATTATCGTATGAGTAAAATCTTAAAAGTCACGTAAAAGAT

6500
     AATCATGCGTCATTTGACTCACGGGTCGTTATAGTTCAAAATCAGTGACACTTACCGCATTGACAAGCACGCCTCAGCCGAGCTCCAAGCGGGCGACTG

6600
     AGATGTCCTAAATTGCAAACAGCGACGGATTCGCGCTATTTAGAAAGAGAGAGCAATATTCAAGAATGCATGCGTCAATTTTACGCAGACTATCTTTCT
                                                                                       RIGHT TERMINAL REPEAT        >
```

*FIG. 2(C1) CONT.*

6700
AGGGTAATCTAGAGGATCCCTCTAGATTAACCCTAGAAAGATAATCATATTGTGACGTACGTTAAAGATAATCATGCGTAAAATTGACGCCATGTGTTTTT
                >                            LEFT TERMINAL REPEAT

6800
ATCGGTCTGTATATCGAGGTTTATTTATTAATTGAATAGATATTAAGTTTTATTATATTACACTTACATACTAATAATAAATTCAACAAACAATTAT

6900
TTATGTTTTATTTATTATTAAAAAACAAAAACTCAAAAATTTCTCTAAAGTAACAAAACTTTAAACATTCTCTCTTTTACAAAATAAACTTATTT

7000
TGTACTTTAAAAACAGTCATGTTGTATTATAAAATAAGTAATTAGCTTAACTTATACATAATAGAAACAAATTATACTTATTAGTCAGTCCAGAAACAAC
<D  T  W  F  C  S
   ORF1 C-TER

7100
TTTGGCACATATCAATATTATGCTCTCGACAAATAACTTTTTTGCATTTTTTGCACGATGCATTGCCTTTCGCCTTATTTTAGAGGGCAGTAAGTACA
<Q  C  M  D  I  N  H  E  R  C  I  V  K  K  C  K  K  C  S  A  N  A  K  R  R  I  K  S  P  C  Y  T  C
                                 ORF1 C-TERM

7200
GTAAGTACGTTTTTCATTACTGGCTCTTCAGTACTGTCATCTGATGTACCAGGCACTTCATTTGGCAAAATATTAGAGATATTATCGCCAAATATCTC
<Y  T  R  K  K  M  V  P  E  E  T  S  D  D  S  T  G  P  V  E  N  P  L  I  N  S  I  N  D  R  L  Y  R
                                 ORF1 C-TERM

7300
TTCAAAGTAGGAGCTTCTAAACGTTACGCATAAACGATGACGTCAGGCTCATGTAAAGTTTCTCATAAATTTTTTGCGACTTTGAACCTTTCTCCCT
<K  L  T  P  A  E  L  R  N  R  M  F  S  S  T  L  S  M  Y  L  N  R  M  F  K  K  R  S  Q  V  K  E  G  K
                                 ORF1 C-TERM

*FIG. 2(C1) CONT.*

```
7400
TGCTACTGACATTATGGCTGTATATAATAAAGAATTATGCAGGCAATGTTTATCATTCCGTACAATAATGCCATAGGCCACCTATTCGTCTTCCTACT
 S  S  V  N  H  S  Y  I  I  F  S  N  I  C  A  I  N  I  M  G  Y  L  L  A  M  P  W  R  N  T  K  R  S
                                     ORF1 C-TERM

7500
GCAGGTCATCACAGAACACATTTGTCTAGCGTGTCCACTCCGCCCTTTAGTTTGATTATAATACATAACCATTTGCGGTTTACCGTACTTTGTTGATA
 C  T  M  V  S  C  M  Q  D  L  T  D  V  G  G  K  T  Q  N  Y  Y  M  V  M  Q  P  P  K  G  T  S  E  N  I
                                     ORF1 C-TERM

7600
GAAGCATCCTCATCACAAGATGATAATAAGTATACCATCTTAGCTGGCTTCGGTTTATATGAGAGAGAGTAAGGGGTCGTCAAAACAAAACATCGATG
 S  A  D  E  D  C  S  S  L  L  Y  V  M  K  A  P  K  P  K  Y  S  V  L  T  L  P  G  D  F  C  F  M  S  T
                                     ORF1 C-TERM

TTCCCACTGGCCTGGAGGCGACTGTTTTCAGTACTTCCGTATCTCGCGTTGTTTGATCGCACGGTACC --(SEQ ID NO:57)--
 G  V  P  R  S  R  S  N  K  L  V  E  P  I  E  R  K  N  S  R  V  T  G --(SEQ ID NO:62)--
                ORF1 C-TERM
```

FIG. 2(C1) CONT.

pIAO-P/L-Lambda-2.2kb
Sequence Range: 1 to 9984

100
AACGCGCGGGGAGAGGCGGTTTGCGTATTGGGCGCTCTTCCGCTTCCTCGCTCACTGACTCGCTGCGCTCGGTCGTTCGGCTGCGGCGAGCGGTATCAGC

200
TCACTCAAAGGCGGTAATACGGTTATCCACAGAATCAGGGGATAACGCAGGAAAGAACATGTGAGCAAAAGGCCAGCAAAAGGCCAGGAACCGTAAAAAG
   >ori
   ─┼──

300
GCCGCGTTGCTGGCGTTTTTCCATAGGCTCCGCCCCCCTGACGAGCATCACAAAAATCGACGCTCAAGTCAGAGGTGGCGAAACCCGACAGGACTATAAA

400
GATACCAGGCGTTTCCCCCTGGAAGCTCCCTCGTGCGCTCTCCTGTTCCGACCCTGCCGCTTACCGGATACCTGTCCGCCTTTCTCCCTTCGGGAAGCGT

500
GGCGCTTTCTCAATGCTCACGCTGTAGGTATCTCAGTTCGGTGTAGGTCGTTCGCTCCAAGCTGGGCTGTGTGCACGAACCCCCCGTTCAGCCCGACCGC

600
TGCGCCTTATCCGGTAACTATCGTCTTGAGTCCAACCCGGTAAGACACGACTTATCGCCACTGGCAGCAGCCACTGGTAACAGGATTAGCAGAGCGAGGT

700
ATGTAGGCGGTGCTACAGAGTTCTTGAAGTGGTGGCCTAACTACGGCTACACTAGAAGGACAGTATTTGGTATCTGCGCTCTGCTGAAGCCAGTTACCTT

800
CGGAAAAAGAGTTGGTAGCTCTTGATCCGGCAAACAAACCACCGCTGGTAGCGGTGGTTTTTTTGTTTGCAAGCAGCAGATTACGCGCAGAAAAAAAGGA

900
TCTCAAGAAGATCCTTTGATCTTTTCTACGGGGTCTGACGCTCAGTGGAACGAAAACTCACGTTAAGGGATTTTGGTCATGAGATTATCAAAAGGATCT

FIG. 2(C2)

```
1000
TCACCTAGATCCTTTAAATTAAAAATGAAGTTTTAAATCAATCTAAAGTATATATGAGTAAACTTGGTCTGACAGTTACCAATGCTTAATCAGTGAGGC
                                                            <W  H  K  I  L  S  A
                                                                 AMP RESIST

1100
ACCTATCTCAGGCGATCTGTCTATTTCGTTCATCCATAGTTGCCTGACTCCCCCGTCGTGTAGATAACTACGGATACGGGAGGGCTTACCATCTGGCCCCAGT
< G  I  E  A  I  Q  R  N  R  E  D  M  T  A  Q  S  G  T  T  Y  I  V  V  I  R  S  P  K  G  D  P  P  G  L
<                            AMP RESIST

1200
GCTGCAATGATACCGGGAGACCCACGGCTCCACCGGCTCCAGATTTATCAGCAATAAACCAGCCAGCCCGGAAGGGCCGAGGCGCAGAAGTGGTCCTGCAACTT
< A  A  I  I  G  R  S  G  R  E  G  A  G  S  K  D  A  I  F  W  G  A  P  L  A  S  R  L  L  P  G  A  V  K
<                            AMP RESIST

1300
TATCCGGCCCTCCATCCAGTCTATTAATTGTTGCCGGAAGCTAGAGTAAGTAGTTCGCCAGTAATAGTTTGGCCAACGTTGTGTGCCATTGCTACAGGCAT
< D  A  E  M  W  D  I  L  Q  Q  R  S  A  L  T  L  L  E  G  T  L  L  K  R  L  T  T  A  M  A  V  P  M
<                            AMP RESIST

1400
CGTGGTGTCACGCTCGTCGTTGGTATGGCTTCATTCAGCTCCGGTTCCCAACGATCAAGGCGAGTTACATGATCCCCATGTTGTGCAAAAAGCGGTT
< T  T  D  R  E  D  N  P  I  A  E  N  L  E  P  E  W  R  D  L  R  T  V  H  D  G  M  N  H  L  F  A  T
<                            AMP RESIST

1500
AGTTCCTTCGGTCCCTTCCGATCGTTGTCAGAAGTAAGTCCAGTGTTATCACTCATGGTTATGGCAGCAGCACTGCATAATTCTCTTACTGTCATGCCAT
< L  E  K  P  G  G  I  T  T  L  L  L  N  A  A  T  N  D  S  M  T  I  A  A  S  C  L  E  R  V  T  M  G  D
<                            AMP RESIST

1600
CCGTAAGATGCTTTCTGTGACTGGTGAGTACTCAACCAAGTCATTCTGAGAATAGTGTATGCGGCGACCGAGTTGCTCTTGCCCGGCGTCAATACGGGA
< T  L  H  K  E  T  V  P  S  Y  E  V  L  D  N  Q  S  Y  H  I  R  R  G  L  Q  E  Q  G  A  D  I  R  S
<                            AMP RESIST
```

*FIG. 2(C2) CONT.*

```
1700
TAATACCGCGGCCACATAGCAGAACTTAAAAGTGCTCATCATTGGAAAACGTTCTTCGGGGGAAAACTCTCAAGGATCTTACCGCTGTGTTGAGATCCAGT
<L V A G C L L V K F T S M M P F R E E P R F S E L I K G S N L D L
                                    AMP RESIST

1800
TCGATGTAACCCACTCTGCCACCCAACTGATCTTCAGCATCTTTACTTTCACCAGCGTTTCTGGGTGAGCAAAAACAGGAAGGCAAAATGCCGCAAAAA
<E I Y G V R A G L Q D E A D K V K V L T E P H A F V P L C F A A F F
                                    AMP RESIST

1900
AGGGAATAAGGGCGACACGGAAATGTTGAATACTCATATACTCTTCCTTTTCAATATTATTGAAGCATTTATCAGGGTTATTGTCTCATGAGCGGATACAT
<P I L A V R F H Q I S M --(SEQ ID NO:58)--
          AMP RESIST

2000
ATTTGAATGTATTAGAAAATAAACAAATAGGGGTTCCGCGCACATTTCCCGAAAAGTGCCACCTGAGCTCTAAGAAACCATTATTATCATGACATTA

2100
ACCTATAAAAATAGGCGTATCACGGGCCCTGAGGTGAACCAATTGTCACACGTAATATTACGACAACTACCGTGCACAGGCTTTGATAACTCCTTCACG
<R Y F Y A Y * P A R L H V L Q * V Y Y * S L * R A C A K I V G E R
                    ORF1 N-TERM [SPLIT]

2200
TAGTATTCACCGAGTGCTACCGTTGGTGTTCCTCTTCCCAAATAAGGCATTCCATTATCATATACTTCGTACCACTGTCACACATCATGAGGA
<L I * R T T S R Q D T N R K G F L A N W K D Y V E Y W Q * V D H P
            ORF1 N-TERM [SPLIT]

2300
TTTTTATTCCATACTTACTTGGCTTGTTTGGGATATACATCCTAAACGGACACCGTCCTCTAAAACCAAGTAACTGTTCATCTATGGTCAAATGAGCCCC
<N K N W * K A Q K P Y V D * V S V T R * F W T V T * R H D F S G R
                ORF1 N-TERM [SPLIT]
```

FIG. 2(C2) CONT.

```
2400
TGGAGTGTAATTTTGTATGCACTGATGATGGATAAAGAGATCCCATATTTTCTAACAGGAGTAAATACATCGTTTTCTCGAAGTGTGGGCCTATACTTTTG
 S  H  L  K  T  H  V  S  P  Y  L  S  G  M  N  K  *  C  S  Y  I  C  R  K  R  S  T  H  A  T  Y  R  Q
                                          ORF1 N-TERM [SPLIT]

2500
TCATCCATTCTAAGACATCGTATCAAAAAATCCAAAGACGATCCACAGACTCATTACAGAGACGTACACATTGACAAAGATCGATCCAAAGAGGTCATCTG
 G  N  *  S  M  T  D  F  F  G  F  R  D  V  S  E  N  C  L  R  V  C  Q  C  L  D  I  W  L  P  *  R
                                          ORF1 N-TERM [SPLIT]

2600
TGGACATGTGGTTATCTTTTCTCACTGCTGTCATTACCAGAATACCAAAGAAAGCATAGATTTCATCTTCATTCGTGTCACGAAATGTAGCACCTGTCAT
 H  V  H  P  *  R  K  E  S  S  D  N  G  S  Y  W  L  F  C  L  N  *  R  *  E  H  *  S  I  Y  C  R  D  Y
                                          ORF1 N-TERM [SPLIT]

2700
AGATTCCCGACGTTCAATGATATCTCAGATTTGTCCATTTTACAATTTGCGAAATTATCTCATCAGTAAAAATAGTTTGAAGCATAAAAGTGGGTCA
 I  G  S  T  E  I  I  D  *  C  K  D  M  K  C  N  A  F  N  D  *  *  Y  F  I  T  Q  L  M  F  T  P  *
                                          ORF1 N-TERM [SPLIT]

2800
TATATATTGCGGCACATACGGCTCGGACCTCTTTGAGATCTGACAATGTTCAGTGCAGAGACTCGGCTACCGCTCGTCCTGTGACTTTGAAGTTAAATTCAGAT
 I  Y  Q  P  V  Y  A  D  S  R  K  S  I  Q  C  H  E  T  C  L  S  P  *  R  E  H  V  K  F  N  --(SEQ ID NO:59)--
                                          ORF1 N-TERM [SPLIT]

2900
ATAAAGAGCTGAAAATCATTTGATTTTCGCTCTAACATACCACCCTAAAGATTATAAATTAATGAATTATTAAAATACGTACAACAATTGTCTGTAAA

3000
TCAACAACGCACAGAATCTAGCGCTTAATAAAATGTACTAATAACAATGTATCGTGTTTAATACGCCGGACCAGTGAACAGAGTGCGTCTGGTGCAAAC

3100
TCCTTTACTTTGAACACCAGGAAACTTCAAGGAGAATTCCTCCTCTTCAGCAGAGTCGGTACCGGTCACCCGGGGATCCCCCTGCCCGGTTATTATT
```

*FIG. 2(C2) CONT.*

```
3200
ATTTTGACACCAGACCAACTGGTAATGTAGCGACCGGCTCAGCTGGAATTCGCCGATACTGACGGGCTCCAGGAGTGTCGCCACCAATCCCCAT
<K  Q  C  W  V  L  Q  Y  H  Y  R  G  A  S  L  Q  F  E  A  S  V  S  P  S  W  S  D  D  G  G  I  G  M
v                                                     LACZ

3300
ATGGAAACCGTCGATATTCAGCCATGTGCCTTCTTCCGGTGCAGCAGATGGCGATGCTGGTTGTTGCTGTGTTGACTGTGTTAGCGGCTGATGTTG
<H  F  G  D  I  N  L  W  T  G  E  E  A  H  L  L  H  R  H  S  T  E  M  L  Q  Q  Q  S  Y  R  S  I  N
v                                                     LACZ

3400
AACTGGAAGTCGCCGCCACTGGTCTGTGGGCCCTCCCGCAGCCGTTTCGCTCGGAAGACGTACGGGGTATACATGT
<F  Q  F  D  G  R  W  Q  H  P  G  Y  N  L  E  R  T  G  C  R  L  G  N  E  S  P  F  V  Y  P  T  Y  M  D
v                                                     LACZ

3500
CTGACAAATGGCAGATCCCAGGCGTCAAAACAGGGCAGTAAGGCGTCGGGATAGTTTTCTTGGCCCTAATCCGAGCCAGTTTACCCGCTCTGCTAC
<S  L  P  L  D  W  R  D  F  C  A  A  T  L  R  D  P  Y  N  E  Q  P  G  L  G  L  W  N  V  R  E  A  V
v                                                     LACZ

3600
CTGCGCCACAGCTGGAGTTCAGGCCCAATCCGCGGTGTATCGCTCGCCACTTCAACATCAACGGTTGACCACTACCATCAATC
<Q  A  L  Q  C  N  L  G  I  R  A  P  H  P  T  D  S  A  V  E  V  D  V  T  I  A  M  Q  G  S  G  D  I
v                                                     LACZ

3700
CGGTAGTAGTTTTCCCGGCTGATAAATAAGTTTTCCCCTGATGCGTGAGCGGTCGTAATCAGCACCGCAAGTGTATCTGCCGTGCACT
<R  Y  T  K  R  S  I  F  L  T  K  G  Q  H  Q  W  A  H  A  T  T  I  L  V  A  D  A  L  T  D  A  T  C  Q
v                                                     LACZ

3800
GCAACAACGCTGCTTCGGCTGGTAATGGGCCCTTCCAGGCGTTCGACCCAGGCGTTAGGGTCAATGGGTGCGTCACTTACGCCAATGTCGTT
<L  A  A  E  A  Q  Y  H  G  A  A  K  W  R  E  V  W  A  N  P  D  I  R  T  A  E  S  V  G  I  D  N
v                                                     LACZ
```

FIG. 2(C2) CONT.

```
3900
ATCCAGCGGTGCACGGGGTGAACTGATCGCGCAGCAGTTGTTTTTATCGCCAATCCACATCTGTGAAGAAAGCCTGACTGGCGGTTAAAT
<D  L  P  A  R  T  F  Q  D  R  L  P  T  L  L  Q  K  K  D  G  I  W  M  Q  S  L  F  G  S  Q  R  N  F
                                                LACZ

4000
TGCCAACGCTTATTACCCAGCTCGATGCAAAAATCCATTTCGCTGGTCAGATGCCGTTCAGATGCGGATGGCGTGGGAGCGTCACACTGAGTTTT
<Q  W  R  K  N  G  L  E  I  C  F  D  M  E  S  T  L  H  P  I  A  H  S  A  A  P  L  T  V  S  L  N  E
                                                LACZ

4100
CCGCCAGAGACGCCACTGCTGCCAGGCGCTGATGTGCCCGGCTTCGATGCTCTGACACATGCGGTCGCCGTTCGCGTACGGTACTGTGAGCCAGAGTTGCCCGGC
<A  L  R  W  Q  Q  W  A  S  I  H  G  A  E  S  W  A  T  A  N  P  Q  V  V  R  V  T  L  W  L  Q  G  A
                                                LACZ

4200
GCTCTCCGGCTGCGGTAGTTCAGGCAGTTCAATCAACTGTTTACCTTGTGAGCGACATCCAGAGGCACTTCACCGTCGAAGGTGAAGCGCTTACCATCCAGC
<S  E  P  Q  P  L  E  P  L  E  I  L  Q  K  G  Q  P  A  V  D  L  P  V  E  G  S  A  L  P  K  G  D  L
                                                LACZ

4300
GCACCATCCAGTGCAGGAGCTCGTTATCGCTATGACGGAACAGGTATTCGCTGGTCACTTCGATGGTTTGCCCGGATAAACGAACTGAAAACTGCT
<A  V  M  W  H  L  L  E  N  D  S  H  R  F  L  Y  E  S  T  V  E  I  T  Q  G  S  L  R  F  Q  F  F  Q
                                                LACZ

4400
GCTGGTGTGTTTGCTTCCGTCAGCGCTGGATGGGCGTCGGCAAAGACTCGGCAAATGCCGTTCATACAGAACCGTTCGGCGTATCGCCAAAATC
<Q  H  K  A  E  T  L  A  P  H  P  T  R  D  A  F  V  L  G  N  M  C  F  Q  R  D  N  P  T  D  G  F  D
                                                LACZ

4500
ACGGCCCGTAAGCCCGACCAGGGTTGCCGTTTCATCATATATTTAATCAGCGACTGATCCCCAGTCCCAGAGACGAAGCCCCTGTAAACGGGGATACTGA
<G  G  Y  A  S  W  P  N  G  N  E  D  Y  K  I  L  S  Q  D  V  W  D  W  V  F  G  G  Q  L  R  P  Y  Q
                                                LACZ
```

*FIG. 2(C2) CONT.*

```
4600
CGAAACGCCTGCCAGTATTAGCGAAACCGCCAAGACTGTTACCCATGCCGTTGGGCCGTGCTCTCCAGGTAGCGAAA
 <R  F  A  Q  W  Y  K  A  F  G  G  L  S  N  G  M  A  H  A  Y  E  C  L  I  L  P  R  T  E  G  P  L  S  L
                                      LACZ

4700
GCCATTTTTGATGACCATTTCGGCACACAGTTCCGGGAAGGGCTGTCTTCATCCACGCGCGTACATGCCGCAAATAATATCGTTGGCCGTGTGTCGGC
 <W  K  K  I  S  W  K  P  V  A  P  F  P  Q  D  E  D  V  R  A  Y  M  P  C  I  I  D  T  A  T  T  D  A
 V  V                                 LACZ

4800
TCCGCCGCCTTCATACTGCGACCGGGCGGCGGAAGGATCGACAGATTTGATCGCGCTGATTAGCGCCGTGATTCATTCCCAGC
 <G  G  E  Y  Q  V  P  R  S  P  D  V  S  K  I  W  R  Y  L  A  D  H  N  A  G  H  G  S  E  N  G  L
 V  V                                 LACZ

4900
GACCAGATGATCACACTCGGGTGATTACGACTTCCGCTTGCCACCATTCCGGTAGCCAGCGCGGATCATCGGTCAGACGAT
 <S  W  I  I  V  S  P  H  N  R  D  R  Q  V  M  R  T  V  R  E  S  M  A  P  L  W  R  P  D  D  T  L  R  N
 V  V                                 LACZ

5000
TCATTGGCACCATGCCGTGGTTCAATATTGGCTTCATCCACAGCCGTGCACAGCCGTGTATCCACAGCGGATGTTCGGATAATG
 <M  P  V  M  G  H  T  E  I  N  A  E  D  V  V  Y  I  G  Y  R  D  C  L  T  Y  W  L  P  H  N  P  Y  H
 V  V                                 LACZ

5100
CGAACAGCGCACGGGCGTTAAAGTTGTTCTGCTTCATCAGCAGGATATCCTGCAGTCATCCATGACCTGACCATGCAGAGGATGATGCTCG
 <C  R  V  A  N  F  N  Q  K  M  L  L  I  D  Q  V  M  T  Q  E  D  M  V  Q  G  H  L  P  H  H  E
 V  V                                 LACZ

5200
TGACGGTTAACGCCCTCGAATCAGCAACGGCTTGCCGTTCAGCAGCAGACCATTTCAATCCGCACCTCGCGGAAACCGACATCGCAGGCTTCTGCTT
 <H  R  N  V  G  R  I  L  L  P  K  G  N  L  L  L  G  N  E  I  R  V  E  R  F  G  V  D  C  A  E  A  E
 V  V                                 LACZ
```

*FIG. 2(C2) CONT.*

```
5300
CAATCAGCGTGCCGTCGGCGGTGTGCAGTTCAACCACCGCACGATAGAGATTCGGGATTTCGGGCTCCACAGTTTCGGGTTTTGACGTTCAGACGTAG
<I  T  G  D  D  A  T  H  L  E  V  V  A  R  Y  L  N  P  I  E  A  S  W  L  K  P  N  E  V  N  L  R  L
                                                LACZ

5400
TGTGACGGCGATCGGACATAACCACCGCTCATCGATAATTTCACCGCCGAAAGGCGCGGTCCCTGGGACCTGCGTTTCACCCTGCCATAAAGAAACT
<T  V  R  D  A  Y  G  G  R  E  D  I  I  E  G  G  F  P  A  T  G  S  A  V  Q  T  E  G  Q  W  L  S  V
                                                LACZ

5500
GTTACCCGTAGTAGTCACGCCAACTCGCCGCACATCTGAACTTCAGCTTGGGCTGAAATCATCATTAAAGGCGAGTGGCAACATGGAAAT
<T  V  R  L  Y  D  R  L  E  G  C  M  Q  V  E  A  E  L  V  A  R  S  F  D  D  N  F  R  T  A  V  H  F  D
                                                LACZ

5600
CGCTGATTTGTGTAGTCGGTTTATGCAGCAACGAGAGACGTCACGGCGAAAATGCCGCTCATCCGCTGATCTTCCAGATAATCCGCTCACTCCA
<S  I  Q  T  T  P  K  H  L  S  V  D  R  F  I  G  S  M  R  W  M  D  Q  D  E  L  Y  S  G  D  S  W
                                                LACZ

5700
ACGCAGCACCATCACCGGAGGCGGTTTCTCCGGCGTAAAAATGCGCTCAGGTCAAATTCAGACGGCAAACGACTGTCCTGGCCGTAACCGACCCAG
<R  L  V  M  V  A  L  R  N  E  G  A  R  L  F  A  S  L  D  F  E  S  P  L  R  S  D  Q  G  Y  G  V  W
                                                LACZ

5800
CGCCCGTTGCACCACAGATGAAACGCCCAGTTAACGCCATCAACAAAATAATTCGCGTCTGGCCTTCATCAACATTAAATGTGAGCG
<R  G  N  C  W  L  H  F  A  S  N  V  G  D  F  I  I  R  T  Q  G  E  Q  L  W  S  E  D  V  N  E  T  L  S
                                                LACZ

5900
AGTAACAACCCCGTCGGATTCTCCGTGGGAACAAACGGCGGATTGACCGTAATGGGCCGATCGTTTGGTGTGTAGAATGGGATAGTTACGTTGTTACCGTAACGTGCATCTG
<Y  C  G  T  P  N  E  T  P  P  N  V  T  I  P  Y  T  V  N  T  Y  I  P  A  D  Y  G  H  M  Q
                                                LACZ
```

FIG. 2(C2) CONT.

```
6000
CCAGTTTGAGGGGACGACGACGGGATCCGTTTTTTATTACAAAACTGTTACGAAAACAGTAAAATACTTATTATTCGGACCAACAATGTTATTCTTA
<W  N  S  P  V  V  V  P  D  T  K  K  N  C  F  Q  *   S  F  L  L  I  S  I  *  E  S  W  C --(SEQ ID NO:60)--
<R  *  Y  D  E  T  A  L  D  L  N  Q  *    F  G  I  F  R  T  T  *  Y  C  K  T  R  R  I  N  *  *  A
                                 LacZ                            <V  L  L  T  *  E  *
                                                                  <  ORF1 N-TERM [S

6100
CCTCTAATAGTCCCTCTGTGGCAAGGTCAAGATTCTGTAGAAGCCAATGAAGAACCTGGTTGTTCAATAACATTTGTTCGTCTAATATTCACTACGCT
                                                              ORF1 N-TERM [SPLIT]

6200
TGACGGTTGGCTGACACTTCATGTCTACCTCATCTATAAACGCTTTCTCTGTATCGCTCTGGACGTCTTCACTTACGTGATCTGATATTCACTGTCAGAATC
<Q  R  Q  S  V  S  *  T  G  *  R  Y  V  S  R  R  Y  R  E  P  R  R  *  K  R  S  R  I  N  *  Q  *  F  G
                                                             ORF1 N-TERM [SPLIT]

6300
CTCACCAACAAGCTCGTCATCGCCTTGCAGAGAGCAGAGAGGATATGCTCATCGTCTAAAGAACATCCCATTTTATTATATATTAGTCACGATATCTAT
<W  C  A  R  *  R  R  A  S  S  C  L  P  Y  A  *  R  R  F  F  M  G  X --(SEQ ID NO:61)--
                                                            ORF1 N-TERM [SPLIT]

6400
AACAAGAAAATATATATATAATAAGTTATCACGTAAGTAGAAACATGAAATAACATATTAATTATCGTATGAGTTAAATCTTAAAGTCACGTAAAAGAT

6500
AATCATGCGTCATTTGACTCACGGGTCGTTATAGTTCAAAATCAGTGACACTTACCGCATTGACAAGCACGCCTCAGCCGAGCTCCAAGCGGGCGACTG

6600
AGATGTCCTAAATTGCAAACAGCGACGGATTCCGCGTCAATTTACGCAGAGACTATCTTTCT
                                                RIGHT TERMINAL REPEAT       >
```

```
7000
TCGACCTTCTAATCCTATCTGACCATTATAATTTTTTAGAATGTGTTCATAAGAAAGCTCTGAATCAACGGACTGCGATAATAAGTGTGGTATCCAGAA
<S  R  R  I  R  D  S  W  *  L  K  K  S  H  N  *  L  F  A  R  F  *  R  V  A  I  I  L  P  P  I  W  F
         EA59 (525); CODON START=1; DB XREF=PID:G215132; TRA
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]

7100
TTTGTCACTTCAAGTAAAACACCTCACGAGTTAAAACACCTAAGTTCTCACCGAATGTCTCAATATCCGGACGGATAATATTTATTGCTTCTCTTGACC
<K  D  S  *  T  F  V  G  *  S  N  F  C  R  L  E  *  R  I  D  *  Y  G  S  P  Y  Y  K  N  S  R  R  V
         EA59 (525); CODON START=1; DB XREF=PID:G215132; TRA
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]

7200
GTAGGACTTTCCACATGCAGGATTTTGGAACCTCTTGCAGTACTGGGAATGAGTTGCAATTATTGCTACACCATTGCGTGCATCGAGTAAGTCGCT
<T  P  S  E  V  H  L  I  K  S  G  R  A  T  S  S  P  F  S  N  C  N  N  S  C  W  Q  T  C  R  T  L  R  K
         EA59 (525); CODON START=1; DB XREF=PID:G215132; TRA
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]
```

*FIG. 2(C2) CONT.*

```
7300
TAATGTTCGTAAAAAGCAGAGAGCAAAGTGGATGCAGATGAACCTCTGGTTCATCGAATAAAACTAATGACTTTTCGCCAACGACATCTACTAATCTT
<I  N  T  F  F  C  L  A  F  T  S  A  S  S  G  R  T  *  R  I  F  S  I  V  K  R  W  R  C  R  S  I  K
        EA59 (525);  CODON_START=1; DB_XREF=PID:G215132;  TRA
        MRNA-PL (ALT.; VIA T'J4 TERMINATOR)  [SPLIT]
        MRNA-PL (ALT.; VIA T'J3 TERMINATOR)  [SPLIT]
        MRNA-PL (ALT.; VIA T'J2 TERMINATOR)  [SPLIT]
        MRNA-PL (ALT.; VIA T'J1 TERMINATOR)  [SPLIT]

7400
GTGATAGTAAATAAAACAATTGCATGTCCAGAGCTCATTCGAAGCAGATATTCTGGATATTGTCATAAAACAATTAGTGAATTATCATCGTCCACTT
<H  Y  Y  I  F  C  N  C  T  W  L  E  N  S  A  S  I  E  P  Y  Q  *  L  V  I  *  H  I  *  R  G  S
        EA59 (525);  CODON_START=1; DB_XREF=PID:G215132;  TRA
        MRNA-PL (ALT.; VIA T'J4 TERMINATOR)  [SPLIT]
        MRNA-PL (ALT.; VIA T'J3 TERMINATOR)  [SPLIT]
        MRNA-PL (ALT.; VIA T'J2 TERMINATOR)  [SPLIT]
        MRNA-PL (ALT.; VIA T'J1 TERMINATOR)  [SPLIT]

7500
GAATCTGTGTCGTTCATTACGTCTTAACTCTTCATATTTAGAAATGAGGCTGATGAGTTCCATATTTGAAAAGTTTCATCACTAGTTTTTGATAGC
<S  D  T  T  *  T  K  V  R  *  I  *  F  H  P  Q  H  T  G  Y  K  F  L  K  *  *  K  T  K  Q  Y  S
        EA59 (525);  CODON_START=1; DB_XREF=PID:G215132;  TRA
        MRNA-PL (ALT.; VIA T'J4 TERMINATOR)  [SPLIT]
        MRNA-PL (ALT.; VIA T'J3 TERMINATOR)  [SPLIT]
        MRNA-PL (ALT.; VIA T'J2 TERMINATOR)  [SPLIT]
        MRNA-PL (ALT.; VIA T'J1 TERMINATOR)  [SPLIT]
```

```
7900
AATCATTCAAAATTGTTGTTTACCACACCCATTCCGCCCGATAAAAGCATGAATGTTCGTGCTGGGCATAGAATTAACCGTCACCTCAAAAGGT
<D N W E F N N N * W V W E A R Y F C S H E H Q A Y F * G D G * F T
             EA59 (525); CODON START=1; DB XREF=PID:G215132; TRA
             MRNA-PL (ALT.; VIA T'J4 TERMINATOR) [SPLIT]
             MRNA-PL (ALT.; VIA T'J3 TERMINATOR) [SPLIT]
             MRNA-PL (ALT.; VIA T'J2 TERMINATOR) [SPLIT]
             MRNA-PL (ALT.; VIA T'J1 TERMINATOR) [SPLIT]
v        v   v   v   v

8000
ATAGTTAAATCACTGAATCCGGGAGCACTTTTTCTATTAAATGAAAAGTGGAAATCTGACAATTCTGGCAAACCATTTAACACACGTGCGAACTGTCCAT
<Y N F * Q I R S C K K * I F L P F R V I R A F W K V C T R V T W
             EA59 (525); CODON START=1; DB XREF=PID:G215132; TRA
             MRNA-PL (ALT.; VIA T'J4 TERMINATOR) [SPLIT]
             MRNA-PL (ALT.; VIA T'J3 TERMINATOR) [SPLIT]
             MRNA-PL (ALT.; VIA T'J2 TERMINATOR) [SPLIT]
             MRNA-PL (ALT.; VIA T'J1 TERMINATOR) [SPLIT]
v        v   v   v   v

8100
GAATTTCTGAAAGAGTTACCCCCTCTAAGTAATGAGGTGTTAAGGACGCTTTCATTTCAATGTCGGCTAATCGATTGGCCATACTACTAAATCCTGAAT
<S N R F S N G R * T I L H * P R K * K * H R S I S K A M S S F G S Y
             EA59 (525); CODON START=1; DB XREF=PID:G215132; TRA
             MRNA-PL (ALT.; VIA T'J4 TERMINATOR) [SPLIT]
             MRNA-PL (ALT.; VIA T'J3 TERMINATOR) [SPLIT]
             MRNA-PL (ALT.; VIA T'J2 TERMINATOR) [SPLIT]
             MRNA-PL (ALT.; VIA T'J1 TERMINATOR) [SPLIT]
v        v   v   v   v
```

*FIG. 2(C2) CONT.*

```
8200
AGCTTAAGAAGGTTATGTTTAAAACCATCGCTTAATTTGCTGAGATTAACATAGTCAATGCTTTCACCTTAAGGAAAAAACATTTCAGGGAGTTGA
<S * S  P * T * F  W R K I Q Q S * C L L * H K * R L F F V N * P T S
                                 EA59 (525); CODON START=1; DB XREF=PID:G215132; TRA
                                 MRNA-PL (ALT.; VIA T'J4 TERMINATOR) [SPLIT]
                                 MRNA-PL (ALT.; VIA T'J3 TERMINATOR) [SPLIT]
                                 MRNA-PL (ALT.; VIA T'J2 TERMINATOR) [SPLIT]
                                 MRNA-PL (ALT.; VIA T'J1 TERMINATOR) [SPLIT]

8300
CTGAATTTTTTATCTATTAATGAATAAGTGCTTACTTCTCTTTTTGACCTACAAAACCAATTTAACATTTCCGATATGCATTTTTCACCATGCTCAT
<Q I K * R N I F L H K S R R K S R C F W N * C K R Y R M K * W A *
                                 EA59 (525); CODON START=1; DB XREF=PID:G215132; TRA
                                 MRNA-PL (ALT.; VIA T'J4 TERMINATOR) [SPLIT]
                                 MRNA-PL (ALT.; VIA T'J3 TERMINATOR) [SPLIT]
                                 MRNA-PL (ALT.; VIA T'J2 TERMINATOR) [SPLIT]
                                 MRNA-PL (ALT.; VIA T'J1 TERMINATOR) [SPLIT]

8400
CAAAGACAGTAAGATAAAACATTGTAACAAAGGAATAGTCATTCCAACCATCTGCTCGTAGGAATGCCTTATTTTTTCTACTGCAGGAATATACCCGCC
<* L C Y S L V N Y C L F L * E L W R S T P I G * K K R S C S Y V --(SEQ ID NO:65)--
                                 EA59 (525); CODON START=1; DB XREF=PID:G215132; TRA
                                 MRNA-PL (ALT.; VIA T'J4 TERMINATOR) [SPLIT]
                                 MRNA-PL (ALT.; VIA T'J3 TERMINATOR) [SPLIT]
                                 MRNA-PL (ALT.; VIA T'J2 TERMINATOR) [SPLIT]
                                 MRNA-PL (ALT.; VIA T'J1 TERMINATOR) [SPLIT]
```

FIG. 2(C2) CONT.

```
8500
TCTTTCAATAACACTAAAACTCCAACATATAGTAACCCTTAATTTTATTAAAATAACCGCAATTTATTGGGCGGCAACACAGGATCTCTCTTTTAAGTTAC
                         MRNA-PL (ALT.; VIA T'J4 TERMINATOR)    [SPLIT]
                         MRNA-PL (ALT.; VIA T'J3 TERMINATOR)    [SPLIT]
                         MRNA-PL (ALT.; VIA T'J2 TERMINATOR)    [SPLIT]
                         MRNA-PL (ALT.; VIA T'J1 TERMINATOR)    [SPLIT]

8600
TCTCTATTACATACGTTTTCCATCTAAAAATTAGTAGTATTGAACTTAACGGGGCATCGTATTGTAGTTTTCCATATATTTAGCTTTCTGCTTCCTTTTGGA
                         MRNA-PL (ALT.; VIA T'J4 TERMINATOR)    [SPLIT]
                         MRNA-PL (ALT.; VIA T'J3 TERMINATOR)    [SPLIT]
                         MRNA-PL (ALT.; VIA T'J2 TERMINATOR)    [SPLIT]
                         MRNA-PL (ALT.; VIA T'J1 TERMINATOR)    [SPLIT]

8700
TAACCCCACTGTTATTCATGTTGCATGGTGCACTGTGTTTATACCAACGATATAGTCTATTAATGCATATATAGTATCGCCGAACGATTAGCTCTTCAGGCTT
                         MRNA-PL (ALT.; VIA T'J4 TERMINATOR)    [SPLIT]
                         MRNA-PL (ALT.; VIA T'J3 TERMINATOR)    [SPLIT]
                         MRNA-PL (ALT.; VIA T'J2 TERMINATOR)    [SPLIT]
                         MRNA-PL (ALT.; VIA T'J1 TERMINATOR)    [SPLIT]

8800
CTGAAGAAGCGTTTCAAGTACTAATAAGCCGATAGATAGCCACGGACTTCGTAGCCATTTTTCATAAGTGTTAACTTCCGCTCCTCGCTCATAACAGACA
                         MRNA-PL (ALT.; VIA T'J4 TERMINATOR)    [SPLIT]
                         MRNA-PL (ALT.; VIA T'J3 TERMINATOR)    [SPLIT]
                         MRNA-PL (ALT.; VIA T'J2 TERMINATOR)    [SPLIT]
                         MRNA-PL (ALT.; VIA T'J1 TERMINATOR)    [SPLIT]
```

*FIG. 2(C2) CONT.*

```
8900
TTCACTACAGTTATGGCGGAAAGGTATGCATGCTGGGTGTGGGGAAGTCGTGAAAGAAGAAGTCAGCTGCTGCGTCGTTTGACATCACTGCTATCTTCTTA
                                                        MRNA-PL (ALT.; VIA T'J4 TERMINATOR) [SPLIT]
                                                        MRNA-PL (ALT.; VIA T'J3 TERMINATOR) [SPLIT]
                                                        MRNA-PL (ALT.; VIA T'J2 TERMINATOR) [SPLIT]
                                                        MRNA-PL (ALT.; VIA T'J1 TERMINATOR) [SPLIT]
9000
CTGGTTATGCAGGTCGTAGTGGGTGGCCACACAAAGCTAGATTAACCCTAGAAAGATAATCATATTGTGACGTACGTTAAAGATAATCATGCGTAAAAATTG
  MRNA-PL (ALT.; VIA T'J4 TERM
  MRNA-PL (ALT.; VIA T'J3 TERM
  MRNA-PL (ALT.; VIA T'J2 TERM
  MRNA-PL (ALT.; VIA T'J1 TERM
                                                              LEFT TERMINAL REPEAT                    >
9100
ACGCATGTGTTTTATCGGTCTGTATATCGAGGTTTATTATTAATTTGAATAGATATTAAGTTTTATTATATTACACTTACACTACTAATAATAAAATTC
  >
9200
AACAAACAATTATTTATTGTTTATTATTTATTAAAAAAAAAACAAAAACTCAAAATTCTTCTAAAGTAACAAAAACTTTAAACATTCTCTCTTTTACAA
9300
AAATAAACTTATTTGTACTTTAAAAAACAGTCATGTTGTATTATAAAATAAGTAATTAGCTTAACTTATACATAATAGAAACAAATTATACTTATTAGTC
                                                                                                  <D
9400
AGTCCAGAAACAACTTTGGCACATATCAATATTATGCTCTCGACAAATAACTTTTTGCATTTTTGCACGATGCATTGCCTTTCGCCTTATTTAGAG
<T  W  F  C  S  Q  C  M  D  I  N  H  E  R  C  I  V  K  K  C  K  K  C  S  A  N  A  K  R  R  I  K  S
                          ORF1 C-TERM
```

```
9500
GGGCAGTAAGTACAGTAAGTACGTTTTTCATTACTGGCTCTTCAGTACTGTCATCTGATGTACCAGGCACTTCATTGGCAAAATATTAGAGATATTAT
 P  C  Y  T  C  Y  T  R  K  K  M  V  P  E  E  T  S  D  D  S  T  G  P  V  E  N  P  L  I  N  S  I  N  D
                                                  ORF1 C-TERM

9600
CGGCCAAATATCTCTTCAAAGTAGGAGCTTCTAAACGGTTACGCATAAACGATGAGCTCAGGCTCATGTAAAGTTTCTCATAAATTTTTGGCACTTTG
 R  L  Y  R  K  L  T  P  A  E  L  R  N  R  M  F  S  S  T  L  S  M  Y  L  N  R  M  F  K  K  R  S  Q
                                                  ORF1 C-TERM

9700
AACCTTTTCTCCCTTGCTACTGACATTATGGCTGTATATAAAAGAATTTATGCAGGCAATGTTTATCATTCCGTACAATAATGCCATAGGCCACCTA
 V  K  E  G  K  S  S  V  N  H  S  Y  I  I  F  S  N  I  C  A  I  N  I  M  G  Y  L  L  A  M  P  W  R
                                                  ORF1 C-TERM

9800
TTCGTCTTTCCTACTGCAGTCATCACAGAACACATTGGTCTAGCGTGTCCACTCCGCCTTTAGTTTGATTATAATACATAACCATTGCGGTTTACCGG
 N  T  K  R  S  C  T  M  V  S  C  M  Q  D  L  T  D  V  G  G  K  T  Q  N  Y  Y  M  V  M  Q  P  K  G  T
                                                  ORF1 C-TERM

9900
TACTTTCGTTGATAGAAGCATCCTCATCAAGATGATAATAAGTATACCATCTTAGCTGCTTCGGTTATATGAGACGAGAGTAAGGGGTCCGTCAAA
 S  E  N  I  S  A  D  E  D  C  S  S  L  L  Y  V  M  K  A  P  K  P  K  Y  S  V  L  T  L  P  G  D  F
                                                  ORF1 C-TERM

ACAAAAACATCGATGTCCCACTGGCCTGGAGCGACTGTTTTCAGTACTTCCGTATCTCGCGTTGTTTGATCGCACGGTACC    --(SEQ ID NO:63)--
 C  F  M  S  T  G  V  P  R  S  R  S  N  K  L  V  E  P  I  E  R  K  N  S  R  V  T  G    --(SEQ ID NO:66)--
                                                  ORF1 C-TERM
```

FIG. 2(C2) CONT.

ITR Cartridge Sequence        Sequence Range: 1 to 707

```
                                                   50
GGATCCCATGCGTCAATTTTACGCAGACTATCTTTCTAGGGTTAATCTAG
         RIGHT TERMINAL REPEAT        >
                                                  100
CTGCATCAGGATCATATCGTCGGGTCTTTTTTCCGGCTCAGTCATCGCCC
                                                  150
AAGCTGGCGCTATCTGGGCATCGGGGAGGAAGAAGCCCGTGCCTTTTCCC
                                                  200
GCGAGGTTGAAGCGGCATGGAAAGAGTTTGCCGAGGATGACTGCTGCTGC
                                                  250
ATTGACGTTGAGCGAAAACGCACGTTTACCATGATGATTCGGGAAGGTGT
                                                  300
GGCCATGCACGCCTTTAACGGTGAACTGTTCGTTCAGGCCACCTGGGATA
                                                  350
CCAGTTCGTCGCGGCTTTTCCGGACACAGTTCCGGATGGTCAGCCCGAAG
                                                  400
CGCATCAGCAACCCGAACAATACCGGCGACAGCCGGAACTGCCGTGCCGG
                                                  450
TGTGCAGATTAATGACAGCGGTGCGGCGCTGGGATATTACGTCAGCGAGG
                                                  500
ACGGGTATCCTGGCTGGATGCCGCAGAAATGGACATGGATACCCCGTGAG
                                                  550
TTACCCGGCGGGCGCGCCTCGTTCATTCACGTTTTTGAACCCGTGGAGGA
                                                  600
CGGGCAGACTCGCGGTGCAAATGTGTTTTACAGCGTGATGGAGCAGATGA
                                                  650
AGATGCTCGACACGCTGCAGAACACGCAGCTAGATTAACCCTAGAAAGAT
                                                     >
                                                  700
AATCATATTGTGACGTACGTTAAAGATAATCATGCGTAAAATTGACGCAT
                LEFT TERMINAL REPEAT           >
```

GGGATCC --(SEQ ID NO:40)--
      _>

FIG. 3(C1)

pXL-Bac
Sequence Range: 1 to 3662

100
CTAAATTGTAAGCGTTAATATATTTGTTAAATTTTTGTTAAATCAGCTCATTTTTTAACCAATAGGCCGAAATCGGCAAAATCCCTTAT

200
AAATCAAAAGAATAGACCGAGATAGGGTTGAGTGTTGTTCCAGTTTGGAACAAGAGTCCACTATTAAAGAACGTGGACTCCAACGTCAAAGGGCGAAAAA

300
CCGTCTATCAGGGCGATGGCCCACTACGTGAACCATCACCCTAATCAAGTTTTTTGGGGTCGAGGTGCCGTAAAGCACTAAATCGGAACCCTAAAGGGAG

400
CCCCCGATTTAGAGCTTGACGGGGAAAGCCGGCGAACGTGGCGAGAAAGGAAGGGAAGCGAAAGGAGCGGGCGCTAGGGCGCTGGCAAGTGTAGCG

500
GTCACGCTGCGCGTAACCACCACACCCGCCGCTAATGCGCCGCTTAATGCGCCGCTACAGGGCGCGTCCCATTCGCCATTCAGGCTGCGCAACTGTTGGGAAGGGCGAT

600
CGGTGCGGGCCTCTTCGCTATTACGCCAGCTGGCGAAAGGGGGATGTGCTGCAAGGCGATTAAGTTGGGTAACGCCAGGGTTTTCCCAGTCACGACGTTG

700
TAAAACGACGGCCAGTGAGCGCGCGTAATACGACTCACTATAGGGCGAATTGGGTACCGGGCCCCCCTCGAGGTCGACGGTATCGATAAGCTTGATATCGAATTCCTGC

800
CAGATGAAGATGCTCGACACGCTGCAGAACACGCTGCAGATTAACCCTAGAAAGATAATCATATTGTGACGTAGTAAAGATAATCATGCGTAAAATT
                                                                        LEFT TERMINAL REPEAT

>MCS_of_pBSII

900
GACGCGATGGATCTGTAATACGACTCACTATAGGGCGAATTGGGTACCGGGCCCCCCTCGAGGTCGACGGTATCGATAAGCTTGATATCGAATTCCTGC

FIG. 3(C2)

```
2100
ACCAGGGGCGTTCCCCCTGGAAGCTCCCCTGTGCGCTCTCCTGTTCCGACCCTGCCGCTTACCGGATATACCTGTCCGCCTTTCTCCCCTTCGGGAAGCGTGGC

2200
GCTTTCTCATAGCTCACGCTGTAGGTATCTCAGTTCGGTGTAGGTCGTTCGCTCCAAGCTGGGCTGTGTGCACGAACCCCCCGTTCAGCCCGACCGCTGC

2300
GCCTTATCCGGTAACTATCGTCTTGAGTCCAACCCGGTAAGACAGACTTATCGCCACTGGCAGCAGCCACTGGTAACAGGATTAGCAGAGCGAGGTATG

2400
TAGGCGGTGCTACAGAGTTCTTGAAGTGGTGGCCTAACTACGGCTACACTAGAAGGACAGTATTTGGTATCTGCGCTCTGCTGAAGCCAGTTACCTTCGG

2500
AAAAAGAGTTGGTAGCTCTTGATCCGGCAAACAAACCACCGCTGGTAGCGGTGGTTTTTTTGTTTGCAAGCAGCAGATTACGCGCAGAAAAAAGGATCT

2600
CAAGAAGATCCTTTGATCTTTTCTACGGGGTCTGACGCTCAGTGGAACGAAAACTCACGTTAAGGGATTTTGGTCATGAGATTATCAAAAAGGATCTTCA
                                                                    <ColE1_origin 2700
CCTAGATCCTTTTAAATTAAAAATGAAGTTTTAAATCAATCTAAAGTATATATGAGTAAACTTGGTCTGACAGTTACCAATGCTTAATCAGTGAGGCACC
                                                                                        <  AMPCILLIN RESISTAN 2800
TATCTCAGCGATCTGTCTATTTCGTTCATCCATAGTTGCCTGACTCCCCGTCGTGTAGATAACTACGATACGGGAGGGCTTACCATCTGGCCCCAGTGCT
<       AMPCILLIN RESISTANCE 2900
GCAATGATACCGCGAGACCCACGCTCACCGGCTCCAGATTTATCAGCAATAAACCAGCCAGCCGGAAGGGCCGAGCGCAGAAGTGGTCCTGCAACTTTAT
<       AMPCILLIN RESISTANCE
```

*FIG. 3(C2) CONT.*

```
3000
CCGCCCTCCATCCAGTCTATTAATTGTTGCCGGGAAGCTAGAGTAAGTAGTTCGCCAGTTAATAGTTTGCCGAACGTTGTTGCCATTGCTACAGGCATCGT
     |                                          AMPCILLIN RESISTANCE                                  |
3100
GGTGTCACGCTCGTCGTTGGTATGGCTTCATTCAGCTCCGGTTCCCAACGATCAAGGGCGAGTTACATGATCCCCCATGTTGTGCAAAAAAGCGGTTAGC
     |                                          AMPCILLIN RESISTANCE                                  |
3200
TCCTTCGGTCCTCCGATCGTTGTCAGAAGTAAGTTGGCCCGCAGTGTTATCACTCATGGTTATGGCAGCACTGCATAATTCTCTTACTGTCATGCCATCCG
     |                                          AMPCILLIN RESISTANCE                                  |
3300
TAAGATGCTTTTCTGTGACTGGTGAGTACTCAACCAAGTCATTCTGAGAATAGTGTATGCGGCGACCGAGTGCTCTTGCCCGGCGTCAATACGGGATAA
     |                                          AMPCILLIN RESISTANCE                                  |
3400
TACCGCGCCACATAGCAGAACTTTAAAAGTGCTCATCATTGGAAAACGTTCTTCGGGGCGAAAACTCTCAAGGATCTTACCGCTGTTGAGATCCAGTTCG
     |                                          AMPCILLIN RESISTANCE                                  |
3500
ATGTAACCCACTCGTGCACCCAACTGATCTTCAGCATCTTTTACTTTCACCAGCGTTTCTGGGTGAGCAAAAACAGGAAGGCAAAATGCCGCAAAAAAGG
     |                                          AMPCILLIN RESISTANCE                                  |
3600
GAATAAGGGCGACACGGAAATGTTGAATACTCATACTCTTCCTTTTTCAATATTATTGAAGCATTTATCAGGGTTATTGTCTCATGAGCGGATACATATT
     |            AMPCILLIN RESISTANCE           |

TGAATGTATTTAGAAAAATAAACAAATAGGGGTTCCGCGCACATTTCCCCGAAAAGTGCCAC --(SEQ ID NO:41)--
```

*FIG. 3(C2) CONT.* pBSII-hs-orf
Sequence Range: 1 to 5533

```
100  CTAAATTGTAAGCGTTAATATTTGTTAAATTTTTGTTAAATCAGCTCATTTTTTAACCAATAGGCCGAAATCGGCAAAATCCCTTAT
200  AAATCAAAAGAATAGACCGAGATAGGGTTGAGTGTTGTTCCAGTTTGGAACAGAGTCCACTATTAAAGAACGTGGACTCCAACGTCAAAGGGCGAAAAA
300  CCGTCTATCAGGGCGATGGCCCACTACGTGAACCATCACCCTAATCAAGTTTTTTGGGGTCGAGGTGCCGTAAAGCACTAAATCGGAACCCTAAAGGGAG
400  CCCCCGATTTAGAGCTTGACGGGGAAAGCCGGCGAACGTGGCGAGAAAGGAAGGGAAGAAAGCCGAAAGGAGCGGGGCGCTGGCAAGTGTAGCG
500  GTCACGCTGCGCGTAACCACCACACCCGCCGCGCTTAATGCGCCGCTACAGGGCGCGTCCCATTCGCCATTCAGGCTGCGCAACTGTTGGGAAGGGCGAT
600  CGGTGCGGGCCTCTTCGCTATTACGCCAGCTGGCGAAAGGGGGATGTGCTGCAAGGCGATTAAGTTGGGTAACGCCAGGGTTTTCCCAGTCACGACGTTG
700  TAAAACGACGGCCAGTGAGCGCGCGTAATACGACTCACTATAGGGCGAATTGGGTACCGGGCCCCCCCTCGAGGTCGACGGTATCGATAAGCTATCCAGT
800  GCAGTAAAAAAATAAAAAAAAATATGTTTTTTAAATCTACATTCTCCAAAAAAAGGGTTTTATTAACTTACATACATAGAATTGATCCCCGATCCCC
900  CTAGAATCCCAAAACAAACTGGTTATTGTGTAGGTCATTTGTTTGGCAGAAGAAACTCGAGAAATTCTCTGGCCGTTATTCGTATTCTCTCTTTC
1000 TTTTTGGGTCTCCCCTCTGCACTAATGCTCTCTCACTCTGTCACACAGTAAACGCATACTGCTCTCGTTGTTCGAGAGAGCGCCCTCGAATGTTCG
1100 CGAAAAGAGCGCCGAGTATAAATAGAGCGCTTCGTCTACGAGGCGACAATTCAATTCAAACAAGCAAGTGAACACGTCGCTAAGCCGAAAGCTAAGCAA
```

FIG. 5(B)

```
1200
ATAAACAAGCGCAGCTGAACAAGCTAAACAATCTGCAGTAAAGTGCAAGTTAAAGTGAATCAATTAAAAGTAACCAGCAACCAAGTAAATCAACTGCAAC
                                                                <hsp70_promoter
1300
TACTGAAATCTGCCAAGAAGTAATTATTGAATACAAGAGAGAACTCTGAATAGGGAATTGGGAATTCCTGCAGCCCGGGGATCCTATATAATAAAATG
1400
GGTAGTTCTTTAGACGATGAGCATATCCTCTCTGCTCTTCTGCAAAGCGATGAGCTTGTTGGTGAGGATTCTGACAGTGAAATATCAGATCACGTAA
1500
GTGAAGATGACGTCCAGAGCGATACAGAAGAAGCGTTTATAGATGAGGTACATGAAGTGCAGCCAACGTCAAGCGGTAGTGAAATATTAGACGAACAAAA
1600
TGTTATTGAACAACCAGGTTCTTCATTGGCTTCTAACAGAATCTTGACCTTGCCACAGAGGACTATTAGAGGTAAGAATAAACATTGTTGGTCAACTTCA
1700
AAGTCCACGAGGCGTAGCCGAGTCTCTGCACTGAACATTGTCAGATCTCAAAGAGGTCCGACGCGTATGTGCCGAATATATATGACCCACTTTTATGCT
1800
TCAAACTATTTTTTACTGATGAGATAATTTCGGAAATTGTAAAATGGACAAAATGCTGAGATATCATTGAAACGTCGGGAATCTATGACAGTGCTACATT
1900
TCGTGACACGAATGAAGATGAAATCTATGCTTTCTTTGGTATTCTGGTAATGAGTCGTGATCGTTTGATTTTTGATACGATGTCTTAGAATGGATGACAAAGTATACGGCCACAC
2000
CGATCTTTGTCAATGTGTACGTCTCCTGTAATGAGTCGTGATCGTTTGATTTTTGATACGATGTCTTAGAATGGATGACAAAGTATACGGCCACAC
2100
TTCGAGAAAACGATGTATTACTCCTGTTAGAAAAATATGGGATCTCTTTATCCATCAGTGCATACAAATTACACTCCAGGGGCTCATTTGACCATAGA
2200
TGAACAGTTACTTGGTTTTAGAGGACGGTGTCCGTTTAGGATGTATATCCCAAACAAGCCAAGTAAGTATGGAATAAAATCCTCATGATGTGTGACAGT
```

FIG. 5(B) CONT.

```
2300
GGTACGAAGTATATGATAAATGGAATGCCTTATTTGGGAAGAGGAACACAGACCAACGGAGTACCACTCGGTGAATACTACGTGAAGGAGTTATCAAAGC
2400
CTGTGCACGGTAGTTGTCGTAATATTACGTGTGACAATTGGTTCACCTCAATCCCTTTGGCAAAAAACTTACTACAGAACCGTATAAGTTAACCATTGT
2500
GGGAACCCGTGCGATCAAACAAACGCGAGATACCGGAAGTACTGAAAAACAGTCGCTCCAGGCCAGTGGGAACATCGATGTTTGTTTGACGGACCCCTT
2600
ACTCTCGTCTCATATAAACCGAAGCCAGCTAAGATGGTATACTTATTATCATCTTGTGATGAGGATGCTTCTATCAACGAAAGTACGGTAAACCGCAAA
2700
TGGTTATGTATTATAATCAAACTAAAGGCGGAGTGGACACGCTAGACCAAATGTGTTCTGTGATGACCTGCAGTAGGAAGACGAATAGGTGGCCTATGGC
2800
ATTATTGTACGGAATGATAAACATTGCCTGACGTCATCGTTTATGCGTAAGCGTTTAGAAGCTCCTACTTGAAGAGATATTGCCGATAATATCTCTAATA
2900
TTTATGAGAAACCTTTACATGAGCCTGACGTCATCGTTTATGCGTAAGCGTTTAGAAGCTCCTACTTGAAGAAAAACGTACTTACTGTACTGCCCCTCTAAAATAAGGCG
3000
TTTTGCCAAATGAAGTGCCTGGTACATCAGATGACAGTACTGAAGAGCCAGTAATGAAAAAACGTACTTACTGTACTGCCAAGTTGTTTCTGACTGACTAATAAGTATAAT
3100
AAAGGCAAATCGTCGTGCAAAAAATGCAAAAAAGTTATTGTCGAGAGCATAATATTGTCGAGAGCATAATATTGTCGAGAGCATAATATTGT
3200
TTGTTTCTATTATGTATAAGTTAAGCTAATTACTTATTTTATAATACAACATGACTGTTTTTAATAAATAAACATAAATAAATTGTTTGTTGAATTGGATCCACTA
3300
GTTTAAAAGTTTGTTACTTTAGAAGAAATTTGAGTTTTTGTTTTTTTGTTCCCTTTGTTCCCTTTAGTGAGGGTTAATTGCCGCTTGGCGTAATCATGGTCATAGCTGTTTCCTG
3400
GTTCTAGAGCGGCCGCCACCGCGGTGGAGCTCCAGCTTTTGTTCCCTTTAGTGAGGGTTAATTGCCGCTTGGCGTAATCATGGTCATAGCTGTTTCCTG
```

FIG. 5(B) CONT.

```
3500
     TGTGAAATTGTTATCCGCTCACAATTCCACACAACATACGAGCCGGAAGCATAAAGTGTAAAGCCTGGGGTGCCTAATGAGTGAGCTAACTCACATTAAT
3600
     TGCGTTGCGCTCACTGCCCGCTTTCCAGTCGGGAAACCTGTCGTGCCAGCTGCATTAATGAATCGGCCAACGCGCGGGGAGAGGCGGTTTGCGTATTGGG
3700
     CGCTCTTCCGCTTCCTCGCTCACTGACTCGCTGCGCTCGGTCGTTCGGCTGCGGCGAGCGGTATCAGCTCACTCAAAGGCGGTAATACGGTTATCCACAG
3800
     AATCAGGGGATAACGCAGGAAAGAACATGTGAGCAAAAGGCCAGCAAAAGGCCAGGAACCGTAAAAAGGCCGCGTTGCTGGCGTTTTTCCATAGGCTCCG
3900
     CCCCCCTGACGAGCATCACAAAAATCGACGCTCAAGTCAGAGGTGGCGAAACCCGACAGGACTATAAAGATACCAGGCGTTTCCCCCTGGAAGCTCCCTC
4000
     GTGCGCTCTCCTGTTCCGACCCTGCCGCTTACCGGATACCTGTCCGCCTTTCTCCCTTCGGGAAGCGTGGCGCTTTCTCATAGCTCACGCTGTAGGTATC
4100
     TCAGTTCGGTGTAGGTCGTTCGCTCCAAGCTGGGCTGTGTGCACGAACCCCCCGTTCAGCCCGACCGCTGCGCCTTATCCGGTAACTATCGTCTTGAGTC
4200
     CAACCCGGTAAGACACGACTTATCGCCACTGGCAGCAGCCACTGGTAACAGGATTAGCAGAGCGAGGTATGTAGGCGGTGCTACAGAGTTCTTGAAGTGG
4300
     TGGCCTAACTACGGCTACACTAGAAGGACAGTATTTGGTATCTGCGCTCTGCTGAAGCCAGTTACCTTCGGAAAAAGAGTTGGTAGCTCTTGATCCGGCA
4400
     AACAAACCACCGCTGGTAGCGGTGGTTTTTTTGTTTGCAAGCAGCAGATTACGCGCAGAAAAAAAGGATCTCAAGAAGATCCTTTGATCTTTTCTACGGG
4500
     GTCTGACGCTCAGTGGAACGAAAACTCACGTTAAGGGATTTTGGTCATGAGATTATCAAAAAGGATCTTCACCTAGATCCTTTTAAATTAAAAATGAAGT
```

*FIG. 5(B) CONT.*

<CoIE1_origin

4600
TTTAAATCAATCTAAAGTATATATGAGTAAACTTGGTCTGACAGTTACCAATGCTTAATCAGTGAGGCACCTATCTCAGCGATCTGTCTATTTCGTTCAT
AMPCILLIN RESISTANCE

4700
CCATAGTTGCCTGACTCCCCGTCGTGTAGATAACTACGATACGGGAGGGCCTTACCATCTGGCCCCAGTGCTGCAATGATACCGCGAGACCCACGCTCACC
AMPCILLIN RESISTANCE

4800
GGCTCCAGATTTATCAGCAATAAACCAGCCAGCCGGAAGGGCCGAGCGCAGAAGTGGTCCTGCAACTTTATCCGCCTCCATCCAGTCTATTAATTGTTGC
AMPCILLIN RESISTANCE

4900
CGGGAAGCTAGAGTAAGTAGTTCGCCAGTTAATAGTTTGCGCAACGTTGTTGCCATTGCTACAGGCATCGTGGTGTCACGCTCGTCGTTTGGTATGGCTT
AMPCILLIN RESISTANCE

5000
CATTCAGCTCCGGTTCCCAACGATCAAGGCGAGTTACATGATCCCCCATGTTGTGCAAAAAAGCGGTTAGCTCCTTCGGTCCTCCGATCGTTGTCAGAAG
AMPCILLIN RESISTANCE

5100
TAAGTTGGCCGCAGTGTTATCACTCATGGTTATGGCAGCACTGCATAATTCTCTTACTGTCATGCCATCCGTAAGATGCTTTTCTGTGACTGGTGAGTAC
AMPCILLIN RESISTANCE

5200
TCAACCAAGTCATTCTGAGAATAGTGTATGCGGCGACCGAGTTGCTCTTGCCCGGCGTCAATACGGGATAATACCGCGCCACATAGCAGAACTTTAAAAG
AMPCILLIN RESISTANCE

5300
TGCTCATCATTGGAAAACGTTCTTCGGGGCGAAAACTCTCAAGGATCTTACCGCTGTTGAGATCCAGTTCGATGTAACCCACTCGTGCACCCAACTGATC
AMPCILLIN RESISTANCE

FIG. 5(B) CONT.

5400
TTCAGCATCTTTACTTTCACCAGCGTTTCTGGGTGAGCAAAAACAGGAAGGCAAAATGCCGCAAAAAAGGGAATAAGGGCGACACGGAAATGTTGAATA >
                                           AMPCILLIN RESISTANCE
5500
CTCATACTCTTCCTTTTTCAATATTATTGAAGCATTTATCAGGGTTATTGTCTCATGAGCGGATACATATTTGAATGTATTTAGAAAAATAAACAAATAG
  >
GGGTTCCGCGCCACATTTCCCCGAAAAGTGCCAC --(SEQ ID NO:42)--

*FIG. 5(B) CONT.*

Sequence Range: 1 to 4971

100
CTAAATTGTAAGCGTTAATATTTGTTAAATTTTTGTTAAATCAGCTCATTTTTAACCAATAGCCGAAATCGGCAAATCCCTTAT

200
AAATCAAAAGAATAGACCGAGATAGGTTGAGTGTGTTCCAGTTTGAACAAGAGTCCACTATTAAAGAACGTGACTCCAAAGGGCGAAAAA

300
CCGTCTATCAGGGCGATGCCCACTACGTGAACCATCACCCTAATCAAGTTTTTGGGGTCGAGGTGCCGTAAAGCACTAAATCGGAACCCTAAAGGGAG

400
CCCCCGATTTAGAGCTTGACGGGGAAAGCCGGCGAACGTGGCGAGAAAGGAAGAAAGCGAAAGGAGAGCGGGCGTAGGGCGCTGGCAAGTGTAGCG

500
GTCACGCTGCGCGTAACCACCACACCCGCCGCGCTTAATGCGCCGCTACAGGGCGCGTCCCATTCAGGCTGCCGCAACTGTTGGGAAGGGCGAT

600
CGGTGCGGGCCTCTTCCGCTATTACGCCAGCTGGCGAAAGGGGGATGTGCTGCAAGGCGATTAAGTGGGTAACGCCAGGGTTTTCCCAGTCACGACGTTG

700
TAAAACGACGGCCAGTGAGCGCGCGTAATACGACTCACTATAGGGCGAATTGGGTACCGGGCCCCCCCTCGAGGTCGACGGTATCGATAAGCTTGATATC

800
GAATTCCTGCAGCCCGGGGATCCTATATATAAATGGGTAGTTCTTTAGACGATGAGCATACAGAAGAAGCCGTTTATAGATGAGTACATGAAGTGCAG

900
TGGTGAGGATTCTGACAGTGAAATATCAGATCACGTAAGTGAAGATGACGTCCAGAGCCGATACAGAAGAAGCCGTTTATAGATGAGTACATGAAGTGCAG

1000
CCAACGTCAAGCGGTAGTGAAATATTAGACGAACAAAATGTTATTGAACAACCAGGTTCTTCATTGGCTTCTAACAGAATCTTGACCTTGCCACAGAGGA

1100
CTATTAGAGGTAAGAATAAACATTGTTGGTCAACTTCAAAGTCCACGAGGCGTAGCCGAGTCCTGCACTGAACATTGTCAGATCTCAAAGAGGTCCGAC

FIG. 6(B)

```
1200
GCGTATGTGCCGCAATATATGACCACTTTTATGCTTCAAACTATTTTTACTGATGAGATAATTCGGAAATTGTAAAATGGACAAATGCTGAGATA
1300
TCATTGAAACGTCGGGAATCTATGACAGGTGCTACATTTCGTGACACGAATGAAGATGAAATCTATGCTTTCTTTGGTATTCTGGTAATGACAGCAGTGA
1400
GAAAAGATAACCACATGTCCACAGATGACCTCTTTGATCGATCTTTGTCAATGGTGTACGTCTCTGTAATGAGTCGTTTTGATTTTTTGATACG
1500
ATGTCTTAGAATGGATGACAAAAGTATACGGCCCACACTTCGAGAAAAACGATGTATTACTCCCTGTTAGAAAAATATGGGATCTCTTTATCCATCAGTGC
1600
ATACAAAATTACACTCCAGGGGCTCATTGACCATAGATGAACAGTTACTGTTTTAGAGGACGGTGTCCGTTTAGGATGTATATCCCAAACAAGCCAA
1700
GTAAGTATGGAATAAAAATCCTCATGTGTGACAGTGGTACGAAGTATATGATAAATGCCTTATTTGGAAGAGGAACAGACCAACGGAGT
1800
ACCACTCGGTGAATACTACGTGAAGGAGTTATCAAAGCCTGTGCACGGTAGTTGTCGTAATATTACGTCTGTGACAATTGTTCACCTCAATCCCTTTGGCA
1900
AAAAACTTACTACAAGAACCGTATAAGTTAACCATTGTGGGAACCGGAGATACCGGAAGCCAGCTAAGATGGTATACTTATTATCATCTTGTGATGA
2000
CAGTGGGAACATCGATGTTTGTTTGACGGAACCCCTTACTCTCGTCTCATATAAACCGAAGCCAGCTAAGATGGTATACTTATTATCATCTTGTGATGA
2100
GGATGCTTCTATCAACGAAAGTACCGGTGAAACCGTAAACTAAAGGCGGAGTGGACACGCTAGACCAAATGTGTTCTGTG
2200
ATGACCTGCAGTAGGAAGACGAATAGGTGCCTATGGCCATTATTGTACGGAATGATAAACATTGCCTGCATAAATTCTTTATTATATACAGCCATAATG
2300
TCAGTAGCAAGGGAGAAAAGGTTCAAAGTCGCAAAAAATTTATGAGAAACCTTTACATGAGCCTGACGTCATCGTTTATGCGTAAGCGTTAGAAGCTCC
```

*FIG. 6(B) CONT.*

2400 TACTTTGAAGAGATATTTGCGCGATAATATCTCTAATATTTTGCCAAATGAAGTGCCTGGTACATCAGATGACAGTACTGAAGAGCCAGTAATGAAAAAA

2500 CGTACTTACTGTACTTACTGCCCCTCTAAAATAAGGCGAAATGCATCGTGCAAAAAAATGCAAAAAAGTATTTGTCGAGAGCATATAATATTGATA

2600 TGTGCCAAAGTTGTTTCTGACTGAATAAGTATAATTGTTTCTATTATGTATAAGTAAGCTAATTACTTATTTTATAATACAACATGACTGTTTT

2700 AAAGTACAAAATAAGTTTATTTTGTAAAAGAGAGAATGTTAAAAGTTTTGTTACTTTAGAGAAATTTGAGTTTTTGTTTTTTTAATAAATAAAT

2800 AAACATAAATAAATTGTTTGTTGAATTTGGATCCACTAGTTCTAGAGCGGCCGCCACCGGGTGGAGCTCCAATTCCACACAACATACGAGCCG

2900 TGCGCGTTGGCGTAATCATGGTCATAGCTGTTTCCTGTGTGAAATTGTTATCCGCTCACTGCCCGCTTTCCAGTCGGGAAACCTGTCGTGCCAGCTGCATTAATGAA

3000 GCCTGGGGTGCCTAATGAGTGAGCTAACTCACATTAATTGCGTTGCGCTCACTGCCCGCTTTCCAGTCGGGAAACCTGTCGTGCCAGCTGCATTAATGAA
 >ColE1_origin 3100 TCGGCCAACGCGCGGGGAGAGGCGGTTTGCGTATTGGGCGCTCTTCCGCTTCCTCGCTCACTGACTCGCTGCGCTCGGTCGTTCGGCTGCGGCGAGCGGT 3200 ATCAGCTCACTCAAAGGCGGTAATACGGTTATCCACAGAATCAGGGGATAACGCAGGAAAGAACATGTGAGCAAAAGGCCAGCAAAAGGCCAGGAACCGT 3300 AAAAAGGCCGCGTTGCTGGCGTTTTTCCATAGGCTCCGCCCCCCTGACGAGCATCACAAAAATCGACGCTCAAGTCAGAGGTGGCGAAACCCGACAGGAC 3400 TATAAAGATACCAGGCGTTTCCCCCTGGAAGCTCCCTCGTGCGCTCTCCTGTTCCGACCCTGCCGCTTACCGGATACCGTCCGCCTTTCTCCCTTCGGG

*FIG. 6(B) CONT.*

```
3500
AAGCCGTGGCGCTTTCTCATAGCTCACGCTGTAGGTATCTCAGTTCGGTGTAGGTCGTTCGCTCCAAGCTGGGCTGTGTGCACGAACCCCCCGTTCAGCCC

3600
GACCGCTGCGCCTTATCCGGTAACTATCGTCTTGAGTCCAACCCGGTAAGACACGACTTATCGCCACTGGCAGCAGCCACTGGTAACAGGATTAGCAGAG

3700
CGAGGTATGTAGGCGGTGCTACAGAGTTCTTGAAGTGGTGGCCTAACTACGGCTACACTAGAAGGACAGTATTTGGTATCTGCGCTCTGCTGAAGCCAGT

3800
TACCTTCGGAAAAAGAGTTGGTAGCTCTTGATCCGGCAAACAAACCACCGCTGGTAGCGGTGGTTTTTTTGTTTGCAAGCAGCAGATTACGCGCAGAAAA

3900
AAAGGATCTCAAGAAGATCCTTTGATCTTTTCTACGGGGTCTGACGCTCAGTGGAACGAAAACTCACGTTAAGGGATTTTGGTCATGAGATTATCAAAAA

4000
GGATCTTCACCTAGATCCTTTTAAATTAAAAATGAAGTTTTAAATCAATCTAAAGTATATATGAGTAAACTTGGTCTGACAGTTACCAATGCTTAATCAG
         >                                                                                      _____
4100
TGAGGCACCTATCTCAGCGATCTGTCTATTTCGTTCATCCATAGTTGCCTGACTCCCCGTCGTGTAGATAACTACGATACGGGAGGGCTTACCATCTGGC
_____
                                    AMPCILLIN RESISTANCE
4200
CCCAGTGCTGCAATGATACCGCGAGACCCACGCTCACCGGCTCCAGATTTATCAGCAATAAACCAGCCAGCCGGAAGGGCCGAGCGCAGAAGTGGTCCTG
_____
                                    AMPCILLIN RESISTANCE
4300
CAACTTTATCCGCCTCCATCCAGTCTATTAATTGTTGCCGGGAAGCTAGAGTAAGTAGTTCGCCAGTTAATAGTTTGCGCAACGTTGTTGCCATTGCTAC
_____
                                    AMPCILLIN RESISTANCE
4400
AGGCATCGTGGTGTCACGCTCGTCGTTTGGTATGGCTTCATTCAGCTCCGGTTCCCAACGATCAAGGCGAGTTACATGATCCCCCATGTTGTGCAAAAAA
_____
                                    AMPCILLIN RESISTANCE
```

*FIG. 6(B) CONT.*

4500
GCGGGTTAGCTCCTTCGGTCCTCCGATCGTTGTTCTCAGAAGTAAGTTGGCCGCAGTGTTATCACTCATGGTTATGGCAGCACTGCATAATTCTCTTACTGTCA
　　　　　　　　　　　　　　　　　　　　　AMPCILLIN RESISTANCE                                           ^

4600
TGCCATCCGTAAGATGCTTTTCTGTGACTGGTGAGTACTCAACCAAGTCATTCTGAGAATAGTGTATGCGGCGACCGAGTTGCTCTTGCCCGGCGTCAAT
　　　　　　　　　　　　　　　AMPCILLIN RESISTANCE                                                        ^

4700
ACGGGATAATACCGCGCCACATAGCAGAACTTTAAAAGTGCTCATCATTGGAAAACGTTCTTCGGGGCGAAAACTCTCAAGGATCTTACCGCTGTTGAGA
　　　　　　　　AMPCILLIN RESISTANCE                                                                     ^

4800
TCCAGTTCGATGTAACCCACTCGTGCACCCAACTGATCTTCAGCATCTTTTACTTTCACCAGCGTTTCTGGGTGAGCAAAAACAGGAAGGCAAAATGCCG
　　　　　　AMPCILLIN RESISTANCE                                                                         ^

4900
CAAAAAAGGGAATAAGGGCGACACGGAAATGTTGAATACTCATACTCTTCCTTTTTCAATATTATTGAAGCATTTATCAGGTTATTGTCTCATGAGCGG
　　　　　　　AMPCILLIN RESISTANCE                                                       ^

ATACATATTTGAATGTATTTAGAAAAATAAACAAATAGGGGTTCCGCGCACATTTCCCCGAAAAGTGCCAC -- (SEQ ID NO:43)--

*FIG. 6(B) CONT.*

Sequence Range: 1 to 5523

100
CTAAATTGTAAGCGTTAATATTTGTTAAATTTTGTTAAATCAGCTCATTTTTTAACCAATAGGCCGAAATCGGCAAAATCCCTTAT

200
AAATCAAAAGAATAGACCGAGATAGGGTTGAGTGTTGTTCCAGTTTGGAACAAGAGTCCACTATTAAAGAACGTCCAAGCGTCAAAGGGCGAAAAA

300
CCGTCTATCAGGGCGATGGCCCACTACGTGAACCATCACCCTAATCAAGTTTTTGGGGTCGAGGTGCCGTAAAGCACTAAATCGAACCCTAAAGGGAG

400
CCCCCGATTTAGAGCTTGACGGGGAAAGCCGGCGAACGTGGCGAGAAAGGAAGGGAAGAAAGCGAAAGGAGCGGGCGCTAGGGCGCTGGCAAGTGTAGCG

500
GTCACGCTGCGCGTAACCACCACACCCCGCGCGCTTAATGCGCCGCTACAGGGCGCGTCCCATTCAGGCTGCGCAACTGTTGGGAAGGGCGAT

600
CGGTGCGGGCCCTCTTCGCTATTACGCCAGCTGAGCGCCGTAATACGACTCACTATAGGGCGAATTGTGCTCAAGGCGATTAAGTTGGGTAACGCCAGGGTTTTCCCAGTCACGACGTTG

700
TAAAACGACGGCCAGTGAGCGCGCGTAATACGACTCACTATAGGGCGAATTGTGATAAAATGAACGGATACAGTGCCCGACTTATCATTAAATCTCGAGGTCGACGGTATCGATAAGCTTCGATGT

800
CTTTGTGATGCGCCGACATTTTTGTAGTTATTGATAAAATGAACGGATACAGTGCCCGTACTTTGGCTTCAAAGTTTTGCGCACAGACAAAATGTGCCACACTTGCAGCTCTGCATG

900
ATTGTCCGTGTGCGCTAGCATGCCCGCTAACGGACCTCGTACTTTGGCTTCAAAGTTTTGCGCACAGACAAAATGTGCCGCCGAATGCAGCTGATCACGTACGCT

1000
TGTGCGCGTTACCACAACCCCAACCGGCGCAGTGTACTTGTTGTATGCAAATAAATCTCGATAAAGGCCGGGCGGAATGCAGCTGATCACGTACGCT

1100
CCTCGCGTGTTCCGTTCAAGGACGGGTGTTATCGACCTCAGATTAATGTTATCGGCCGACTGTTTCGTATCCGCTCACCAAACGCGTTTTTGCATTAACAT

*FIG. 8(B)*

```
1200
TGTATGTCGGCGGATGTTCTATATCTAATTTGAATAAATAAACGCGTTGTTTTAGAGGGCATATAAAGAAATATTGTTATCGTGTTCGCC
1300
ATTAGGGCAGTATAAATTGACGTTCATGTTGGATATTGTTTCAGTTGCAAGTGAATTCCTGCAGCCCGGGGATCCTATATATAAATGGTAGTTCTT
1400
TAGACGATGAGCATATCCCTCTGCTCTTCTGCAAAGGCGATGACGAGCTTGTTGGTGAGGATTCTGACAGTGAAATATCAGATCACGTAAGTGAAGATGA
1500
CGTCCAGAGCGATACAGAAGAAGCGTTTATAGATGAGGTACATGAAGTGCAGCCAACGTCAAGGGGTAGTGAAATATTAGACGAACAAAATGTTATTGAA
1600
CAACCAGGTTCTTCATTGGCTTCTAACAGAATCTTGACCTTGCCACAGAGGACTATTAGAGAGGTAAGAATAAACATTGTTGGTCAACTTCAAAGTCCACGA
1700
GGCGTAGCCGAGTCTCTGCACTGAACATTGTCAGATCTCAAAGAGGTCCGACGCGTATGTGCCGCAATATATGACCCACTTTTATGCTTCAAACTATT
1800
TTTTACTGATGAGATAATTTCGGAAATTGTAAAATGGACAAAATGCTGAGATATCATTGAAACGTCGGGAATCTATGACAGGTGCTACATTTCCTGACACG
1900
AATGAAGATGAAATCTATGCTTTCTTTGGTATTCTGGTAATGACAGCAGTGAGAAAAGATAACCACATGTCCACAGATGACCTCTTTGATCGATCTTTGT
2000
CAATGGTGTACGTCTCTGTAATGAGTCGTGAAAGTATATGGATCTCTTAGATACGATGTCTTAGAATGATGACAAAAGTATACGGCCCACACTTCGAGAAAA
2100
CGATGTATTACTCCTGTTAGAAAAATATGGGATCTCTTTATCCATCACAAAATTACACTCCAGGGGCTCATTTGACCATAGATGAACAGTTA
2200
CTTGGTTTTAGAGGACGGTGTCCGTTTAGGAGTGTATATCCCAAAACAAGCCAAGTAAGTATGGAATAAAAATCCTCATGATGTGTGACAGTGGTACGAAGT
2300
ATATGATAAATGGAATGCCTTATTGGGAAGAGAACACAGACCAACGGAGTACCACTCGGTGAATACTACGTGAAGGAGTTATCAAAGCCTGTGCACGG
```

*FIG. 8(B) CONT.*

2400 TAGTTGTCGTAATATTACGTGTGACAATTGGTTCACCTCAATCCCTTTGGCAAAAAACTTACTACAAGAACCGTATAAGTTAACCATTGTGGGAACCGTG
2500 CGATCAAACAAACGGAGATACCGAAGTACTGAAAAACAGTGCCTCCAGGCCAGTGGGAACATCGATGTTTTGTTTGACGGACCCCTTACTCTCGTCT
2600 CATATAAACCGAAGCCAGCTAAGATGGTATACTTATTATCATCTTGTGATGAGGATGCTTCTATCAACGAAGTACCGGTAAACCGCTAAACCGCAAATGGTTATGTA
2700 TTATAATCAAACTAAAGGCGGAGTGGACACGCTAGACCAAATGTGTTCTGTGATGACCTGCAGTAGGAAGAGAATAGTGGCCTATGCATTATTGTAC
2800 GGAATGATAAACATTGCCTGCATAAATTCTTTTATTATATACAGCCATAATGTCAGTAGCAAGGGAGAAAAAGTTCAAAGTGCAAAAAATTTATGAGAA
2900 ACCTTTACATGAGCCTGACGTCATCGATGACAGTACTGAAGAGCCAGTAATGAAAAAACGTACTACTGCCCCTCTAAAATAAGGCGAAAGGCAAAT
3000 TGAAGTGCCTGGTACATCAGATGACAGTACTGAAGAGCCAGTAATGAAAAAACGTACTACTGCTACTGCCCCTCTAAAATAAGGCGAAAGGCAAAT
3100 GCATCGTGCAAAAATGCAAAAAAGTTATTGTCGAGAGCATAATATTGATATGTGCCAAAGTTGTTTCTGACTGATAATAAGTATAATTGTTTCTAT
3200 TATGTATAAGTTAAGCTAATTACTTATTTTATAATACAACATGACTGTTTTAAAGTACAAAATAAGTTTATTTTGTAAAAGAGAATGTTAAAAGT
3300 TTTGTTACTTTAGAAGAAATTTGAGTTTTTGTTTTTTTTAATAATAAACATAAATAATTGTTGTTGAATTGGATCCACTAGTTCTAGAGC
3400 GGCCGCCACCGGGGTGGAGCTCCAGCTTTTGTTCCCTTTAGTGAGGGTTAATTGCGCGCTTGGCGTAATCATGGTCATAGCTGTTCCTGTGTGAAATTG

*FIG. 8(B) CONT.*

```
3500
TTATCCGCTCACAATTCCACACAACATACGAGCCCGGAAGCATAAAGTGTAAAGCCTGGGGTGCCTAATGAGTGAGCTAACTCACATTAATTGCGTTGCGC
>ColE1_origin
3600
TCACTGCCCGCTTTCCAGTCGGGAAACCTGTCGTGCCAGCTGCATTAATGAATCGGCCAACGCGCGGGGAGAGGCGGTTTGCGTATTGGGCGCTCTTCCG
3700
CTTCCTCGCTCACTGACTCGCTGCGCTCGGTCGTTCGGCTGCGGCGAGCGGTATCAGCTCACTCAAAGGCGGTAATACGGTTATCCACAGAATCAGGGGA
3800
TAACGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGAC
3900
GAGCATCACAAAAATCGACGCTCAAGTCAGAGGTGGCGAAACCCGACAGGACTATAAAGATACCAGGCGTTTCCCCCTGGAAGCTCCCTCGTGCGCTCTC
4000
CTGTTCCGACCCTGCCGCTTACCGGATACCTGTCCGCCTTTCTCCCTTCGGGAAGCGTGGCGCTTTCTCATAGCTCACGCTGTAGGTATCTCAGTTCGGT
4100
GTAGGTCGTTCGCTCCAAGCTGGGCTGTGTGCACGAACCCCCCGTTCAGCCCGACCGCTGCGCCTTATCCGGTAACTATCGTCTTGAGTCCAACCCGGTA
4200
AGACACGACTTATCGCCACTGGCAGCAGCCACTGGTAACAGGATTAGCAGAGCGAGGTATGTAGGCGGTGCTACAGAGTTCTTGAAGTGGTGGCCTAACT
4300
ACGGCTACACTAGAAGGACAGTATTTGGTATCTGCGCTCTGCTGAAGCCAGTTACCTTCGGAAAAAGAGTTGGTAGCTCTTGATCCGGCAAACAAACCAC
4400
CGCTGGTAGCGGTGGTTTTTTTGTTTGCAAGCAGCAGATTACGCGCAGAAAAAAAGGATCTCAAGAAGATCCTTTGATCTTTTCTACGGGGTCTGACGCT
4500
CAGTGGAACGAAAACTCACGTTAAGGGATTTTGGTCATGAGATTATCAAAATGAAGTTTTAAATCAA
4600
TCTAAAGTATATATGAGTAAACTTGGTCTGACAGTTACCAATGCTTAATCAGTGAGGCACCTATCTCAGCGATCTGTCTATTTCGTTCATCCATAGTTGC
                                AMPCILLIN RESISTANCE
```

*FIG. 8(B) CONT.*

4700
CTGACTCCCCGTCGTGTAGATAACTACGATACGGGAGGGCTTACCATCTGGCCCCAGTGCTGCAATGATACCGCGAGACCCACGCTCACCGGCTCCAGAT
         AMPCILLIN RESISTANCE                                                                       >

4800
TTATCAGCAATAAACCAGCCAGCCGGAAGGGCCGAGCGCAGAAGTGGTCCTGCAACTTTATCCGCCTCCATCCAGTCTATTAATTGTTGCCGGGAAGCTA
         AMPCILLIN RESISTANCE                                                                       >

4900
GAGTAAGTAGTTCGCCAGTTAATAGTTTGCGCAACGTTGTTGCCATTGCTACAGGCATCGTGGTGTCACGCTCGTCGTTTGGTATGGCTTCATTCAGCTC
         AMPCILLIN RESISTANCE                                                                       >

5000
CGGTTCCCAACGATCAAGGCGAGTTACATGATCCCCCATGTTGTGCAAAAAAGCGGTTAGCTCCTTCGGTCCTCCGATCGTTGTCAGAAGTAAGTTGGCC
         AMPCILLIN RESISTANCE                                                                       >

5100
GCAGTGTTATCACTCATGGTTATGGCAGCACTGCATAATTCTCTTACTGTCATGCCATCCGTAAGATGCTTTTCTGTGACTGGTGAGTACTCAACCAAGT
         AMPCILLIN RESISTANCE                                                                       >

5200
CATTCTGAGAATAGTGTATGCGGCGACCGAGTTGCTCTTGCCCGGCGTCAATACGGGATAATACCGCGCCACATAGCAGAACTTTAAAAGTGCTCATCAT
         AMPCILLIN RESISTANCE                                                                       >

5300
TGGAAAACGTTCTTCGGGGCGAAAACTCTCAAGGATCTTACCGCTGTTGAGATCCAGTTCGATGTAACCCACTCGTGCACCCAACTGATCTTCAGCATCT
         AMPCILLIN RESISTANCE                                                                       >

5400
TTTACTTTCACCAGCGTTTCTGGGTGAGCAAAAACAGGAAGGCAAAATGCCGCAAAAAAGGGAATAAGGGCGACACGGAAATGTTGAATACTCATACTCT
         AMPCILLIN RESISTANCE                                                                       >

5500
TCCTTTTTCAATATTATTGAAGCATTTATCAGGGTTATTGTCTCATGAGCGGATACATATTTGAATGTATTTAGAAAAATAAACAAATAGGGGTTCCGCG
CACATTTCCCCGAAAAGTGCCAC --(SEQ ID NO:44)--

*FIG. 8(B) CONT.* p3XP3-DsRed-orf
Sequence Range: 1 to 6984

```
100
TAGTTATTAATAGTAATCAATTACGGGGTCATTAGTTCATATAGCCCATATATGGAGTTCCGCGTTACATAACTTACGGTAAATGGCCCGCCTGGCTGACCG
                                                        CMV PROMOTER

200
CCCAACGACCCCCGCCCATTGACGTCAATAATGACGTATGTTCCCATAGTAACGCCAATAGGGACTTTCCATTGACGTCAATGGGTGGAGTATTTACGGT
                                                        CMV PROMOTER

300
AAACTGCCCACTTGGCAGTACATCAAGTGTATCATATGCCAAGTACGCCCCCTATTGACGTCAATGACGGTAAATGGCCCGCCTGGCATTATGCCCAGTA
                                                        CMV PROMOTER

400
CATGACCTTATGGGACTTTCCTACTTGGCAGTACATCTACGTATTAGTCATCGCTATTACCATGGTGATGCGGTTTTGGCAGTACATCAATGGGCGTGGA
                                                        CMV PROMOTER

500
TAGCGGTTTGACTCACGGGGATTTCCAAGTCTCCACCCCATTGACGTCAATGGGAGTTTGTTTTGGCACCAAAATCAACGGGACTTTCCAAAATGTCGTA
                                                        CMV PROMOTER

600
ACAACTCCGCCCCATTGACGCAAATGGGCGGTAGGCGTGTACGGTGGGAGGTCTATATAAGCAGAGCTGGTTTAGTGAACCGTCAGATCCGCTAGCGCTA
                                                        CMV PROMOTER

700
CCGGACTCAGATCCTATATAATAAAATGGGTAGTTCTTTAGACGATGAGCATATCCTCTCTGCTCTTCTGCAAAGCGATGACGAGCTTGTTGGTGAGGAT
                                                                                                        PIGGYBAC ORF

800
TCTGACAGTGAAATATCAGATCACGTAAGTGAAGATGACGTCCAGAGCGATACAGAAGAAGGCGTTTATAGATGAGGTACATGAAGTGCAGCCAACGTCAA
PIGGYBAC ORF
```

*FIG. 9(B)*

```
900
GCGGTAGTGAAATATTAGACGAACAAAATGTTATTGAACAACCAGGTTCTTCATTGGCTTCTAACAGAATCTTGACCTTGCCACAGAGGACTATTAGAGG
     PIGGYBAC ORF

1000
TAAGAATAAACATTGTTGGTCAACTTCAAAGTCCACGAGGGTAGCCGAGTCTCTGCACTGAACATTGTCAGATCTCAAAGAGGTCCGACGCGTATGTGC
     PIGGYBAC ORF

1100
CGCAATATATATGACCCACTTTTATGCTTCAAACTATTTTTACTGATGAGATAATTTCGGAAATTGTAAAATGGACAAATGCTGAGATATCATTGAAAC
     PIGGYBAC ORF

1200
GTCGGGAATCTATGACAGGTGCTACATTTCGTGACACGAATGAAGATGAAATCTATGCTTTCTTTGGTATTCTGGTAATGACAGCAGTGAGAAAGATAA
     PIGGYBAC ORF

1300
CCACATGTCCACAGAGATGACCTCTTTGATCGATCTTTGTCAATGGTGTACGTCTCTGTAATGAGTCGTGATCGTTTTGATTTTTGATACGATGTCTTAGA
     PIGGYBAC ORF

1400
ATGGATGACAAAAGTATACGGCCCCACACTTCCAGAAAACGATGTATTTACTCCTGTTAGAAAAATATGGGATCTCTTTATCCATCAGTGCATACAAAATT
     PIGGYBAC ORF

1500
ACACTCCAGGGGCTCATTTGACCATAGATGAACAGTTACTTGGTTGTTTTAGAGGACGGTGTCCGTTAGGATGTATATCCCAAACAAGCCAAGTAAGTATGG
     PIGGYBAC ORF

1600
AATAAAAAATCCTCATGATGTGTGACAGTGGTACGAAGTATATGAATAAATGGAATGCCTTATTTGGGAAGAGAGAACACAGACCAACGGAGTACCACTCGGT
     PIGGYBAC ORF

1700
GAATACTACGTGAAGGAGTTATCAAAGCCTGTGCACGGTAGTTGTCGTAATATTACGTGTGACAATTGGTTCACCTCAATCCCTTTGGCAAAAAACTTAC
     PIGGYBAC ORF
```

*FIG. 9(B) CONT.*

```
1800
TACAAGAACCGTATAAGTTAACCATTGTGGAACCGTGCGATCAAACAAACGCGAGATACCGGAAGTACTGAAAACAGTCGCTCCAGCCAGTGGGAAC
                                             PIGGYBAC ORF

1900
ATCGATGTTTGTTTGACGACCCCTTACTCTCGTCTCATATAAACCGAAGCCAGCTAAGATGGTATACTTATTATCATCTTGTGATGAGGATGCTTCT
                                             PIGGYBAC ORF

2000
ATCAACGAAAGTACCGGTAAACCGCTAAACAACTAAAGGCGGAGTGGACACGCTAGACCAAATGTGTTCTGTGATGACCTGCA
                                             PIGGYBAC ORF

2100
GTAGGAAGACGAATAGGTGGCCTATGGCATTATTGTACGGAATGATAAACATTGCCTGCATAAATTCTTTATTATATACAGCCATAATGTCAGTAGCAA
                                             PIGGYBAC ORF

2200
GGGAGAAAAGGTTCAAAGTCGCAAAAAATTTATGAGAAACCTTTACATGAGCCTGACGTCATCGTTTATGCGTAAGCGTTTAGAAGCTCCTACTTTGAAG
                                             PIGGYBAC ORF

2300
AGATATTTGCGCGATAATATCTCTAATATTTTTGCCAAATGAAGTGCCTGGTACATCAGATGACAGTACTGAAGAGCCAGTAATGAAAAACGTACTTACT
                                             PIGGYBAC ORF

2400
GTACTTACTGCCCCTCTAAATAAGGCGAAATGCATCTGTCAAAAAATGCAAAAAAGTTATTGTCGAGAGCATAATATTGATATGTGCCAAAG
                                             PIGGYBAC ORF

2500
TTGTTTCTGACTGACTAATAAGTATATAATTGTTTCTATTATGTATAAGTTAAGCTAATTACTTATTTTATAATACAACATGACTGTTTTTAAAGTACAAA
                                             PIGGYBAC ORF

2600
ATAAGTTTATTTTGTAAAGAGAGAATGTTTAAAGTTTGTTACTTTAGAAGAAATTTGAGTTTTGTTTTTTAATAAATAAACATAAAT
                                             PIGGYBAC ORF
```

FIG. 9(B) CONT.

```
2700
AAATTGTTTGTTGAATTTGGATCTCGAGGTTCCCACAATGGTTAATTCGAGCTCGCCCGGGATCTAATTCAATTAGAGCTAAT
     PIGGYBAC ORF          >                                        3XP3 PROMOTER
2800
TCAATTAGAGCTAAGCTTATCGATTTCGAACCCTCGACCGCCCGGAGTATAAATAGAGGCGCTTCGTCTACGGAGCGACAATTCAATTCAAACAAGCAAA
                                                                              3XP3 PROMOTER
2900
GTGAACACGTCGCTAAGCGAAAGCTAAGCAAATAAACAAGGCAGCTGAACAAGCTAAACAATCGGGTACCGCTAGAGTCGACGGTACCGCGGGCCCGG
                                     3XP3 PROMOTER
3000
GATCCACCGGTCGCCACCATGAATTCTGCAGTCGACGGTACCGCGGGCCCGGGATCCACCGTGCCTCCTCCAAGAACGTCATCAAG
     3XP3 PROMOTER      >                                          DSRED GENE
3100
GAGTTCATGCGCTTCAAGGTGCGCATGGAGGGCCACGAGTTCGAGATCGAGGGCGAGGGCGAGGGCCGCCCTACGAGGGCCACAACA
                                                  DSRED GENE
3200
CCGTGAAGCTGAAGGTGACCAAGGGCGGCCCCCTGCCCTTCGCCTGGGACATCCTGTCCCCCCAGTTCCAGTACGGCTCCAAGGTGTACGTGAAGCACCC
                                                              DSRED GENE
3300
CGCCGACATCCCCGACTACAAGAAGCTGTCCTTCCCCGAGGGCTTCAAGTGGGAGCGCGTGATGAACTTCGAGGACGGCGGCGTGGTGACCGTGACCCAG
                                                              DSRED GENE
3400
GACTCCTCCCTGCAGGACGGCTGCTTCATCTACAAGGTGAAGTTCATCGGCGTGAACTTCCCCTCCGACGGCCCCGTAATGCAGAAGAAGACCATGGCT
                                                              DSRED GENE
```

*FIG. 9(B) CONT.*

```
3500
GGGAGGGCCCTCCACCGAGCGCCTGTACCCCGCGACGGCGCTGCTGAAGGGCGAGATCCACAAGGCCCTGAAGCTGAAGGACGGCGGCCACTACCTGGTGGA
                                                                 DSRED GENE                            >

3600
GTTCAAGTCCATCTACATGGCCAAGAAGCCCGTGCAGCTGCCCGGCTACTACTACGTGGACTCCAAGCTGGACATCACCTCCCACAACGAGGACTACACC
                                                                 DSRED GENE                          >

3700
ATCGTGGAGCAGTACGAGCGCACCGAGGGCCGCCACCACCTGTTCCTGTAGGGCCCGACTCTAGATCATAATCAGCCATACCACATTTGTAGAGGTTT
                 DSRED GENE                          >

3800
TACTTGCTTTAAAAAACCTCCCACACCTCCCCCTGAACCTGAAACATAAAATGAATGCAATTGTTGTTGTTAACTTGTTTATTGCAGCTTATAATGGTTA

3900
CAAATAAAGCAATAGCATCACAAATTTCACAAATAAAGCATTTTTTCACTGCATTCTAGTTGTGGTTTGTCCAAACTCATCAATGTATCTTAAGGCGTA
>f1_single-strand_DNA_origin 4000
AATTGTAAGCGTTAATATTTTGTTAAAATTCGCGTTAAATTTTTGTTAAATCAGCTCATTTTTTAACCAATAGGCCGAAATCGGCAAAATCCCTTATAAA 4100
TCAAAAGAATAGACCGAGATAGGGTTGAGTGTTGTTCCAGTTTGGAACAGAGTCCACTATTAAAGAACGTGGACTCCAACGTCAAAGGGCGAAAAACCG 4200
TCTATCAGGGCGATGCCCACTACGTGAACCATCACCCTAATCAAGTTTTTGGGGTGAGGTGCCGTAAAGCACTAAATCGGAACCCTAAAGGGAGCCC 4300
CCGATTTAGAGCTTGACGGGGAAAGCCGGCGAACGTGGCGAGAAAGGAAGGGAAGAAAGGAGCGGGCGCTAGGGCGCTGGCAAGTGTAGCGGTC
```

FIG. 9(B) CONT.

```
4400
ACGCTGCGCGTAACCACCACACCCGCCGCGCGCTTAATGCGCCGCGCTCAGGGCGCGTCAGTGGCACTTTTCGGGGAAATGTGCGGGAACCCCTATTTGTT
     >Bacerial_promoter_for_expressioin_of_Kan_resistance_gene 4500
TATTTTTCTAAATACATTCAAATATGTATCCGCTCATGAGACAATAACCCTGATAAATGCTTCAATAATATATTGAAAAAGGAAGAGTCCTGAGGCGGAAAG
                                  >SV40_early_promoter_and_origin_of_replication 4600
AACCAGCTGTGTGGAATGTGTGTCAGTTAGGGTGTGGAAAGTCCCCAGGCTCCCCAGCAGGCAGAAGTATGCAAAGCATGCATCTCAATTAGTCAGCAACCA 4700
GGTGTGTGGAAAGTCCCCAGGCTCCCCAGCAGGCAGAAGTATGCAAAGCATGCATCTCAATTAGTCAGCAACCATAGTCCCGCCCCTAACTCCGCCCATCCC 4800
GCCCCTAACTCCGCCCAGTTCCGCCCATTCTCCGCCCCATGGCTGACTAATTTTTTTTATTTATGCAGAGGCCGAGGCCGCCTCGGCCTCTGAGCTATTC 4900
CAGAAGTAGTGAGGAGGCTTTTTTGGAGGCCTAGGCTTTTGCAAAGATCGATCAAGAGACAGGATCGAGGATCGTTTCGCATGATTGAACAAGATGGATTG 5000
CACGCAGGTTCTCCGGCCGCTTGGGTGGAGAGGCTATTCGGCTATGACTGGGCACAACAGACAATCGGCTGCTCTGATGCCGCCGTGTTCCGGCTGTCAG
                                                           KANAMYCIN RESISTANCE GENE 5100
CGCAGGGGCGCCCGGTTCTTTTTGTCAAGACCGACCTGTCCGGTGCCCTGAATGAACTGCAAGACGAGGCAGCGCGGCTATCGTGGCTGGCCACGACGGG
                                                           KANAMYCIN RESISTANCE GENE 5200
CGTTCCTTGCGCAGCTGTGCTCGACGTTGTCACTGAAGCGGGAAGGGACTGGCTGCTATTGGGCGAAGTGCCGGGGCAGGATCTCCTGTCATCTCACCTT
                                                           KANAMYCIN RESISTANCE GENE
```

*FIG. 9(B) CONT.*

```
5300
GCTCCTGCCGAGAAAGTATCCATCATGGCTGATGCAATGCGGCGGCTGCATACGCTTGATCCGGCTACCTGCCCATTCGACCACCAAGCGAAACATGCA
                              KANAMYCIN RESISTANCE GENE
5400
TCGAGCGAGCACGTACTCGGATGAAGCCGGTCTTGTCGATCAGGATGATCTGGACGAAGAGCATCAGGGGCTCGCGCCAGCCGAACTGTTCGCCAGGCT
                              KANAMYCIN RESISTANCE GENE
5500
CAAGGCGAGCATGCCCGACGGCGAGGATCTCGTCGTGACCCATGGCGATGCCTGCTTGCCGAATATCATGGTGGAAAATGGCCGCTTTTCTGGATTCATC
                              KANAMYCIN RESISTANCE GENE
5600
GACTGTGGCCGGCTGGGTGTGGCGGACCGCTATCAGGACATAGCGTTGGCTACCCGTGATATTGCTGAAGAGCTTGGCGGCGAATGGGCTGACCGCTTCC
                              KANAMYCIN RESISTANCE GENE
5700
TCGTGCTTTACGGTATCGCCGCTCCCGATTCGCAGCGCATCGCCTTCTATCGCCTTCTTGACGAGTTCTTCTGAGCGGGACTCTGGGGTTCGAAATGACC
                              KANAMYCIN RESISTANCE GENE
5800
GACCAAGCGACGCCCAACCTGCCATCACGAGATTTCGATTCCACCGCCGCCTTCTATGAAAGGTTGGGCTTCGGAATCGTTTTCCGGGACGCCGGCTGGA
5900
TGATCCTCCAGCGCGGGGATCTCATGCTGGAGTTCTTCGCCCACCCTAGGGGGAGGCTAACTGAAACACGGAAGGAGACAATACCGGAAGGAACCCGCGC
>Herpes_simplex_virus_(HSV)_thymidine_kinase_(TK)_polyA_signals
6000
TATGACGGCAATAAAAAGACAGAATAAAACGCACGGTGTTGGGTCGTTTGTTCATAAACGCGGGGTTCGGTCCCAGGGCTGGCACTCTGTCGATACCCCA
6100
CCGAGACCCCATTGGGGCCAATATACGCGCGGTTTCTTCCTCTTCCTTTTCCCCACCCCCACCCCCCAAGTTCGGGTGAAGGCCCAGGCTCGCAGCCAACGTCGGGG
```

FIG. 9(B) CONT.

>pUC_plasmid_replication_origin

```
6200 CGGCAGGCCCTGCAATAGCCTCAGGTTACTCATATATACTTTAGATTGATTTAAAACTTCATTTTTAATTTAAAAGGATCTAGGTGAAGATCCTTTTTGA
6300 TAATCTCATGACCAAAATCCCTTAACGTGAGTTTTCGTTCCACTGAGCGTCAGACCCCGTAGAAAAGATCAAAGGATCTTCTTGAGATCCTTTTTTTCTG
6400 CGCGTAATCTGCTGCTTGCAAACAAAAAAACCACCGCTACCAGCGGTGGTTTGTTTGCCGGATCAAGAGCTACCAACTCTTTTTCCGAAGGTAACTGGCT
6500 TCAGCAGAGCGCAGATACCAAATACTGTCCTTCTAGTGTAGCCGTAGTTAGGCCACCACTTCAAGAACTCTGTAGCACCGCCTACATACCTCGCTCTGCT
6600 AATCCTGTTACCAGTGGCTGCTGCCAGTGGCGATAAGTCGTGTCTTACCGGGTTGGACTCAAGACGATAGTTACCGGATAAGGCGCAGCGGTCGGGCTGA
6700 ACGGGGGGTTCGTGCACACAGCCCAGCTTGGAGCGAACGACCTACACCGAACTGAGATACCTACAGCGTGAGCTATGAGAAAGCGCCACGCTTCCCGAAG
6800 GGAGAAAGGCGGACAGGTATCCGGTAAGCGGCAGGGTCGGAACAGGAGAGCGCACGAGGGAGCTTCCAGGGGGAAACGCCTGGTATCTTTATAGTCCTGT
6900 CGGGTTTCGCCACCTCTGACTTGAGCGTCGATTTTTGTGATGCTCGTCAGGGGGGCGGAGCCTATGGAAAAACGCCAGCAACGCGGCCTTTTTACGGTTC
    CTGGCCTTTTGCTGGCCTTTTGCTCACATGTTCTTTCCTGCGTTATCCCCTGATTCTGTGGATAACCGTATTACCGCCATGCAT --(SEQ ID NO:45)--
```

*FIG. 9(B) CONT.*

Sequence Range: 1 to 4613

```
100
AGCGCCCAATACGCCAAACCGCCTCTCCCCGGCGTTGGCCGATTCATTAATGCAGCTGGCACGACAGTTCCCGACTGGAAAGCGGGCAGTGAGCGCAA

200
CGCAATTAATGTGAGTTAGCTCACTCATTAGGCACCCCAGGCTTTACACTTTATGCTTCCGGCTCGTATGTTGTGTGGAATTGTGAGCGGATAACAATTT

300
CACACAGGAAACAGCTATGACCATGATTACGCCAAGCTTGGTACCGAGCTCGGATCCACTAGTAACGGCCGCCAGTGTGCTGGAATTCGGCTTGATCCC
                                                                                              >
400
ATGGGTCAATTTACGCAGACTATCTTTCTAGGGTTAATCTAGCTGCATCAGGATCATATCGTCGGGTCTCTTTTTCCGGCTCAGTCATCGCCCAAGCTGG
 L  H  Q  D  H  I  V  G  S  F  F  R  L  S  H  R  P  S  W>
 B (CAPSID COMPONENT;533); CODON_START=1; DB_XREF=P >
 L  H  Q  D  H  I  V  G  S  F  F  R  L  S  H  R  P  S  W>
        PROCESSED B; CODON_START=1 [SPLIT]
        RIGHT TERMINAL REPEAT        >

500
CGCTATCTGGGCATCGGGGAGGAAGAAGCCCGTGCCTTTTCCCGCGAGGTTGAAGCGGCATGGAAAGAGTTTGCCGAGGATGACTGCTGCATTGACG
 R  Y  L  G  I  G  E  E  E  A  R  A  F  S  R  E  V  E  A  A  W  K  E  F  A  E  D  D  C  C  I  D>
                   B (CAPSID COMPONENT;533); CODON_START=1; DB_XREF=PID:G215108; TRA [SPLIT]
 R  Y  L  G  I  G  E  E  E  A  R  A  F  S  R  E  V  E  A  A  W  K  E  F  A  E  D  D  C  C  I  D>
                        PROCESSED B; CODON_START=1 [SPLIT]
```

*FIG. 10(B)*

```
600
TTGAGCCGAAAACGCACGTTTACCATGATGATTCGGGAAGTGTGGCCATGCACGCCTTTAACGGTGAACTGTTCGTTCAGGCCACCTGGGATACCAGTTC
 V  E  R  K  R  T  F  T  M  M  I  R  E  G  V  A  M  H  A  F  N  G  E  L  F  V  Q  A  T  W  D  T  S  S>
 ────────────────────────────────────────────────────────────────────────────────────────────────────
 B (CAPSID COMPONENT;533); CODON_START=1; DB_XREF=PID:G215108; TRA [SPLIT]                            ^
 V  E  R  K  R  T  F  T  M  M  I  R  E  G  V  A  M  H  A  F  N  G  E  L  F  V  Q  A  T  W  D  T  S  S>
 ────────────────────────────────────────────────────────────────────────────────────────────────────
              PROCESSED B; CODON_START=1 [SPLIT]                                                     ^

700
GTCGCGGCTTTTCCGGACACAGTTCCGGATGTCAGCCCGAAGCGCATCAGCAACCCGAACAATACCGGCGACAGCCGAACTGCCGCCGTGCCGGTGTGCAG
 S  R  L  F  R  T  Q  F  R  M  V  S  P  K  R  I  S  N  P  N  N  T  G  D  S  R  N  C  R  A  G  V  Q>
 ────────────────────────────────────────────────────────────────────────────────────────────────────
 B (CAPSID COMPONENT;533); CODON_START=1; DB_XREF=PID:G215108; TRA [SPLIT]                            ^
 S  R  L  F  R  T  Q  F  R  M  V  S  P  K  R  I  S  N  P  N  N  T  G  D  S  R  N  C  R  A  G  V  Q>
 ────────────────────────────────────────────────────────────────────────────────────────────────────
              PROCESSED B; CODON_START=1 [SPLIT]                                                     ^

800
ATTAATGACAGCGGTGCGGCGCTGGGCTATTACGTCAGCGAGGACGGGTACCCTGGCTGGATGCCGCAGAAATGGACATGGATACCCGTGAGTTACCCG
 I  N  D  S  G  A  A  L  G  Y  Y  V  S  E  D  G  Y  P  G  W  M  P  Q  K  W  T  W  I  P  R  E  L  P>
 ────────────────────────────────────────────────────────────────────────────────────────────────────
 B (CAPSID COMPONENT;533); CODON_START=1; DB_XREF=PID:G215108; TRA [SPLIT]                            ^
 I  N  D  S  G  A  A  L  G  Y  Y  V  S  E  D  G  Y  P  G  W  M  P  Q  K  W  T  W  I  P  R  E  L  P>
 ────────────────────────────────────────────────────────────────────────────────────────────────────
              PROCESSED B; CODON_START=1 [SPLIT]                                                     ^

900
GCGGGGCGCGGCCTCGTTCATTCACGTTTTGAACCCGTGGAGGACGGGCAGACTCGCGGTGCAAATGTGTTTTACAGCGTGATGGAGCAGATGAAGATGCT
 G  G  R  A  S  F  I  H  V  F  E  P  V  E  D  G  Q  T  R  G  A  N  V  F  Y  S  V  M  E  Q  M  K  M  L>
 ────────────────────────────────────────────────────────────────────────────────────────────────────
 B (CAPSID COMPONENT;533); CODON_START=1; DB_XREF=PID:G215108; TRA [SPLIT]                            ^
 G  G  R  A  S  F  I  H  V  F  E  P  V  E  D  G  Q  T  R  G  A  N  V  F  Y  S  V  M  E  Q  M  K  M  L>
 ────────────────────────────────────────────────────────────────────────────────────────────────────
              PROCESSED B; CODON_START=1 [SPLIT]                                                     ^
```

FIG. 10(B) CONT.

1000
CGACACGCTGCAGAACACGCGCAGCTAGATTAACCCTAGAAAGATAATCATATTGTGACGTACGTTAAAGATAATCATGCGTAAAATTGACGCATGGGATCC
 D  T  L  Q  N  T  Q> --(SEQ ID NO:47)--
 B (CAPSID COMPO     >
D  T  L  Q  N  T  Q> --(SEQ ID NO:47)--
 PROCESSED B; CO     >
                     LEFT TERMINAL REPEAT                                                  >

1100
AAGCCGAATTCTGCAGATATCCATCACACTGGCGGCCGCTCGAGCATGCATCTAGAGGGCCCAATTCGCCCTATAGTGAGTCGTATTACAATTCACTGGC

1200
CGTCGTTTTACAACGTCGTGACTGGGAAAACCCTGGCGTTACCCAACTTAATCGCCTTGCAGCACATCCCCCTTTCGCCAGCTGGCGTAATAGCGAAGAG

1300
GCCCGCACCGATCGCCCTTCCCAACAGTTGCGCAGCCTGAATGGCGAATGGCGCCTGATGCGGTAGGGCGTGTGGTGGTTACGC

1400
GCAGCGTGACCGCTACACTTGCCAGCGCCCTAGCGCCCGCTCCTTTCGCTTTCTTCCCTTCCTTTCTCGCCACGTTCGCCGGCTTTCCCCGTCAAGCTCT

1500
AAATCGGGGGCTCCCTTTAGGGTTCCGATTTAGAGCTTTACGGCACCTCGACCGCAAAAAACTTGATTTGGGTGATGGTTCACGTAGTGGGCCATCGCCC

1600
TGATAGACGGTTTTTCGCCCTTTGACGTTGGAGTCCACGTTCTTTAATAGTGGACTCTTGTTCCAAACTGGAACAACACTCAACCCTATCGCGGTCTATT

1700
CTTTTGATTTATAAGGGATTTTGCCGATTTCGGCCTATTGGTTAAAAAATGAGCTGATTTAACAAATTCAGGGGCTGCTAAAGGAAGCGGAAC

1800
ACGTAGAAAGCCAGTCCGCAGAAACGGTGCTGACCCCGGATGAATGCAGCTACTGGGCTATCTGGACAAGGGAAAACCAAGCGCAAAGAGAAAGCAGG

FIG. 10(B) CONT.

```
1900
TAGCTTGCAGTGGGCTTACATGGCGATAGCTAGACTGGGCGGTTTTATGGACAGCAAGCGAACCGAATTGCCAGCTGGGGCGCCCTCTGGTAAGGTTGG
2000
GAAGCCCTGCAAAGTAAACTGGATGGCTTTCTTGCCGCCAAGGATCTGATGGCGCAGGGGATCAAGATCTGATCAAGAGACAGGATGAGGATCGTTTCGC
2100
ATGATTGAACAAGATGGATTGCACGCAGGTTCTCCGGCCGTTCCCGCCGCTTGGGTGGAGAGGCTATTCGGCTATGACTGGGCACACAACAGACAATCGGCTGCTCTGATG
2200
CCGGCCGTGTTCCGGCTGTCAGCGCAGGGGCGCCCGGTTCTTTTTGTCAAGACCGACCTGTCCGGTGCCCTGAATGAACTGCAGGACGAGGCAGCGCGGCT
2300
ATCGTGGCTGGCCACGACGGGCGTTCCTTGCGCAGCTGTGCTCGACGTTGTCACTGAAGCGGGAAGGGACTGGCTGCTATTGGGCGAAGTGCCGGGGCAG
2400
GATCTCCTGTCATCTCGCCTTGCTCCTGCCGAGAAAGTATCCATCATGGCTGATGCAATGCGGCGGCTGCATACGCTTGATCCGGCTACCTGCCCATTCG
2500
ACCACCAAGCGAAACATCGCATCGAGCGAGCACGTACTCGGATGAAGCCGGTCTTGTCGATCAGGATGATCTGGACGAAGAGCATCAGGGGCTCGCGCC
2600
AGCCGAACTGTTCGCCAGGCTCAAGGCGCGCATGCCCGACGGCGAGGATCTCGTCGTGACCCATGGCGATGCCTGCTTGCCGAATATCATGGTGGAAAAT
2700
GGCCGCTTTTCTGGATTCAACGACTGTGGCCGGCTGGGTGTGGCGGACCGCTATCAGGACATAGCGTTGGCTACCCGTGATATTGCTGAAGAGCTTGGCG
2800
GCGAATGGGCTGACCGCTTCCTCGTGCTTTACGGTATCGCCGCTCCCGATTCGCAGCGCATCGCCTTCTATCGCCTTCTTGACGAGTTCTTCTGAATTGA
2900
AAAAGGAAGAGTATGAGTATTCAACATTTCCGTGTCGCCCTTATTCCCTTTTTTGCGGCATTTTGCCTTCCTGTTTTTGCTCACCCAGAAACGCTGGTGA
```

*FIG. 10(B) CONT.*

```
3000
AAGTAAAAGATGCTGAAGATCAGTTGGGTGCACGAGTGGGTTACATGAACTGAAGATCCTTGAGAGTTTTCGCCCGAAGAACG
3100
TTTTCCAATGATGAGCACTTTTAAAGTTCTGCTATGTCATACACTATTATCCCGTATTGACGCCGGGCAAGAGCAACTCGGTCGCCGGGCGGGTATTCT
3200
CAGAATGACTTGGTTGAGTACTCACCAGTCACAGAAAAGCATCTTACGGATGGCATGACAGTAAGAGAATTATGCAGTGCTGCCATAACCATGAGTGATA
3300
ACACTGCGGCCAACTTACTTCTGACAACGATCGGAGGACCGAAGGAGCTAACCGCTTTTTTGCACAACATGGGGATCATGTAACTCGCCTTGATCGTTG
3400
GGAACCGGAGCTGAATGAAGCCATACCAAACGACGAGAGTGACACCACGATGCCTGTAGCAATGCCAACAAGTTGCGCAAACTATTAACTGGCGAACTA
3500
CTTACTCTAGCTTCCCGGCAACAATTAATAGACTGGATGGAGGCGGATAAAGTTGCAGGACCACTTCTGCGCTCCGGCTATCGTAGTTATCTACACGACGGG
3600
CTGATAAATCTGGAGCCGTGGGTGAGCGTGGGCTCGCGGTATCATTGCAGCACTGGGGCCAGATGGTAAGCCCTCCCGTATCGTAGTTATCGTCAGACCAAGTTACTCATATATA
3700
GAGTCAGGCAACTATGGATGAACGAAATAGACAGATCGCTGAGATAGTGCCTCACTGATTAAGCATTGTAACTGTCAGACCAAGTTACTCATATATA
3800
CTTTAGAGATTGATTAAAACTTCATTTTTAATTTAAAAGGATCTAGGTGAAGATCCTTTTGATAATCTCATGACCAAAATCCCTTAACGTGAGTTTTCGT
3900
TCCACTGAGCGTCAGACCCCGTAGAAAAGATCAAAGGATCTTCTTGAGATCCTTTTTTTCTGCGCGTAATCTGCTGCTTGCAAACAAAAAAACCACCGCT
4000
ACCAGCGGTGGTTTGTTTGCCGGATCAAGAGCTACCAACTCTTTTTCCGAAGGTAACTGGCTTCAGCAGAGCGCAGATACCAAATACTGTCCTTCTAGTG
```

FIG. 10(B) CONT.

```
4100
TAGCCCGTAGTTAGGCCACCACTTCAAGAACTCTGTAGCACCGCCTACATACCTCGCTCTGCTAATCCTCGTTACCAGTGGCTGCTGCCAGTGGCGATAAGT
4200
CGTGCTCTTACCGGGTTGGACTCAAGACGATAGTTACCGGATAAGGCGCAGCGGTCGGGCTGAACGGGGGGTTCGTGCACAGCCCAGCTTGGAGCGAAC
4300
GACCTACACCGAACTGAGATACCTACAGCGTGAGCATTGAGAAAGCGCCACGCTTCCCGAAGGGAGAAAGGCGGACAGGTATCCGGTAAGCGGCAGGGTC
4400
GGAACAGGAGAGCGCACGAGGGAGCTTCCAGGGGGAAACGCCTGGTATCTTTATAGTCCTGTCGGGTTTCGCCACCTCTGACTTGAGCGTCGATTTTTGT
4500
GATGCTCGTCAGGGGGGCGGAGCCTATGGAAAAAACGCGGCCTTTTTACGGTTCCTGGCCTTTTGCTGGCCTTTTGCTCACATGTTCTTTCC
4600
TGCGTTATCCCCTGATTCTGTGGATAACCGTATTACCGCCTTTGAGTGAGCTGATACCGCTCGCCGCAGCCGAACGACCGAGCGCAGCGAGTCAGTGAGC

GAGGAAGCGGAAG  --(SEQ ID NO:46)--
```

*FIG. 10(B) CONT.* p(PZ)-Bac-EYFP
Sequence Range: 1 to 8999

100
ACCGAAGTATACACTTAAATTCAGTGCACGTTTGCTTGTTGAGAGGAAAGGTTGTGTGCGGACGAATTTTTTTTGAAAACATTAACCCTTACGTGGAAT

200
AAAAAAAATGAAATATTGCAAATTTTGCTGCAAAGCTGTGACTGGAGTAAAATTAATTCACGTGCCGAAGTGTGCTATTAAGAGAAAATTGTGGGAGCA

300
GAGCCTTGGGTGCAGCCTTGTGTGAAAACTCCCAAATTTGTGATAATCCCACTTTAATGATTCGCAGTGGAAGGCTGCACCTGCAAAAGGTCAGACATTTAAA

400
AGGAGGCGACTCAACGCAGATGCCGTACCTAGTAAAGTGATAGAGCCTGAACCAGAAAAGATAAAAGAAGGCTATACCAGTGGGAGTACACAAACAGAGT

500
AAGTTTGAATAGTAAAAAAAAATCATTTATGTAAACAATAACGTGACTGTGCGGTTAGGTCCTGTTCATTGTTTAATGAAATAAGAGCTTGAGGGAAAAAA

600
TTCGTACTTTGGAGTACGAAATGCTTCGTTTAGAGCAGCAGCCGAATTCACTGGCCGTCGTGACTGGGAAAACCCTGGCGTTACCCA

700
ACTTAATCGCCTTGCAGCACATCCCCCTTTCGCCACCAGAAGGCCCGCACCGATCGCCCTTCCAACAGTTGCCGCAGCCTGAATGGC

800
GAATGGCGCTTTGCCTGGTTTCCGGCACCAGAAGCGGTGCCGGAAAGCTGGCTGGAGTGCGATCTTCCTGAGGCCGATACTGTCGTCGTCCCCTCAAACT

900
GGCAGATGCACGGTTACGATGGCCCATCTACACCAACTATACCCATTACGGTCAACCTGAAGCCAGAAGGCCAGACGCGAATTATTTTGATGCCGTTAACTGGCGTTAACGGG

1000
CTCGCTCACATTTAATGTTGATGAAAGCTGGCTACAGGAAGGCCAGACGCGAATTATTTTTGATGGCGTTAACTGGCGTTAACGGG

1100
CGCTGGGTCGGTTACGGCCAGGACAGTCGTTTGCCGTCTGAATTGACCTGAGCGCATTTTACGCGCCGAGAAAACCGCCTGCGGTGATGGTGCTGC

FIG. 12(B)

```
1200
GTTGGAGTGACGGGCAGTTATCTGGAAGATCAGGATATGTGGCGGATGAGCGGCATTTCCGTGACGTCTCGTTGCTGCATAAACCGACTACACAAATCAG
1300
CGATTTCCATGTGCCACTCGCTTTAATGATGATTTCAGCCGCGCTGTACTGGAGGCTGAAGTTCAGATGTGCGGCGAGTTGCGTGACTACCTACGGGTA
1400
ACAGTTTCTTTATGGCAGGGTGAAAACGCAGTTGCCCAGCGGCACCGCGCCTTTCGGCGGTGAAATTATCGATGAGCGTGGTGGTTATGCCGATCGCTCA
1500
CACTACGTCTGAACGTCGAAAACCCGAAACTGTGGAGCGCCCGAAATCTCTATCGTGCCGGTGGTTGAACTGCACACCGCCGACGGCACGCTGAT
1600
TGAAGCAGAAGCCTGCCGATGTCGGTTTCCGCGAGGTGCGATTGAAAATGGTCTGCTGAACCGCCGTTGCTGATTCGAGGCGTTAACCGT
1700
CACGAGCATCATCCTCTGCATGGTCAGGTCATGGATGAGCAGACGATGGTGCAGGATATCCTGCTGATGAAGCAGAACAACTTTAACGCCGTGCCGCTGTT
1800
CGCATTATCCGAACCATCCGCTGTGCCGACCGCTGTGCCGCTACGGCCTGTATGTGGTGGATGAAGCCAATATTGAAACCCACGGCATGGTGCCAAT
1900
GAATCGGTCTGACCGATGATCCCGCTGGCTACCGGCGATGAGCGAACGGTAACGCGAATGTGCAGCGCGATCGTAATCACCCGAGTGTGATCATCTGG
2000
TCGCTGGGGAATGAATCAGGCCACGCGCGCTAATCACGACGCGTATCGCTGGATCAAATCTGTCGATCCTTCCCGCCGGTGCAGTATGAAGGCGGCG
2100
GAGCCCGACACCACGGCCACCGATATTATTGCCCGATGTACGGCCGTGATGAAGACCAGCCCTTCCCGGCTGTGCCGAAATGGTCCATCAAAAAATG
2200
GCTTTCGCTACCTGGAGAGACGGCCCGCTGATCCTTTGCGAATACGCCACGCGATGGTAACAGTGTTCGGCGGTTTCGCTAAATACTGGCAGGCGTTT
2300
CGTCAGTATCCCCGTTTACAGGGCGCTTCGTCTGGGACTGGGTGGATCAGTCGCTGATTAAATATGAAAACGGCAACCGTGTGCGGCTTACGGCG
```

*FIG. 12(B) CONT.*

2400
GTGATTTGGCGATACGCCGAACGATGCCAGTTCTGTATGAACGGTCTGTCTTTGCCGACCGCCACGCCGCATCCAGCGCTGACGGAAGCAAAACACCA

2500
GCAGCAGTTTTTCCAGTTCCGTTTATCGGGCAAACCATCGAAGTGACCAGCGAATACCTGTTCCGTCATAGCGATAACGAGCTCCTGCACTGGATGGTG

2600
GCGCTGGATGGTAAGCCGCTGGCAAGCGGTGAAGTGCCTCTGGATGTCGCTCCACAAGGTAAACAGTTGATTGAACTGCCTGAACTACCGCAGCCGGAGA

2700
GCGCCGGGCAACTCTGGCTCACAGTACGCGTAGTGCAACCGAACGGCATGGTCAGAACGGACCAGCGCTGGCAGCAGTGGCGTCTGGC

2800
GGAAAACCTCAGTGTGACGCTCCCCGCCGGTCCCACGCCATCTGACCACCAGCGAAATGGATTTTTGCATCGAGCTGGGTAATAAGCGTTGG

2900
CAATTTAACCGCCAGTCAGGCTTTCTTTCACAGATGTGGATTGGCGATAAAAAACAACTGCTGACGCCGTCGCCGATCAGTTCACCCGTGCACCGCTGG

3000
ATAACGACATTGGCGTAAGTGAAGCGACCCGCATTGACCCTAACGCTGGGTCGAACGCTGGAAGGCGGGCCATTACCAGGCGAAGCAGCGTTGTT

3100
GCAGTGCACGGGCAGATACACTTGCTGTCGATGCGTGCTGATTACGACGGTCTGATTACCGTTGCCAGCATCAGGGGAAAACCTTATTTATCAGCCGGAAAACCTAC

3200
CGGATTGATGGTAGTGGTCAAATGGCGATTAGGGCCGCAAGAAAAACTATCCGACCGCCTTACTGCGCTGTTTGACCGCTGGGATCTGCCATTGTC

3300
AGGTAGCAGAGCGGGTAAACTGGCTCGGATTAGGGCCGCAAGAACGGTCTGCGCTGCGGACGCGCGAATTGAATTATGGCCCACACCAGTGGCGGGCGACTTCCAG

3400
AGACATGTATACCCCGTACGTCTTCCCGAGCGAAACAGCCATCGCCATCTGCTGCACCGGAAGAAGGCACATGGCTGAATATCGACGGTTTCC

3500
TTCAACATCAGCCGCTACAGTCAACAGCAACTGATGGAAACCAGCCATCGCCATCTGCTGCACCGGAAGAAGGCACATGGCTGAATATCGACGGTTTCC

FIG. 12(B) CONT.

3600
ATATGGGGATTGGTGGCGACGACTCCTGGAGCCCGTCAGTATCGGGCTATCGAGCGCCGGTCGCTACCATTACCAGTTGGTCTCGTGTCGGGG

3700
ATCCGTCGACTAAGGCCAAAGAGTCTAATTTTGTTCATCAATGGGTTATAACATATGGGTTATATTATAAGTTGTTTAAGTTTTGAGACTGATAAG

3800
AATGTTTCGATCGAATATTCCATAGAACAACAATAGTATTACCTAATTACCAAGTCTTAATTTAGCAAAAATGTTATTGCTTATAGAAAAATAAATTAT

3900
TTATTTGAAATTAAAGTCAACTTGTCATTTAATGTCTGTAGACTTTGAAAGTCTTACGATACAATTAGTATCTAATATACATGGGTTCATTCTACAT

4000
TCTATATTAGTGATGATTCTTAGCTAGTAATACATTTAATTATATTCGGCTTTGATGATTTTCTGATTTTTCCGAACGGATTTCGTAGACCCTTT

4100
CGATCTCATAATGGCTCATTTTATTGCGATGACGGTCAGGAGAGCTCCACTTTGAATTCTGTTCGCAGACCGCATTGTAGCACATAGCCGGGAC

4200
ATCCGGTTTGGGAGATTTCCAGTCTCTGTTGCAATTGGTTTTCGGGAATGCGTTGCAGGCGCATACGCTCTATATCCTCCGAACGGCGCTGTTGACC

4300
CTAGCATTTACATAAGGATCAGCAGCAAAATTGCCTCGCTTCATTGCCCGGAATCACAGCAATCAGATGTCCCTTTCGGTTACGATGGATATTCAGT

4400
GCGAACCGCACACAAAGCTCTCGCCGCCACACTCCACACTGATATGGTCGTCGCCGCATATGGATCTTAAGTCGTTGGACTGCACAAAG

4500
CTCTTGCTGCACATTTTGCAGGAGTACGCCCTTTGACCCGTTGTCAATCGCATGTGCGCGCCAGCTTGTTCTGCGAAATAAACTTCTTGGACTGCACAAAG



4500
CTCTTGCTGCACATTTTGCAGGAGTACGCCCTTTGACCCGTTGTCAATCGCATGTGCGCGCCAGCTTGTTCTGCGAAATAAACTTCTTGGAGCAGATGC

4600
GGCCGCCCGGGGTGGGCGAAGAACTCCAGCATGAGGATCATCCAGCGGCGCTCCCGGAAAACGATTCCGAAGCCCAACCTTTCAT

4700
AGAAGGCGGCGGTGGAATCGAAATCTGTGATGGCAGGTTGGGCGTCGCTTGGTCGTCATTCGAACCCCAGAGTCCCGCTCAGAAGAACTCGTCAAGA

FIG. 12(B) CONT.

```
4800
AGGCGATAGAAGGCGATGCGCTGCGAATCGGGAGCGGCGATACCGTAAAGCACGAGGAAGCGGTCAGCCATTCGCCGCCAAGCTCTTCAGCAATATCAC
4900
GGGTAGCCAACGCTATGTCCTGATAGCGGTCCGCCACACCCAGCCGGCCCACAGTCGATGAATCCAGAAAAGCGGCCATTTCCACCATGATATTCGGCAA
5000
GCAGGCATGCGCCATGGTCACGACGAGATCCTCGCCGTCGGGCATGCGCGCCCTTGAGCCTGGCGAACAGTTCGGCTGGCGGAGCCCCTGATGCTCTTCG
5100
TCCAGATCATCCTGATCGACAAGACCGGCTTCCATCCGAGTACGTGCTCGCTCGATGCGATGTTTCGCTTGGTGGTCGAATGGGCAGGTAGCCGGATCAA
5200
GCGTATGCAGCCGCCATTGCATCAGCCATGATGGATACTTTCTCGGCAGGAGCAAGCTGAGACAAGGAGATCCTGCCCCGGCACTTCGCCAATAG
5300
CAGCCAGTCCCTTCCCGCTTCAGTGACAACGTCGAGCAGCTGCGCAAGGAACGCCCGTCGTGGCCAGCCACGATAGCCGCGCTGCCTCGTCCTGCAGT
5400
TCATTCAGGGCACCGGACAGGTCGGTCTTGACAAAAGAACCGGGCGCCCCTGCCGCTGACAGCCGGAACACGCCGATTGTCTGTT
5500
GTGCCCAGTCATAGCCGAATAGCCTCTCCACCCAAGCGGCCGGAGAACCTGCGTGCAATCATCTGTTCAATCATGCGAAACGATCCTCATCCTGCTCTC
5600
TTGATCAGATCTTGATCCCCTGCGCCATCAGATCCTTGGCGCAAGAAAGCCATCCAGTTACTTTGCAGGGCTTCCCAACCTTACCAGAGGCGCCCCA
5700
GCTGGCAATTCCGGTTCGCTTGCTTGCTGTCCATAAAACCGCCAGTCTAGCTATCGCCATGTAAGCCCACTGCAAGCTACCTGCTTTCTCTTTGCGCTTGCGT
5800
TTTCCCTTGTCCAGATAGCCCAGTAGCTGACATTCATCCGGGTCAGCACGTTCTGCGGACTGGCTTTCACGTGTTCCGCTTCCTTTAGCAGCCCTT
5900
GCGCCCTGAGTGCTTGCGGCAGCGTGAAGCTAATTCATGGTTATAAATTTTGTTAAATCAGCTCATTTTTAACCAATAGGCCGAAATCGGCAAAATCC
```

FIG. 12(B) CONT.

6000
CTTATAAATCAAAAGAATAGCCCGAGATAGGGTTGAGTGTTGTTGTTCCAGTTTGGAACAAGAGTCCACTATTAAAGAACGTGGACTCCAACGTCAAAGGGCG
6100
AAAAACCGTCTATCAGGGCGATGCCCGGATCAGCTTATGCGGTGTGAAATACCGCACAGATGCGTAAGGAGAAAATACCGCATCAGGCGCTCTTCCGCTT
6200
CCTCGCTCACTGACTCGCTGCGCTCGGTCGTTCGGCTGCGGCGAGCGGTATCAGCTCACTCAAAGGCGGTAATACGGTTATCCACAGAATCAGGGGATAA
6300
CGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGACGAG
6400
CATCACAAAAATCGACGCTCAAGTCAGAGGTGGCGAAACCCGACAGGACTATAAAGATACCAGGCGTTTCCCCCTGGAAGCTCCCTCGTGCGCTCTCCTG
6500
TTCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTA
6600
GGTCGTTCGCTCCAAGCTGGGCTGTGTGCACGAACCCCCCGTTCAGCCCGACCGCTGCGCCTTATCCGGTAACTATCGTCTTGAGTCCAACCCGGTAAGA
6700
CACGACTTATCGCCACTGGCAGCAGCCACTGGTAACAGGATTAGCAGAGCGAGGTATGTAGGCGGTGCTACAGAGTTCTTGAAGTGGTGGCCTAACTACG
6800
GCTACACTAGAAGGACAGTATTTGGTATCTGCGCTCTGCTGAAGCCAGTTACCTTCGGAAAAAGAGTTGGTAGCTCTTGATCCGGCAAACAAACCACCGC
6900
TGGTAGCGGTGGTTTTTTTGTTTGCAAGCAGCAGATTACGCGCAGAAAAAAAGGATCTCAAGAAGATCCTTTGATCTTTTCTTACTGAACGGTGATCCCCA
7000
CGGGAATTGCGGCCGCGGAATTCTCATGTTTGACAGCTTATCATCGATAAGCTGGCCGCTCTAGAACTAGTGTCCCACAATGGTTAATTCGAGCTCGCC  >
                                                                                      3XP3-EYFP MARKER
7100
CGGGGATCTAATTCAATTAGAGACTAATTCAATTAGAGCTAATTCAATTAGGATCCAAGCTTATCGATTTCGAACCCCTGACCGCCGGAGTATAAATAGA  >
                                                                                      3XP3-EYFP MARKER

```
7200
GGCGCTTCGTCGTCTACGGAGGCGACAATTCAATTCAAACAAGCAAAGTGAACACGTGCTAAGCGAAAGCTAAGCAAATAAACAAGCGAGCTGAACAAGCTA
                                                     3XP3-EYFP MARKER

7300
AACAATCGGGTACCGCTAGAGTCGACGGTACGATCCACCGGTCGCCACCATGGTGAGCAAGGGCGAGGAGCTGTTCACCGGGGTGGTGCCCATCCTGGT
                                                     3XP3-EYFP MARKER

7400
CGAGCTGGACGGCGACGTAAACGGCCACAAGTTCAGCGTGTCCGGCGAGGGCGAGGGCGATGCCACCTACGGCAAGCTGACCCTGAAGTTCATCTGCACC
                                                     3XP3-EYFP MARKER

7500
ACCGGCAAGCTGCCCGTGCCCTGGCCCACCCTCGTGACCACCTTCGGCTACGGCCTGCAGTGCTTCGCCCGCTACCCCGACCACATGAAGCAGCACGACT
                                                     3XP3-EYFP MARKER

7600
TCTTCAAGTCCGCCATGCCCGAAGGCTACGTCCAGGAGCGCACCATCTTCTTCAAGGACGACGGCAACTACAAGACCCGCGCCGAGGTGAAGTTCGAGGG
                                                     3XP3-EYFP MARKER

7700
CGACACCCTGGTGAACCGCATCGAGCTGAAGGGCATCGACTTCAAGGAGGACGGCAACATCCTGGGGCACAAGCTGGAGTACAACTACAACAGCCACAAC
                                                     3XP3-EYFP MARKER

7800
GTCTATATCATGGCCGACAAGCAGAAGAACGGCATCAAGGTGAACTTCAAGATCCGCCACAACATCGAGGACGGCAGCGTGCAGCTCGCCGACCACTACC
                                                     3XP3-EYFP MARKER

7900
AGCAGAACACCCCCATCGGCGACGGCCCCGTGCTGCTGCCCGACAACCACTACCTGAGCTACCAGTCCGCCCTGAGCAAAGACCCCAACGAGAAGCGCGA
                                                     3XP3-EYFP MARKER

8000
TCACATGGTCCTGCTGGAGTTCGTGACCGCCGCCGGGATCACTCTCGGCATGGACGAGCTGTACAAGTAAAGCGGCCGCGACTCTAGATCATAATCAGCC
                                                     3XP3-EYFP MARKER
```

*FIG. 12(B) CONT.*

```
8100
ATACCACATTTGTAGAGGTTTTACTTGCTTTAAAAAAACCTCCCACACCTCCCCCTGAACCTGAAACATAAAATGAATGCAATTGTGTTGTTAACTTGTT
                                                         3XP3-EYFP MARKER                              >
8200
TATTGCAGCTTATAATGGTTACAAATAAAGCAATAGCATCACAAATTTCACAAATTTTTTCACTGCATTCTAGTTGTGGTTTGTCCAAACTC
                                                         3XP3-EYFP MARKER                              >
8300
ATCAATGTATCTTAAAGTCTTATCGATACGCGTTATCGGCACTAGTGGATCCCATGCGTCAATTTTACGCATGATTATCTTTAAGCTAGTCACAATATGATT
                                                         <  LEFT TERMINAL REPEAT
8400
ATCTTTCTAGGGTTAATCTAGCTGCCGTTCTGCAGCGTGTCGAGCATCTTCATCGCTCCATCACGCTGTAAACACATTTGCACCGCGAGTCTGCCCG
              3XP3-EYFP MARKER                    >
                                                 <
8500
TCCTCCACGGGTTCAAAAACGTGAATGAACGAGGGCGCCCCGGGTAACTCACGGGGTATCCATGTCCATTTCTGCGGCATCCAGCCAGGATACCCGT
8600
CCTCGCTGACGTAATATCCCAGCGCCACCGGCCACCGGCAGTTCCGGCTGTCGCCGGTATTGTTCGGGTTGCTGATGCG
8700
CTTCGGGCTGACCATCCGGAACTGTCCGGAAAGCCGGACGAACTGGTATCCCAGTGGCCTGAACAGTCACCGTTAAAGGCGTGCATGCC
8800
ACACCCTTCCCGAATCATCATGGTAAACGTGCGTTTCGCTCAACGTGCGTTTTCGCTCAACGTCATCCTCGGCAAACTCTTTCCATGCGCTTCAACCTCGC
8900
GGGAAAAGGCACGGGCTTCTTCTCCCCGATGCCCAGATAGCGCCAGCTTGGGCGATGACTGAGCCGGAAAAAAAGACCCGACGATGATCCTGATGCAG
CTAGATTAACCCTAGAAAGATAGTCTGCGTAAAATTGACGCGCATGGGATCCCCCCCGGGCTGCAGGAATTCGATATCAAGCTTATCGATACCGTCGAAGCTT
       RIGHT TERMINAL REPEAT                                                         --(SEQ ID NO:48)--
                                                 <
```

*FIG. 12(B) CONT.* p(PZ)-Bac-ECFP
Sequence Range: 1 to 9012

100
ACCGAAGTATACACTTAAATTCAGTGCACGTTTGCTTGTTGAGAGGAAAGTTGTGTGCGGACGAATTTTTTTTGAAAACATTAACCCTTACGTGAAT

200
AAAAAAAAATGAAATATTGCAAATTTGCTGCAAAGCTGTGACTGGGAGTAAAATTAATTCACGTGCCGAAGTGTGCTATTAAGAGAAAATTGTGGAGCA

300
GAGCCCTTGGGTGCAGCCTTGGTGTGCAAATTTGTGATACCCACTTTAATGATTCGCAGTGGAAGGCTCAAAAGGTCAGACATTTAAA

400
AGGAGGGGACTCAACGCAGATGCCGAAACCTCGAACCAGAAAGATAAAGAGGCTATACCAGTGGAGTACACAAACAGAGT

500
AAGTTTGAATAGTAAAAAAATCATTTATGTAAACAATAACGTGACTGTGCGTTAGTCCTGTTCATTGTTAATGAAATAAGAGCTTGAGGGAAAAAA

600
TTCGTACTTTGGAGTACGAAATGCGTCGTTAGAGCAGCCGAATTCACTGGCCGTCGTTTACACAGTCGTGACTGGGAAACCCTGGCGTTACCCA

700
ACTTAATCGCCTTGCAGCACATCCCCCTTTCGCCAGCTGGCGTAATAGCGAAGAGGCCCGCACCGATCGCCCTTCCCAACAGTTGCGCAGCCTGAATGGC

800
GAATGGCGCTTTGCCTGGTTTCCGGCACCAGAAGCGGTGCCGGAAAGCTGGCTGGAGTGCGATCTTCCTGAGGCCGATACTGTCGTCGTCCCCTCAAACT

900
GGCAGATGCACGGTTACGATGCGCCCATCTACACCAACGTAACCTATCCCATTACGGTCAATCCGCCGTTTGTTCCCACGGAGATCCGACGGGTTGTTA

1000
CTCGCTCACATTTAATGTTGATGAAAGCTGGCTACAGGAAGGCCAGACGCGAATTATTTGATGGCGTTAACTGGTTTCATCGTGGTGCAACGGG

1100
CGCTGGGTCGGTTACGGCCAGGACAGTCGTTTGCCGTCTGAATTGACCTGAGCGCATTTTTACGCGCCGGAGAAAACCGCCTCGCGGTGATGGTGCTGC

FIG. 13(B)

```
1200
GTTGGAGTGACGGCAGTTATCTGGAAGATCAGGATATGTGGCGGATGAGCGGCATTTTCCGTGACGTCTCGTTGCTGCTGCATAAACCGACTACACAAATCAG
1300
CGATTTCCATGTTGCCACTCGCTTTAATGATGATTTCAGCCGCTGTACTGGAGGCTGAAGTTCAGATGTGCGGCGAGTTGCGTGACTACCTACGGGTA
1400
ACAGTTTCTTTATGGCAGGGTGAAAACGCAGGTCGCCAGCGGCGGCCTTTCGGCGGTGAAATTATCGATGAGCGTGGTTATGCCGATCGCTCA
1500
CACTACGGTCTGAAACGTCGATGTCGGTTCCGCGAGGTGCGGATTGAAAATGTCTGCTGCTGAACGGCAAGCCGTTGCTGATTCGAGGCGTTAACCGT
1600
TGAAGCAGAAGCCTGCGATGTCGGTTTCCGCGAGGTGCGGATTGAAAATGTCTGCTGCTGAACGGCAAGCCGTTGCTGATTCGAGGCGTTAACCGT
1700
CACGAGCATCATCCTCTGCAGTGGTCAGTTCATGATGAGCAGACGATGTGCAGGATATCCTGCTGATGAAGCAGAACAACTTTAACGCCGTGCCGTGTT
1800
CGCATTATCCGAACCATCCGCTGGTACACGCTGTGCCACCGGCTACCGGCGATGAGCGGAATGTGCAGGCGGATCGTAATCACCGAGTGTGATCATCTGG
1900
GAATCGTCTGACCGATGATCAGGCCACGGCCACCGATATTATTTGCCCGATGTACGGCCCTGATCCTTCCCGCCGGTGCAGTATGAAGGCGGCG
2000
TCGCTGGGGAATGAATCAGGCCACGGCCACCGATATTATTTGCCCGATGTACGGCCCTGATCCTTCCCGCCGGTGCAGTATGAAGGCGGCG
2100
GAGCCGACACCACGGCGCCCGCTGAGAGACGGCCCGCTGATCCTTTGCGAATACGCCCACGCGATGGTAACAGTCTTGGCGGTTTCGCTAAATACTGGCAGGCGTTT
2200
GCTTTCGCTACCTGAGAGACGGCCCGCTGATCCTTTGCGAATACGCCCACGCGATGGTAACAGTCTTGGCGGTTTCGCTAAATACTGGCAGGCGTTT
2300
CGTCAGTATCCCCGTTTACAGGGGCTTCGTCTGGGACTGGGTGATCAGTCGCTGATTAAATATGATGAAAACGGCAACCCGTGGTCGGCTTACGGCCG
```

FIG. 13(B) CONT.

2400 GTGATTTTGGGCGATACGCCGAACGATGCCAGTTCTCTGTATGAACGGTCTGTCTTTGCCGACCGCCATCCAGGCGCTGACGGAAGCAAAACACCA

2500 GCAGCAGTTTTTCCAGTTCCGTTATCGGGCAAACCATCGAAGTGACCAGCGAATACCTGTTCCGTCATAGCGATAACGAGCTCCTGCACTGGATGGTG

2600 GCGCTGGATGGTAAGCCGCTGGCAAGCGGTGAAGTGCCTCTGGATGTCGCTCCACAGGTAAACAGTTGATTGAACTGCCTGAACTACCGCAGCCGGAGA

2700 GCGCCGGGCAACTCTGGCTCACAGTACGGCGTAGTGCAACGAACGCGACCCATGGTCAGAAGCCGACCCATCAGCGCCTGGCAGCAGTGGCGTCTGGC

2800 GCGAAAACCTCAGTGTGACGCTCCCCGCCGTCCCACGCCATCTGACCACCAGCGAAATGGATTTTGCATCGAGCTGGGTAATAAGCGTTGG

2900 CAATTTAACCGCCAGTCAGGCTTTCTTTCACAGATGTGGATTGGGATAAAAAACAACTGCTGACGCCCTGGGTCGAACGCTAACGCCTCACCGCTGG

3000 ATAACGACATTGGGCGTAAGTGAAGCGACCCGCATTGACCTGACGTGCTGATTACGACCGGTCGATGCGGTGCTGAAGTGCGAGCGCTCACGCGTTGAAGTGGGAGCGATACACCGCGAAAACCTAC

3100 GCAGTGCACGGCAGATACACTTGCTGCATCAGGGGAAAACCTTATTTATCAGCCGGAAAACCTAC

3200 CGGATTGATGTAGTGTCAAATGGCGATTACCGTTGATGTTGAAGTGCCTGAACTGCCAGCTGGCGC

3300 AGGTAGCAGAGCGGGTAAACTGCTCGGATTAGGCCCGCAAGAGAAAACTATCCCGACCGCCCTTACTGCCGCCTGTTTTTGACCGCTGGGATCTGCCATTGTC

3400 AGACATGTATACCCGTACGTCTTCCCGAGCGAAAACGGTCGTCTGCGCTGCGGGACGCGCGAATTGAATTATGCCCCACACCAGTGGCCGGGCGACTTCCAG

3500 TTCAAACATCAGCCGCTACAGTCAACAGCAACTGATGAAACCATCCGCCATCTGCTGCACGCGGAAGAAGGCACATGGCTGAATATCGACGTTTCC

FIG. 13(B) CONT.

```
3600
ATATGGGGATTGGTGCGACGACTCCTGGAGCCCGTCAGTATCGGCGGAATTCCAGCTGAGCGCCGGTCGCTACCATTACCAGTTGGTCTGGTGTCGGGG
3700
ATCCGTCGACTAAGGCCAAAGAGTCTAATTTTGTTCATCAATGGGTTATAACATATGGGTTATATTATAAGTTGTTTTAAGTTTTTGAGACTGATAAG
3800
AATGTTTCGATCGAATATTCCATAGAACACAATAGTATTACCTAATTACCAAGTCTTAATTTAGCAAAAATGTATTGCTTATAGAAAAATAAATTAT
3900
TTATTTGAAATTTAAAGTCAACTTGTCATTTAAGTCTTGTAGACTTTTGAAAGTCTTACGATACAACAATTAGTATCTAATATACATGGTTCATTCTACAT
4000
TCTATATTAGTGATGATTTCTTTAGCTAGTAATACATTTAATTATATTCGGCTTTGATGATTTTCTGATTTTTCCGAACGGATTTCGTAGACCCTTT
4100
CGATCTCATAATGGCTCATTTATTGCGATGAGCGTCAGGAGAGCTCCACTTTTGAATTCTGTTGCCAGACCGCATACGCTCTATATCCTCCGAACGGCGCTGGTTGACC
4200
ATCCGGTTTGGGGAGATTTCCAGTCTCTGTTGCAATTGGTTTCGGGAATGCGTTGCAGGCCGCATACGCTCTATATCCTCCGAACGGCGCTGGTTGACC
4300
CTAGCATTTACATAAGGATCAGCAGCAAAATTGCCTCTGCTTCATTGCCCGATGATGGTCGTCGCCCTGTGGCCGCCGCATATGGATCTTAAGTCGTTGACTGCACAAAG
4400
GCGAACCGCACACAAAGCTCTCGCCGCACTCCACACTGATAGGTCGTCGCAATCGCATGTGTCGGCGCCAGTTGTTCTGCGAAATAAACTTCTTGGAGCAGATGC
4500
CTCTTGCTGCACATTTTGCAGGAGTACGGCCCTTTGACCCGTGTGCGAAGACTCCAGCATGAGATCCCGGCGTCCCCGGAAAACGATTCCGAAGCCCAACCTTTCAT
4600
GGCCGCCGGGGTGGGCGAAGAACTCCAGCATGAGATCCCGGCGTCCCCGGAAAACGATTCCGAAGCCCAACCTTTCAT
4700
AGAAGGCGGCGGTGGAATCGAATCTCGTGATGCAGGTTGGGCGTCGCTTGGTCGTCGTCATTTCGAACCCAGAGTCCCGCTCAGAAGAACTCGTCAAGA
```

FIG. 13(B) CONT.

```
4800
AGGCGATAGAAGGCGATGCGCTGGAATCGGGAGGCGGCGATACCGTAAAGCACGAGGAAGCGGTCAGCCTTCATTCGCCGCCAAGCTCTTCAGCAATATCAC
4900
GGGTAGCCAACGCTATGTCCTGATAGCGGTCCGCCACACCCAGCCGGCCACAGTCGATGAATCCAGAAAAGCGGCCATTTCCACCATGATATTCGGCAA
5000
GCAGGCCATCGCCATGGTCACGACGAGATCCGCCGTGGGCATGCGGCGCCTTGAGCCTGGCGAACAGTTCGGCTGGCTGGCGAGCCCTGATGCTCTTCG
5100
TCCAGATCATCATCCTGATCGACAGACCGGCTTCCATCCGAGTACGTGCTCTCGTCGATGCGATGTTTCGCTTGGTGGTCGAATGGGCAGGTAGCCGATCAA
5200
GCGTATGCAGCCGCGCCATTGCATCAGCCATGATGATACTTTCTCGGCAGGAGCAAGGTGAGATGACAGGAGATCTGCCCCGGCACTTCGCCCAATAG
5300
CAGCCAGTCCCTTCCCGCTTCAGTGACAACGTCGAGCAACAGCTGCGCAAGGAACCCGTCGTGCCAGCCACGATAGCCGGCGCTGTCCTGCCTGTCCTGCAGT
5400
TCATTCAGGGCACCGGACAGGTCGGTCTTGACAAAAAGAACCGGGCCCCTGCGCTGACAGCCGAACCTGCGTGCAATCATCTTGTTCAATCATGCCGATTGTCTGTT
5500
GTGCCCAGTCATAGCCGAATAGCCTCTCCCAAGCCCTTGGCGGCAAGAAAGCCATCCAGTTACTTTGCAGGGCTTCCCAACCTTACCAGAGGGCGCCCCA
5600
TTGATCAGATCTTGATCCCCTGCGCTTGCTTGCTGTGTCCATAAACCGCCCAGTCTAGCTATCGCCATGTAAGCCACTGCAAGCTACCTGCTTTCTCTTTGCGCTTGCGT
5700
GCTGGCAATTCCGGTTCGCTTGCTGCAGATAGCCCAGTAGCTGACATTCATCCGGGTCAGCACCGTTTCTGCGGACTGGCTTTCTACGTGTTCCGCTTCCTTTAGCAGCCCTT
5800
TTTCCCCTTGTCCAGATAGCCCAGTAGCTGACATTCATCCGGGTCAGCTAATTCATGGTTATAAATTTTGTTAAATCAGCTCATTTTTAACCAATAGGCCGAAATCGGCAAAATCC
5900
GCGCCCTGAGTGCTTGCGGCAGCGTGAAGCTAATTCATGGTTATAAATTTTGTTAAATCAGCTCATTTTTAACCAATAGGCCGAAATCGGCAAAATCC
```

*FIG. 13(B) CONT.*

```
6000
CTTATAAATCAAAAGAATAGCCCGAGATAGGGTTGAGTGTTGTTCCAGTTTGGAACAAGAGTCCACTATTAAAGAACGTGGACTCCAACGTCAAAGGGCG
6100
AAAAACCGTCTATCAGGGGCGATGGCCCGATCAGCTTATGCGGTGTGAAATACCGCACAGATGCGTAAGGAGAAAATACCGCATCAGGCGCTCTTCCGCTT
6200
CCTCGCTCACTGACTCGCTGCGCTCGGTCGTTCGGCTGCGGCGAGCGGTATCAGCTCACTCAAAGGCGGTAATACGGTTATCCACAGAATCAGGGGATAA
6300
CGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGACGAG
6400
CATCACAAAAATCGACGCTCAAGTCAGAGGTGGCGAAACCCGACAGGACTATAAAGATACCAGGCGTTTCCCCCTGGAAGCTCCCTCGTGCGCTCTCCTG
6500
TTCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTA
6600
GGTCGTTCGCTCCAAGCTGGGCTGTGTGCACGAACCCCCCGTTCAGCCCGACCGCTGCGCCTTATCCGGTAACTATCGTCTTGAGTCCAACCCGGTAAGA
6700
CACGACTTATCGCCACTGGCAGCAGCCACTGGTAACAGGATTAGCAGAGCGAGGTATGTAGGCGGTGCTACAGAGTTCTTGAAGTGGTGGCCTAACTACG
6800
GCTACACTAGAAGGACAGTATTTGGTATCTGCGCTCTGCTGAAGCCAGTTACCTTCGGAAAAAGAGTTGGTAGCTCTTGATCCGGCAAACAAACCACCGC
6900
TGGTAGCGGTGGTTTTTTTGTTTGCAAGCAGCAGATTACGCGCAGAAAAAAAGGATCTCAAGAAGATCCTTTGATCTTTTCTACTGAACGGTGATCCCCA
7000
CCGGAATTGCGGCCGCGGAATTCTCATGTTTGACAGCTTATCATCGATAAGCTGGCCCTCTAGAACTAGTGTTCCCACAATGGTTAATTCGAGCTCGCC⟩
                                                                                            3XP3-EYFP MARKER
7100
CGGGGATCTAATTCAATTAGAGACTAATTCAATTAGAGCTAATTCAATTAGGATCCAAGCTTATCGATTTCGAACCCTCGACCGCCGCCGGAGTATAAATAGA⟩
3XP3-EYFP MARKER
```

*FIG. 13(B) CONT.*

```
7200
GGCGGCTTCGTCGTCTACGGAGCGACAATTCAATTCAAACAAGCAAAGTGAACACGTCGCTAAGCGAAAGCTAAGCAAATAAACAAGCGCAGCTGAACAAGCTA >
                                           3XP3-EYFP MARKER
7300
AACAATCGGGGTACCGCTAGAGTCGACGGTACGATCCACCGGTCGCCACCATGGTGAGCAAGGGCGAGGAGCTGTTCACCGGGGTGGTGCCCATCCTGGT >
                                           3XP3-EYFP MARKER
7400
CGAGCTGGACGGCGACGTAAACGGCCACAAGTTCAGCGTGTCCGGCGAGGGCGAGGGCGATGCCACCTACGGCAAGCTGACCCTGAAGTTCATCTGCACC >
                                           3XP3-EYFP MARKER
7500
ACCGGCAAGCTGCCCGTGCCCTGGCCCACCCTCGTGACCACCCTGACCTGCAGTGCTTCAGCCGCTACCCCGACCACATGAAGCAGCACGACT >
                                           3XP3-EYFP MARKER
7600
TCTTCAAGTCCGCCATGCCCGAAGGCTACGTCCAGGAGCGCACCATCTTCTTCAAGGACGACGGCAACTACAAGACCCGCGAGGTGAAGTTCGAGGG >
                                           3XP3-EYFP MARKER
7700
CGACACCCTGGTGAACCGCATCGAGCTGAAGGGCATCGACTTCAAGGAGGACGGCAACATCCTGGGGCACAAGCTGGAGTACAACTACATCAGCCACAAC >
                                           3XP3-EYFP MARKER
7800
GTCTATATCACCGCCGACAAGCAGAAGAACGGCATCAAGGCCAACTTCAAGATCCGCCACAACATCGAGGACGGCAGCGTGCAGCTCGCCGACCACTACC >
                                           3XP3-EYFP MARKER
7900
AGCAGAACACCCCCATCGGCGACGGCCCCGTGCTGCTGCCCGACAACCACTACCTGAGCACCCAGTCCGCCCTGAGCAAAGACCCCAACGAGAAGCGCGA >
                                           3XP3-EYFP MARKER
8000
TCACATGGTCCTGCTGGAGTTCGTGACCGCCGCGGGATCACTCCGGCATGGACGAGCTGTACAAGTAAAGCGGCCGCGACTCTAGATCATAATCAGCC >
                                           3XP3-EYFP MARKER
```

*FIG. 13(B) CONT.*

```
8100
ATACCACATTTGTAGAGGTTTTACTTGCTTTAAAAAACCTCCCACACCTCCCCCTGAACCTGAAACATAAATGAATGCAATTGTTGTTGTTAACTTGTT
                                                 3XP3-EYFP MARKER
8200
TATTGCAGCTTATAATGTTACAAATAAAGCAATAGCATTCACAAATTCACAAATAAAGCATTTTTTCACTGCATTCTAGTTGTGTTTGTCCAAACTC
                                              3XP3-EYFP MARKER
8300
ATCAATGTATCTTAAAGCTTATCGATACCGGTGTACGGCCGCGGCCCTAGGCCGCGGCCGGCCCGATTGGATCCATGGCGTCAATTTACGCATGATTATCTTTAACGTACG
              3XP3-EYFP MARKER                                                              LEFT TERMINAL REPEAT
8400
TCACAATATGATTATCTTTCTAGGGTTAATCTAGCTGCGTGTTCTGCAGCTGCTGAGCATCTTCATCTGCTCCATCACGCTGTAAACACATTTGCACC
    LEFT TERMINAL REPE
8500
GCGAGTCTGCCCGTCCTCCACGGGTTCAAAAACGTGAATGAACGAGGCGCGCCCGGGTAACTCAGGGTATCCATGTCCATTTCTGCGGCATCCAG
8600
CCAGGATACCCGTCCTCGCTGACGTAATATCCAGCGACCATCCGGAACTGTGTCCGGAAAAGCCGGACGAACTGTATCCAGGTGGCCTGAACGAACAGTTCACCGTTAAA
8700
GGTTGCTGATGCGCTTCGGGCTGACCTTCTGGGCTGTAGCGTCCAACGTGCGTTTCGCTGCAACGTGCATCATGGTAAACGTGCGTTCTTCCCGAAATCATCAGCAGCCGGATGACTGAGCCGGTATTGTTCG
8800
GGCGTGCATGGCCAGCCTGGGCGCTTGGGCAGATAGCCGCCAGCTTGGGCGATGACTGAGCCGGAAAAAAGACCCGACGATAT
8900
GCTTCAACCTCGGGAAAAGCACGGCGTTCTTCCTCCCCGATGCCCAGCTTGGGCGATGACTGAGCCGGAAAAAAGACCCGACGATAT
9000
GATCCTGATGCAGCTAGATTAACCCTAGAAAGATAGTCTGCGTAAAATTGACGCATGGGATCCCCCGGCCTGCAGGAATTCGATATCAAGCTTATCGATA

CCGTCGAAGCTT --(SEQ ID NO:49)--
```

FIG. 13(B) CONT.

P(P2)-Bac-EGFP
Sequence Range: 1 to 9013

```
        100
ACCGAAGTATACACTTAAATTCAGTGCACGTTTGCTTGTTGAGAGAAAGGTTGTGTGCCGACGAATTTTTTTTGAAAAACATTAACCCTTACGTGGAAT
        200
AAAAAAAATGAAATATTGCAAATTTGCTGCAAAGCTGTGACTGGAGTAAAATTAATTCAGTGCCGAAGTGTGCTATTAAGAGAAAATTGTGGGAGCA
        300
GAGCCCTTGGGTGCAGCCTTGGTGCGAAAACTCCCAAATTTGTGATACCCACTTTAATGATTCGCAGTGGAAGGCTGCACCTGCAAAAGTCAGACATTTAAA
        400
AGGAGGCGACTCAAACGCAGATGCCGTACCTAGTAAAGTGATAGAGCCTGAACCAGAAAAGATAAAGAAGGCTATACCAGTGGAGTACACAAACAGAGT
        500
AAGTTTGAATAGTAAAAAAAATCATTTATGTAACAATAACGTGACTGTGCGTTAGGTCCTGTCCTGTTCATTGTTAATGAAATAAGAGCTTGAGGGAAAAAA
        600
TTCGTACTTTGGAGTACGAAATGCGTCGTTTAGAGCAGCAGCCGAATTCACTGGCCCTCGTTTACACGTCGTTGACTGGGAAAACCCTGGCGTTACCCA
        700
ACTTAATCGCCTTGCAGCACATCCCCCTTTCGCCAGCTGGCGTAATAGCGAAGAGGCCCGCACCGATCGCCCTTCCCAACAGTTGCGCAGCCTGAATGGC
        800
GAATGGCGCTTTGCCTGGTTTCCGGCACCAGAAGCGGTGCCGGAAAGCTGGCTGGAGTGCGATCTTCCTGAGGCCGATACTGTCGTCGTCCCCTCAAACT
        900
GGCAGCAGATGCACGGGTTACGATGCGCCCATCTACACCAACGTAACCTATCCCATTACGGTCAATCCGCCGTTTGTTCCCACGGAGAATCCGACGGGTTA
        1000
CTCGCTCACATTTAATGTTGATGAAAGCTGGCTACAGGAAGGCCAGACGCGAATTATTTTTGATGGCGTTAACTCGGCGTTTCATCTGTGGTGCAACGGG
        1100
CGCTGGGTCGGTTACGGCCAGGACAGTCGTTTGCCGTCGAATTGACCTGAGCGCATTTTTACGCGCCGGAGAAAACCGCCTCGCGGTGATGGTGCTGC
```

FIG. 14(B)

```
1200
GTTGGAGTGACGGCAGTTATCTGGAAGATCAGGATATGTGGCGATGAGCGGCATTTCCGTGACGTCTCGTTGCTGCTGCATAAACCGACTACACAAATCAG
1300
CGATTTCCATGTTGCCACTCGCTTTAATGATGATTTCAGCCCGCTGTACTGGAGGCTGAAGTTCAGATGTGCGGCGAGTTGCGTGACTACCTACGGGTA
1400
ACAGTTTCTTTATGGCAGGTGAAACGCAGTTCGCCAGCGCACCGGCGCCTTTCGGCGGTGAAATTATCGATGAGCGTGGTGGTTATGCCGATCGGTCA
1500
CACTACGTCTGAACGTCGAAAACCCGAATCTGGAGCGCCCGAATCTCTATCGTGCGGTGGTTGAACTGCACACCGCCGACGCACGCTGAT
1600
TGAAGCAGAAGCCTGCGATGTCGGTTCCGCGAGGTGCCGATTGAAAAATGGTCTGCTGCTGAACGCCAAGCCGTTGCTGATTCGAGGCGTTAACCGT
1700
CACGAGCATCATCCCTGCATGGTCAGGTCATGGATGAGCAGACGATGGTGCAGGATATCCTGCTGATGAAGCCAATATTGAAACCACGGCATGGTGCCAAT
1800
CGCATTATCCGAACCATCCGCTGTGGTACACGCTGCTGCCACCGGATGAGCGGAACGCGTAACGCCGAATGGTGCAGCGCGATCGTAATCACCGAGTGTGATCATCTGG
1900
GAATCGTCTGACCGATGATCCGCTGGCTACCGGCGATGAGCGGAACGCGTAACGCCGAATGGTGCAGCGCGATCGTAATCACCGAGTGTGATCATCTGG
2000
TCGCTGGGGAATGAATCAGGCCACGCGCTAATCACGACGCGCTGTATCGCTGATCAAATCTGTCGATCCTTCCCGCCGGTGCAGTATGAAGGCGGCG
2100
GAGCCGACACCACGGCCACCGATATTATTGCCCGATGTACCCGGTGGATGAAGACCAGCCCTTCCCGGCTGTGCCGAAATGGTCATCAAAAAATG
2200
GCTTTCGCTACCTGGAGAGACGCGCCCGCTGATCCTTGCCAATACGCCCACGCGATGGGTAACAGTCTTGGCGGTTTCGCTAAATACTGCCAGGCGTTT
2300
CGTCAGTATCCCCGTTACAGGGGCTTCGTCTGGGACTGGGTGGATCAGTCAGTCGCTGATTAAATATGATGAAAACGGCAACCCGTGTCGGCTTACGGGCG
```

FIG. 14(B) CONT.

```
2400
GTGATTTGGCGATACGCCGAACGATCGCCAGTTCTGTATGAACGGTCTGGTCTTTGCCGACCGCACGCCGCATCCAGCGCTGACGGAAGCAAAACACCA
2500
GCAGCAGTTTTCCAGTTCCGTTATCCGGCAAACCATCGAAGTGACCAGCGAATACCTGTTCCGTCATAGCGATAACGAGCTCCTGCACTGATGGTG
2600
GCGCTGGATGGTAAGCCGCTGGCAAGCGGTGAAGTGCCTCTGGATGTCGCGCAAGGTAAACAGTGTGATTGAACTGCCTGAACTACCGCAGCCGGAGA
2700
GCGCCGGGCAACTCTGGCTCACAGTACGCGTAGTGCAACCGAACGCGACCGCATGGTCAGAAGCCGGGCACATCAGGCCTGGCAGCAGTGGGCTCTGGC
2800
GGAAAACCTCAGTGTGACGCTCCCCCCGCGTCCCACGCCATCTGAGCTCTCCGATAAAAAACAACTGCTGACGCCGATCAGTTCACCCGTGCACCGCTGG
2900
CAATTTAACCGCCAGTCAGGCTTTCTCTTTCACAGATGTGGATTGGCGATAAAAAAACAACTGCTGGGTCGAACGCTGGAAGCGGCCATTACCAGGCCGAAGCAGCGTTGTT
3000
ATAACGACATTGGGCGTAAGTGAAGCGACCCGCATTGACCCTAACGCCTGATGCGGTGCTGATTACGACCGCTCACGCGGTGGCAGCATCAGGGGAAAACCTTATTTATCAGCCGGAAAACCTAC
3100
GCAGTGCACGGCAGATACACTTGCTGATGCGGTGCTGATTACGACCGCTCACGCGGTGGCAGCATCAGGGGAAAACCTTATTTATCAGCCGGAAAACCTAC
3200
CGGATTGATGGTAGTGGTCAAATGGCGATTACCGTTGATGTTGAAGTGGCGAGCGATACACCGCATCCGGCGGATTGGCCTGAACTGCCAGCTGGCGC
3300
AGGTAGCAGAGCGGGTAAACTGGCTCGATTAGGCGCCGAAGAAAACTATCCCGACGCCTTACTGCGCTGCGCTGCGGGACGCTCGCGTGTTTGACCGCTGGGATCGCCATTGTC
3400
AGACATGTATACCCCGTACGTCTTCCCGAGCGAAAACGGTCTGCGCTGCGGGACGCGCGAATTGAATTATGGCCACCAGTGGCGGCGACTTCCAG
3500
TTCAACATCAGCCGCTACAGTCAACAGCAACTGATGAAACCAGCCATCGCTGCACCGCGAAGAAGGCACATGGCTGAATATCGACGGTTTCC
```

*FIG. 14(B) CONT.*

```
3600
ATATGGGGATTGGTGTGGGCGACGACTCCTGGAGCCCGTCAGTATCGGGGGAATTCCAGCTGAGCGGCCGGTCGCTACCATTACCAGTTGGTCTGGTGTCGGGG
3700
ATCCGTCGACTAAGGCCAAAGAGTCTAATTTTGTTCATCAATGGGTTATAACATATGGTTATATATTATAAGTTGTTTAAGTTTTTGAGACTGATAAG
3800
AATGTTTCGATCGAATATTCCATAGAACAACAATAGTATTACCTAATTACCAAGTCTTAATTTAGCAAAAATGTTATTGCTTATAGAAAAATAAATTAT
3900
TTATTTGAAATTAAAGTCAACTTGTCATTTAATGTCTTGTAGACTTTTGAAAGTCTTACGATACAATTAGTATCTAATATACATGGTTCATTCTACAT
4000
TCTATATTAGTGATGATTTCTTAGCTAGTAATACATTTTAATTATATTCGGCTTTGATGATTTTCGATTTTTTCGAACGGATTTCGTAGACCCTTT
4100
CGATCTCATAAATGGCTCATTTATTGCCATGACGGTCAGGAGAGCTCCACTTTGAATTTCTGTTCGCAGACACCGCATTGTAGCACATAGCGGGAC
4200
ATCCGGTTTGGGGAGATTTTCCAGTCTCTCGTTGCAATTGGTTTTCGGGAATGCGTTGCAGGCGCATACGCTCTATATCCTCCGAACGGCGCTGGTTGACC
4300
CTAGCATTTACATAAGGATCAGCCGAATCACAGCAATCAGATGTCCCTTTCGGTTACGATGGATATTCAGT
4400
GCGAACCGCACACAAAGCTCTCGCCCGCCCTGTGGGCGCCGCCATATGGATCTTAAGGTCGTTGGACTGCACAAAG
4500
CTCTTGCTGCACATTTGCAGGAGTACGGCCTTTGACCCGTGTGCCTGTGCAATCGCATGTCGCCAGCTTGTTCTGCGAAATAAACTTCTTGGAGCAGATGC
4600
GGCCGCCGGGGTGGGCGAAGAACTCCAGCATGAGAATCCCGCGCTGGAGATCATCAGCCGGCGTCCCGGAAAACGATTCCGAAGCCCAACCTTTCAT
4700
AGAAGGCGCGGCGGTTGGGAATCGAAATCTCGATGGCAGGTTGGGCGTCGCTTGGTCGGTCATTTCGAACCCCAGAGTCCCGCTCAGAAGAACTCGTCAAGA
4800
AGGCGATAGAAGGCGATGCGCTGCGAATCGGGAGCGGCGATACCGTAAAGCACGAGGAAGCGGTCAGCCCATTCGCCGCCAAGCTCTTCAGCAATATCAC
```

*FIG. 14(B) CONT.*

```
4900
GGGTAGCCAACGCTATGTCCTGATAGCGGTCCGCCACACCCAGCCGGCCACAGTCGATGAATTCAGAAAAGCGGCCATTTTCCACCATGATATTCGGCAA
5000
GCAGGCCATGCGCCATGGGTCACGACGAGATCCTCGCCCGTCGGGCATGCGCGCCCTTGAGCCTGGCCGGAACAGTTCGGCTGGCTGGCCGAGCCCCTGATGCTCTTCG
5100
TCCAGATCATCCTGATCGACAAGACCGGCTTCCATCCGAGTACGTGCTCCGTTGTGGTGCTTGGTGTTGTGGTCAGGTAGCCGGATCAA
5200
GCTATGCAGCCGCCATTGCATCAGCCATGATGATACTTTCTCGGAGCAAGGTGAGATGACAGGAGATCCTGCCCCGCACTTCGCCAATAG
5300
CAGCCAGTCCCTTCCCGCTTCAGTGACAACGTCGGTCTTGACAAAAAGAACCGGCCGCGGAAGAACGCCCGTGCGCAAGAACGCCCGTGCGCTGCCAGCCACGATAGCCGCTGCCTCGTCCTGCAGT
5400
TCATTCAGGGCACCGGACAGTCGGTCTTGACAAAAAGAACCGGCCGCGGAGAACCTGCGTGCAATCATCTTGTTCAATCATGCGAAACGATCCTCATCCTGTCTC
5500
GTGCCCAGTCATAGCCCGAATAGCCTCTCCACCCAAGCCGGCCCGGAGAACCTGCGTGCAATCATCCAGTTACTTTGCAGGGCTTCCCAACCTTACCAGAGGGCGCCCCA
5600
TTGATCAGATCTTGATCCCCTGCGCCATCAGATCCTTGGGCCAAGAAAGCCATCCAGTTACTTTGCAGGGCTTCCCAACCTTACCAGAGGGCGCCCCA
5700
GCTGGCAATTCCGGTTCGCTTGCTGTCGTCCATAAAACGCCCAGTCTAGCTATCGCCAGTAAGCCCACTGCAAGCTACCTGCTTCTCTTTGCGCTTGCGT
5800
TTTCCCTTGTCCAGATAGCCCAGTAGCTGACATTCATCCGGGTCAGCACCGTTCTGCGACTGGCTTCTACGTGTTCCGCTTCCTTAGCAGCCCTT
5900
GCGCCCTGAGTGCTGCGGCAGCGTGAAGCTAATTCATGGTTATAAATTTTGTTAAATCAGCTCATTTTTAACCAATAGCCGAAATCGGCAAAATCC
6000
CTTATAAATCAAAAGAATAGCCCGAGATAGGGTTGAGTGTTGTTCCAGTTTGGAACAGAGTCCACTATTAAAGAACGTGGACTCCAACGTCAAAGGGCG
6100
AAAAACCGTCTATCAGGCGATGCCCGATCAGCTTATGCGGTGTGAAATACCGCACAGATGCGTAAGGAGAAAATACCGCATCAGGCGCTCTTCCGCTT
```

*FIG. 14(B) CONT.*

```
6200
CCTCGCTCACTGACTCGCTGCCGCTCGGTCGTTCGGCTGCGGCGAGCGGTATCAGCTCACTCAAAGGCGGTAATACGGTTATCCACAGAATCAGGGGATAA
6300
CGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGACGAG
6400
CATCACAAAAATCGACGCTCAAGTCAGAGGTGGCGAAACCCGACAGGACTATAAAGATACCAGGCGTTTCCCCCTGGAAGCTCCCTCGTGCGCTCTCCTG
6500
TTCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTA
6600
GGTCGTTCGCTCCAAGCTGGGCTGTGTGCACGAACCCCCCGTTCAGCCCGACCGCTGCGCCTTATCCGGTAACTATCGTCTTGAGTCCAACCCGGTAAGA
6700
CACGACTTATCGCCACTGGCAGCAGCCACTGGTAACAGGATTAGCAGAGCGAGGTATGTAGGCGGTGCTACAGAGTTCTTGAAGTGGTGGCCTAACTACG
6800
GCTACACTAGAAGGACAGTATTTGGTATCTGCGCTCTGCTGAAGCCAGTTACCTTCGGAAAAAAGAGTTGGTAGCTCTTGATCCGGCAAACAAACCACCGC
6900
TGGTAGCGGTGGTTTTTTGTTTGCAAGCAGCAGATTACGGCAGAAAAAAAGGATCTCAAGAAGATCCTTTGATCTTTTCTACGAACGGTGATCCCCA
7000
CCGGAATTGCCGGCGGAATTCTCATGTTGACAGCTTATCATCGATAAGCTGGCCGCTCTAGAACTAGTGTTCCCACAATGGTTAATTCGAGCTCGCC
                                                                                3XP3-EYFP MARKER
7100
CGGGGATCTAATTCAATTAGAGACTAATTCAATTAGAGATCCAAGCTTATCGATTTCGAACCCTCGACCGCCGGAGTATAAATAGA
3XP3-EYFP MARKER
7200
GGCGCTTCGTCTACGGAGCGACAATTCAATTCAAACAAGCAAAGTGAACACGTCGCTAAGCGAAAGCTAAGCAAATAAACAAGCCAGCTGAACAAGCTA
3XP3-EYFP MARKER
```

*FIG. 14(B) CONT.*

```
7300
AACAATCGGGTACCGCTAGAGTCGACGGTACCGCGGGCCCGGGATCCACCGGTCGCCACCATGGTGAGCAAGGGCGAGGAGCTGTTCACCGGGGTGGTG
          3XP3-EYFP MARKER

7400
CCCATCCTGGTCGAGCTGGACGGCGACGTAAACGGCCACAAGTTCAGCGTGTCCGGCGAGGGCGAGGGCGATGCCACCTACGGCAAGCTGACCCTGAAGT
          3XP3-EYFP MARKER

7500
TCATCTGCACCACCGGCAAGCTGCCCGTGCCCTGGCCCACCCTCGTGACCACCTTCGGCTACGGCGTGCAGTGCTTCAGCCGCTACCCCGACCACATGAA
          3XP3-EYFP MARKER

7600
GCAGCACGACTTCTTCAAGTCCGCCATGCCCGAAGGCTACGTCCAGGAGCGCACCATCTTCTTCAAGGACGACGGCAACTACAAGACCCGCGCCGAGGTG
          3XP3-EYFP MARKER

7700
AAGTTCGAGGGCGACACCCTGGTGAACCGCATCGAGCTGAAGGGCATCGACTTCAAGGAGGACGGCAACATCCTGGGGCACAAGCTGGAGTACAACTACA
          3XP3-EYFP MARKER

7800
ACAGCCACAACGTCTATATCATGGCCGACAAGCAGAAGAACGGCATCAAGGTGAACTTCAAGATCCGCCACAACATCGAGGACGGCAGCGTGCAGCTCGC
          3XP3-EYFP MARKER

7900
CGACCACTACCAGCAGAACACCCCCATCGGCGACGGCCCCGTGCTGCTGCCCGACAACCACTACCTGAGCACCCAGTCCGCCCTGAGCAAAGACCCCAAC
          3XP3-EYFP MARKER

8000
GAGAAGCGCGATCACATGGTCCTGCTGGAGTTCGTGACCGCCGCGGGGATCACTCTCGGCATGGACGAGCTGTACAAGTAAAGCGGCCGACTCTAGAT
          3XP3-EYFP MARKER

8100
CATAATCAGCCATACCACATTTGTAGAGGTTTTACTTGCTTTAAAAAACCTCCCACACCTCCCCCTGAACCTGAAACATAAAATGAATGCAATTGTTGTT
          3XP3-EYFP MARKER
```

FIG. 14(B) CONT.

```
8200
GTTAACTTGTTTATTGCAGCTTATAATGGTTACAAATAAAGCAATAGCATCACAAATTTCACAAATAAAGCATTTTTTCACTGCATTCTAGTGTGTT
                                                    3XP3-EYFP MARKER

8300
TGTCCAAACTCATCAATGTATCTTAAAGCTTATCGATACGGTACGGGCGCCTAGTGGATCCCATGCCTCAATTTACGCATGATTATCTTAACGTAC
         3XP3-EYFP MARKER                                                   LEFT TERMINAL REPEAT

8400
GTCACAATAATGATTATCTTTCTAGGGTTAATCTAGCTGCCGTGTTCTGCAGCCTGTCGAGCATCTTCATCTGCTCCATCACGCTGTAAAACACATTGCAC
      LEFT TERMINAL REPEAT

8500
CGGGAGTCTGCCCGTCCTCCACGGGTCAAAAAACGTGAATGAAGGAGGCGCCCGGGTAACTCACGGGGTATCCATGTCCATTTCTGCGGCATCCA

8600
GCCAGGATACCCGTCCTCGCTGAGCTAATATCCCAGCGCCGCTGTCATTAATCTGCACACCGGCAGTTCCGGCGTGTCGCCGGTATTGTTC

8700
GGGTTGCTGATGCGCTTCGGGCTGACCATCATGGTAAACGTGCGTTTCGCTCAACGTCAATGCAGCAGTCATCCTCGCAAACTCTTTCCATGC

8800
AGGCGTGCATGCCACACCTTCCCGAATCATCATGGTAAACGTGCGCCAGCTTGGGCGATGACTGAGCCGGAAAAAAGACCCGACGATA

8900
CGCTTCAACCTGCGGGAAAAGGCACGGCTTCTTCCTCCCCGATGCCCAGATAGCCCAGCTTGGGCGATGACTGAGCCGGAAAAAAGACCCGACGATA

9000
TGATCCTGATGCAGCTAGATTAACCCTAGAAAGATAGTCTGCGTAAAATTGACGCATGGGATCCCCCGGGCTGCAGGAATTCGATATCAAGCTTATCGAT
                                                                            RIGHT TERMINAL REPEAT

ACCGTCGAAGCTT --(SEQ ID NO:50)--
```

FIG. 14(B) CONT.

```
pXL-Bac-EYFP
Sequence Range: 1 to 4951
     100
     CTAAATTGTAAGCGTTAATATTTTGTTAAATTTTCGCGTTAAATCAGCTCATTTTTTAACCAATAGGCCGAAATCGGCAAAATCCCTTAT
     200
     AAATCAAAAGAATAGACCGAGATAGGGTTGAGTGTTGTTCCAGTTTGGAACAAGAGTCCACTATTAAAGAACGTGGACTCCAACGTCAAAGGGCGAAAAA
     300
     CCGTCTATCAGGGCGATGCCCACTACGTGAACCATCACCCTAATCAAGTTTTTTGGGGTCGAGGTGCCGTAAAGCACTAAATCGAACCCTAAAGGGAG
     400
     CCCCCGATTTAGAGCTTGACGGGGAAAGCCGGCGAACGTGGCGAGAAAGGAAGGGAAGAAAGCGAAAGGAGCGGGCGCTAGGGCGCTGGCAAGTGTAGCG
     500
     GTCACGCTGCGCGTAACCACCACACCCGCCGCGCTTAATGCGCCGCTACAGGGCGCGTCCCATTCGCCATTCAGGCTGCGCAACTGTTGGGAAGGGCGAT
     600
     CGGTGCGGGCCTCTTCGCTATTACGCCAGCTGGCGAAAGGGGGATGTGCTGCAAGGCGATTAAGTTGGGTAACGCCAGGGTTTTCCCAGTCACGACGTTG
     700
     TAAAACGACGGCCAGTGAGCGCGCGTAATACGACTCACTATAGGGCGAATTGGGTACACTTACAGGATACCCGTCTCGCTGACGTAAT
     800
     ATCCCAGCGCCACCGCTGTCATTAATCTGCACACCCGGCCAGTTCCGGCTGTGCCGCCGGTATTGTTCGGGTTGCTGATGCCGCTTCGGGCTGACCAT
     900
     CCGGAACTGTGTCCGGAAAGCCGACGAACCGTGATCCCAGTGGCCTGAACGACAGTTCACCGTTAAAGGCGTGCATGGCCACACCTTCCGAATC
     1000
     ATCATGGTAAACGTGCGTTTCGCTCAACGTCAATGCAGCAGCGTCATCCTCGGCAAACTCTTTCCATGCCGTTCAACCTCGCGGAAAAGGCACGGG
     1100
     CTTCTTCCCTCCCCGATGCCCAGATAGCGCAGCTTGGGCGATGACTGAGCCGGAAAAAAAAGACCCGACGATATGATCCTGATGCAGCTAGATTAACCCTAG
     1200
     AAAGATAGTCTGCGTAAAATTGACGCATGATCTAATTAACCCTCACTAAAGGGAACAAAAGCTGGAGCTCCACGCGGTGGCGGCCGCTCTAGAACTAGT
     ← RIGHT TERMINAL REPEAT
```

FIG. 15(B)

```
1300
GTTCCCACAATGGTTAATTCGAGCTCGCCCGGGATCTAATTAGAGACTAATTCAATTAGATCCAAGCTTATCGATTTC
                                 3XP3-EYFP MARKER
1400
GAACCCTCGACGCGCCGGAGTATAAATAGAGGCGCTTCGTCTACGGAGCGACAATTCAATTCAAACAAGCAAAGTGAACACGTCGCTAAGGCGAAAGCTAAG
                                 3XP3-EYFP MARKER
1500
CAAATAAACAAGGCGAGCTGAACAAGCTAAACAATCGGGGTACCGCTAGAGTCGACGTCGACGATCCACCGTCGCGCCACCATGGTGAGCAAGGGCGAGGAG
                                 3XP3-EYFP MARKER
1600
CTGTTCACCGGGGTGGTGCCCATCCTGGTCGAGCTGGACGGCGACGTAAACGGCCACAAGTTCAGCGTGTCCGGCGAGGGCGAGGGCGATGCCACCTACG
                                 3XP3-EYFP MARKER
1700
GCAAGCTGACCCTGAAGTTCATCTGCACCACCGGCAAGCTGCCCGTGCCCTGGCCCACCCTCGTGACCACCTTCGGCTACGGCCTGCAGTGCTTCGCCCG
                                 3XP3-EYFP MARKER
1800
CTACCCCGACCACATGAAGCAGCACGACTTCTTCAAGTCCGCCATGCCCGAAGGCTACGTCCAGGAGCGCACCATCTTCTTCAAGGACGACGGCAACTAC
                                 3XP3-EYFP MARKER
1900
AAGACCCGCGCCGAGGTGAAGTTCGAGGGCGACACCCTGGTGAACCGCATCGAGCTGAAGGGCATCGACTTCAAGGAGGACGGCAACATCCTGGGGCACA
                                 3XP3-EYFP MARKER
2000
AGCTGGAGTACAACTACAACAGCCACAACGTCTATATCATGGCCGACAAGCAGAAGAACGGCATCAAGGTGAACTTCAAGATCCGCCACAACATCGAGGA
                                 3XP3-EYFP MARKER
```

*FIG. 15(B) CONT.*

2100
CGGCAGCGTGCAGCTCGCCGACCACTACCAGCAGAACACCCCCATCGGGCGACGGCCCCGTGCTGCTGCCCGACAACCACTACCTGAGCTACCAGTCCGCC
         3XP3-EYFP MARKER

2200
CTGAGCAAAGACCCCAACGAGAAGCGCGATCACATGGTCCTGCTGGAGTTCGTGACCGCCGCCGGGATCACTCTCGGCATGGACGAGCTGTACAAGTAAA
         3XP3-EYFP MARKER

2300
GCGGCCGCGACTCTAGATCATAATCAGCCATACCACATTTGTAGAGGTTTACTTGCTTTAAAAAACCTCCCACACCTCCCCCTGAACCTGAAACATAAA
         3XP3-EYFP MARKER

2400
ATGAATGCAATTGTGTTGTTAACTTGTTTATTGCAGCTTATAAATGGTTACAAATAAAGCAATAGCATCACAAATTTCACAAATAAAGCATTTTTTCAC
         3XP3-EYFP MARKER

2500
TGCATTCTAGTTGTGGTTTGTCCAAACTCATCAATGTATCTTAAAGCTTATCGATACCGTCGACCTCGAGGGGGGGCCCGGTACCCAATTCGCCCTATAGTGAGTCGTATTAAGATCACGCGTAGATCCAT
                                        LEFT TERMINAL REPEAT

2600
GAATTCGATATCAAGCTTATCGATACCGTCGACCTCGAGGGGGGGCCCGGTACCCAATTCGCCCTATAGTGAGTCGTATTAAGATCACGCGTAGATCCAT

2700
GCGTCAATTTTACGCATGATTATCTTTAACGTACGTCACAATATGATTATCTTTCTAGGGTTAATCTAGCTGCGTTCTGCAGGTGTCGAGCATCTTC

2800
ATCTGCTCCATCACGCTGTAAACACATTTGCACCGGAGTCTGCCCGTCCGGAGTCTGCCCTCCTCCACGGGTTCAAAAACGTGAATGAACGAGGCGCTTGGCGTAATCAT

2900
GGTCATAGCTGTTTCCTGTGTGAAATTGTTATCCGCTCACAATTCCACACAACATACGAGCCGGAAGCATAAAGTGTAAAGCCTGGGGTGCCTAATGAGT

FIG. 15(B) CONT.

3000
GAGCTAACTCACATTAATTGCGTTGCGCTCACTGCCCGCTTTCCAGTCGGGAAACCTGTCGTGCCAGCTGCATTAATGAATCGGCCAACGCGCGGGGAGA
>ColE1_origin
|----

3100
GGCGGGTTTGCGTATTGGGCGCTCTTCCGCTTCCTCGCTCACTGACTCGCTGCGCTCGGTCGTTCGGCTGCGGCGAGCGGTATCAGCTCACTCAAAGGCGG

3200
TAATACGGTTATCCACAGAATCAGGGGATAACGCAGGAAAGAACATGTGAGCAAAAGGCCAGCAAAAGGCCAGGAACCGTAAAAAGGCCGCGTTGCTGGC

3300
GTTTTTCCATAGGCTCCGCCCCCCTGACGAGCATCACAAAAATCGACGCTCAAGTCAGAGGTGGCGAAACCCGACAGGACTATAAAGATACCAGGCGTTT

3400
CCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTCATA

3500
GCTCACGCTGTAGGTATCTCAGTTCGGTGTAGGTCGTTCGCTCCAAGCTGGGCTGTGTGCACGAACCCCCCGTTCAGCCCGACCGCTGCGCCTTATCCGG

3600
TAACTATCGTCTTGAGTCCAACCCGGTAAGACACGACTTATCGCCACTGGCAGCAGCCACTGGTAACAGGATTAGCAGAGCGAGGTATGTAGGCGGTGCT

3700
ACAGAGTTCTTGAAGTGGTGGCCTAACTACGGCTACACTAGAAGGACAGTATTTGGTATCTGCGCTCTGCTGAAGCCAGTTACCTTCGGAAAAAGAGTTG

3800
GTAGCTCTTGATCCGGCAAACAAACCACCGCTGGTAGCGGTGGTTTTTTTGTTTGCAAGCAGCAGATTACGCGCAGAAAAAAAGGATCTCAAGAAGATCC

3900
TTTGATCTTTTCTACGGGGTCTGACGCTCAGTGGAACGAAAACTCACGTTAAGGGATTTTGGTCATGAGATTATCAAAAAGGATCTTCACCTAGATCCTT

4000
TTAAATTAAAAATGAAGTTTTAAATCAATCTAAAGTATATATGAGTAAACTTGGTCTGACAGTTACCAATGCTTAATCAGTGAGGCACCTATCTCAGCGA
                                                                         AMPCILLIN RESISTANCE ———>

*FIG. 15(B) CONT.*

```
4100
TCTGTGTCTATTTCGTTCATCCATAGTTGCCTGACTCCCCGTCGTGTAGATAACTACGATACGGGAGGGCTTACCATCTGGCCCCAGTGCTGCAATGATACC
                                                          AMPCILLIN RESISTANCE

4200
GCGAGACCCACGCTCACCGGCTCCAGATTTATCAGCAATAAACCAGCCAGCCGGAAGGGCCGAGCGCAGAAGTGGTCCTGCAACTTTATCCGCCTCCATC
                                                          AMPCILLIN RESISTANCE

4300
CAGTCTATTAATTGTTGCCGGGAAGCTAGAGTAAGTTCGCCAGTTAATAGTTTGCGCAACGTTGTTGCCATTGCTACAGGCATCGTGGTGTCACGCT
                                                          AMPCILLIN RESISTANCE

4400
CGTCGTTTGGTATGGCTTCATTCAGCTCCGGTTCCCAACGATCAAGGCGAGTTACATGATCCCCCATGTTGTGCAAAAAAGCGGTTAGCTCCTTCGGTCC
                                                          AMPCILLIN RESISTANCE

4500
TCCGATCGTTGTCAGAAGTAAGTTGGCCGCAGTGTTATCACTCATGGTTATGGCAGCACTGCATAATTCTCTTACTGTCATGCCATCCGTAAGATGCTTT
                                                          AMPCILLIN RESISTANCE

4600
TCTGTGACTGGTGAGTACTCAACCAAGTCATTCTGAGAATAGTGTATGCGGCGACCGAGTTGCTCTTGCCCGGCGTCAATACGGGATAATACCGCGCCAC
                                                          AMPCILLIN RESISTANCE

4700
ATAGCAGAACTTTAAAAGTGCTCATCATTGGAAAACGTTCTTCGGGGCGAAAACTCTCAAGGATCTTACCGCTGTTGAGATCCAGTTCGATGTAACCCAC
                                                          AMPCILLIN RESISTANCE

4800
TCGTGCACCCAACTGATCTTCAGCATCTTTTACTTTCACCAGCGTTTCTGGGTGAGCAAAAACAGGAAGGCAAAATGCCGCAAAAAAGGGAATAAGGGCG
                                                          AMPCILLIN RESISTANCE

4900
ACACGGAAATGTTGAATACTCATACTCTTCCTTTTTCAATATTATTGAAGCATTTATCAGGGTTATTGTCTCATGAGCGGATACATATTTGAATGTATTT
         AMPCILLIN RESISTANCE      >

AGAAAAATAAACAAATAGGGGTTCCGCGCACATTTCCCCGAAAAGTGCCAC  -- (SEQ ID NO:51)--

FIG. 15(B) CONT.
``` pXL-Bac-EGFP
Sequence Range: 1 to 4952

100
CTAAATTGTAAGCGTTAATATTTTGTTAAATTTTCGCGTTAAATTTGCGTTAAATCAGCTCATTTTTTAACCAATAGGCCGAAATCGGCAAAATCCCTTAT

200
AAATCAAAAGAATAGACCGAGATAGGGTTGAGTGTTGTTCCAGTTTGGAACAAGAGTCCACTATTAAAGAACGTGGACTCCAACGTCAAAGGGCGAAAAA

300
CCGTCTATCAGGGCGATGGCCCACTACGTGAACCATCACCCTAATCAAGTTTTTTGGGGTCGAGGTGCCGTAAAGCACTAAATCGGAACCCTAAAGGGAG

400
CCCCCGATTTAGAGCTTGACGGGGAAAGCCGGCGAACGTGGCGAGAAAGGAAGGGAAGAAAGCGAAAGGAGCGGGCGCTAGGGCGCTGGCAAGTGTAGCG

500
GTCACGCTGCGCGTAACCACCACACCCGCCGCTTAATGCGCCGCTACAGGGCGCGTCCCATTCGCCATTCAGGCTGCGCAACTGTTGGGAAGGGCGAT

600
CGGTGCGGGCCTCTTCGCTATTACGCCAGCTGGCGAAAGGGGGATGTGCTGCAAGGCGATTAAGTTGGGTAACGCCAGGGTTTTCCCAGTCACGACGTTG

700
TAAAACGACGGCCAGTGAGCGCGCCCGCGGGTAACTCACGCGGTATCCATGTCCATTCGCCGCTGTCGCCCGCTGTTGTTCGCCAGATACCCGTCTCGACGTAAT

800
ATCCCAGCGCGCACGCTGTCATTAATCTGCACACGGTATCCCAGTGCTGACGCCTGGCCTGAACGAACAGTCACCGTTAAAGGCGTGCATGGCCACACCTTCCCGAATC

900
CCGGAACTGTGTCCGGAAAGCCGCGAACTGGTATCCCGCTTCAAGCGTGCGCCTTCAACCTCGGGAAAAGGCACGGG

1000
ATCATGGTAAACGTGCGTTTCGCTCAACGTCAATGCAGCAGCAGTCATCCGGCAAACTCTTTCCATGCCGCTTCAACCTCGGGAAAAGGCACGGG

1100
CTTCTTCCTCCCCGATGCCCAGATAGCGCCAGCTTGGGCGATGACTGAGCCGGAAAAAGACCCGACGATATGATCCTGATGCAGCTAGATTAACCCTAG

FIG. 16(B)

```
1200 AAAGATAGTCTGCGTAAAATTGACGCCATGATCTAATTAACCCTCACTAAAGGGAACAAAAGCTGAGCTCCACCGCGGTGGCGGCCGCTCTAGAACTAGT
     RIGHT TERMINAL REPEAT
1300 GCCGTACGCGTATCGATAAGCTTAAGATACATTGATGAGTTTGGACAAACCACAACTAGAATGCAGTGAAAAAATGCTTTATTGTGAAATTTGTGAT
                                                  3XP3-EGFP MARKER
1400 GCTATTGCTTTATTTGTAACCATTATAAGCTGCAATAAACAAGTTAACAACAATTGCATTCATTTTATGTTTCAGGTTCAGGGGAGGTGTGGGAGG
                                                  3XP3-EGFP MARKER
1500 TTTTTTAAAGCAAGTAAAACCCTCTACAAATGTGGTATGATCTAGAGTCGCGGCCGCTTTACTTGTACAGCTCGTCCATGCCGAGAGTGAT
                                                  3XP3-EGFP MARKER
1600 CCCGGCGGCGGTCACGAACTCCAGCAGGACCATGTGATCGCGCTTCTCGTTGGGGTCTTTGCTCAGGGCGGACTGGGTGCTCAGGTAGTGGTTGTCGGGC
                                                  3XP3-EGFP MARKER
1700 AGCAGCACGGGGCCGTCGCCGATGGGGGTGTTCTGCTGGTAGTGGTCGGCGAGCTGCACGCTGCCGTCCTCGATGTTGTGGCGGATCTTGAAGTTCACCT
                                                  3XP3-EGFP MARKER
1800 TGATGCCGTTCTTCTGCTTGTCGGCCATGATATAGACGTTGTGGCTGTTGTAGTTGTACTCCAGCTTGTGCCCCAGGATGTTGCCGTCCTCCTTGAAGTC
                                                  3XP3-EGFP MARKER
1900 GATGCCCTTCAGCTCGATGCGGTTCACCAGGGTGTCGCCCTCGAACTTCACCTCGGGCGGGTCTTGTAGTTGCCGTCGTCCTTGAAGAAGATGGTGCGC
                                                  3XP3-EGFP MARKER
2000 TCCTGGACGTAGCCTTCGGGCATGGCGGACTTGAAGAAGTCGTGCTGCTTCATGTGGTCGGGGTAGCGGCTGAAGCACTGCACGCCGTAGGTCAGGGTGG
                                                  3XP3-EGFP MARKER
2100 TCACGAGGGTGGGCCAGGGCACGGGCAGCTTGCCGGTGGTGCAGATGAACTTCAGGGTCAGCTTGCCGTAGTGGCATCGCCCTCGCCCTCGCCGGACAC
                                                  3XP3-EGFP MARKER
```

*FIG. 16(B) CONT.*

2200
GCTGAACTTGTGGCCGTTTACGTCGCCGTCCAGCTGCGTCCAGGATGGGCACCACCCCGGTGAACAGCTCCTCGCCCTTGCTCTCGCCCATGTGGCGACCGGT
           3XP3-EGFP MARKER

2300
GGATCCCGGGCCCGCGGTACCGTCGACTCTAGCGGGTACCCCGATTGTTAGCTTGTTCAGCTGCGCTTGTTTATTTGCTTAGCTTTCGCTTAGCGACGTG
           3XP3-EGFP MARKER

2400
TTCACTTTGCTTGTTTGAATTGAATTGTGCTCCGTAGACGAAGCCCTCTATTTATACTCCGGGTCGAGGGTTCGAAATCGATAAGCTTGGATCCTA
           3XP3-EGFP MARKER

2500
ATTGAATTAGCTCTAATTAGTCTCTAATTGAATTAGATCCCGGGGGCCGAGCTCGAATTAACCATTGTGGAACACTAGTGGATCCCCCGGGCTGCA

2600
GGAATTCGATATCAAGCTTATCGATACCGTCGACCTCGAGGGGGGCCCGGTACCCAATTCGCCCTATAGTGAGTCGTATTAAGATCACGCGTAGATCCA
                                                                                          LEFT TERMINAL REPEAT

2700
TGCGTCAATTTTACGCATGATTATCTTTAACGTACGTCACAATATGATTATCTTTCTAGGGTTAATCTAGCTGCGTGTTCTGCAGGCTGTCGAGCATCTT

2800
CATCTGCTCCATCACGCTGTAAACACATTTGCACCGGCGAGTCGCTGCCCGTCCTCCACGGGTTCAAAAACGTGAATGAACGAGGCGCTTGGCGTAATCA

2900
TGGTCATAGCTGTTTCCTGTGTGAAATTGTTATCCGCTCACAATTCCACACAACATACGAGCCGGAAGCATAAAGTGTAAAGCCTGGGGTGCCTAATGAG

3000
TGAGCTAACTCACATTAATTGCGTTGCGCTCACTGCCCGCTTTCCAGTCGGGAAACCTGTCGTGCCAGCTGCATTAATGAATCGGCCAACGCGCGGGGAG
3100
AGGCGGTTTGCGTATTGGGCGCTCTTCCGCTTCCTCGCTCACTGACTCGCTGCGCTCGGTCGTTCGGCTGCGGCGAGCGGTATCAGCTCACTCAAAGGCG
     COLE1 ORIGIN

3200
GTAATACGGTTATCCACAGAATCAGGGGATAACGCAGGAAAGAACATGTGAGCAAAAGGCCAGCAAAAGGCCAGGAACCGTAAAAAGGCCGCGTTGCTGG
                       COLE1 ORIGIN

*FIG. 16(B) CONT.*

```
3300
CGTTTTTTCCATAGGCTCCGCCCCCCTGACGAGCATCACAAAAATCGACGCTCAAGTCAGAGGTGGCGAAACCCGACAGGACTATAAAGATACCAGGCGTT
                                           COLE1 ORIGIN

3400
TCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTCAT
                                           COLE1 ORIGIN

3500
AGCTCACGCTGTAGGTATCTCAGTTCGGTGTAGGTCGTTCGCTCCAAGCTGGGCTGTGTGCACGAACCCCCCGTTCAGCCCGACCGCTGCGCCTTATCCG
                                           COLE1 ORIGIN

3600
GTAACTATCGTCTTGAGTCCAACCCGGTAAGACACGACTTATCGCCACTGGCAGCAGCCACTGGTAACAGGATTAGCAGAGCGAGGTATGTAGGCGGTGC
                                           COLE1 ORIGIN

3700
TACAGAGTTCTTGAAGTGGTGGCCTAACTACGGCTACACTAGAAGGACAGTATTTGGTATCTGCGCTCTGCTGAAGCCAGTTACCTTCGGAAAAAGAGTT
                                           COLE1 ORIGIN

3800
GGTAGCTCTTGATCCGGCAAACAAACCACCGCTGGTAGCGGTGGTTTTTTTGTTTGCAAGCAGCAGATTACGCGCAGAAAAAAAGGATCTCAAGAAGATC
                                           COLE1 ORIGIN

3900
CTTTGATCTTTTCTACGGGGTCTGACGCTCAGTGGAACGAAAACTCACGTTAAGGGATTTTGGTCATGAGATTATCAAAAAGGATCTTCACCTAGATCCT
                                           COLE1 ORIGIN

4000
TTTAAATTAAAAATGAAGTTTTAAATCAATCTAAAGTATATATGAGTAAACTTGGTCTGACAGTTACCAATGCTTAATCAGTGAGGCACCTATCTCAGCG
                                           COLE1 ORIGIN                              AMPICILLIN RESISTANCE

4100
ATCTGTCTATTTCGTTCATCCATAGTTGCCTGACTCCCCGTCGTGTAGATAACTACGATACGGGAGGGCTTACCATCTGGCCCCAGTGCTGCAATGATAC
                                           AMPICILLIN RESISTANCE
```

FIG. 16(B) CONT.

```
4200
CGCGAGACCCCACGCTCACCGGCTCCAGATTTATCAGCAATAAACCAGCCAGCCGGAAGGGCCGAGCGGCAGAAGTGGTCCTGCAACTTTATCCGCCTCCAT
     AMPCILLIN RESISTANCE                                                                              >
4300
CCAGTCTATTAATTGTTGCCGGGAAGCTAGAGTAAGTAGTTCGCCAGTTAATAGTTTGCGCAACGTTGTTGCCATTGCTACAGGCATCGTGGTGTCACGC
     AMPCILLIN RESISTANCE                                                                              >
4400
TCGTGTCGTTTGGTATGGCTTCATTCAGCTCCGGTTCCCAACGATCAAGGCGAGTTACATGATCCCCCATGTTGTGCAAAAAAGCGGTTAGCTCCTTCGGTC
     AMPCILLIN RESISTANCE                                                                              >
4500
CTCCGATCGTTGTCAGAAGTAAGTTGGCCGCAGTGTTATCACTCATGGTTATGGCAGCACTGCATAATTCTCTTACTGTCATGCCATCCGTAAGATGCTT
     AMPCILLIN RESISTANCE                                                                              >
4600
TTCTGTGACTGGTGAGTACTCAACCAAGTCATTCTGAGAATAGTGTATGCGGCGACCGAGTTGCTCTTGCCCGGCGTCAATACGGGATAATACCGCGCCA
     AMPCILLIN RESISTANCE                                                                              >
4700
CATAGCAGAACTTTAAAAGTGCTCATCATTGGAAAACGTTCTTCGGGGCGAAAACTCTCAAGGATCTTACCGCTGTTGAGATCCAGTTCGATGTAACCCA
     AMPCILLIN RESISTANCE                                                                              >
4800
CTCGTGCACCCAACTGATCTTCAGCATCTTTTACTTTCACCAGCGTTTCTGGGTGAGCAAAAACAGGAAGGCAAAATGCCGCAAAAAAGGGAATAAGGGC
     AMPCILLIN RESISTANCE                                                                              >
4900
GACACGGAAATGTTGAATACTCATACTCTTCCTTTTTCAATATTATTGAAGCATTTATCAGGGTTATTGTCTCATGAGCGGATACATATTTGAATGTATT
     AMPCILLIN RESISTANCE         >

TAGAAAAATAAACAAATAGGGGTTCCGCGCACATTTCCCCGAAAAGTGCCAC --(SEQ ID NO:52)--
```

*FIG. 16(B) CONT.* pXL-Bac-ECFP
Sequence Range: 1 to 4941

```
100
CTAAATTGTAAGCGTTAATATTTTGTTAAATTCGCGTTAAATTTTGTTAAATCAGCTCATTTTTTAACCAATAGGCCGAAATCGGCAAAATCCCTTAT
200
AAATCAAAAGAATAGACCGAGATAGGGTTGAGTGTTGTTCCAGTTTGGAACAACAGAGTCCACTATTAAAGAACGTGGACTCCAACGTCAAAGGGCGAAAAA
300
CCGTCTATCAGGGCGATGGCCCACTACGTGAACCATCACCCTAATCAAGTTTTTTGGGGTCGAGGTGCCGTAAAGCACTAAATCGGAACCCTAAAGGGAG
400
CCCCCGATTTAGAGCTTGACGGGGAAAGCCGGCGAACGTGGCGAGAAAGGAAGGGAAGAAAGCGAAAGGAGCGGGCGCTAGGGCGCTGGCAAGTGTAGCG
500
GTCACGCTGCGCGTAACCACCACACCCGCCGCGCTTAATGCGCCGCTACAGGGCGCGTCCATTCGCCATTCAGGCTGCGCAACTGTTGGGAAGGGCGAT
600
CGGTGCGGGCCTCTTCGCTATTACGCCAGCTGGCGAAAGGGGGATGTGCTGCAAGGCGATTAAGTTGGGTAACGCCAGGGTTTTCCCAGTCACGACGTTG
700
TAAAACGACGGCCAGTGAGCGCGCGTAATACGACTCACTATAGGGCGAATTCCATGTCCATTCGCGGCGCCAGCCAGGATACCCGTCTCGCTGACGTAAT
800
ATCCCCAGCGCCGCCACGCTGTCATTAATCTGCACACCGGGTATCCAGTGGCCGGCCTGAACGAACAGTTCACCGTTAAAGGCGTGCATGGCCACACCTTCCCGAATC
900
CCGGAACTGTGTCCGAAAGCCGGCGTTTCGCTCAACGTCAATGCAGCAGCAGTCATCCTCGGCAAACTCTTTCCATGCCGCTTCAACCTCGGGAAAAGCACGGG
1000
ATCATGGTAAACGTGCGTTTCGCTCAACGTCAATGCAGCAGCAGTCATCCTCGGCAAACTCTTTCCATGCCGCTTCAACCTCGGGAAAAGCACGGG
1100
CTTCTTCCTCCCCGATGCCCAGATAGCGCCCAGCTTGGGCGATGACTGAGCCGGAAAAAGACCCGACGATATGATCCTGATCAGCTAGATTAACCCTAG
```

FIG. 17(B)

```
1200
AAGATAGTCTGCGTAAAATTGACGCATGATCTAATTAACCCTCACTAAAGGGAACAAAAGCTGGAGCTCCACCGCGGTGGCGGCCGCTCTAGAACTAGT
     < RIGHT TERMINAL REPEAT       |
1300
GTTCCCACAATGGTTAATTCGAGCTCGCCCGGGGATCTAATTCAATTAGAGACTAATTCAATTAGAGCTAATTCAATTAGAGATCCAAGCTTATCGATTTC
                                                                                        3XP3-ECFP MARKER                                                   >
1400
GAACCCCTCGACCGCCGGAGTATAAATAGAGGGCCTTCGTCTACGGAGCGACAATTCAATTCAAACAAGCAAAGTGAACACGTCGCTAAGCGAAAGCTAAG
                                              3XP3-ECFP MARKER                                                                                              >
1500
CAAATAAACAAGGCGCAGCTGAACAAGCTAAACAATCGGGGTACCGCTAGAGTCGACGGTACGATCCACCGTCGCCACCATGGTGAGCAAGGGCGAGGAG
                                              3XP3-ECFP MARKER                                                                                              >
1600
CTGTTCACCGGGGTGGTGCCCATCCTGGTCGAGCTAAACGGCCACAAGTTCAGCGTGTCCGGCGAGGGCGAGGGCGATGCCACCTACG
                                              3XP3-ECFP MARKER                                                                                              >
1700
GCAAGCTGACCCTGAAGTTCATCTGCACCACCGGCAAGCTGCCCGTGCCCTGGCCCACCCTCGTGACCACCCTGACCTGGGGCGTGCAGTGCTTCAGCCG
                                              3XP3-ECFP MARKER                                                                                              >
1800
CTACCCCGACCACATGAAGCAGCACGACTTCTTCAAGTCCGCCATGCCCGAAGGCTACGTCCAGGAGCGCACCATCTTCTTCAAGGACGACGGCAACTAC
                                              3XP3-ECFP MARKER                                                                                              >
1900
AAGACCCGCGCCGAGGTGAAGTTCGAGGGCGACACCCTGGTGAACCGCATCGAGCTGAAGGGCATCGACTTCAAGGAGGACGGCAACATCCTGGGGCACA
                                              3XP3-ECFP MARKER                                                                                              >
2000
AGCTGGAGTACAACTACATCAGCCACAACGTCTATATCACCGCCGACAAGCAGAAGAACGGCATCAAGGCCAACTTCAAGATCCGCCACAACATCGAGGA
                                              3XP3-ECFP MARKER                                                                                              >
```

*FIG. 17(B) CONT.*

```
2100
CGGCAGCGTGCGAGCTCGCCGCCGACCACTACCAGCAGAGAACACCCCATGGGCGACGGCCCCGTGCTGCTGCCGACAACCACTACCTGAGCACCCAGTCCGCC
                                                3XP3-ECFP MARKER                                        >

2200
CTGAGCAAAGACCCCAACGAGAAGCGCGATCACATGGTCCTGCTGGAGTTCGTGACCGCCGCCGGGATCACTCTCGGCATGGACGAGCTGTACAAGTAAA
                                                3XP3-ECFP MARKER                                        >

2300
GCGGGCCGCGACTCTAGATCATAATCAGCCATACCACATTTGTAGAGGTTTACTTGCTTTAAAAAACCTCCCACACCTCCCCCCTGAACCTGAAACATAAA
                                                3XP3-ECFP MARKER                                        >

2400
ATGAATGCAATTGTTGTTGTTAACTTGTTTATTGCAGCTTATAATGGTTACAAATAAAGCAATAGCATCACAAATTTCACAAATAAAGCATTTTTTTCAC
                                                3XP3-ECFP MARKER                                        >

2500
TGCATTCTAGTTGTGTGGTTTGTCCAAACTCATCAATGTATCTTAAAGCTTATCGATACCGTCGACCTAGTGGATCCCCCGGGCTGCAGGAATTCGATA
                                                3XP3-ECFP MARKER                                 >

2600
TCAAGCTTATCGATACCGTCGACCTCGAGGGGGGGCCCGGTACCCAATTCGCCCTATAGTGAGTCGTATTAAGATCACGCGTAGATCCATGCGTCAATTT
                                                                                                   <

2700
TACGCATGATTATCTTAACGTACGTCACAATATGATTATCTTTCTAGGGTTAATCTAGCTGCGTGTCTGCGAGCATCTTCATCTGCTCCA
      <                     LEFT TERMINAL REPEAT

2800
TCACGCTGTAAACACATTGCACCGGCTCTGCCCGTCCTCCACGGGTTCAAAAACGTGAATGAACGAGGCGCGCTTGGCGTAATCATGGTCATAGCT

2900
GTTTCCTGTGTGAAATTGTTATCCGCTCACAATTCCACACAACATACGAGCCGGAAGCATAAAGTGTAAAGCCTGGGGTGCCTAATGAGTGAGCTAACTC

3000
ACATTAATTGCGTTGCGCTCACTGCCCGCTTTCCAGTCGGGAAACCTGTCGTGCCAGCTGCATTAATGAATCGGCCAACGCGCGGGGAGAGGCGGTTTGC
```

FIG. 17(B) CONT.

>ColE1_origin

3100
GTATTGGGCGGCTCTTCCGCTTCCTCGCTCACTGACTCGCTGCGCTCGGTCGTTCGGCTGCGGCGAGCGGTATCAGCTCACTCAAAGGCGGTAATACGGTT
3200
ATCCACAGAATCAGGGGATAACGCAGGAAAGAACATGTGAGCAAAAGGCCAGCAAAAGGCCAGGAACCGTAAAAAGGCCGCGTTGCTGGCGTTTTTCCAT
3300
AGGCTCCGCCCCCCTGACGAGCATCACAAAAATCGACGCTCAAGTCAGAGGTGGCGAAACCCGACAGGACTATAAAGATACCAGGCGTTTCCCCCTGGAA
3400
GCTCCCTCGTGCGCTCTCCTGTTCCGACCCTGCCGCTTACCGGATACCTGTCCGCCTTTCTCCCTTCGGGAAGCGTGGCGCTTTCTCATAGCTCACGCTG
3500
TAGGTATCTCAGTTCGGTGTAGGTCGTTCGCTCCAAGCTGGGCTGTGTGCACGAACCCCCCGTTCAGCCCGACCGCTGCGCCTTATCCGGTAACTATCGT
3600
CTTGAGTCCAACCCGGTAAGACACGACTTATCGCCACTGGCAGCAGCCACTGGTAACAGGATTAGCAGAGCGAGGTATGTAGGCGGTGCTACAGAGTTCT
3700
TGAAGTGGTGGCCTAACTACGGCTACACTAGAAGGACAGTATTTGGTATCTGCGCTCTGCTGAAGCCAGTTACCTTCGGAAAAAGAGTTGGTAGCTCTTG
3800
ATCCGGCAAACAAACCACCGCTGGTAGCGGTGGTTTTTTTGTTTGCAAGCAGCAGATTACGCGCAGAAAAAAAGGATCTCAAGAAGATCCTTTGATCTTT
3900
TCTACGGGGTCTGACGCTCAGTGGAACGAAAACTCACGTTAAGGGATTTTGGTCATGAGATTATCAAAAAGGATCTTCACCTAGATCCTTTTAAATTAAA
4000
AATGAAGTTTTAAATCAATCTAAAGTATATATGAGTAAACTTGGTCTGACAGTTACCAATGCTTAATCAGTGAGGCACCTATCTCAGCGATCTGTCTATT

——————— AMPCILLIN RESISTANCE ———————>

FIG. 17(B) CONT.

```
4100
TCGTTCATCCATAGTTGCCTGACTCCCCGTGTCGTGTAGATAACTACGATACGGGAGGGCTTACCATCTGGCCCCAGTGCTGCAATGATACCGCGAGACCCA
     AMPCILLIN RESISTANCE

4200
CGCTCACCGGCTCCAGATTTATCAGCAATAAACCAGCAGCCGGAAGGGCCGAGCCGCAGAAGTGGTCCTGCAACTTTATCCGCCTCCATCCAGTCTATTA
     AMPCILLIN RESISTANCE

4300
ATTGTTGCCGGGAAGCTAGAGTAAGTAGTTCGCCAGTTAATAGTTTGCGCAACGTTGTTGCCATTGCTACAGGCATCGTGGTGTCACGCTCGTCGTTTGG
     AMPCILLIN RESISTANCE

4400
TATGGCTTCATTCAGCTCCGGTTCCCAACGATCAAGGCGAGTTACATGATCCCCCATGTTGTGCAAAAAAGCGGTTAGCTCCTTCGGTCCTCCGATCGTT
     AMPCILLIN RESISTANCE

4500
GTCAGAAGTAAGTTGGCCGCAGTGTTATCACTCATGGTTATGGCAGCACTGCATAATTCTCTTACTGTCATGCCATCCGTAAGATGCTTTTCTGTGACTG
     AMPCILLIN RESISTANCE

4600
GTGAGTACTCAACCAAGTCATTCTGAGAATAGTGTATGCGGCGACCGAGTTGCTCTTGCCCGGCGTCAATACGGGATAATACCGCGCCACATAGCAGAAC
     AMPCILLIN RESISTANCE

4700
TTTAAAAGTGCTCATCATTGGAAAACGTTCTTCGGGGCGAAAACTCTCAAGGATCTTACCGCTGTTGAGATCCAGTTCGATGTAACCCACTCGTGCACCC
     AMPCILLIN RESISTANCE

4800
AACTGATCTTCAGCATCTTTTACTTTCACCAGCGTTTCTGGGTGAGCAAAAACAGGAAGGCAAAATGCCGCAAAAAAGGGAATAAGGGCGACACGGAAAT
     AMPCILLIN RESISTANCE

4900
GTTGAATACTCATACTCTTCCTTTTTCAATATTATTGAAGCATTTATCAGGGTTATTGTCTCATGAGCGGATACATATTTGAATGTATTTAGAAAAATAA
     AMPCILLIN R    >

ACAAATAGGGGGTTCCGCGCACATTTCCCCGAAAAGTGCCAC  --(SEQ ID NO:53)--

FIG. 17(B) CONT.
```

PBS-ITR-ECFP
Sequence Range: 1 to 4943

100
CACCCTGACGCGCCCTGTAGCGGCGCATTAAGCGCGGCGGGTGTGGTGGTTACGCGCAGCGTGACCGCTACACTTGCCAGCGCCCTAGCGCCCGCTCCTTT

200
CGCTTTCTTCCCTTCCTTTCTGCACGTTCGCCGGCTTTCCCCGTCAAGCTCTAAATCGGGGGCTCCCTTTAGGGTTCCGATTTAGTGCTTTACGGCAC

300
CTCGACCCCAAAAAACTTGATTAGGGTGATGGTTCACGTAGTGGGCCATCGCCCTGATAGACGGTTTTTCGCCCTTTGACGTTGGAGTCCACGTTCTTTA

400
ATAGTGGACTCTTGTTCCAAACTGGAACAACACTCAACCCTATCTCGGTCTATTCTTTGATTTATAAGGATTTGCCGATTTCGGCCTATTGGTTAAA

500
AAATGAGCTGATTAACAAAAATTTAACGCGAATTTTAACAAAATATTAACGCTTACAATTCCATTCGCCATTCAGGCTGCCAACTGTTGGGAAGGGC

600
GATCGGTGCGGGCCTCTTCGCTATTACGCCAGCTGGCGAAAGGGGGATGTGCTGCAAGGCGATTAAGTTGGGTAACGCCAGGGTTTTCCCAGTCACGACG

700
TTGTAAAACGACGGCCAGTGAATTGTAATACGACTCACTATAGGGCGAATTGGGTACCGGGCCCCCCCTCGAGGTCGACGGTATCGATAAGCTTGATATC

800
GAATTCCTGCAGCCCGGGGGATCCATGGTCATGCGTCAATTTTACGCAGACTATCTTTCTAGGGTTAATCTAGCTGCATCAGGATCATATCTCGGGTCTTTTT
                                     RIGHT TERMINAL REPEAT  ───────────>

900
CCGGCTCAGTCATCGCCAAGCTGCCTATCGGGCGCATCGGGGAGGAAGAAGCCCGTGCCTTTCCCGAGGTTGAAGCGGCATGGAAAGAGTTTGCC

1000
GAGGATGACTGCTGCTGCATTGACGTTGAGCGAAAACGCACGTTTACCATGATGATTCGGGAAGGTGTGGCCATGCACGCCCTTTAACGGTGAACTGTTCG

1100
TTCAGGCCACCTGGGATACCAGTTCGTCGCGGCTTTTTCCGGACACAGTTCGACATGTTCAGCCGAAGCGCATCAGCAACCCGAACAATACCGGCGACAG

*FIG. 18(B)*

1200 CCGGAACTGCCGTGCCGGTGTGCAGATTAATGACAGCGGTGCGGCGCTGGGATATTACGTCAGCGAGGACGGGTATCCTGGCTGATGCCGCAGAAATGG
1300 ACAATGGATACCCCGTGAGTTACCCGGCGCTCGTTCATTCACGTTTTTGAACCCGTGGAGGACGGGCAGACTCGCGGTGCAAATGTGTTTTACAGCGTGA
1400 TGGAGCAGATGAAGATGCTCGACACGCTGCAGAACACGGCAGCTAGAGATTAACCCTAGAAAGATAATCATATTGTGACGTACGTTAAAGATAATCATGCGTA
                                                                        LEFT TERMINAL REPEAT
1500 AAATTGACGCATGGGATCCACTAGTGTTCCCACAATGGTTAATTCGAGCTCGCCCGGGGATCTAATTCAATTAGAGACTAATTCAATTAGAGCTAATTCA
                                                                                                    3XP3-ECFP MARKER
1600 ATTAGGATCCAAGCTTATCGATTTCGAACCCTCGACCGCCGGAGTATAAATAGAGGCGCTTCGTCCTACGGAGGACGACAATTCAATTCAAACAAGCAAAGTG
       3XP3-ECFP MARKER
1700 AACACGTCGCTAAGCGAAAGCTAAGCAACAAATAAACAAGGCAGCTGAACAAGCTAAACAATGCGGGTACCGCTAGAGTGCACGGTACGATCCACCGGTCGC
       3XP3-ECFP MARKER
1800 CACCATGGTGAGCAAGGGCGAGGAGCTGTTCACCGGGGTGGTGCCCATCCTGGTCGAGCTGGACGGCGACGTAAACGGCCACAAGTTCAGCGTGTCCGGC
       3XP3-ECFP MARKER
1900 GAGGGCGAGGGCGATGCCACCTACGGCAAGCTGACCCTGAAGTTCATCTGCACCACCGGCAAGCTGCCCGTGCCCTGGCCCACCCTCGTGACCACCCTGA
       3XP3-ECFP MARKER
2000 CCTGGGGCGTGCAGTGCTTCAGCCGCTACCCCGACCACATGAAGCAGCACGACTTCTTCAAGTCCGCCATGCCCGAAGGCTACGTCCAGGAGCGCACCAT
       3XP3-ECFP MARKER
2100 CTTCTTCAAGGACGACGGCAACTACAAGACCCGCGCCGAGGTGAAGTTCGAGGGCGACACCCTGGTGAACCGCATCGAGCTGAAGGGCATCGACTTCAAG
       3XP3-ECFP MARKER

FIG. 18(B) CONT.

```
2200
GAGGACGGCAACATCCTGGGGCACAAGCTGGAGTACAACTACATCAGCCACAACGTCTATATCACCGCCGACAAGCAGAAGAACGGCATCAAGGCCAACT
                                                    3XP3-ECFP MARKER

2300
TCAAGATCCGCCACACATCGAGGACGGCAGCGTGCAGCTCGCCGACCACTACCAGCAGAACACCCCCATCGGCGACGGCCCCGTGCTGCTGCCCGACAA
                                                    3XP3-ECFP MARKER

2400
CCACTACCTGAGCACCCAGTCCGCCCTGAGCAAAGACCCCAACGAGAAGCGCGATCACATGGTCCTGCTGGAGTTCGTGACCGCCGCCGGGATCACTCTC
                                                    3XP3-ECFP MARKER

2500
GGCATGGACGAGCTGTACAAGTAAAGCGGCCGACTCTAGATCATAAATCAGCCATACCACACATTTGTAGAGGTTTACTTGCTTTAAAAAACCTCCCACA
                                                    3XP3-ECFP MARKER

2600
CCTCCCCCTGAACCTGAAACATAAAATGAATGCAATTGTGTTGTTAACTTGTTTATTGCAGCTTATAATGTTACAAATAAAGCAATAGCATCACAAAT
                                                    3XP3-ECFP MARKER

2700
TTCACAAATAAAGCATTTTTTCACTGCATTCTAGTTGTGTTTGTCCAAACTCATCAATGTATCTTAAAGCTTATCGATACGGCGTACGGCGGCCTAGG
                                                    3XP3-ECFP MARKER

2800
CCGGCCCGATACTAGTTCTAGAGCGGCCGCCACCGCGTGGAGCTCCAGCTTTTGTTCCCTTTAGTGAGGGTTAATTCGAGCTTGGCGTAATCATGGTCA

2900
TAGCTGTTTCCTGTGTGAAATTGTTATCCGCTCACAATTCCACACAACATACGAGCCGGAAGCATAAAGTGTAAAGCCTGGGGTGCCTAATGAGTGAGCT

3000
AACTCACATTAATTGCGTTGCGCTCACTGCCCGCTTTCCAGTCGGGAAACCTGTCGTGCCAGCTGCATTAATGAATCGGCCAACGCGCGGGGAGAGGCGG
```

*FIG. 18(B) CONT.*

>ColE1_origin

3100 TTTGCGTATTGGGCGCTCTTCCGCTTCCTCGCTCACTGACTCGCTGCGCTCGGTCGTTCGGCTGCGGCGAGCGGTATCAGCTCACTCAAAGGCGGTAATA
3200 CGGTTATCCACAGAATCAGGGGATAACGCAGGAAAGAACATGTGAGCAAAAGGCCAGCAAAAGGCCAGGAACCGTAAAAAGGCCGCGTTGCTGGCGTTTT
3300 TCCATAGGCTCCGCCCCCCTGACGAGCATCACAAAAATCGACGCTCAAGTCAGAGGTGGCGAAACCCGACAGGACTATAAAGATACCAGGCGTTTCCCCC
3400 TGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCTCA
3500 CGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAACT
3600 ATCGTCTTGAGTCCAACCCGGTAAGACACGACTTATCGCCACTGGCAGCAGCCACTGGTAACAGGATTAGCAGAGCGAGGTATGTAGGCGGTGCTACAGA
3700 GTTCTTGAAGTGGTGGCCTAACTACGGCTACACTAGAAGGACAGTATTTGGTATCTGCGCTCTGCTGAAGCCAGTTACCTTCGGAAAAAGAGTTGGTAGC
3800 TCTTGATCCGGCAAACAAACCACCGCTGGTAGCGGTGGTTTTTTTGTTTGCAAGCAGCAGATTACGCGCAGAAAAAAAGGATCTCAAGAAGATCCTTTGA
3900 TCTTTTCTACGGGGTCTGACGCTCAGTGGAACGAAAACTCACGTTAAGGGATTTTGGTCATGAGATTATCAAAAAGGATCTTCACCTAGATCCTTTTAAA
4000 TTAAAAATGAAGTTTTAAATCAATCTAAAGTATATATGAGTAAACTTGGTCTGACAGTTACCAATGCTTAATCAGTGAGGCACCTATCTCAGCGATCTGT
                                                                                  AMPCILLIN RESISTANCE
4100 CTATTTCGTTCATCCATAGTTGCCTGACTCCCCGTCGTGTAGATAACTACGATACGGGAGGGCTTACCATCTGGCCCCAGTGCTGCAATGATACCGCGAG
     AMPCILLIN RESISTANCE

*FIG. 18(B) CONT.*

```
4200
ACCCACGCTCACCGGCTCCAGATTTATCAGCAATAAACCAGCCGAGGGGCGAGCCGCAGAAGTGGTCCTGCAACTTTATCCGCCTCCATCCAGTC
         AMPCILLIN RESISTANCE                                                                   >

4300
TATTAATTGTTGCCGGGAAGCTAGAGTAAGTAGTTCGCCAGTTAATAGTTTGCGCAACGTTGTTGCCATTGCTACAGGCATCGTGGTGTCACGCTCGTCG
                                AMPCILLIN RESISTANCE                                               >

4400
TTTGGTATGGCTTCATTCAGCTCCGGTTCCCAACGATCAAGGCGAGTTACATGATCCCCATGTTGTGCAAAAAGCGGTTAGCTCCTTCGGTCCTCCGA
                                AMPCILLIN RESISTANCE                                               >

4500
TCGTTGTCAGAAGTAAGTTGGCCGCAGTGTTATCACTCATGGTTATGGCAGCACTGCATAATTCTCTTACTGTCATGCCATCCGTAAGATGCTTTTCTGT
                                AMPCILLIN RESISTANCE                                               >

4600
GACTGGTGAGTACTCAACCAAGTCATTCTGAGAATAGTGTATGCGGCGACCGAGTTGCTCTTGCCCGGCGTCAATACGGGATAATACCGCGCCACATAGC
                                AMPCILLIN RESISTANCE                                               >

4700
AGAACTTTAAAAGTGCTCATCATTGGAAAACGTTCTTCGGGGCGAAAACTCTCAAGGATCTTACCGCTGTTGAGATCCAGTTCGATGTAACCCACTGTG
                                AMPCILLIN RESISTANCE                                               >

4800
CACCCAACTGATCTTCAGCATCTTTTACTTTCACCAGCGTTTCTGGGTGAGCAAAAACAGGAAGGCAAAATGCCGCAAAAAAGGGAATAAGGGCGACACG
                                AMPCILLIN RESISTANCE                                               >

4900
GAAATGTTGAATACTCATACTCTTCCTTTTTCAATATTATTGAAGCATTATCAGGGTTATTGTCTCATGAGCGGATACATATTTGAATGTATTAGAAA
       AMPCILLIN RESISTANCE   >

AATAAACAAATAGGGGTTCCGCGCACATTTCCCCGAAAAGTGC  --(SEQ ID NO:54)--
```

*FIG. 18(B) CONT.*

```
PBS-ITR-EGFP
Sequence Range: 1 to 4944

100  CACCTGACGGCCCTAGCGGCGCATTAAGCGCGGCGGGTGTGGTGGTTACGCGCAGCGTGACCGCTACACTTGCCAGCGCCCTAGCGCCCGCTCCTTT
200  CGCTTTCTTCCCTTCCTTTCTCGCCACGTTCGCCGGCTTTCCCCGTCAAGCTCTAAATCGGGGGCTCCCTTTAGGGTTCCGATTTAGTGCTTTACGGCAC
300  CTCGACCCCAAAAAACTTGATTAGGGTGATGGTTCACGTAGTGGGCCATCGCCCTGATAGACGGTTTTTCGCCCTTTGACGTTGGAGTCCACGTTCTTTA
400  ATAGTGGACTCTTGTTCCAAACTGGAACACACTCAACCCTATCTCGGTCTATTCTTTTGATTTATAAGGGATTTTGCCGATTTCGGCCTATTGGTTAAA
500  AAATGAGCTGATTTAACAAAAATTTAACGCGAATTTTAACAAATATTAACGCTTACAATTTCCATTCGCCATTCAGGCTGCGCAACTGTTGGGAAGGGC
600  GATCGGTGCGGGCCTCTTCGCTATTACGCCAGCTGGCGAAAGGGGGATGTGCTGCAAGGCGATTAAGTTGGGTAACGCCAGGGTTTTCCCAGTCACGACG
700  TTGTAAAACGACGGCCAGTGAATTGTAATACGACTCACTATAGGGCGAATTGGGTACCGGGCCCCCCCTCGAGGTCGACGGTATCGATAAGCTTGATATC
800  GAATTCCTGCAGCCCGGGGATCCACTAGTTCTAGAGCGGCCGCCACCGCGGTGGAGCTCCAGCTTTTGTTCCCTTTAGTGAGGGTTAATTCTGAGCTTGG
                                                                                      RIGHT TERMINAL REPEAT ———>
900  CGTAATCATGGTCATAGCTGTTTCCTGTGTGAAATTGTTATCCGCTCACAATTCCACACAACATACGAGCCGGAAGCATAAAGTGTAAAGCCTGGGGTGC
1000 CTAATGAGTGAGCTAACTCACATTAATTGCGTTGCGCTCACTGCCCGCTTTCCAGTCGGGAAACCTGTCGTGCCAGCTGCATTAATGAATCGGCCAACGC
1100 GCGGGGAGAGGCGGTTTGCGTATTGGGCGCTCTTCCGCTTCCTCGCTCACTGACTCGCTGCGCTCGGTCGTTCGGCTGCGGCGAGCGGTATCAGCTCACT
```

*FIG. 19(B)*

```
1200
CCGGAACTGCCGTGCGGTGTGCAGATTAATGACAGGCGGTGCGGCGCTGGAGATATTACGTCAGCGAGGAGGACGGGTATCCTGGCTGATGCCGCAGAAATGG
1300
ACAATGGATACCCCGTGAGTTACCCGGGGCCTCGTTCATTCACGTTTTTGAACCCGTGGAGGACGGGCAGACTCGGGTGCAAATGTGTTTACAGCGTGA
1400
TGGAGCAGAGATGAAGATGCTCGACACGCTGAGATTAACCCTAGAAAGATAATCATATTGTGACGTACGTTAAAGATAATCATGCGTA
                                                                         LEFT TERMINAL REPEAT
1500
AAATTGACGCATGGATCCACTAGTGTTCCCACAATGGTTAATTCGAGCTCGCCCGGGGATCTAATTCAATTAGAGACTAATTCAATTAGAGCTAATTCA
            >                                                  3XP3-EGFP MARKER
1600
ATTAGGATCCAAGCTTATCGATTTCGAACCCTCGACCGCCGGAGTATAAATAGAGGCGCTTCGTCTACGAGCGACAATTCAATTCAAACAAGCAAAGTG
                                                             3XP3-EGFP MARKER
1700
AACACGTCGCTAAGCGAAAGCTAAGCAAATAAACAAGCTGAACAAGCTGAAAACAATGGGGTACCGCTAGAGTCGACGGTACCGCGGGCCCGGGAT
                                                             3XP3-EGFP MARKER
1800
CCACCGGTCGCCACCATGGTGAGCAAGGGCGAGGAGCTGTTCACCGGGGTGGTGCCCATCCTGGTCGAGCTGGACGGCGACGTAAACGGCCACAAGTTCA
                                                             3XP3-EGFP MARKER
1900
GCGTGTCCGGCGAGGGCGAGGGCGATGCCACCTACGGCAAGCTGACCCTGAAGTTCATCTGCACCACCGGCAAGCTGCCCGTGCCCTGGCCCACCCTCGT
                                                             3XP3-EGFP MARKER
2000
GACCACCCTGACCTACGGCGTGCAGTGCTTCAGCCGCTACCCCGACCACATGAAGCAGCACGACTTCTTCAAGTCCGCCATGCCCGAAGGCTACGTCCAG
                                                             3XP3-EGFP MARKER
2100
GAGCGCACCATCTTCTTCAAGGACGACGGCAACTACAAGACCCGCGCCGAGGTGAAGTTCGAGGGCGACACCCTGGTGAACCGCATCGAGCTGAAGGGCA
                                                             3XP3-EGFP MARKER
```

*FIG. 19(B) CONT.*

```
2200
TCGACTTCAAGGAGGACGGCAACATCCTGGGCACACAAGCTGGAGTACAACTACAACAGCCACAACGTCTATATCATGGCCGACAAGCAGAAGAACGGCAT
                                                           3XP3-EGFP MARKER
2300
CAAGGTGAACTTCAAGATCCGCCACAACATCGAGGACGGCAGCGTGCAGCTCGCCGACCACTACCAGCAGAACACCCCCATCGGCGACGGCCCCGTGCTG
                                                           3XP3-EGFP MARKER
2400
CTGCCCGACAACCACTACCTGAGCACCCAGTCCGCCCTGAGCAAAGACCCCAACGAGAAGCGCGATCACATGGTCCTGCTGGAGTTCGTGACCGCCGCCG
                                                           3XP3-EGFP MARKER
2500
GGATCACTCTCGGCATGGACGAGCTGTACAAGTAAAGCGGCCGACTCTAGATCATAATCAGCCATACCACATTTGTAGAGGTTTTACTTGCTTTAAAA
                                                           3XP3-EGFP MARKER
2600
AACCTCCCACACCTCCCCCTGAACCTGAAACATAAAATGAATGCAATTGTTGTTGTTAACTTGTTTATTGCAGCTTATAATGGTTACAAATAAAGCAATA
                                                           3XP3-EGFP MARKER
2700
GCATCACAAATTTCACAAATAAAGCATTTTTTCACTGCATTCTAGTTGTGGTTTGTCCAAACTCATCAATGTATCTTAAAGCTTATCGATACCGTCACG
                                                           3XP3-EGFP MARKER
2800
GCGCGCCTAGACTAGTTCTAGAGCGGCCGCCACCGGGTGGAGCTCCAGCTTTTGTTCCCTTTAGTGAGGGTTAATTTCGAGCTTGGCGTAATCATGGTC
2900
ATAGCTGTTTCCTGTGTGAAATTGTTATCCGCTCACAATTCCACACAACATACGAGCCGGAAGCATAAAGTGTAAAGCCTGGGGTGCCTAATGAGTGAGC
3000
TAACTCACATTAATTGCGTTGCGCTCACTGCCCGCTTTCCAGTCGGGAAACCTGTCGTGCCAGCTGCATTAATGAATCGGCCAACGCGCGGGGAGAGGCG
```

*FIG. 19(B) CONT.*

>ColE1_origin

3100 GTTTGCGTATTGGGCGCTCTTCCGCTTCCTCGCTCACTGACTCGCTGCGCTCGGTCGTTCGGCTGCGGCGAGCGGTATCAGCTCACTCAAAGGCGGTAAT

3200 ACGGTTATCCACAGAATCAGGGGATAACGCAGGAAAGAACATGTGAGCAAAAGGCCAGCAAAAGGCCAGGAACCGTAAAAAGGCCGCGTTGCTGGCGTTT

3300 TTCCATAGGCTCCGCCCCCCTGACGAGCATCACAAAAATCGACGCTCAAGTCAGAGGTGGCGAAACCCGACAGGACTATAAAGATACCAGGCGTTTCCCC

3400 CTGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCTC

3500 ACGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAAC

3600 TATCGTCTTGAGTCCAACCCGGTAAGACAGGACTTATCGCCACTGGCAGCAGCCACTGGTAACAGGATTAGCAGAGCGAGGTATGTAGGCGGTGCTACAG

3700 AGTTCTTGAAGTGGTGGCCTAACTACGGCTACACTAGAAGGACAGTATTTGGTATCTGCGCTCTGCTGAAGCCAGTTACCTTCGGAAAAAGAGTTGGTAG

3800 CTCTTGATCCGGCAAACAAACCACCGCTGGTAGCGGTGGTTTTTTTGTTTGCAAGCAGCAGATTACGCGCAGAAAAAAGGATCTCAAGAAGATCCTTTG

3900 ATCTTTTCTACGGGGTCTGACGCTCAGTGGAACGAAAACTCACGTTAAGGGATTTTGGTCATGAGATTATCAAAAAGGATCTTCACCTAGATCCTTTTAA

4000 ATTAAAAATGAAGTTTTAAATCAATCTAAAGTATATATGAGTAAACTTGGTCTGACAGTTACCAATGCTTAATCAGTGAGGCACCTATCTCAGCGATCTG
                                                                              AMPCILLIN RESISTANCE

4100 TCTATTTCGTTCATCCATAGTTGCCTGACTCCCCGTCGTGTAGATAACTACGATACGGGAGGGCTTACCATCTGGCCCCAGTGCTGCAATGATACCGCGA
                                                          AMPCILLIN RESISTANCE

FIG. 19(B) CONT.

```
4200
GACCCACGCGCTCACCGGCTCCAGATTTATCAGCAATAAACCAGCCAGCCGGAAGGGCCGAGCCGCAGAAGTGTCCTGCAACTTTATCCGCCTCCATCCAGT
                                            AMPCILLIN RESISTANCE
4300
CTATTAATTGTTGCCGGGAAGCTAGAGTAAGTAGTTCGCCAGTTAATAGTTTGCGCAACGTTGTTGCCATTGCTACAGGCATCGTGGTGTCACGCTCGTC
                                            AMPCILLIN RESISTANCE
4400
GTTTGGTATGGCTTCATTCAGCTCCGGTTCCCAACGATCAAGGCGAGTTACATGATCCCCATGTTGTGCAAAAAAGCGGTTAGCTCCTTCGGTCCTCCG
                                            AMPCILLIN RESISTANCE
4500
ATCGTTGTCAGAAGTAAGTTGGCCGCAGTGTTATCACTCATGGTTATGGCAGCACTGCATAATTCTCTTACTGTCATGCCATCCGTAAGATGCTTTTCTG
                                            AMPCILLIN RESISTANCE
4600
TGACTGGTGAGTACTCAACCAAGTCATTCTGAGAATAGTGTATGCGGCGACCGAGTTGCTCTTGCCCGGCGTCAATACGGATAATACCGCGCCACATAG
                                            AMPCILLIN RESISTANCE
4700
CAGAACTTTAAAAGTGCTCATCATTGGAAAACGTTCTTCGGGGCGAAAACTCTCAAGGATCTTACCGCTGTTGAGATCCAGTTCGATGTAACCCACTCGT
                                            AMPCILLIN RESISTANCE
4800
GCACCCCAACTGATCTTCAGCATCTTTTACTTTCACCAGCGTTTCTGGGTGAGCAAAAACAGGAAGGCAAAATGCCGCAAAAAAGGGAATAAGGGCGACAC
                                            AMPCILLIN RESISTANCE
4900
GGAAATGTTGAATACTCATACTCTTCCTTTTTCAATATTATTGAAGCATTTATCAGGGTTATTGTCTCATGAGCGGATACATATTTGAATGTATTTAGAA
      AMPCILLIN RESISTANCE          >

AAATAAACAAATAGGGGTTCCGCGCACATTTCCCCGAAAAGTGC --(SEQ ID NO:55)--
```

*FIG. 19(B) CONT.* pBS-ITR-EYFP
Sequence Range: 1 to 4944

100
CACCTGACGCGCCCTGTAGCGCGCACATTAAGCGCGGCGGGTGTGGTGGTTACGCGCAGCGTGACCGCTACACTTGCCAGCGCCCTAGCGCCCGCTCCTTT

200
CGCTTTCTTCCCTTCCTTTCTCGCCACGTTCGCCGGCTTTCCCCGTCAAGCTCTAAATCGGGGGCTCCCTTTAGGGTTCCGATTTAGTGCTTTACGGCAC

300
CTCGACCCCAAAAAACTTGATTAGGGTGATGGTTCACGTAGTGGGCCATCGCCCTGATAGACGGTTTTTCGCCCTTTGACGTTGGAGTCCACGTTCTTTA

400
ATAGTGGACTCTTGTTCCAAACTGGAACAACACTCAACCCTATCTCGGTCTATTCTTTGATTTATAAGGGATTTTGCCGATTTCGGCCTATTGGTTAAA

500
AAATGAGCTGATTTAACAAAAATTTAACGCGAATTTTAACGCTTACAATTTCCATTCGCCATTCAGGCTGCGCAACTGTTGGGAAGGGC

600
GATCGGTGCGGGCCTCTTCGCTATTACGCCAGCTGGCGAAAGGGGGATGTGCTGCAAGGCGATTAAGTTGGGTAACGCCAGGGTTTTCCCAGTCACGACG

700
TTGTAAAACGACGGCCAGTGAATTGTAATACGACTCACTATAGGGCGAATTGGGTACCGGGCCCCCCCTCGAGGTCGACGGTATCGATAAGCTTGATATC

800
GAATTCCTGCAGCCCGGGATCCACTAGTTCTAGAGCGGCCGCCACCGCGGTGGAGCTCCAGCTTTTGTTCCCTTTAGTGAGGGTTAATCTAGCTGCATCAGGATCATATCGTCGGGTCTTTTT
     RIGHT TERMINAL REPEAT   →

900
CCGGCTCAGTCATCGCCCAAGCTGGCGCTATCGGTCGGGAGGAAGAAGCCCGTGCCTTTCCCGAGGTTGAAGCGCATGGAAAGAGTTTGCC

1000
GAGGATGACTGCTGCTGCATTGACGTTGAGCGAAAACGCACGTTTAAGCGGTGTGGCCATGCACGCCTTTAAGGTGAACTGTTCG

1100
TTCAGGCCACCTGGGATACCAGTTCGTCGCGGCTTTTCCGGACAGTTCCGGATGGTCAGCGGACGATGTCAGCAACCCGAAGCGCATCAGCAACATACCGGCGACAG

FIG. 20(B)

```
1200
CCGGAACTGCCGTGCCGGTGTGCAGATTAATGACAGCGGTGCGGGCGCTGGGATATTACGTCAGCGAGGAGGACGGGTATCCTGCTGGATGCCGCAGAAATGG
1300
ACATGGATACCCCGTGAGTTACCCGGCGCTCGTTCATTCACGTTTTTGAACCGGTGCAAATGTGTTTACAGCGTGA
1400
TGGAGCAGATGAAGAGATGCTCGACACGCTCAGAACACGCTAGATTAACCCTAGAAAGATATAATCATATTGTGACGTACGTTAAAGATAATCATGCGTA
                                                                      LEFT TERMINAL REPEAT
1500
AAATTGACGCATGGATCCACTAGTTGTTCCCACAATGGTTAATTCGAGCTCGCCCGGGATCTAATTCAATTAGAGACTAATTCAATTAGAGCTAATTCA
        >                                                                                   >
                                                                                3XP3-EYFP MARKER
1600
ATTAGGATCCAAGCTTATCGATTTCGAACCCTCGACCGCCGGAGTATAAATAGAGGCGCTTCGTCTACGGAGCGACAATTCAATTCAAACAAGCAAAGTG
                                                                3XP3-EYFP MARKER                >
1700
AACACGTCGCTAAGCGAAAGCTAAGCAAATAAACAAGCTGAACAAGCTGACAAGCTAAACAATCGGGGTACCGCTAGAGTCGACGATCCACCGGTCGC
                                                        3XP3-EYFP MARKER                      >
1800
CACCATGGTGAGCAAGGGCGAGGAGCTGTTCACCGGGGTGGTGCCCATCCTGGTCGAGCTGGACGGCGACGTAAACGGCCACAAGTTCAGCGTGTCCGGC
                                                3XP3-EYFP MARKER                              >
1900
GAGGGCGAGGGCGATGCCACCTACGGCAAGCTGACCCTGAAGTTCATCTGCACCACCGGCAAGCTGCCCGTGCCCTGGCCCACCCTCGTGACCACCTTCG
                                        3XP3-EYFP MARKER                                      >
2000
GCTACGGCCTGCAGTGCTTCGCCCGCTACCCCGACCACATGAAGCAGCACGACTTCTTCAAGTCCGCCATGCCCGAAGGCTACGTCCAGGAGCGCACCAT
                                        3XP3-EYFP MARKER                                      >
2100
CTTCTTCAAGGACGACGGCAACTACAAGACCCGCGCCGAGGTGAAGTTCGAGGGCGACACCCTGGTGAACCGCATCGAGCTGAAGGGCATCGACTTCAAG
                        3XP3-EYFP MARKER                                                       >
```

*FIG. 20(B) CONT.*

2200
GAGGACGGCAACATCCTGGGGCACAAGCTGGAGTACAACTACACAACAGCCACAACGTCTATATCATGGCCGACAAGCAGAAGAACGGCATCAAGGTGAACT
                                                         3XP3-EYFP MARKER                                >

2300
TCAAGATCCGCCACAACATCGAGGACGGCAGCGTGCAGCTCGCCGACCACTACCAGCAGAACACCCCCATCGGCGACGGCCCCGTGCTGCTGCCCGACAA
                                                         3XP3-EYFP MARKER                                >

2400
CCACTACCTGAGCTACCAGTCCGCCCTGAGCAAAGACCCCAACGAGAAGCGCGATCACATGGTCCTGCTGGAGTTCGTGACCGCCGCCGGGATCACTCTC
                                                         3XP3-EYFP MARKER                                >

2500
GGCATGGACGAGCTGTACAAGTAAAGCGGCCGCGACTCTAGATCATAATCAGCCATACCACACATTTGTAGAGGTTTTACTTGCTTTAAAAAACCTCCCACA
                                                         3XP3-EYFP MARKER                                >

2600
CCTCCCCCCTGAACCTGAAACATAAAATGAATGCAATTGTTGTTGTTAACTTGTTTATTGCAGCTTATAATGGTTACAAATAAAGCAATAGCATCACAAAT
                                                         3XP3-EYFP MARKER                                >

2700
TTCACAAATAAAGCATTTTTTCACTGCATTCTAGTTGTTGGTTTGTCCAAACTCATCAATGTATCTTAAAGCTTATCGATACGGCGTACGGCGGCCTAGG
                                                         3XP3-EYFP MARKER                                >

2800
CCGGGCCGATCACTAGTTCTAGAGCGGCCGCCACCGCGGTGGAGCTCCAGCTTTTGTTCCCTTTAGTGAGGGTTAATTTCGAGCTTGGCGTAATCATGGTC
                                                         >

2900
ATAGCTGTTTCCTGTGTGAAATTGTTATCCGCTCACAATTCCACACAACATACGAGCCGGAAGCATAAAGTGTAAAGCCTGGGGTGCCTAATGAGTGAGC

3000
TAACTCACATTAATTGCGTTGCGCTCACTGCCCGCTTTCCAGTCGGGAAACCTGTCGTGCCAGCTGCATTAATGAATCGGCCAACGCGCGGGGAGAGGCG

FIG. 20(B) CONT.

>ColE1_origin

3100
GTTTGCGGTATTGGGCGCTCTTCCGCTTCCTCGCTCACTGACTCGCTGCGCTCGGTCGTTCGGCTGCGGCGAGCGGTATCAGCTCACTCAAAGGCGGTAAT

3200
ACGGTTATCCACAGAATCAGGGGATAACGCAGGAAAGAACATGTGAGCAAAAGGCCAGCAAAAGGCCAGGAACCGTAAAAAGGCCGCGTTGCTGGCGTTT

3300
TTCCATAGGCTCCGCCCCCCTGACGAGCATCACAAAAATCGACGCTCAAGTCAGAGGTGGGCGAAACCCGACAGGACTATAAAGATACCAGGCGTTTCCCC

3400
CTGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCTC

3500
ACGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAAC

3600
TATCGTCTTGAGTCCAACCCGGTAAGACACGACTTATCGCCACTGGCAGCAGCCACTGGTAACAGGATTAGCAGAGCGAGGTATGTAGGCGGTGCTACAG

3700
AGTTCTTGAAGTGGTGGCCTAACTACGGCTACACTAGAAGGACAGTATTTGGTATCTGCGCTCTGCTGAAGCCAGTTACCTTCGGAAAAAGAGTTGGTAG

3800
CTCTTGATCCGGCAAACAAACCACCGCTGGTAGCGGTGGTTTTTTTGTTTGCAAGCAGCAGATTACGCGCAGAAAAAAAGGATCTCAAGAAGATCCTTTG

3900
ATCTTTTCTACGGGGTCTGACGCTCAGTGGAACGAAAACTCACGTTAAGGGATTTTGGTCATGAGATTATCAAAAAGGATCTTCACCTAGATCCTTTTAA

4000
ATTAAAAATGAAGTTTTAAATCAATCTAAAGTATATATGAGTAAACTTGGTCTGACAGTTACCAATGCTTAATCAGTGAGGCACCTATCTCAGCGATCTG
                                                                                AMPCILLIN RESISTANCE

4100
TCTATTTCGTTCATCCATAGTTGCCTGACTCCCCGTCGTGTAGATAACTACGATACGGGAGGGCTTACCATCTGGCCCCAGTGCTGCAATGATACCGCGA
AMPCILLIN RESISTANCE

*FIG. 20(B) CONT.*

4200
GACCCACGCTCACCGGCTCTCCAGATTTATCAGCAATAAACCAGCCAGCCGGAAGGGCCGAGCCGCAGAAGTGGTCCTGCAACTTTATCCGCCTCCATCCAGT
    AMPCILLIN RESISTANCE

4300
CTATTAATTGTTGCCGGGAAGCTAGAGTAAGTAGTTCGCCAGTTAATAGTTTGCGCAACGTTGTTGCCATTGCTACAGGCATCGTGGTGTCACGCTCGTC
    AMPCILLIN RESISTANCE

4400
GTTTGGTATGGCTTCATTCAGCTCCGGTTCCCAACGATCAAGGCGAGTTACATGATCCCCCATGTTGTGCAAAAAAGCGGTTAGCTCCTTCGGTCCTCCG
    AMPCILLIN RESISTANCE

4500
ATCGTTGTCAGAAGTAAGTTGGCCGCAGTGTTATCACTCATGTTATGGCAGCACTGCATAATTCTCTTACTGTCATGCCATCCGTAAGATGCTTTTCTG
    AMPCILLIN RESISTANCE

4600
TGACTGGTGAGTACTCAACCAAGTCATTCTGAGAATAGTGTATGCGGCGACCGAGTTGCTCTTGCCCGGCGTCAATACGGGATAATACCGCGCCACATAG
    AMPCILLIN RESISTANCE

4700
CAGAACTTTAAAAGTGCTCATCATTGGAAAACGTTCTTCGGGGCGAAAACTCTCAAGGATCTTACCGCTGTTGAGATCCAGTTCGATGTAACCCACTCGT
    AMPCILLIN RESISTANCE

4800
GCACCCAACTGATCTTCAGCATCTTTTACTTTCACCAGCGTTTCTGGGTGAGCAAAAACAGGAAGGCAAAATGCCGCAAAAAAGGGAATAAGGGCGACAC
    AMPCILLIN RESISTANCE

4900
GGAAATGTTGAATACTCATATACTCTTCCTTTTTCAATATTATTGAAGCATTATCAGGGTTATTGTCTCATGAGCGGATACATATTTGAATGTATTTAGAA
    AMPCILLIN RESISTANCE

AAATAAACAAATAGGGGTTCCGCGCACATTTCCCCGAAAAGTGC--(SEQ ID NO:56)--

*FIG. 20(B) CONT.* pBSII-Act5c-orf
Sequence Range: 1 to 7411

```
100
CTAAATTGTAAGCGTTAATATTTTGTTAAATTTTGTTAAATTCGCGTTAAATTCAGCTCATTTTTAACCAATAGGCCGAAATCGGCAAAATCCCTTAT
200
AAATCAAAGAATAGACCGAGATAGGGTTGAGTGTTGTTCCAGTTTGGAACAAGAGTCCACTATTAAAGAACGTGGACTCCAACGTCAAAGGGCGAAAAA
300
CCGTCTATCAGGGCGATGGCCCACTACGTGAACCATCACCCTAATCAAGTTTTTTGGGGTCGAGGTGCCGTAAAGCACTAAATCGGAACCCTAAAGGGAG
400
CCCCCGATTTAGAGCTTGACGGGGAAAGCCGGTCCAACTGGCGAACGTGGGCGCTAGGGCGCTGGCAAGTGTAGCG
500
GTCACGCTGCGCGTAACCACCACACCCGGCGTTAATGCCGCGCTACAGGGCGCGTCCCATTCGCCATTCAGGCTGCCAACTGTTGGGAAGGGCGAT
600
CGGTGCGGGCCTCTTCGCTATTACGCCAGCTGGCGAAAGGGGATGTGCTGCAAGGCGATTAAGTTGGGTAACGCCAGGGTTTTCCCAGTCACGACGTTG
700
TAAAACGACGGCCAGTGAGCGCGCGTAATACGACTCACTATAGGGCGAATTGGGTACCGGGCCCCCCCTCGAGGTCGACGGTATCGATAAGCTTGATATC
800
GAATTCTAAAAAAAATCATGAATGGCATCAACTCTGAATCAAATCTTTGCAGATGCACCTACTTCTCATTTCCACTGTCACATCATTTTCCAGATCTCG
                                                ACTIN 5C PROMOTER
900
CTGCCTGTTATGTGGCCCACAAACCAAGACACGTTTTATGGCCATTAAAGCTGGCTGATCGTCGCCAAACACCAAATACATATCAATATGTACATTCGAG
   ACTIN 5C PROMOTER
1000
AAAGAAGCGATCAAAGAAGCGTCTCGGGCGAGTAGGAGAATGCGGAGGAGAAGGAGAACGAGCTGATCTAGTATCTCTCCACAATCCAATGCCAACTGA
   ACTIN 5C PROMOTER
```

FIG. 21(B)

```
1100
CCAACTGGCCATATATTCGGAGCAATTTGAAGCCAATTTCCATCGGCCTGGCGATCGCTCCATTCTTGGCTATATGTTTTCACCGTTCCCGGGGCCATTTTC
                                                         ACTIN 5C PROMOTER

1200
AAAGACTCGTCGGTAAGATAAGATTGTGTCACTCGCTGTCTCTTCATTTGTCGAAGAATGCTGAGGAATTCGCGATGACGTCGGCGAGTATTTGAA
                                             ACTIN 5C PROMOTER

1300
GAATGAGAATAATTTGTATTTATACGAAAATCAGTTAGTGGAATTTCTACAAAAACATGTTATCTATAGATAATTTTGTTGCAAAATATGTTGACTATG
                                         ACTIN 5C PROMOTER

1400
ACAAAGATTGTATGTATATACCTTTAATGTATTCTCATTTTCTTATGTATTATAAATGGCAATGATGATACTGATGATATTTAAGATGATGCCAGACCA
                                         ACTIN 5C PROMOTER

1500
CAGGCTGATTTCTCGCGTCTTTTGCCGAACGCAGTGCATGTGCGGTTGTGTTTTTGAATAGTTTCAATTTTCGGACTGTCCGCTTTGATTTCAGTTTC
                                         ACTIN 5C PROMOTER

1600
TTGGCTTATTCAAAAAGCAAAGTAAAGCCAAATACCAAATGCGGCAATACCAAATGCGGCAAAACGTAGTGGAAGGAAAGGGGTGCGGGGCAGCGGAAG
                                         ACTIN 5C PROMOTER

1700
GAAGGGTGGGGCGGGGCCTGTGGGCTCTGTGGCTGCGGCGACGTTGAGCCCACTCCTTTGACCATGTGTGCGTGTGTATTATTCGTG
                                     ACTIN 5C PROMOTER

1800
TCTCGCCACTCGCCGGTTGTTTTTTCTTTTTATCGCTCTCTCTAGCGCCATCTCGTACGCATGCTCAACGCACCGCATGTTGCCGTGTCCTTTATGC
                                     ACTIN 5C PROMOTER

1900
GTCATTTTGGCTCGAAATAGGCAATTATTAAACAAAGATTAGTCAACGAAAACGCTAAAATAAGTCTACAATATGGTTACTTATTGCCATGTGTG
                                     ACTIN 5C PROMOTER
```

*FIG. 21(B) CONT.*

```
2000
TGCAGCCAACGATAGCAACAAAAGCAACAACACAGTGGCTTTCCCCTCTTTCACTTTTGTTTGCAAGCGCGTGCGAGCAAGACGGCACGACCGGCAAACG
                                   ACTIN 5C PROMOTER

2100
CAATTACGCTGACAAAGAGCAGACGAAGTTTTGGCCGAAAAACATCAAGGCGCCTGATACGCATTTGCAATAACAATTGCGATATTTAATATTGTT
                                   ACTIN 5C PROMOTER

2200
TATGAAGCTGTTTGACTTCAAAACACACAAAAAAAAAAATAAAACAAATTATTTGAAAGAGAATTAGGAATCGGACAGCTTATCGTTACGGGCTAACAGC
                                   ACTIN 5C PROMOTER

2300
ACACCGAGACGAAATAGCTTACCTGACGTCACAGCCTCTGGAAGAACTGCCCGCCAAGCAGACGATGCAGAGGACGACATAGAGTAGCGGAGTAGGCCA
                                   ACTIN 5C PROMOTER

2400
GCGTAGTACGCCATGTGCTTGTGTGTGAGGCGTCTCTCTCTCTTCCGTCTCCTGTTGGCCAAACGCATAGACTGCACTGAGAAAATCGATTACCTATTTTTA
                                   ACTIN 5C PROMOTER

2500
TGAATGAATATTTGCACTATTACTATTCAAAACTATTAAGATAGCAATCACATTCAATAGCCAAATACTATACCACCTGAGCGATGCAACGAAATGATCA
                                   ACTIN 5C PROMOTER

2600
ATTTGAGCAAAAATGCTGCATATTAGGACGGCATCATTATAGAAATGCTTCTTGCTGTGTACTTTTCTCTCGTTGGCAGCTGTTTCGCCGTTATTGTT
                                   ACTIN 5C PROMOTER

2700
AAAACCGGCTTAAGTTAGGTGTGTTTTCTACGACTAGTGATGCCCCTACTAGAAGATGTGTTGTTGCACAAATGTCCCTGAATAACCAATTTGAAGTGCAG
                                   ACTIN 5C PROMOTER

2800
ATAGCAGTGTAAACGTAAGCTAATAATTGTTTAATGTTTTAATATCGCTGGACATTACTAATAAACCCACTATAAACACATGTACATATGT
                                   ACTIN 5C PROMOTER
```

*FIG. 21(B) CONT.*

```
2900
ATGTTTTGGCATACAATGAGTAGTTGGGGAAAAAAATGTGTAAAAGCACCGTGACCATCACAGCATAAAGATAACCAGCTGAAGTATCGAATATGAGTAAC
                                                        ──────────────────────────────────────────────>
                                                                    ACTIN 5C PROMOTER

3000
CCCCAAATTGAATCACATGCCGCAACTGATAGAGACCCATGAAGTACACTCTTCATGGCGATATACAAGACACACAAGCACGAACACCCAGTTGCGGA
──────────────────────────────────────────────────────────────────────────────────────────────────>
                ACTIN 5C PROMOTER
                                            >CCATATATGG_element
                                             ┬─────────
                                             │
3100
GGAAATTCTCCGTAAATGAAAACCCAATTCATACCCATATATGTAAAAGTTTTGAACGCGACTTGAGAGCGGAGAGCATTGCGGCTGA
────────────────────────────────────────────────────────────────────────────────────────>
              ACTIN 5C PROMOTER
     >TATA-box
      ┬──────
      │
3200
TAAGGTTTTAGCGCTAAGCGGGCTTTATAAAACGGGCCTTTATAAAACGGGCTGCCGGGACCAGTTTCATATCGGATCCTATATAATAAATGGGTAGTTCTTTAGACGATGAGC
─────────────────────                                                          ────────────────────────────────>
  ACTIN 5C PROMOTER                                                                  IFP2 ORF BAMHI CARTRIDGE 3300
ATATCCTCTCTGCTCTTCTCTGCAAAGCGACGATGACGAGCTTGTTGGTGAGGATTCTGACAGTGAAATATCAGATCGAAATCACGTAAGTGAAGATGAGTCCAGAGCGA
──────────────────────────────────────────────────────────────────────────────────────────────────────────────>
                                          IFP2 ORF BAMHI CARTRIDGE 3400
TACAGAAGAAGCGTTTATAGATGAGGTACATGAAGTCAAGCGTAGTGAAGCGGTAGTGAAATATTAGACGAACAAAATGTTATTGAACAACCAGTTCT
─────────────────────────────────────────────────────────────────────────────────────────────────>
                                        IFP2 ORF BAMHI CARTRIDGE 3500
TCATTGGCTTCTAACAGAATCTTGACCTTGCCACAGAGACTATTAGAGAGGTAAGAATAAACATTGTTGGTCAACTTCAAAGTCCACGAGAGGCGTAGCCGAG
────────────────────────────────────────────────────────────────────────────────────────────────────>
                                        IFP2 ORF BAMHI CARTRIDGE
```

*FIG. 21(B) CONT.*

```
3600
TCTCTGCACTGAACATTGTCAGATCTCAAAGAGGTCCGACGCGTATGTGCCGCAATATATGACCCACTTTTATGCTTCAAACTATTTTTACTGATGA
     IFP2 ORF BAMHI CARTRIDGE

3700
GATAATTTCGGAAATTGTAAAATGGACAAATGCTGAGATATCATTCAAACGTCGGGAATCTATGACAGGTGCTACATTCGTGACACGAATGAAGATGAA
     IFP2 ORF BAMHI CARTRIDGE

3800
ATCTATGCTTTCTTTGGTATTCTCGGTAATGACAGCAGTGAGAAAAGATAACCACATGTCCACAGATGACCTCTTTGATCGATCTTTGTCAATGGTGTACG
     IFP2 ORF BAMHI CARTRIDGE

3900
TCTCTGTAATGAGTCGTGATCGTTTTGATTTTTTGATACGATGTCTTAGAATGGATGACAAAAGTATACGGCCCACACTTCGAGAAAACGATGTATTTAC
     IFP2 ORF BAMHI CARTRIDGE

4000
TCCTGTTAGAAAAAATATGGGATCTCTCTTTATCCATACAGTGCATACAAAATTACACTCCAGGGGCTCATTTGACCATAGATGAACAGTTACTTGGTTTTAGA
     IFP2 ORF BAMHI CARTRIDGE

4100
GGACGGTGTCCGTTTAGGATGTATATCCCAAACAAGCCAAGTAAGTATGGAATAAAATCCTCATGATGTGTGACAGTGGTACGAAGTATATGATAAATG
     IFP2 ORF BAMHI CARTRIDGE

4200
GAATGCCTTATTTGGGAAGAGGAACACAGACCAACGGAGTACCACTCGGTGAATACTACGTGAAGGAGTTATCAAAGCCTGTGCACGGTAGTTGTCGTAA
     IFP2 ORF BAMHI CARTRIDGE

4300
TATTACGTGTGACAATTGGTTCACCTCAATCCCTTTGGCAAAAAACTTACTACAAGAACCGTATAAGTTAACCATTGTGGGAACCGTGCGATCAAACAAA
     IFP2 ORF BAMHI CARTRIDGE

4400
CGCGAGATACCGGAAGTACTGAAAAACAGTCGCTCCAGGCCAGTGGGAACATCGATGTTTTGTTTTGACGGACCCCTTACTCTCGTCTCATATAAACCGA
     IFP2 ORF BAMHI CARTRIDGE
```

*FIG. 21(B) CONT.*

4500
AGCCAGCTAAGATGGTATACTTATTATCATCTTGTGATGAGGATGCTTCTATCAACGAAAGTACCGGTAAACCGCAAATGTTATGTATTATAATCAAAC
         IFP2 ORF BAMHI CARTRIDGE                                                                   >

4600
TAAAGGCGGAGTGGACACGCTAGACCAACAAATGTGTTCTGTGATGACCTGCAGTAGGAAGACGAATAGTGGCCTATGGCATTATTGTACGGAATGATAAAC
         IFP2 ORF BAMHI CARTRIDGE                                                                   >

4700
ATTGCCTGCATAAATTCTTTTATTATATACAGCCATATAATGTCAGTAGCAAGGGAGAAAAAGTTCAAAGTCGCAAAAAATTTATGAGAAACCTTTACATGA
         IFP2 ORF BAMHI CARTRIDGE                                                                   >

4800
GCCTGAGCGTCATCGTTATGCGTAAGCGTTTAGAAGCTCCTACTTTGAAGAGATATTTGCGCGATAATATCTCTAATATTTTGCCAAATGAAGTGCCTGG
         IFP2 ORF BAMHI CARTRIDGE                                                                   >

4900
TACATCAGATGACAGTACTGAAGAGCCAGTAATGAAAAAACGTACTTACTGTACTGCCCCTCTAAAATAAGGCGAAAGGCAAATGCATCGTGCAAA
         IFP2 ORF BAMHI CARTRIDGE                                                                   >

5000
AAATGCAAAAAAGTTATTTGTCGAGAGCATATATTGATATGTGCCAAAGTTGTTTCTGACTGACTAATAAGTATAATTGTTCTATTATGTATAAGTT
         IFP2 ORF BAMHI CARTRIDGE                                                                   >

5100
AAGCTAATTACTTATTTTATAATACAACATGACTGTTTTTAAAGTACAAAATAAGTTTATTTTGTAAAAGAGAGAATGTTTAAAAGTTTTTGTTACTTTA
         IFP2 ORF BAMHI CARTRIDGE                                                                   >

5200
GAAGAAATTTGAGTTTTGTTTGTTTTTTTTAATAAATAAACATAAATAAATTGTTTTGTTGAATTTGGATCCACTAGTTCTAGAGCGGCCGCCACCGC
         IFP2 ORF BAMHI CARTRIDGE                          >

5300
GGTGGAGCTCCAGCTTTGTCCCTTTAGTGAGGGTTAATTGCGCGCTTGGCGTAATCATGGTCATAGCTGTTTCCTGTGTGAAATTGTTATCCGCTCAC

FIG. 21(B) CONT.

```
5400
AATTCCACACAACATACGAGCCGGAAGCATAAAGTGTAAAGCCTGGGGTGCCTAATGAGTGAGCTAACTCACATTAATTGCGTTGCGCTCACTGCCCGCT
5500
TTCCAGTCGGGAAACCTGTCGTGCCAGCTGCATTAATGAATCGGCCAACGCGCGGGGAGAGGCGGTTTGCGTATTGGGCGCTCTTCCGCTTCCTCGCTCA
5600
CTGACTCGCTGCGCTCGGTCGTTCGGCTGCGGCGAGCGGTATCAGCTCACTCAAAGGCGGTAATACGGTTATCCACAGAATCAGGGGATAACGCAGGAAA
5700
GAACATGTGAGCAAAAGGCCAGCAAAAGGCCAGGAACCGTAAAAAGGCCGCGTTGCTGGCGTTTTTCCATAGGCTCCGCCCCCCTGACGAGCATCACAAA
5800
AATCGACGCTCAAGTCAGAGGTGGCGAAACCCGACAGGACTATAAAGATACCAGGCGTTTCCCCCTGGAAGCTCCCTCGTGCGCTCTCCTGTTCCGACCC
5900
TGCCGCTTACCGGATACCTGTCCGCCTTTCTCCCTTCGGGAAGCGTGGCGCTTTCTCATAGCTCACGCTGTAGGTATCTCAGTTCGGTGTAGGTCGTTCG
6000
CTCCAAGCTGGGCTGTGTGCACGAACCCCCCGTTCAGCCCGACCGCTGCGCCTTATCCGGTAACTATCGTCTTGAGTCCAACCCGGTAAGACACGACTTA
6100
TCGCCACTGGCAGCAGCCACTGGTAACAGGATTAGCAGAGCGAGGTATGTAGGCGGTGCTACAGAGTTCTTGAAGTGGTGGCCTAACTACGGCTACACTA
6200
GAAGGACAGTATTTGGTATCTGCGCTCTGCTGAAGCCAGTTACCTTCGGAAAAAGAGTTGGTAGCTCTTGATCCGGCAAACAAACCACCGCTGGTAGCGG
6300
TGGTTTTTTTGTTTGCAAGCAGCAGATTACGCGCAGAAAAAAAGGATCTCAAGAAGATCCTTTGATCTTTTCTACGGGGTCTGACGCTCAGTGGAACGAA
6400
AACTCACGTTAAGGGATTTTGGTCATGAGATTATCAAAAAGGATCTTCACCTAGATCCTTTTAAATTAAAAATGAAGTTTTAAATCAATCTAAAGTATAT
6500
ATGAGTAAACTTGGTCTGACAGTTACCAATGCTTAATCAGTGAGGCACCTATCTCAGCGATCTGTCTATTTCGTTCATCCATAGTTGCCTGACTCCCCGT
```

*FIG. 21(B) CONT.*

6600
CGTGTAGATAACTACGATACGGGAGGGCTTACCATCTGGCCCCAGTGCTGCTGCAATGATACGGCGAGACCCACGCTCACCGGCTCCAGATTTATCAGCAATA
6700
AACCAGCCGAGCCGGAAGGGCCGAGCGCGAGAAGTGGTCCTGCAACTTTATCCGCCTCCATCCAGTCTATTAATTGTTGCCGGGAAGCTAGAGTAAGTAGTT
6800
CGCCAGTTAATAGTTTGCGCAACGTTGTTGCCATTGCTACAGGCATCGTGGTGTCACGCTCGTCGTTTGTGTATGGCTTCATTCAGCTCCGGTTCCCAACG
6900
ATCAAGGCGAGTTACATGATCCCCATGTTGTGCAAAAAAGCGGTTAGCTCCTTCGGTCCTCCGATCGTTGTCAGAAGTAAGTGGCCCAGTGTTATCA
7000
CTCATGGTTATGCAGCACTGCATAATTCTCTTACTGTCATGCCATCCGTAAGATGCTTTCTGTGACTGGTGAGTACTCAACCAAGTCATTCTGAGAAT
7100
AGTGTATGCGGGGCGACCGAGTTGCTCTTGCCCGGGTCAATACGGCGATAATACCGGTTCGATGTAACCCACTCGTGCACCCAACTGATCTTCAGCATCTTTACTTTCACC
7200
TTCGGGGCGAAACTCTCAAGGATCTTACCGCTGTGTGAGATCCAGTTCGATGTAACCCACTCGTGCACCCAACTGATCTTCAGCATCTTTACTTTCACC
7300
AGCGTTTCTGGGTGAGCAAAAACAGGAAGGCAAATGCCGCAAAAAAGGGAATAAGGCGACACGGAAATGTTGAATACTCATACTCTTCCTTTTTCAAT
7400
ATTATTGAAGCATTTATCAGGTTATTGTCTCATGAGCGGATACATATTTGAATGTATTAGAAAAATAAACAATAGGGGTTCCGCGCACATTTCCCG

AAAAGTGCCAC --(SEQ ID NO:67)--

*FIG. 21(B) CONT.*

Sequence Range: 1 to 10333

```
     100
AAGCTTGGGCTGCAGGTCGACGGATCCAAATTCAACAAACAATTTATTGTTTATTATTATTAAAAAAAAACAAAACTCAAATTTCTTCTAAAG
     200
TAACAAAACTTTAAACATTCTCTCTTTTACAAAATAAACTTATTTGTACTTAAAAACAGTCATGTTGTATTATAAAATAAGTAATTAGCTTAACTT
     300
ATACATAATAGAAACAAATTATACTTATTAGTCAGTCAGAAACAACTTGGCACATATCAATATTATGCTCTCGACAAATAACTTTTTGCATTTTTGC
                                          ∨————————————————— PIGGYBAC ORF —————————————————
     400
ACGATGCATTGCCTTTCGCCTTTATTTAGAGGGGCAGTAAGTACGTTTTTTCATTACTGGCTCTTCAGTACTGTCATCTGATGTACCAGG
     ——————————————— PIGGYBAC ORF ———————————————
     500
CACTTCATTTGGCAAAATATATTAGAGATATTATCGCGCAAATATCTTCAAAGTAGGAGCTTCTAAACGCTTACGCATAAACGATGACGTCAGGCTCATG
     ∨———————————————————————— PIGGYBAC ORF ————————————————————————
     600
TAAAGGTTTCTATAAATTTTTGCGACTTTGAACCTTTTCTCCCTTGCTACTGACATTATGGCTGTATATAATAAAAGAATTTATGCAGGCAATGTTTA
     ∨———————————————————————— PIGGYBAC ORF ————————————————————————
     700
TCATTCCGTACAATAATGCCATAGGCCACCTATTCGTCTTCCTACTGCAGTCATCACAGAACACATTGGTCTAGCGTGTCCACTCCGCCTTTAGTTTG
     ∨———————————————————————— PIGGYBAC ORF ————————————————————————
     800
ATTATAATACATAACCATTGCGGTTTACCGGTACTTTCGTTGATAGAAGCATCCTCATCACAAGATGATAATAAGTATACCATCTTAGCTGGCTTCGGT
     ∨———————————————————————— PIGGYBAC ORF ————————————————————————
     900
TTATATGAGACGAGAGTAAGGGTCCGTCAAAACAAAAACATCGATGTCCCACTGGCCTGGAGCGACTGTTTTCAGTACTACTTCCGTATCTCGCGTTTGT
     ∨———————————————————————— PIGGYBAC ORF ————————————————————————
```

FIG. 22

```
1000
TTGATCGGCACGGTTCCCACAATGGTTAACTTATACGGTTCTTGTAGTAAGTTTTTGCCAAAGGGATTGAGGTGAACCAATGTCACACGTAATATTACG
          PIGGYBAC ORF

1100
ACAACTACCGTGCACAGGCTTTGATAACTCCTTCACGTAGTATTCACCGAGTGGTACTCCGTTGGTCTGTGTTCCTCTTCCCAAATAAGGCATTCCATTT
          PIGGYBAC ORF

1200
ATCATATACTTCGTACCACTGTCACACATCATGAGGATTTTTTATTCCATACTTACTTGGCTTGTTGTTTGGGATATACATCCTAAACGGACACCGTCCTCTAA
          PIGGYBAC ORF

1300
AACCAAGTAACTGTTCATCTATGGTCAAATGAGCCCCCTGGAGTGTAATTTTGTATGCACTGATGATAAAGAGATCCCATATTTTTCTAACAGGAGTAAA
          PIGGYBAC ORF

1400
TACATCGTTTTCTCGAAGTGTGGGCCCGTATACTTTGTCATCCATTCTAAGACATGTATCAAAAAAATCAAAACGATCACGACTCATTACAGAGACGTAC
          PIGGYBAC ORF

1500
ACCATTGACAAAGATCGATCAAAGAGGTCATCTGTGGACATGGTTATCTTTTCTCACTGCTGTCATTACCAGAATACCAAAGAAAGCATAGATTTCAT
          PIGGYBAC ORF

1600
CTTCATTCGTGTCACGAAATGTAGCACCTGTCATAGATTCCCGACGTTTCAAATGATATCTCAGCATTGTCCATTTTACAATTCCGAAATTATCTCATC
          PIGGYBAC ORF

1700
AGTAAAAAATAGTTTGAAGCATAAAAGTGGGTCATATATATATTGCCGCACATACGCGTCGGACCTCTTTGAGATCTGACAATGTTCAGTGCAGAGACTCGG
          PIGGYBAC ORF

1800
CTACGCCCTCGTGGACTTTGAAGTTGACCAACAATGTTTATTCTTACCTCTAATAGTCCCTCTGTGGCAAGTCAAGATTCTGTTAGAAGCCAATGAAGAAC
          PIGGYBAC ORF
```

FIG. 22 CONT.

```
1900
CTGGTTGTTCAATAACATTTGTTCGTCTAATATTTCACTACCGCTTGACGTTGGCTGCACTTCATGTACCTCATCTATAAACGCTTCTTCTGTATCGCT
V————————————————————————————————————————————————————————————————————————————————————————————————
         PIGGYBAC ORF
2000
CTGGACGTCATCTTCACTTACGTGATCTGATATTTCACTGTCAGAATCCTCACCAACAAGCTCGTCATCGCTTTGCAGAAGAGCAGAGAGGATATGCTCA
V————————————————————————————————————————————————————————————————————————————————————————————————
         PIGGYBAC ORF
2100
TCGTCTAAAGAACTACCCATTTATTATATAGGATCCCCGACACCAGACCAACTGGTAATGGTAGCGACCGGCGCTCAGCTGGAATTAGGCCTTCTAGAC
V————————————
    PIGGYBAC ORF
2200
CGGGGCCGCAGATCTGTTAACGAATTCCCAATTCCCTATTCAGAGTTCTCTCTTGTATTCAATAATTACTTCTTGGCAGATTTCAGTAGTTGCAGTTGA
V————————————————————————————————————————————————————————————————————————————————————————————————
         HSP 70 PROMOTER
2300
TTTACTTGGTTGCTGGTTACTTTTTAATTGATTCACTTTAACTTGCACTTTACTGCAGATTGTTGTTAGCTTGTGCGCTTGTTTATTGCTTAGCTT
V————————————————————————————————————————————————————————————————————————————————————————————————
         HSP 70 PROMOTER
2400
TCGCTTAGCGACGTGTTCACTTTGCTTGTTGTTTGAATTGAATTGTGCGCTCCGTAGACGAAGCGCTCTATTTATACTCCGGCGCTCTTTTCGCGAACATTCGA
V————————————————————————————————————————————————————————————————————————————————————————————————
         HSP 70 PROMOTER
2500
GGCGCGCTCTCTCGAACCAACGAGAGCAGTATGCCGTTTACTGTGTGACAGAGTGAGAGAGCATTAGTGCAGAGAGGGAGACCCAAAAGAAAAGAGAGA
V————————————————————————————————————————————————————————————————————————————————————————————————
         HSP 70 PROMOTER
2600
ATAACGAATAACGGCCCAGAGAAATTTCTCGAGTTTTCTTCTGCCAAACAAATGACCTACCACAATAACCAGTTTGTTTTGGGATTCTAGGGGGATCGGGG
V————————————————————————————————————————————————————————————————————————————————————————————————
         HSP 70 PROMOTER
2700
ATCAATTCTAGTATGTATGTAAGTTAATAAAAAACATATTTTTTTATTTTTTACTGCACTGGATATCA
V—————————
```

*FIG. 22 CONT.*

2800 TTGAACTTATCTGATCAGTTTTAAATTTACTTCGATCCAAGGGTATTTGAAGTACCAGTTCTTTCGATTACCTCTCACTCAAAATGACATTCCACTCAA
2900 AGTCAGGCGCTGTTGCCTCCTTCTCTGTCCACAGAAATATGCCCGTCTCTTTCGCCGTCCGCTGCCTATCTCTTTCGCCACCGTTTGTAGCGTTACCTA
3000 GCGTCAATGTCCGCCTTCAGTTGCACTTTGTCAGGCGGTTTCGTGACGAAGCTCCAAGCGGTTTACGCCATCAATTAAACACAAAGTGCTGTGCCAAAACT
3100 CCTCTCGCTTCTTATTTTGTTTGTTTTTGAGTGATTGGGGTGGTGATTGGTTTTGGGTGGGTAAGCAGGGAAAGTGTGAAAATCCGGCAATGGGC
3200 CAAGAGGATCAGGAGCTATTAATTCGCGGAGCAGCAAACACCCATCTGCCGAGCATCTGAACAATGTGAGTAGTACATGCATACATCTTAAGTTCAC
3300 TTGATCTATAGGAACTGCAATTGCAACATCAAATTGCTGCGCGGCGTGAGAACTGCGACCCACAAAAATCCCAAACGCAATCGCACAACAAATAGTGAC
3400 ACGAAACAGATTATTCGGTAGCTGTGCTCGCTATATAAGACAATTTTAAGATCATATCATGATCAAGACATCTAAAGGCATTCATTTCGACTACATT
3500 CTTTTTTACAAAAAATATAACAACCAGATATTTTAAGCTGATCCTAGATGCACAAAAATAATAAAGTATAAACCTACTTCGTAGGATACTTCGTTTT
3600 GTTCGGGGTTAGATGAGCATAACGCTTGTAGTTGATATTTGAGATCCCCTATCATTGCAGGGTGACAGCGGGCTTCGACAGCTGCATTAACCAGG
3700 GCTTCGGGCAGGCCAAAAACTACGGCACGCTCCTGCCACCCAGCCCGGGCCTCCGGTTCAGGGAGCGGCCAACTAGCCGAGAACCTCACCTATGC
3800 CTGGCACAATATGGACATCTTTGGGGCGGTCAATCAGCCGGGCCTGGTCAACCGGACTGGGAGCGGACAACGAGCGCCGACTATTCTGCAACGAGCGACAC
3900 ATACCGGCGCCCAGGAAACATTGCTCAAGAAACGGTGAGTTCTATTCGCAGTCGGCTGATCTGTGTGAAATCTTAATAAAGGGTCCAATTACCAATTTG

*FIG. 22 CONT.*

```
4000
AAACTCAGTTTGCGGGCGTGGCCTATCGGGGCGAACTTTTGGCCGTGATGGGCGCAGTTCCGGTGCCGGAAAGACGACCCTGCTGCCTTTCGA
4100
TCGCCGCAGGGCATCCAAGTATCGCCATCCGGGATGCGACTGCTCAATGGCCAACCTGTGGACGCCAAGGAGATGCAGGCCAGTGCGCCTATGTCCAGC
4200
AGGATGACCTCTTTATCGGCTCCCTAACGGCCAGGGAACACCTGATTTTCCAGGCCATGGTGCGGATGCCACGACATCTGACCTATCGGCAGCGAGTGGC
4300
CCGCGTGGATCAGGTGATCCAGAGAGCTTTCGCTCAGCAAATGTCAGCACACGATCATCGGTGTGCCCGGCAGGGTGAAAGGTCTGTCCGGCGGAGAAAGG
4400
AAGCGTCTGCATTCGCCTCCGAGGCACTAACCGATCCGCCGCTTCTGATCTGCGATGAGCCCACCTCCAGCCGTCTGTTGAGCTCTTTGACAAGATCCTTCT
4500
TCCAGGTGCTGAAGAAGCTGTCGCAGAAGGGCAAGACCGTCATCCTGACCATTCATCAGCCGTCGACTTCTTTCCTAGTGAGTCGATGTGTTATTAAGGTATCTAGCATTA
4600
GATGGCCGAGGGCAGGTAGCTTTCTTGGGCACTCCCAGCGAAGCCGTCGACTTCTTTCCTAGTGAGTCGACTTTTACGTACAGGTGTTGGCCGTTGTGCCCGGACGG
4700
CATTACATCTCAACTCCTATCCAGCGTGGGTGCCCAGTGTCCTACCAACTACAATCCGGGACTTTTACGTACAGGTGTTGGCCGTTGTGCCCGGACGG
4800
GAGATCGAGTCCCGTGATCGGATCGCCAAGATATGCGACAATTTGCTATTAGCAAAGTAGCCCGGGATATGGAGCAGTTGTTGGCCACCAAAAATTGG
4900
AGAAGCCACTGGAGCAGCCGGGAGAATGGGTACACCTACAAGGCCACCTGGTTCATGCAGTTCCCGGGCGGTCCTGTGGCCGATCCTGGCTGTCGGTGCTCAA
5000
GGAACCACTCCTCGTAAAGTGGCGACTTATTCAGACAACGGTGAGTGTTCCAGTGGAAACAAATGATATAACGCTTACAATTCTTGAAACAAATTCGC
5100
TAGATTTTAGTTAGAATTGCCTGATTCCACACCCTTCTAGTTTTTTTCAATGAGATGTATAGTTTATAGTTTGCAGAAATAAATAAATTCATTTAA
```

FIG. 22 CONT.

```
5200 CTCGCGGAACATGTTGAAGATATGAATATTAATGAGAGATGCGAGTAACATTTTAATTTGCAGATGGTTGCCATCTTGATTGGCCTCATCTTTTTGGGCCAAC
5300 AACTCACGCAAGTGGGCGTGATGAATATCAACGGAGCCATCTCCCTCTTCCTGACCAACATGACCTTTCAAAACGTCTTTGCCACGATAAATGTAAGTCT
5400 TGTTTAGAATACATTTGCATATTAATAAATTTACTAACTTTCTAATGAATCGATTTAGTGTTCACCTCAGAGCTGCCAGTTTTTATGAGGGAGGC
5500 CCGAAGTCGACTTTATCGCTGTGACACATACTTTCTGGGCAAAACGATTGCCGAATTACCGCTTTTTCTCACAGTGCCACTGTCTTCACGGCGATTGCC
5600 TATCCCGATGATCGGACTGGGGGCCGGAGTGCTGCACTTCTTCAACTGCCTGGCGCTGGTCACTCTCTGGTGGCCAATGTGTCAACGTCCTTCGGATATCTAA
5700 TATCCTGGGCCCAGCTCCCTCGACCCTCGATGGCGCTGTCGTGGGTCCGGTTATCATACATTCCTGCTCTTGGCGGCTTCTTCTTGAACTCGGGCTC
5800 GGTGCCAGTATACCTCAAATGGTTGTCGTACCTCTCATGGTTCCGTACCGCAAGGTCATCCTGGAGACGCTTAACTTCTCCGCGCAAGGAGTAGCCGACTACGTGG
5900 ATTAGCTGCACATCGTCGAACACCAGCTGCCCAGTTCGGGCTGCCTCCGATCTGCCGCTGGACTACGTGG
6000 GTCTGGGCCATTCTCATCGTGAGCTTCCGGTGCTCCGCATATCGGCTCTAAGACTTCGGGCCCCTCAAAAAGCTAATGTAATTATATTGTGCCAATAAAAACAAGATATGA
6100 CTTGTTTTTTTTTTTACCATTATTACCATCGTCGTTACTGTTATTGCCCCTCAAAAAGCTAATGTAATTATATTGTGCCAATAAAAACAAGATATGA
6200 CCTATAGAATACAAGTATTTCCCCTTCGAACATCCCCACAAGTAGAGACTTTGTCTTCTTCTAACCAAAGACTTACACACCTGCATACCTTACATCAA
6300 AAACTCGTTTATCGCTACATAAAAACACCGGATATATTTTATATACATACTTTTCAAATCGCGGCCCCTCTTCATAATTCACCTCCACCACCACCAGT
```

*FIG. 22 CONT.*

```
6400 TTCGTAGTTGCTCTTTCGCTGTCTCCCACCCGCTCTCCGCAACACATTCACCTTTTGTCGACGACCTTGGAGGCGACTGTCGTTAGTTCCGCGATTCG
6500 GTTCGCTCAAATGGTTCCGAGTGGTTCATTCGTCTCAATAGAAATTAGTAATAAATATTTGTATGTACAATTTATTGCTCCAATATATTTGTATATAT
6600 TTCCCTCACAGCTATATTTATTCTAATTAATTATGACTTTTTAAGGTAATTTTTGTGACCTGTTCCGAGTGATTAGCGTTACAATTTGAACTGAAA
6700 GTGACATCCAGTGTTGTTCCTTGTGTAGATGCATCTCAAAAAAAATGGTGGGCATAATAGTGTGTTTATATATATCAAAATAACAACTATAATAATAA
6800 GAATACATTTAATTTAGAAAATGCTTGGATTTCACTGGAACTAGAATTAATTCGGCTGCTGCTCTAAACGACGCATTCGTACTCCAAAGTACGAATTT
6900 TTCCCTCAAGCTCTTATTTCATTAAACAATGAACAGGACCTAACGCACAGTCACGTTATTGTTTACATAAATGATTTTTTTACTATTCAAACTTACTC
7000 TGTTTGTGTACTCCCACTGGTATAGCCTTTCTTTTCTGGTTCAGGCTCTATCACTTACTAGGTACGGCATCGCGTTGAGTCGCCTCCTTTTA
7100 AATGTCTGACCTTTGCAGGTGCAGCCTTCCACTGCGAATCTTTAAAGTGGTATCACAAATTGGGAGTTTCACCAAGGCTGCACCCAAGGCTCTGCT
7200 CCCACACAATTTTCTCTTAATAGCACACTTCGGCACGTGAATTAATTTTACTCCAGTCACAGCTTTGCAGCAAAATTGCAATATTTCATTTTTTTATTC
7300 CACGTAAGGGTTAATGTTTTCAAAAAAAATTCGTCCGCACAACCTTCCTCTCAACAAGCAAACGTGCACTGAATTAAGTGTATACTTCGGTAAGC
7400 TTCGGCTATCGACGGGACCACCTTATGTTATTTCATCATGGGCCAGATCGGCGGCGAGATCGGCAGTCCAGTGAAGTTAAGCGTCTCCAGGAT
7500 GACCTTGCCCGAACTGGGGCACGTGGTGTTCGACGATGCAGCTAATTCGCCCCGGCTCCCATTGGTTAATCAGCAGACCCTCGTTGGCG
```

*FIG. 22 CONT.*

```
7600
TAACGGAACCATGAGAGTACGACAACCATTTGAGGTATACTGGCACCCGAGTTCAAGAAGAAGGCGTTTTTCCATAGGCTCCGCCCCCCTGACG
7700
AGCATCACAAAAATCGACGCTCAAGTCAGAGAGGTGGGCGAAACCCGACAGGACTATAAAGATACCAGGCGTTTCCCCCTGGAAGCTCCCTGCGCTCTCC
7800
TGTTCCGACCCTGCCGCTTACCGGATACCTGTCCGCCTTTCTCCCTTCGGGAAGCGTGGCGCTTTCTCAATGCTCACGCTGTAGGTATCTCAGTTCGGTG
7900
TAGGTCGTTCGCTCCAAGCTGGGCTGTGTGCACGAACCCCCCGTTCAGCCCGACCGCTGCCGCCTTATCCGGTAACTATCGTCTTGAGTCCAACCCGGTAA
8000
GACAGACTTATCGCCACTGGCAGCAGCCACTGGTAACAGGATTAGCAGAGCGAGGTATGTAGGCGGTGCTACAGAGTTCTTGAAGTGGTGGCCTAACTA
8100
CGGCTACACTAGAAGGACAGTATTTGGTATCTGCGCTCTGCTGAAGCCAGTTACCTTCGGAAAAAAAGAGTTGGTAGCTCTTGATCCGGCAAACAAACCACC
8200
GCTGGTAGCGGTGGTTTTTTGTTGCAAGCAGCAGATTACGCGCAGAAAAAAAGGATCTCAAGAAGATCCTTTGATCTTTTCTACGGGGTCTGACGCTC
8300
AGTGGAACGAAAACTCACGTTAAGGGATTTTGGTCATGAGATTATCAAAATGAAGTTTAAATCAAT
8400
CTAAAGTATATATGAGTAAACTTGGTCTGACAGTTACCAATGCTTAATCAGTGAGGCACCTATCTCAGCGATCTGTCTATTTCGTTCATCCATAGTTGCC
8500
TGACTCCCCGTCGTGTAGATAACTACGATACGGGAGGGCCTTACCATCTGGCCCCAGTGCTGCAATGATACCGCGAGACCCACGCTCACCGGCTCCAGATT
8600
TATCAGCAATAAACCAGCCAGCCGGAAGGGCCGAGCGCAGAAGTGGTCCTGCAACTTATCCGCCTCCATCCAGTCTATTAATTGTTGCCGGGAAGCTAG
8700
AGTAAGTAGTTCGCCAGTTAATAGTTTGCGCAACGTTGTTGCCATTGCTACAGGCATCGTGGTGTCACGCTCGTCGTTTGGTATGGCTTCATTCAGCTCC
```

*FIG. 22 CONT.*

```
8800 GGTTCCCAACGATCAAGGCGAGTTACATGATCCCCATGTGTGCAAAAAGCGGTTAGCTCCTCCTTCGGTCCTCCGATCGTTGTCAGAAGTAAGTTGGCCG
8900 CAGTGTTATCACTCATGGTTATGGCAGCACTGCATAATTCTCTTACTGTCATATGCCATCCGTAAGATGCTTTCTGTGACTGGTGAGTACTCAACCAAGTC
9000 ATTCTGAGAATAGTGTATGCGGGCACCGAGTTGCTCTTGCCCGGCGTCAATACGGGATAATACCGCCACATAGCAGAACTTTAAAAGTGCTCATCATT
9100 GGAAAACGTTCTTCGGGGCGAAAACTCTCAAGGATCTTACCGCTGTTGAGATCCAGTTCGATGTAACCCACTCGTGCACCCAACTGATCTTCAGCATCTT
9200 TTACTTTCACCAGCGTTTCTGGGTGAGCAAAAACAGGAAGGCAAATGCCGCAAAAAAGGGAATAAGGGCGACACGGAAATGTTGAATACTCATACTCTT
9300 CCTTTTTCAATATTATTGAAGCATTTATCAGGGTTATTGTCTCATGAGCGGATACATATTTGAATGTATTAGAAAAATAAACAAATAGGGGTTCCGCGC
9400 ACATTTCCCCGAAAAGTGCCACCTGACGTCTAAGAAACCATTATTATCATGACATTAACCTATAAAAATAGGCGTATCACGAGGCCCTTTCGTCTCGCGC
9500 GTTTCGGTGATGACGGTGAAAACCTCTGACACATGCAGCTCCCGGAGACGGTCACAGCTTGTCTGTAAGCGGATGCCGGGAGCAGACAAGCCCGTCAGG
9600 CGCGTCAGCGGGTGTTGGCGGGTGTCGGGGCTGGCTTAACTATGCGGCATCAGAGCAGATTGTACTGAGAGTGCACCATATGCGGTGTGAAATACCGCAC
9700 CGAATCGCCGCGAACTAACGACAGTCGCCTCCAAGTCGTCGAACAAAAGGTGAATGTGTTGCGGAGACAGGCGAAAGAGCAACTACGAA
9800 ACGTGGTGTGGTGAGGTGAATTATGAAGAGGGGCGCGCGATTGAAAAGTATGTATATAAAAATATATCCGGTGTTTATGTAGCGATAAACGAGTTT
9900 TTGATGTAAGGTATGCAGGTGTGTAAGTCTTTTGGTTAGAGAAGACAAATCCAAAGTCTACTTGTGGGGATGTTCGAAGGGGAAATACTTGTATTCTATAGG
```

*FIG. 22 CONT.*

```
10000
TCATATCTTGTGTTTTATTGGCACAAATATAATTACATTAGCTTTTTGAGGGGCAATAAACACGATAAACAGTAAACACGATGGTAATAATGGTAAAAAAAAACAAG
10100
CAGTTATTTCGGATATATGTCGGCTACTCCCTTGCGTCGGGCCCGAAGTCTTAGAGCCAGATATGCGAGCACCCGGAAGCTCACGATGAGAATGGCCAGAC
10200
CATGATGAAATAACATAAGGTGGTCCCGTCGGCAAGAGACATCCACTTAACGTATGCTTGCAATAAGTGCGAGTGAAAGGAATAGTATTCTGAGTGTCGT
10300
ATTGAGTCTGAGTGAGACAGCGATATGATTGTTGATTAACCCTTAGCATGTCCGTGGGGTTTGAATTAACTCATAATATTAATTAGACGAAATTATTTT
AAAGTTTTATTTTTAATAATTGCCGAGTACGCA --(SEQ ID NO:68)--
```

*FIG. 22 CONT.*

```
Natural piggyBac orf      1  ATGGGTAGTT CTTTAGACGA TGAGCATATC CTCTCTGCTC TTCTGCAAAG
Optimized piggyBac orf    1  ATGGGTAGca gccTgGAtGA TGAaCATATC CTgagcGCgC TgCTgCAgAG Natural piggyBac orf     51  CGATGACGAG CTTGTTGGTG AGGATTCTGA CAGTGAAATA TCAGATCACG
Optimized piggyBac orf   51  CGAcGAcGAa CTgGTTGGTG AaGATAgcGA cAGcGAAATc agcGATCACG Natural piggyBac orf    101  TAAGTGAAGA TGACGTCCAG AGCCGATACAG AAGAAGCGTT TATAGATGAG
Optimized piggyBac orf  101  TgAGCGAAGA cGAcGTtCAG AGCCGATACCG AAGAAGCGTT cATcGACGAa Natural piggyBac orf    151  GTACATGAAG TGCAGCCAAC GTCAAGCGGT AGTGAAATAT TAGACGAACA
Optimized piggyBac orf  151  GTtCACGAAG TGCAGCCCGAC cagcCAGCGGT AGCGAAATcc TgGAtGAACA Natural piggyBac orf    201  AAATGTTATT GAACAACCAG GTTCTTCATT GGCTTCTAAC AGAATCTTGA
Optimized piggyBac orf  201  gAACGTTATc GAACAgCCGG GTagcagccT GGCgagcAAC cGtATCcTGA Natural piggyBac orf    251  CCTTGCCACA GAGGACTATT AGAGGTAAGA ATAAACATTG TTGGTCAACT
Optimized piggyBac orf  251  CCCTGCCgCA GcGcACCcATc cGtGGTAAaA ACAAACAcTG TTGGagcACc Natural piggyBac orf    301  TCAAAGTCCA CGAGGGCGTAG CCGAGTCTCT GCACTGAACA TTGTCAGATC
Optimized piggyBac orf  301  agcAAaagCA CccGCcCGTAG CCCgTGTTagc GCgCTGAACA TTGTtcGtag Natural piggyBac orf    351  TCAAAGAGGT CCGACGCGTA TGTGCCGCAA TATATATGAC CCACTTTTAT
Optimized piggyBac orf  351  cCAgcGcGGT CCGACCCGTA TGTGCCGCAA cATcTAcGAt CCgCTgcTgT Natural piggyBac orf    401  GCTTCAAACT ATTTTTTACT GATGAGATAA TTTCGGAAAT TGTAAAATGG
Optimized piggyBac orf  401  GCTTCAAACT gTTcTTcACc GATGAaATcA TcagcGAAAT cGTgAAATGG
```

*FIG. 23*

```
Natural piggyBac orf      451  ACAAATGCTG AGATATCATT GAAACGTCGG GAATCTATGA CAGGTGCTAC
Optimized piggyBac orf    451  ACCAAcGCcG AaATcagcCT GAAACGTCGc GAAagcATGA CcGGcGCgAC Natural piggyBac orf      501  ATTTCGTGAC ACGAATGAAG ATGAAATCTA TGCTTTCTTT GGTATTCTGG
Optimized piggyBac orf    501  cTTcCGcGAt ACCAACGAAG ATGAaATCTA CGCcTTCTTc GGTATcCTGG Natural piggyBac orf      551  TAATGACAGC AGTGAGAAAA GATAACCACA TGTCCACAGA TGACCTCTTT
Optimized piggyBac orf    551  TgATGACcGC ggTGcGtAAA GATAACCACA TGagCACCGA TGAtCTgTTT Natural piggyBac orf      601  GATCGATCTT TGTCAATGGT GTACGTCTCT GTAATGAGTC GTGATCGTTT
Optimized piggyBac orf    601  GATCGtagcc TGagcATGGT tTACGTtagc GTtATGAGCC GtGAcCGTTT Natural piggyBac orf      651  TGATTTTTTG ATACGATGTC TTAGAATGGA TGACAAAAGT ATACGGCCCA
Optimized piggyBac orf    651  cGATTTtcTG ATcCGTtGTC TgcGtATGGA TGAtAAAAGc ATcCGcCCgA Natural piggyBac orf      701  CACTTCGAGA AAACGATGTA TTTACTCCTG AAATTACACT CCAGGGGCTC ATTTGACCAT
Optimized piggyBac orf    701  CcCTgCGcGA AAACGATGTg TTcACcCCgG TTcGCAAAAT CCgGGCGCgC AcCTGACCAT Natural piggyBac orf      751  TTTATCCATC AGTGCATACA AAATTACACA AGTGCATACA TTAGAGGACG GTGTCCGTTT AGGATGTATA
Optimized piggyBac orf    751  TTcATCCAcC AGTGCATcCA gAAcTACACc AGTGCATcCA TTcGtGGtCG cTGTCCgTTT cGTATGTAcA Natural piggyBac orf      801  AGATGAACAG TTACTTGGTT TTAGAGGACG GTGTCCGTTT AGGATGTATA
Optimized piggyBac orf    801  cGATGAACAG cTgCTgGGTT TTcGtGGtCG cTGTCCgTTT cGTATGTAcA Natural piggyBac orf      851  TCCCAAACAA GCCAAGTAAG TATGGAATAA AAATCCTCAT GATGTGTGAC
Optimized piggyBac orf    851  TCCCgAACAA aCCgAGcAAa TACGGtATcA AAATCCTgAT GATGTGTGAC
```

FIG. 23 CONT.

| | | | | | | |
|---|---|---|---|---|---|---|
| Natural piggyBac orf | 901 | AGTGGTACGA | AGTATATGAT | AAATGGAATG | CCTTATTTGG | GAAGAGGAAC |
| Optimized piggyBac orf | 901 | AGcGGTACCa | AgTacATGAT | cAAcGGtATG | CCgTATcTGG | GtcGtGGtAC |
| Natural piggyBac orf | 951 | ACAGACCAAC | GGAGTACCAC | TCGGTGAATA | CTACGTGAAG | GAGTTATCAA |
| Optimized piggyBac orf | 951 | CCAGACCAAC | GGtGTgCCgC | TgGGTGAATA | CTACGTGAAa | GAAcTgagcA |
| Natural piggyBac orf | 1001 | AGCCTGTGCA | CGGTAGTTGT | CGTAATATTA | CGTGTGACAA | TTGGTTCACC |
| Optimized piggyBac orf | 1001 | AaCCgGTGCA | CGGTAGcTGT | CGTAAcATcA | CCTGTGACAA | CTGGTTCACC |
| Natural piggyBac orf | 1051 | TCAATCCCTT | TGGCAAAAAA | CTTACTACAA | GAACCGTATA | AGTTAACCAT |
| Optimized piggyBac orf | 1051 | agcATCCCgc | TGGCgAAAAA | CCTgCTgCAg | GAACCGTATA | AacTgACCAT |
| Natural piggyBac orf | 1101 | TGTGGGAACC | GTGCGATCAA | ACAAACGCGA | GATACCCGGAA | GTACTGAAAA |
| Optimized piggyBac orf | 1101 | cGTGGGtACC | GTtCGTagcA | ACAAACGtGA | aATCCCGGAA | GTgCTGAAAA |
| Natural piggyBac orf | 1151 | ACAGTCGCTC | CAGGCCAGTG | GGAACATCGA | TGTTTTGTTTT | GACGGACCC |
| Optimized piggyBac orf | 1151 | ACAGcCGtag | CcGtCCgGTG | GGcACCagcA | TGTTcTGTTTc | GAtGGtCCg |
| Natural piggyBac orf | 1201 | CTTACTCTCG | TCTCATATAA | ACCGAAGCCA | GCTAAGATGG | TATACTTATT |
| Optimized piggyBac orf | 1201 | CTgACcCTgG | TtagcTACaA | ACCGAAaCCG | GCgAAaATGGTg | TACcTgcT |
| Natural piggyBac orf | 1251 | ATCATCTTGT | GATGAGGATG | CTTCTATCAA | CGAAAGTACC | GGTAAACCGC |
| Optimized piggyBac orf | 1251 | gagcagcTGc | GACGAaGACG | CgagcATCAA | CGAAAAGCACC | GGTAAACCGC |
| Natural piggyBac orf | 1301 | AAATGGTTAT | GTATTATAAT | CAAACTAAAG | GCGGAGTGGA | CACGCTAGAC |
| Optimized piggyBac orf | 1301 | AgATGGTTAT | GTACTACaAC | CAGACcAAAG | GCGGtGTGGA | CACcCTGGAt |

FIG. 23 CONT.

```
Natural piggyBac orf      1351  CAAATGTGTT CTGTGATGAC CTGCAGTAGG AAGACGAATA GGTGGCCTAT
Optimized piggyBac orf    1351  CAgATGTGCa gcGTtATGAC CTGCAGccGc AAaACcAACc GCTGGCCgAT Natural piggyBac orf      1401  GGCATTATTG TACGGAATGA TAAACATTGC CTGCATAAAT TCTTTTATTA
Optimized piggyBac orf    1401  GGCgcTgcTG TACGGtATGA TcAACATCGC CTGCATcAAc agcTTTATcA Natural piggyBac orf      1451  TATACAGCCA TAATGTCAGT AGCAAGGGAG AAAAGGTTCA AAGTCGCAAA
Optimized piggyBac orf    1451  TcTACAGCCA TAAcGTtAGc AGCAAaGGtG AAAAaGTTCA gAGCCGCAAA Natural piggyBac orf      1501  AAATTTATGA GAAACCTTTA CATGAGCCTG ACGTCATCGT TTATGCGTAA
Optimized piggyBac orf    1501  AAATTTATGc GtAACCTgTA CATGAGCCCTG ACcagcagcT TcATGCGTAA
```



```
Natural piggyBac orf      1351  CAAATGTGTT CTGTGATGAC CTGCAGTAGG AAGACGAATA GGTGGCCTAT
Optimized piggyBac orf    1351  CAgATGTGCa gcGTtATGAC CTGCAGccGc AAaACcAACc GCTGGCCgAT Natural piggyBac orf      1401  GGCATTATTG TACGGAATGA TAAACATTGC CTGCATAAAT TCTTTTATTA
Optimized piggyBac orf    1401  GGCgcTgcTG TACGGtATGA TcAACATCGC CTGCATcAAc agcTTTATcA Natural piggyBac orf      1451  TATACAGCCA TAATGTCAGT AGCAAGGGAG AAAAGGTTCA AAGTCGCAAA
Optimized piggyBac orf    1451  TcTACAGCCA TAAcGTtAGc AGCAAaGGtG AAAAaGTTCA gAGCCGCAAA Natural piggyBac orf      1501  AAATTTATGA GAAACCTTTA CATGAGCCTG ACGTCATCGT TTATGCGTAA
Optimized piggyBac orf    1501  AAATTTATGc GtAACCTgTA CATGAGCCCTG ACcagcagcT TcATGCGTAA Natural piggyBac orf      1551  GCGTTTAGAA GCTCCCTACTT TGAAGAGATA TTTGCGCGAT AATATCTCTA
Optimized piggyBac orf    1551  aCGTcTgGAA GCCCCGACcc TGAAacGttA TcTGCGCGAT AacATCagcA Natural piggyBac orf      1601  ATATTTTGCC AAATGAAGTG CCTGGTACAT CAGATGACAG TACTGAAGAG
Optimized piggyBac orf    1601  AcATcCTGCC gAACGAAGTG CCgGGTACca gcGATGATAG cACCGAAGAa Natural piggyBac orf      1651  CCAGTAATGA AAAAACGTAC TTACTGTACT TACTGCCCCT CTAAAATAAG
Optimized piggyBac orf    1651  CCgGTgATGA AAAAACGTAC cTACTGTACC TACTGCCCga gcAAAATCCG Natural piggyBac orf      1701  GCGAAAGGCA AATGCATCGT GCAAAAAATG CAAAAAAGTT ATTTGTCGAG
Optimized piggyBac orf    1701  cCGtAAaGCg AACGCgagcT GCAAAAAATG CAAAAAAGTT ATcTGTCGtG Natural piggyBac orf      1751  AGCATAATAT TGATATGTGC CAAAGTTGTT TCTGA-- (SEQ ID NO:69)--
Optimized piggyBac orf    1751  AaCATAACAT CGATATGTGC CAgAGcTGTT TCTGA-- (SEQ ID NO:70)--
```

FIG. 23 CONT.

FIG. 24
A. pCaSpeR-hs-orf
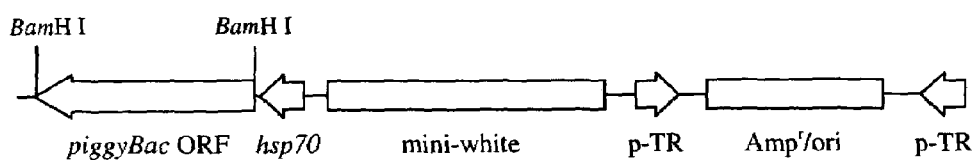
B. p(PZ)-Bac-EYFP
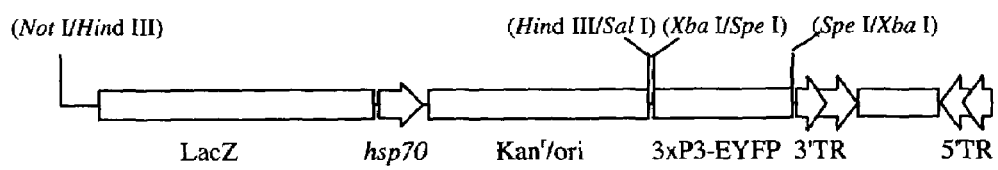
C. pBSII-ITR1.1k-ECFP
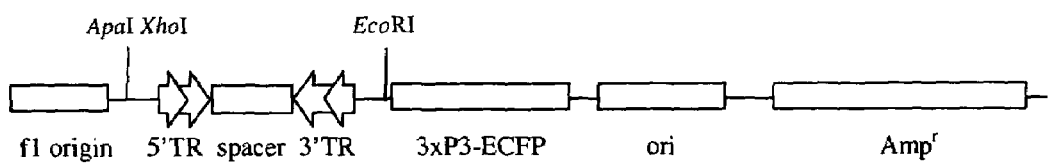
D. pXL-BacII-ECFP
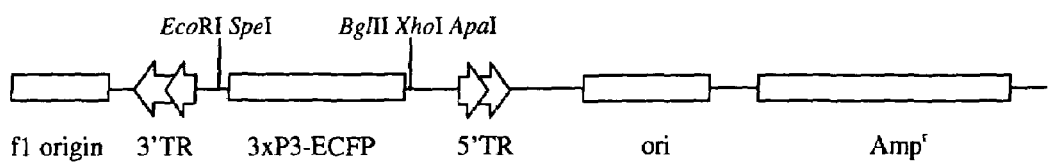

FIG. 26
A
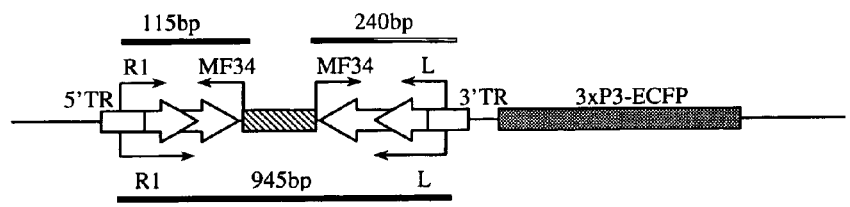
B
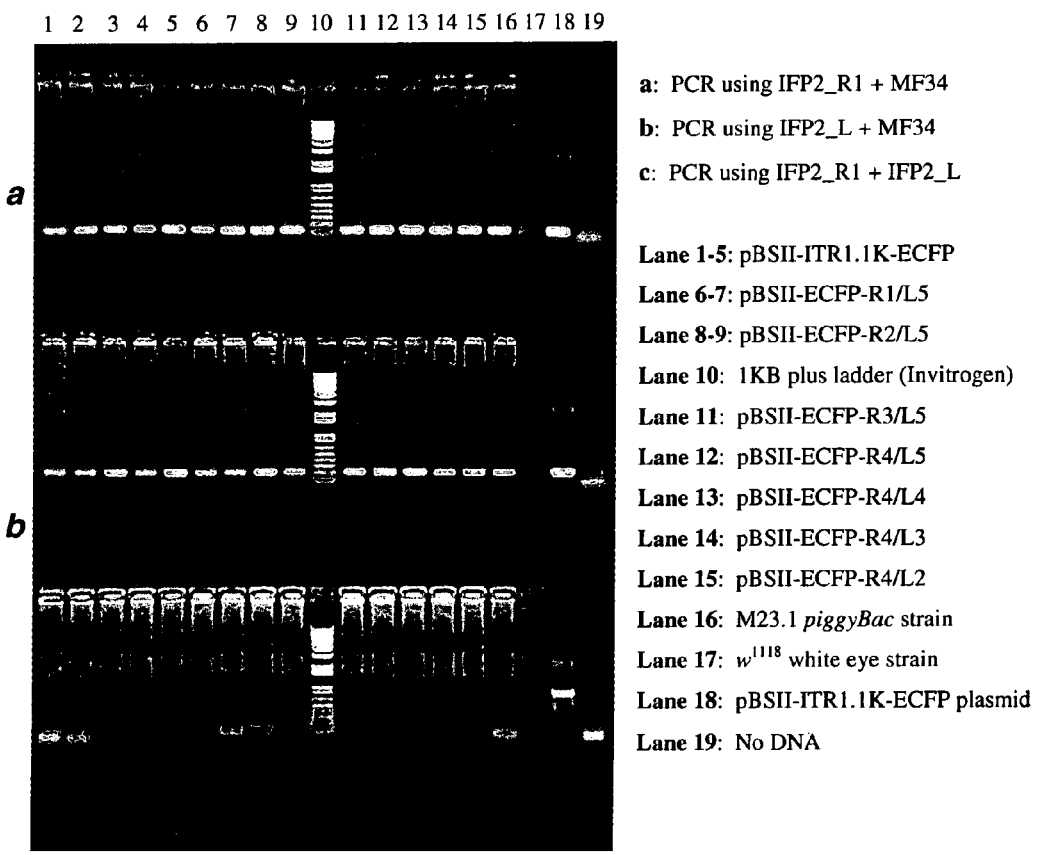
a: PCR using IFP2_R1 + MF34
b: PCR using IFP2_L + MF34
c: PCR using IFP2_R1 + IFP2_L
Lane 1-5: pBSII-ITR1.1K-ECFP
Lane 6-7: pBSII-ECFP-R1/L5
Lane 8-9: pBSII-ECFP-R2/L5
Lane 10: 1KB plus ladder (Invitrogen)
Lane 11: pBSII-ECFP-R3/L5
Lane 12: pBSII-ECFP-R4/L5
Lane 13: pBSII-ECFP-R4/L4
Lane 14: pBSII-ECFP-R4/L3
Lane 15: pBSII-ECFP-R4/L2
Lane 16: M23.1 *piggyBac* strain
Lane 17: $w^{1118}$ white eye strain
Lane 18: pBSII-ITR1.1K-ECFP plasmid
Lane 19: No DNA Southern Hybridization of the transformed strains

SEQUENCE LISTING

```
<160> NUMBER OF SEQ ID NOS: 70

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
ggatcccatg cgtcaatttt acgca                                              25

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
acgactagtg ttcccacaat ggttaattcg                                         30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 3
acgactagtg ccgtacgcgt atcgataagc                                         30

<210> SEQ ID NO 4
<211> LENGTH: 15
<212> TYPE: DNA
<213> ORGANISM: Artificial Sequence
```

```
<220> FEATURE:
<223> OTHER INFORMATION: Description of Artificial Sequence: Primer

<400> SEQUENCE: 4
gcttgataag aagag                                                    15

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 5
gcatgttgct tgctatt                                                  17

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 6
acgtaagctt cgatgtcttt gtgatgcgcc                                    30

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 7
acggaattca cttgcaactg aaacaatatc c                                  31

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 8
actctcgagg ttcccacaat ggttaattcg                                    30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
actgaattca tggtggcgac cggtggatcg                                    30

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 10
ggatcctcta gattaaccct agaaagata                                     29
```

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 11
gaaagggccc gtgatacgcc tatttttata ggtt                    34

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 12
aatcggtacc aacgcgcggg gagaggcggt ttgcg                   35

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 13
ccaagggccc tgacgtgaac cattgtcaca cgt                     33

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 14
tgtgggtacc gtcgatcaaa caaacgcgag ataccg                  36

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cgtcaatttt acgcagacta tctttctagg g                       31

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ttaaccctag aaagatagtc tgcgtaaaat tgacgcatg               39

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtacgtcaca atatgattat ctttctaggg                                    30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ttaaccctag aaagataatc atattgtgac                                    30

<210> SEQ ID NO 19
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 19
ttaattaacc ctagaaagat agtctgcgta aaattgacgc atg                     43

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 20
ttaattaacc ctagaaagat aatcatattg tgac                               34

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctagtactag tgcgccgcgt acgtctagag acgcgcagtc tagaad                  46

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttctagactg cgcgtctcta gacgtacgcg gcgcactagt actagd                  46

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Primer

```
<400> SEQUENCE: 23
gatgacctgc agtaggaaga cgd                                              23

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 24
gactctagac gtacgcggag cttaacccta gaaagatad                             39

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggattccatg cgtcaattttt acgcad                                          26

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 26
ggatcctcga tatacagacc gataaaaaca catgd                                 35

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 27
ggtaccattg caaacagcga cggattcgcg ctatd                                 35

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 28
acgcgtagat cttaatacga ctcactatag gg                                    32

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 29
acgcgtagat ctaattaacc ctcactaaag gg                                    32

<210> SEQ ID NO 30
```

-continued

<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 30
cctcgatata cagaccgata aaacacatg                                   29

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 31
gcacgcctca gccgagctcc aagggcgac                                   29

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 32
ggatccctca aaatttcttc taaagta                                     27

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 33
ggatccctca aaatttcttc taaagta                                     27

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 34
gcacgcctca gccgagctcc aagcggcgac                                  30

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Plasmid
      insertion sequence

<400> SEQUENCE: 35
ttaatctaga ggatcctcta gattaa                                      26

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Plasmid
      insertion sequence

```
<400> SEQUENCE: 36
ttaatctaga cgtacgcgga gcttaa                                          26

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Plasmid
      insertion sequence

<400> SEQUENCE: 37
ttaatctagc tagtactaga actagattaa                                      30

<210> SEQ ID NO 38
<211> LENGTH: 48
<212> TYPE: DNA
<213> ORGANISM: Artificial Sequence
<220> FEATURE:
<223> OTHER INFORMATION: Description of Artificial Sequence: Plasmid
      insertion sequence

<400> SEQUENCE: 38
ttaatctagt tctagacgta cgcggcgcac tagtactagc tagattaa                  48

<210> SEQ ID NO 39
<211> LENGTH: 63
<212> TYPE: DNA
<213> ORGANISM: Artificial Sequence
<220> FEATURE:
<223> OTHER INFORMATION: Description of Artificial Sequence: Plasmid
      insertion sequence

<400> SEQUENCE: 39
ttaatctagt tctagactgc gcgtctctag acgtacgcgg cgcactagta ctagctagat     60
taa                                                                   63

<210> SEQ ID NO 40
<211> LENGTH: 707
<212> TYPE: DNA
<213> ORGANISM: Artificial Sequence
<220> FEATURE:
<223> OTHER INFORMATION: Description of Artificial Sequence: ITR
      Cartridge sequence

<400> SEQUENCE: 40
ggatcccatg cgtcaatttt acgcagacta tctttctagg gttaatctag ctgcatcagg     60
atcatatcgt cgggtctttt ttccggctca gtcatcgccc aagctggcgc tatctgggca    120
tcggggagga agaagcccgt gccttttccc gcgaggttga agcggcatgg aaagagtttg    180
ccgaggatga ctgctgctgc attgacgttg agcgaaaacg cacgtttacc atgatgattc    240
gggaaggtgt ggccatgcac gcctttaacg gtgaactgtt cgttcaggcc acctgggata    300
ccagttcgtc gcggcttttc cggacacagt tccggatggt cagcccgaag cgcatcagca    360
acccgaacaa taccggcgac agccggaact gccgtgccgg tgtgcagatt aatgacagcg    420
gtgcggcgct gggatattac gtcagcgagg acgggtatcc tggctggatg ccgcagaaat    480
ggacatggat accccgtgag ttacccggcg ggcgcgcctc gttcattcac gttttttgaac   540 ccgtggagga cgggcagact cgcggtgcaa atgtgtttta cagcgtgatg gagcagatga    600
agatgctcga cacgctgcag aacacgcagc tagattaacc ctagaaagat aatcatattg    660
```

| | |
|---|---|
| tgacgtacgt taaagataat catgcgtaaa attgacgcat gggatcc | 707 |

<210> SEQ ID NO 41
<211> LENGTH: 3662
<212> TYPE: DNA
<213> ORGANISM: Artificial Sequence
<220> FEATURE:
<223> OTHER INFORMATION: Description of Artificial Sequence: pXL-Bac
     sequence

<400> SEQUENCE: 41

| | |
|---|---|
| ctaaattgta agcgttaata ttttgttaaa attcgcgtta aattttgtt aaatcagctc | 60 |
| atttttaac caataggccg aaatcggcaa atcccttat aaatcaaaag aatagaccga | 120 |
| gataggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta atcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggt tttcccagt cacgacgttg | 600 |
| taaaacgacg gccagtgagc gcgcctcgtt cattcacgtt tttgaacccg tggaggacgg | 660 |
| gcagactcgc ggtgcaaatg tgttttacag cgtgatggag cagatgaaga tgctcgacac | 720 |
| gctgcagaac acgcagctag attaacccta gaaagataat catattgtga cgtacgttaa | 780 |
| agataatcat gcgtaaaatt gacgcatggg atctgtaata cgactcacta tagggcgaat | 840 |
| tgggtaccgg gccccccctc gaggtcgacg gtatcgataa gcttgatatc gaattcctgc | 900 |
| agcccggggg atccactagt tctagagcgg ccgccaccgc ggtggagctc cagcttttgt | 960 |
| tccctttagt gagggttaat tagatcccat gcgtcaattt tacgcagact atctttctag | 1020 |
| ggttaatcta gctgcatcag gatcatatcg tcgggtcttt tttccggctc agtcatcgcc | 1080 |
| caagctggcg ctatctgggc atcggggagg aagaagcccg tgccttttcc cgcgaggttg | 1140 |
| aagcggcatg gaaagagttt gccgaggatg actgctgctg cattgacgtt gagcgaaaac | 1200 |
| gcacgtttac catgatgatt cggaaggtg tggccatgca cgcctttaac ggtgaactgt | 1260 |
| tcgttcaggc cacctgggat accagttcgt cgcggctttt ccggacacag ttccggatgg | 1320 |
| tcagcccgaa gcgcatcagc aacccgaaca ataccggcga cagccggaac tgccgtgccg | 1380 |
| gtgtgcagat taatgacagc ggtgcggcgc tgggatatta cgtcagcgag gacgggtatc | 1440 |
| ctggctggat gccgcagaaa tggacatgga taccccgtga gttacccggc gggcgcgctt | 1500 |
| ggcgtaatca tggtcatagc tgtttcctgt gtgaaattgt tatccgctca caattccaca | 1560 |
| caacatacga gccggaagca taaagtgtaa agcctggggt gcctaatgag tgagctaact | 1620 |
| cacattaatt gcgttgcgct cactgcccgc tttccagtcg ggaaacctgt cgtgccagct | 1680 |
| gcattaatga atcggccaac gcgcggggag aggcggtttg cgtattgggc gctcttccgc | 1740 |
| ttcctcgctc actgactcgc tgcgctcggt cgttcggctg cggcgagcgg tatcagctca | 1800 |
| ctcaaaggcg gtaatacggt tatccacaga atcaggggat aacgcaggaa agaacatgtg | 1860 |
| agcaaaaggc cagcaaaagg ccaggaaccg taaaaaggcc gcgttgctgg cgttttccca | 1920 |
| taggctccgc cccctgacg agcatcacaa aaatcgacgc tcaagtcaga ggtggcgaaa | 1980 |

```
cccgacagga ctataaagat accaggcgtt tccccctgga agctccctcg tgcgctctcc   2040
tgttccgacc ctgccgctta ccggatacct gtccgccttt ctcccttcgg gaagcgtggc   2100
gctttctcat agctcacgct gtaggtatct cagttcggtg taggtcgttc gctccaagct   2160
gggctgtgtg cacgaaccCC ccgttcagcc cgaccgctgc gccttatccg gtaactatcg   2220
tcttgagtcc aacccggtaa gacacgactt atcgccactg gcagcagcca ctggtaacag   2280
gattagcaga gcgaggtatg taggcggtgc tacagagttc ttgaagtggt ggcctaacta   2340
cggctacact agaaggacag tatttggtat ctgcgctctg ctgaagccag ttaccttcgg   2400
aaaaagagtt ggtagctctt gatccggcaa acaaaccacc gctggtagcg gtggtttttt   2460
tgtttgcaag cagcagatta cgcgcagaaa aaaggatctc aagaagatcc tttgatcttt   2520
tctacgggg tctgacgctc agtggaacga aaactcacgt taagggattt tggtcatgag   2580
attatcaaaa aggatcttca cctagatcct tttaaattaa aaatgaagtt ttaaatcaat   2640
ctaaagtata tatgagtaaa cttggtctga cagttaccaa tgcttaatca gtgaggcacc   2700
tatctcagcg atctgtctat ttcgttcatc catagttgcc tgactccccg tcgtgtagat   2760
aactacgata cgggagggct taccatctgg ccccagtgct gcaatgatac cgcgagaccc   2820
acgctcaccg gctccagatt tatcagcaat aaaccagcca gccggaaggg ccgagcgcag   2880
aagtggtcct gcaactttat ccgcctccat ccagtctatt aattgttgcc gggaagctag   2940
agtaagtagt tcgccagtta atagtttgcg caacgttgtt gccattgcta caggcatcgt   3000
ggtgtcacgc tcgtcgtttg gtatggcttc attcagctcc ggttcccaac gatcaaggcg   3060
agttacatga tcccccatgt tgtgcaaaaa agcggttagc tccttcggtc ctccgatcgt   3120
tgtcagaagt aagttggccg cagtgttatc actcatggtt atggcagcac tgcataattc   3180
tcttactgtc atgccatccg taagatgctt ttctgtgact ggtgagtact caaccaagtc   3240
attctgagaa tagtgtatgc ggcgaccgag ttgctcttgc ccggcgtcaa tacgggataa   3300
taccgcgcca catagcagaa ctttaaaagt gctcatcatt ggaaaacgtt cttcggggcg   3360
aaaactctca aggatcttac cgctgttgag atccagttcg atgtaaccca ctcgtgcacc   3420
caactgatct tcagcatctt ttactttcac cagcgtttct gggtgagcaa aaacaggaag   3480
gcaaaatgcc gcaaaaaagg gaataagggc gacacggaaa tgttgaatac tcatactctt   3540
cctttttcaa tattattgaa gcatttatca gggttattgt ctcatgagcg gatacatatt   3600
tgaatgtatt tagaaaaata acaaataggg gttccgcgc acatttcccc gaaaagtgcc   3660
ac                                                                 3662
```

<210> SEQ ID NO 42
<211> LENGTH: 5533
<212> TYPE: DNA
<213> ORGANISM: Artificial Sequence
<220> FEATURE:
<223> OTHER INFORMATION: Description of Artificial Sequence:
      pBSII-hs-orf sequence

<400> SEQUENCE: 42

```
ctaaattgta agcgttaata ttttgttaaa attcgcgtta aattttttgtt aaatcagctc     60
attttttaac cataggccg aaatcggcaa atcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt ttttttgggt cgaggtgccg taaagcacta aatcggaacc ctaaagggag    300
```

-continued

```
ccccgattt agagcttgac ggggaaagcc ggcgaacgtg gcgagaaagg aagggaagaa       360
agcgaaagga gcgggcgcta gggcgctggc aagtgtagcg gtcacgctgc gcgtaaccac       420
cacacccgcc gcgcttaatg cgccgctaca gggcgcgtcc cattcgccat tcaggctgcg       480
caactgttgg gaagggcgat cggtgcgggc ctcttcgcta ttacgccagc tggcgaaagg       540
gggatgtgct gcaaggcgat taagttgggt aacgccaggg ttttcccagt cacgacgttg       600
taaaacgacg gccagtgagc gcgcgtaata cgactcacta tagggcgaat tgggtaccgg       660
gccccccctc gaggtcgacg gtatcgataa gctatccagt gcagtaaaaa ataaaaaaaa       720
aatatgtttt tttaaatcta cattctccaa aaagggttt tattaactta catacatact       780
agaattgatc cccgatcccc ctagaatccc aaaacaaact ggttattgtg gtaggtcatt       840
tgtttggcag aagaaaactc gagaaatttc tctggccgtt attcgttatt ctctcttttc       900
tttttgggtc tccctctctg cactaatgct ctctcactct gtcacacagt aaacggcata       960
ctgctctcgt tggttcgaga gagcgcgcct cgaatgttcg cgaaaagagc gccggagtat      1020
aaatagagcg cttcgtctac ggagcgacaa ttcaattcaa acaagcaaag tgaacacgtc      1080
gctaagcgaa agctaagcaa ataaacaagc gcagctgaac aagctaaaca atctgcagta      1140
aagtgcaagt taaagtgaat caattaaaag taaccagcaa ccaagtaaat caactgcaac      1200
tactgaaatc tgccaagaag taattattga atacaagaag agaactctga atagggaatt      1260
gggaattcct gcagcccggg ggatcctata ataaaaatg ggtagttctt tagacgatga       1320
gcatatcctc tctgctcttc tgcaaagcga tgacgagctt gttggtgagg attctgacag      1380
tgaaatatca gatcacgtaa gtgaagatga cgtccagagc gatacagaag aagcgtttat      1440
agatgaggta catgaagtgc agccaacgtc aagcggtagt gaaatattag acgaacaaaa      1500
tgttattgaa caaccaggtt cttcattggc ttctaacaga atcttgacct tgccacagag      1560
gactattaga ggtaagaata acattgttg gtcaacttca aagtccacga ggcgtagccg       1620
agtctctgca ctgaacattg tcagatctca aagaggtccg acgcgtatgt gccgcaatat      1680
atatgaccca cttttatgct tcaaactatt ttttactgat gagataattt cggaaattgt      1740
aaaatggaca aatgctgaga tatcattgaa acgtcgggaa tctatgacag gtgctacatt      1800
tcgtgacacg aatgaagatg aaatctatgc tttctttggt attctggtaa tgacagcagt      1860
gagaaaagat aaccacatgt ccacagatga cctctttgat cgatctttgt caatggtgta      1920
cgtctctgta atgagtcgtg atcgtttga tttttttgata cgatgtctta gaatggatga     1980
caaaagtata cggcccacac ttcgagaaaa cgatgtattt actcctgtta gaaaaatatg      2040
ggatctcttt atccatcagt gcatacaaaa ttacactcca ggggctcatt tgaccataga      2100
tgaacagtta cttggtttta gaggacggtg tccgtttagg atgtatatcc caaacaagcc      2160
aagtaagtat ggaataaaaa tcctcatgat gtgtgacagt ggtacgaagt atatgataaa      2220
tggaatgcct tatttgggaa gaggaacaca gaccaacgga gtaccactcg gtgaatacta      2280
cgtgaaggag ttatcaaagc ctgtgcacgg tagttgtcgt aatattacgt gtgacaattg      2340
gttcacctca atccctttgg caaaaaactt actacaagaa ccgtataagt taaccattgt      2400
gggaaccgtg cgatcaaaca aacgcgagat accggaagta ctgaaaaaca gtcgctccag      2460
gccagtggga acatcgatgt tttgttttga cggaccccctt actctcgtct catataaacc      2520
gaagccagct aagatggtat acttattatc atcttgtgat gaggatgctt ctatcaacga      2580
aagtaccggt aaaccgcaaa tggttatgta ttataatcaa actaaaggcg gagtggacac      2640
gctagaccaa atgtgttctg tgatgacctg cagtaggaag acgaataggt ggcctatggc      2700
```

```
attattgtac ggaatgataa acattgcctg cataaattct tttattatat acagccataa    2760
tgtcagtagc aagggagaaa aggttcaaag tcgcaaaaaa tttatgagaa acctttacat    2820
gagcctgacg tcatcgttta tgcgtaagcg tttagaagct cctactttga agagatattt    2880
gcgcgataat atctctaata ttttgccaaa tgaagtgcct ggtacatcag atgacagtac    2940
tgaagagcca gtaatgaaaa aacgtactta ctgtacttac tgcccctcta aaataaggcg    3000
aaaggcaaat gcatcgtgca aaaatgcaaa aaagttatt tgtcgagagc ataatattga    3060
tatgtgccaa agttgtttct gactgactaa taagtataat ttgtttctat tatgtataag    3120
ttaagctaat tacttatttt ataatacaac atgactgttt ttaaagtaca aaataagttt    3180
atttttgtaa aagagagaat gtttaaaagt tttgttactt tagaagaaat tttgagtttt    3240 tgttttttt taataaataa ataaacataa ataaattgtt tgttgaattt ggatccacta    3300
gttctagagc ggccgccacc gcggtggagc tccagctttt gttcccttta gtgagggtta    3360
attgcgcgct tggcgtaatc atggtcatag ctgtttcctg tgtgaaattg ttatccgctc    3420
acaattccac acaacatacg agccggaagc ataaagtgta aagcctgggg tgcctaatga    3480
gtgagctaac tcacattaat tgcgttgcgc tcactgcccg ctttccagtc gggaaacctg    3540
tcgtgccagc tgcattaatg aatcggccaa cgcgcgggga gaggcggttt gcgtattggg    3600
cgctcttccg cttcctcgct cactgactcg ctgcgctcgg tcgttcggct gcggcgagcg    3660
gtatcagctc actcaaaggc ggtaatacgg ttatccacag aatcagggga taacgcagga    3720
aagaacatgt gagcaaaagg ccagcaaaag gccaggaacc gtaaaaaggc cgcgttgctg    3780 gcgttttcc ataggctccg ccccctgac gagcatcaca aaaatcgacg ctcaagtcag    3840
aggtggcgaa acccgacagg actataaaga taccaggcgt ttccccctgg aagctccctc    3900
gtgcgctctc ctgttccgac cctgccgctt accggatacc tgtccgcctt tctcccttcg    3960
ggaagcgtgg cgctttctca tagctcacgc tgtaggtatc tcagttcggt gtaggtcgtt    4020
cgctccaagc tgggctgtgt gcacgaaccc cccgttcagc ccgaccgctg cgccttatcc    4080
ggtaactatc gtcttgagtc aacccggta agacacgact tatcgccact ggcagcagcc    4140
actggtaaca ggattagcag agcgaggtat gtaggcggtg ctacagagtt cttgaagtgg    4200
tggcctaact acggctacac tagaaggaca gtatttggta tctgcgctct gctgaagcca    4260
gttaccttcg gaaaaagagt tggtagctct tgatccggca acaaaccac cgctggtagc    4320 ggtggttttt ttgtttgcaa gcagcagatt acgcgcagaa aaaaggatc tcaagaagat    4380 cctttgatct tttctacggg gtctgacgct cagtggaacg aaaactcacg ttaagggatt    4440
ttggtcatga gattatcaaa aaggatcttc acctagatcc ttttaaatta aaatgaagt    4500 tttaaatcaa tctaaagtat atatgagtaa acttggtctg acagttacca atgcttaatc    4560
agtgaggcac ctatctcagc gatctgtcta tttcgttcat ccatagttgc ctgactcccc    4620
gtcgtgtaga taactacgat acgggagggc ttaccatctg gccccagtgc tgcaatgata    4680
ccgcgagacc cacgctcacc ggctccagat ttatcagcaa taaccagcc agccggaagg    4740 gccgagcgca gaagtggtcc tgcaacttta tccgcctcca tccagtctat taattgttgc    4800
cgggaagcta gagtaagtag ttcgccagtt aatagtttgc gcaacgttgt tgccattgct    4860
acaggcatcg tggtgtcacg ctcgtcgttt ggtatggctt cattcagctc cggttcccaa    4920
cgatcaaggc gagttacatg atcccccatg ttgtgcaaaa aagcggttag ctccttcggt    4980
cctccgatcg ttgtcagaag taagttggcc gcagtgttat cactcatggt tatggcagca    5040
```

-continued

```
ctgcataatt ctcttactgt catgccatcc gtaagatgct tttctgtgac tggtgagtac    5100
tcaaccaagt cattctgaga atagtgtatg cggcgaccga gttgctcttg cccggcgtca    5160
atacgggata ataccgcgcc acatagcaga actttaaaag tgctcatcat tggaaaacgt    5220
tcttcggggc gaaaactctc aaggatctta ccgctgttga gatccagttc gatgtaaccc    5280
actcgtgcac ccaactgatc ttcagcatct tttactttca ccagcgtttc tgggtgagca    5340
aaaacaggaa ggcaaaatgc cgcaaaaaag gaataaggg cgacacggaa atgttgaata    5400
ctcatactct cctttttca atattattga agcatttatc agggttattg tctcatgagc     5460
ggatacatat ttgaatgtat ttagaaaaat aaacaaatag gggttccgcg cacatttccc    5520
cgaaaagtgc cac                                                       5533
```

<210> SEQ ID NO 43
<211> LENGTH: 4971
<212> TYPE: DNA
<213> ORGANISM: Artificial Sequence
<220> FEATURE:
<223> OTHER INFORMATION: Description of Artificial Sequence:
      pBSII-IFP2-orf sequence

<400> SEQUENCE: 43

```
ctaaattgta agcgttaata ttttgttaaa attcgcgtta aattttttgtt aaatcagctc    60 attttttaac caataggccg aaatcggcaa aatcccttat aaatcaaaag aatagaccga    120 gataggttg agtgttgttc cagtttggaa caagagtcca ctattaaaga acgtggactc     180
caacgtcaaa gggcgaaaaa ccgtctatca gggcgatggc ccactacgtg aaccatcacc    240
ctaatcaagt ttttggggt cgaggtgccg taaagcacta atcggaacc ctaaagggag      300 cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg aagggcgat cggtgcgggc ctcttcgcta ttacgccagc tggcgaaagg     540
gggatgtgct gcaaggcgat taagttgggt aacgccaggg ttttcccagt cacgacgttg    600
taaaacgacg gccagtgagc gcgcgtaata cgactcacta tagggcgaat tgggtaccgg    660 gcccccctc gaggtcgacg gtatcgataa gcttgatatc gaattcctgc agcccgggg     720 atcctatata ataaaatggg tagttcttta gacgatgagc atatcctctc tgctcttctg    780
caaagcgatg acgagcttgt tggtgaggat tctgacagtg aaatatcaga tcacgtaagt    840
gaagatgacg tccagagcga tacagaagaa gcgtttatag atgaggtaca tgaagtgcag    900
ccaacgtcaa gcggtagtga atatattgac gaacaaatg ttattgaaca accaggttct    960
tcattggctt ctaacagaat cttgaccttg ccacagagga ctattagagg taagaataaa    1020
cattgttggt caacttcaaa gtccacgagg cgtagccgag tctctgcact gaacattgtc    1080
agatctcaaa gaggtccgac gcgtatgtgc cgcaatatat atgacccact tttatgcttc    1140
aaactatttt ttactgatga gataaatttcg gaaattgtaa aatggacaaa tgctgagata    1200
tcattgaaac gtcgggaatc tatgacaggt gctacatttc gtgacacgaa tgaagatgaa    1260
atctatgctt tctttggtat tctggtaatg acagcagtga gaaagataa ccacatgtcc     1320 acagatgacc tctttgatcg atctttgtca atggtgtacg tctctgtaat gagtcgtgat    1380
cgttttgatt tttgatacg atgtcttaga atgatgaca aagtatacg gcccacactt      1440 cgagaaaacg atgtatttac tcctgttaga aaaatatggg atctctttat ccatcagtgc    1500
```

-continued

```
atacaaaatt acactccagg ggctcatttg accatagatg aacagttact tggttttaga   1560
ggacggtgtc cgtttaggat gtatatccca acaagccaa gtaagtatgg aataaaaatc    1620
ctcatgatgt gtgacagtgg tacgaagtat atgataaatg gaatgcctta tttgggaaga   1680
ggaacacaga ccaacggagt accactcggt gaatactacg tgaaggagtt atcaaagcct   1740
gtgcacggta gttgtcgtaa tattacgtgt gacaattggt tcacctcaat cccttttggca  1800 aaaaacttac tacaagaacc gtataagtta accattgtgg gaaccgtgcg atcaaacaaa   1860
cgcgagatac cggaagtact gaaaaacagt cgctccaggc cagtgggaac atcgatgttt   1920
tgttttgacg gacccctac tctcgtctca tataaaccga agccagctaa gatggtatac    1980
ttattatcat cttgtgatga ggatgcttct atcaacgaaa gtaccggtaa accgcaaatg   2040
gttatgtatt ataatcaaac taaggcgga gtggacacgc tagaccaaat gtgttctgtg    2100
atgacctgca gtaggaagac gaataggtgg cctatggcat tattgtacgg aatgataaac   2160
attgcctgca taaattcttt tattatatac agccataatg tcagtagcaa gggagaaaag   2220
gttcaaagtc gcaaaaaatt tatgagaaac ctttacatga gcctgacgtc atcgtttatg   2280
cgtaagcgtt tagaagctcc tactttgaag agatatttgc gcgataatat ctctaatatt   2340
ttgccaaatg aagtgcctgg tacatcagat gacagtactg aagagccagt aatgaaaaaa   2400
cgtacttact gtacttactg cccctctaaa ataaggcgaa aggcaaatgc atcgtgcaaa   2460
aaatgcaaaa aagttatttg tcgagagcat aatattgata tgtgccaaag ttgtttctga   2520
ctgactaata agtataattt gtttctatta tgtataagtt aagctaatta cttatttat    2580 aatacaacat gactgttttt aaagtacaaa ataagtttat ttttgtaaaa gagagaatgt   2640
ttaaaagttt tgttacttta gaagaaattt tgagtttttg tttttttta ataaataaat    2700 aaacataaat aaattgtttg ttgaatttgg atccactagt tctagagcgg ccgccaccgc   2760
ggtggagctc cagcttttgt tccctttagt gagggttaat tgcgcgcttg gcgtaatcat   2820
ggtcatagct gtttcctgtg tgaaattgtt atccgctcac aattccacac aacatacgag   2880
ccggaagcat aaagtgtaaa gcctggggtg cctaatgagt gagctaactc acattaattg   2940
cgttgcgctc actgcccgct ttccagtcgg gaaacctgtc gtgccagctg cattaatgaa   3000
tcggccaacg cgcggggaga ggcggtttgc gtattgggcg ctcttccgct tcctcgctca   3060
ctgactcgct gcgctcggtc gttcggctgc ggcgagcggt atcagctcac tcaaaggcgg   3120
taatacggtt atccacagaa tcaggggata acgcaggaaa gaacatgtga gcaaaaggcc   3180
agcaaaaggc caggaaccgt aaaaaggccg cgttgctggc gtttttccat aggctccgcc   3240
cccctgacga gcatcacaaa aatcgacgct caagtcagag gtggcgaaac ccgacaggac   3300
tataaagata ccaggcgttt cccctggaa gctccctcgt gcgctctcct gttccgaccc    3360
tgccgcttac cggatacctg tccgcctttc tcccttcggg aagcgtggcg ctttctcata   3420
gctcacgctg taggtatctc agttcggtgt aggtcgttcg ctccaagctg ggctgtgtgc   3480
acgaaccccc cgttcagccc gaccgctgcg ccttatccgg taactatcgt cttgagtcca   3540
acccggtaag acacgactta tcgccactgg cagcagccac tggtaacagg attagcagag   3600
cgaggtatgt aggcggtgct acagagttct tgaagtggtg cctaactac ggctacacta    3660 gaaggacagt atttggtatc tgcgctctgc tgaagccagt taccttcgga aaagagttg    3720 gtagctcttg atccggcaaa caaaccaccg ctggtagcgg tggttttttt gtttgcaagc   3780
agcagattac gcgcagaaaa aaaggatctc aagaagatcc tttgatcttt tctacggggt   3840
ctgacgctca gtggaacgaa aactcacgtt aagggatttt ggtcatgaga ttatcaaaaa   3900
```

-continued

```
ggatcttcac ctagatcctt ttaaattaaa aatgaagttt taaatcaatc taaagtatat       3960
atgagtaaac ttggtctgac agttaccaat gcttaatcag tgaggcacct atctcagcga       4020
tctgtctatt tcgttcatcc atagttgcct gactccccgt cgtgtagata actacgatac       4080
gggagggctt accatctggc cccagtgctg caatgatacc gcgagaccca cgctcaccgg       4140
ctccagattt atcagcaata aaccagccag ccggaagggc cgagcgcaga agtggtcctg       4200
caactttatc cgcctccatc cagtctatta attgttgccg gaagctaga gtaagtagtt       4260 cgccagttaa tagtttgcgc aacgttgttg ccattgctac aggcatcgtg gtgtcacgct       4320
cgtcgtttgg tatggcttca ttcagctccg gttcccaacg atcaaggcga gttacatgat       4380
cccccatgtt gtgcaaaaaa gcggttagct ccttcggtcc tccgatcgtt gtcagaagta       4440
agttggccgc agtgttatca ctcatggtta tggcagcact gcataattct cttactgtca       4500
tgccatccgt aagatgcttt tctgtgactg gtgagtactc aaccaagtca ttctgagaat       4560
agtgtatgcg gcgaccgagt tgctcttgcc cggcgtcaat acgggataat accgcgccac       4620
atagcagaac tttaaaagtg ctcatcattg gaaaacgttc ttcggggcga aaactctcaa       4680
ggatcttacc gctgttgaga tccagttcga tgtaacccac tcgtgcaccc aactgatctt       4740
cagcatcttt tactttcacc agcgtttctg ggtgagcaaa aacaggaagg caaaatgccg       4800
caaaaaaggg aataagggcg acacggaaat gttgaatact catactcttc cttttcaat       4860 attattgaag catttatcag ggttattgtc tcatgagcgg atacatattt gaatgtattt       4920
agaaaaataa acaaataggg gttccgcgca catttccccg aaaagtgcca c              4971
```

<210> SEQ ID NO 44
<211> LENGTH: 5523
<212> TYPE: DNA
<213> ORGANISM: Artificial Sequence
<220> FEATURE:
<223> OTHER INFORMATION: Description of Artificial Sequence: pBSII-IEI-orf sequence

<400> SEQUENCE: 44

```
ctaaattgta agcgttaata ttttgttaaa attcgcgtta aattttttgtt aaatcagctc        60 attttttaac caataggccg aaatcggcaa atcccttat aaatcaaaag aatagaccga       120
gatagggttg agtgttgttc cagtttggaa caagagtcca ctattaaaga acgtggactc       180
caacgtcaaa gggcgaaaaa ccgtctatca gggcgatggc ccactacgtg aaccatcacc       240
ctaatcaagt tttttggggt cgaggtgccg taaagcacta aatcggaacc ctaaagggag       300
cccccgattt agagcttgac ggggaaagcc ggcgaacgtg gcgagaaagg aagggaagaa       360
agcgaaagga gcgggcgcta gggcgctggc aagtgtagcg gtcacgctgc gcgtaaccac       420
cacacccgcc gcgcttaatg cgccgctaca gggcgcgtcc cattcgccat tcaggctgcg       480
caactgttgg gaagggcgat cggtgcgggc ctcttcgcta ttacgccagc tggcgaaagg       540
gggatgtgct gcaaggcgat taagttgggt aacgccaggg ttttcccagt cacgacgttg       600
taaaacgacg gccagtgagc gcgcgtaata cgactcacta tagggcgaat tgggtaccgg       660
gccccccctc gaggtcgacg gtatcgataa gcttcgatgt ctttgtgatg cgccgacatt       720
tttgtaggtt attgataaaa tgaacggata cagttgcccg acattatcat taaatccttg       780
gcgtagaatt tgtcgggtcc attgtccgtg tgcgctagca tgcccgctaa cggacctcgt       840
acttttggct tcaaaggttt tgcgcacaga caaaatgtgc cacacttgca gctctgcatg       900
tgtgcgcgtt accacaaatc ccaacggcgc agtgtacttg ttgtatgcaa ataaatctcg       960
```

-continued

```
ataaaggcgc ggcgcgcgaa tgcagctgat cacgtacgct cctcgtgttc cgttcaagga   1020
cggtgttatc gacctcagat taatgtttat cggccgactg ttttcgtatc cgctcaccaa   1080
acgcgttttt gcattaacat tgtatgtcgg cggatgttct atatctaatt tgaataaata   1140
aacgataacc gcgttggttt tagagggcat aataaaagaa atattgttat cgtgttcgcc   1200
attagggcag tataaattga cgttcatgtt ggatattgtt tcagttgcaa gtgaattcct   1260
gcagcccggg ggatcctata taataaaatg gtagttctt tagacgatga gcatatcctc   1320
tctgctcttc tgcaaagcga tgacgagctt gttggtgagg attctgacag tgaaatatca   1380
gatcacgtaa gtgaagatga cgtccagagc gatacagaag aagcgtttat agatgaggta   1440
catgaagtgc agccaacgtc aagcggtagt gaaatattag acgaacaaaa tgttattgaa   1500
caaccaggtt cttcattggc ttctaacaga atcttgacct tgccacagag gactattaga   1560
ggtaagaata acattgttg gtcaacttca aagtccacga ggcgtagccg agtctctgca   1620
ctgaacattg tcagatctca aagaggtccg acgcgtatgt gccgcaatat atatgaccca   1680
cttttatgct tcaaactatt ttttactgat gagataattt cggaaattgt aaaatggaca   1740
aatgctgaga tatcattgaa acgtcgggaa tctatgacag gtgctacatt tcgtgacacg   1800
aatgaagatg aaatctatgc tttctttggt attctggtaa tgacagcagt gagaaaagat   1860
aaccacatgt ccacagatga cctctttgat cgatctttgt caatggtgta cgtctctgta   1920
atgagtcgtg atcgttttga ttttttgata cgatgtctta aatggatga caaaagtata   1980 cggcccacac ttcgagaaaa cgatgtattt actcctgtta gaaaaatatg ggatctcttt   2040
atccatcagt gcatacaaaa ttacactcca ggggctcatt tgaccataga tgaacagtta   2100
cttggtttta gaggacggtg tccgtttagg atgtatatcc caaacaagcc aagtaagtat   2160
ggaataaaaa tcctcatgat gtgtgacagt ggtacgaagt atatgataaa tggaatgcct   2220
tatttgggaa gaggaacaca gaccaacgga gtaccactcg gtgaatacta cgtgaaggag   2280
ttatcaaagc ctgtgcacgg tagttgtcgt aatattacgt gtgacaattg gttcacctca   2340 atcccttttgg caaaaaactt actacaagaa ccgtataagt taaccattgt gggaaccgtg   2400
cgatcaaaca aacgcgagat accggaagta ctgaaaaaca gtcgctccag gccagtggga   2460
acatcgatgt tttgttttga cggaccccctt actctcgtct catataaacc gaagccagct   2520
aagatggtat acttattatc atcttgtgat gaggatgctt ctatcaacga agtaccggt   2580 aaaccgcaaa tggttatgta ttataatcaa actaaaggcg gagtggacac gctagaccaa   2640
atgtgttctg tgatgacctg cagtaggaag acgaataggt ggcctatggc attattgtac   2700
ggaatgataa acattgcctg cataaattct tttattatat acagccataa tgtcagtagc   2760
aagggagaaa aggttcaaag tcgcaaaaaa tttatgagaa acctttacat gagcctgacg   2820
tcatcgttta tgcgtaagcg tttagaagct cctactttga agagatattt gcgcgataat   2880
atctctaata ttttgccaaa tgaagtgcct ggtacatcag atgacagtac tgaagagcca   2940
gtaatgaaaa aacgtactta ctgtacttac tgcccctcta aaataaggcg aaaggcaaat   3000
gcatcgtgca aaaaatgcaa aaaagttatt tgtcgagagc ataatattga tatgtgccaa   3060
agttgtttct gactgactaa taagtataat ttgtttctat tatgtataag ttaagctaat   3120
tacttatttt ataatacaac atgactgttt ttaaagtaca aaataagttt attttttgtaa   3180 aagagagaat gtttaaaagt tttgttactt tagaagaaat tttgagtttt tgttttttt    3240 taataaaataa ataaacataa ataaattgtt tgttgaattt ggatccacta gttctagagc   3300
```

-continued

```
ggccgccacc gcggtggagc tccagctttt gttcccttta gtgagggtta attgcgcgct    3360
tggcgtaatc atggtcatag ctgtttcctg tgtgaaattg ttatccgctc acaattccac    3420
acaacatacg agccggaagc ataaagtgta aagcctgggg tgcctaatga gtgagctaac    3480
tcacattaat tgcgttgcgc tcactgcccg ctttccagtc gggaaacctg tcgtgccagc    3540
tgcattaatg aatcggccaa cgcgcgggga gaggcggttt gcgtattggg cgctcttccg    3600
cttcctcgct cactgactcg ctgcgctcgg tcgttcggct gcggcgagcg gtatcagctc    3660
actcaaaggc ggtaatacgg ttatccacag aatcagggga taacgcagga aagaacatgt    3720
gagcaaaagg ccagcaaaag gccaggaacc gtaaaaaggc cgcgttgctg gcgttttcc     3780 ataggctccg cccccctgac gagcatcaca aaaatcgacg ctcaagtcag aggtggcgaa    3840
acccgacagg actataaaga taccaggcgt ttccccctgg aagctccctc gtgcgctctc    3900
ctgttccgac cctgccgctt accggatacc tgtccgcctt ctcccttcg ggaagcgtgg     3960 cgctttctca tagctcacgc tgtaggtatc tcagttcggt gtaggtcgtt cgctccaagc    4020
tgggctgtgt gcacgaaccc cccgttcagc ccgaccgctg cgccttatcc ggtaactatc    4080
gtcttgagtc caacccggta agacacgact tatcgccact ggcagcagcc actggtaaca    4140
ggattagcag agcgaggtat gtaggcggtg ctacagagtt cttgaagtgg tggcctaact    4200
acggctacac tagaaggaca gtatttggta tctgcgctct gctgaagcca gttaccttcg    4260
gaaaaagagt tggtagctct tgatccggca acaaaccac cgctggtagc ggtggttttt     4320
ttgtttgcaa gcagcagatt acgcgcagaa aaaaaggatc tcaagaagat cctttgatct    4380
tttctacggg gtctgacgct cagtggaacg aaaactcacg ttaagggatt ttggtcatga    4440
gattatcaaa aaggatcttc acctagatcc ttttaaatta aaaatgaagt tttaaatcaa    4500
tctaaagtat atatgagtaa acttggtctg acagttacca atgcttaatc agtgaggcac    4560
ctatctcagc gatctgtcta tttcgttcat ccatagttgc ctgactcccc gtcgtgtaga    4620
taactacgat acgggagggc ttaccatctg gccccagtgc tgcaatgata ccgcgagacc    4680
cacgctcacc ggctccagat ttatcagcaa taaaccagcc agccggaagg gccgagcgca    4740
gaagtggtcc tgcaacttta tccgcctcca tccagtctat taattgttgc cgggaagcta    4800
gagtaagtag ttcgccagtt aatagtttgc gcaacgttgt tgccattgct acaggcatcg    4860
tggtgtcacg ctcgtcgttt ggtatggctt cattcagctc cggttcccaa cgatcaaggc    4920
gagttacatg atcccccatg ttgtgcaaaa aagcggttag ctccttcggt cctccgatcg    4980
ttgtcagaag taagttggcc gcagtgttat cactcatggt tatggcagca ctgcataatt    5040
ctcttactgt catgccatcc gtaagatgct tttctgtgac tggtgagtac tcaaccaagt    5100
cattctgaga atagtgtatg cggcgaccga gttgctcttg cccggcgtca atacgggata    5160
ataccgcgcc acatagcaga actttaaaag tgctcatcat tggaaaacgt tcttcggggc    5220
gaaaactctc aaggatctta ccgctgttga gatccagttc gatgtaaccc actcgtgcac    5280
ccaactgatc ttcagcatct tttactttca ccagcgtttc tgggtgagca aaaacaggaa    5340
ggcaaaatgc cgcaaaaaag gaataagggc gacacggaa atgttgaata ctcatactct    5400
tcctttttca atattattga agcatttatc agggttattg tctcatgagc ggatacatat    5460
ttgaatgtat ttagaaaaat aaacaaatag gggttccgcg cacatttccc cgaaaagtgc    5520
cac                                                                 5523
```

<210> SEQ ID NO 45
<211> LENGTH: 6984

<212> TYPE: DNA
<213> ORGANISM: Artificial Sequence
<220> FEATURE:
<223> OTHER INFORMATION: Description of Artificial Sequence:
    pBXP3-DsRed-orf sequence

<400> SEQUENCE: 45

| | | | | | |
|---|---|---|---|---|---|
| tagttattaa | tagtaatcaa | ttacggggtc | attagttcat | agcccatata | tggagttccg | 60 |
| cgttacataa | cttacggtaa | atggcccgcc | tggctgaccg | cccaacgacc | cccgcccatt | 120 |
| gacgtcaata | atgacgtatg | ttcccatagt | aacgccaata | gggactttcc | attgacgtca | 180 |
| atgggtggag | tatttacggt | aaactgccca | cttggcagta | catcaagtgt | atcatatgcc | 240 |
| aagtacgccc | cctattgacg | tcaatgacgg | taaatggccc | gcctggcatt | atgcccagta | 300 |
| catgacctta | tgggactttc | ctacttggca | gtacatctac | gtattagtca | tcgctattac | 360 |
| catggtgatg | cggttttggc | agtacatcaa | tgggcgtgga | tagcggtttg | actcacgggg | 420 |
| atttccaagt | ctccacccca | ttgacgtcaa | tgggagtttg | ttttggcacc | aaaatcaacg | 480 |
| ggactttcca | aaatgtcgta | acaactccgc | cccattgacg | caaatgggcg | gtaggcgtgt | 540 |
| acggtgggag | gtctatataa | gcagagctgg | tttagtgaac | cgtcagatcc | gctagcgcta | 600 |
| ccggactcag | atcctatata | ataaaatggg | tagttcttta | gacgatgagc | atatcctctc | 660 |
| tgctcttctg | caaagcgatg | acgagcttgt | tggtgaggat | tctgacagtg | aaatatcaga | 720 |
| tcacgtaagt | gaagatgacg | tccagagcga | tacagaagaa | gcgtttatag | atgaggtaca | 780 |
| tgaagtgcag | ccaacgtcaa | gcggtagtga | aatattagac | gaacaaaatg | ttattgaaca | 840 |
| accaggttct | tcattggctt | ctaacagaat | cttgaccttg | ccacagagga | ctattagagg | 900 |
| taagaataaa | cattgttggt | caacttcaaa | gtccacgagg | cgtagccgag | tctctgcact | 960 |
| gaacattgtc | agatctcaaa | gaggtccgac | gcgtatgtgc | cgcaatatat | atgacccact | 1020 |
| tttatgcttc | aaactatttt | ttactgatga | gataaatttcg | gaaattgtaa | aatggacaaa | 1080 |
| tgctgagata | tcattgaaac | gtcgggaatc | tatgacaggt | gctacatttc | gtgacacgaa | 1140 |
| tgaagatgaa | atctatgctt | tctttggtat | tctggtaatg | acagcagtga | gaaaagataa | 1200 |
| ccacatgtcc | acagatgacc | tctttgatcg | atctttgtca | atggtgtacg | tctctgtaat | 1260 |
| gagtcgtgat | cgtttttgatt | ttttgatacg | atgtcttaga | atggatgaca | aaagtatacg | 1320 |
| gcccacactt | cgagaaaacg | atgtatttac | tcctgttaga | aaaatatggg | atctctttat | 1380 |
| ccatcagtgc | atacaaaatt | acactccagg | ggctcatttg | accatagatg | aacagttact | 1440 |
| tggttttaga | ggacggtgtc | cgtttaggat | gtatatccca | aacaagccaa | gtaagtatgg | 1500 |
| aataaaaatc | ctcatgatgt | gtgacagtgg | tacgaagtat | atgataaatg | gaatgcctta | 1560 |
| tttgggaaga | ggaacacaga | ccaacggagt | accactcggt | gaatactacg | tgaaggagtt | 1620 |
| atcaaagcct | gtgcacggta | gttgtcgtaa | tattacgtgt | gacaattggt | tcacctcaat | 1680 |
| cccctttggca | aaaaacttac | tacaagaacc | gtataagtta | accattgtgg | gaaccgtgcg | 1740 |
| atcaaacaaa | cgcgagatac | cggaagtact | gaaaaacagt | cgctccaggc | cagtgggaac | 1800 |
| atcgatgttt | tgttttgacg | gaccccttac | tctcgtctca | tataaaccga | agccagctaa | 1860 |
| gatggtatac | ttattatcat | cttgtgatga | ggatgcttct | atcaacgaaa | gtaccggtaa | 1920 |
| accgcaaatg | gttatgtatt | ataatcaaac | taaaggcgga | gtggacacgc | tagaccaaat | 1980 |
| gtgttctgtg | atgacctgca | gtaggaagac | gaataggtgg | cctatggcat | tattgtacgg | 2040 |
| aatgataaac | attgcctgca | taaattcttt | tattatatac | agccataatg | tcagtagcaa | 2100 |
| gggagaaaag | gttcaaagtc | gcaaaaaatt | tatgagaaac | ctttacatga | gcctgacgtc | 2160 |

```
atcgtttatg cgtaagcgtt tagaagctcc tactttgaag agatatttgc gcgataatat    2220
ctctaatatt ttgccaaatg aagtgcctgg tacatcagat gacagtactg aagagccagt    2280
aatgaaaaaa cgtacttact gtacttactg cccctctaaa ataaggcgaa aggcaaatgc    2340
atcgtgcaaa aaatgcaaaa aagttatttg tcgagagcat aatattgata tgtgccaaag    2400
ttgtttctga ctgactaata agtataattt gtttctatta tgtataagtt aagctaatta    2460
cttattttat aatacaacat gactgttttt aaagtacaaa ataagtttat ttttgtaaaa    2520
gagagaatgt ttaaaagttt tgttacttta gaagaaattt tgagtttttg ttttttttta    2580
ataaataaat aaacataaat aaattgtttg ttgaatttgg atctcgaggt tcccacaatg    2640
gttaattcga gctcgcccgg ggatctaatt caattagaga ctaattcaat tagagctaat    2700
tcaattagga tccaagctta tcgatttcga accctcgacc gccggagtat aaatagaggc    2760
gcttcgtcta cggagcgaca attcaattca acaagcaaa gtgaacacgt cgctaagcga    2820
aagctaagca aataaacaag cgcagctgaa caagctaaac aatcggggta ccgctagagt    2880
cgacggtacc gcgggcccgg gatccaccgg tcgccaccat gaattctgca gtcgacggta    2940
ccgcgggccc gggatccacc ggtcgccacc atggtgcgct cctccaagaa cgtcatcaag    3000
gagttcatgc gcttcaaggt gcgcatggag ggcaccgtga acggccacga gttcgagatc    3060
gagggcgagg gcgagggccg ccctacgag ggccacaaca ccgtgaagct gaaggtgacc    3120
aagggcggcc ccctgccctt cgcctggac atcctgtccc cccagttcca gtacggctcc    3180
aaggtgtacg tgaagcaccc cgccgacatc cccgactaca gaagctgtc cttccccgag    3240
ggcttcaagt gggagcgcgt gatgaacttc gaggacggcg gcgtggtgac cgtgacccag    3300
gactcctccc tgcaggacgg ctgcttcatc tacaaggtga agttcatcgg cgtgaacttc    3360
ccctccgacg gccccgtaat gcagaagaag accatgggct gggaggcctc caccgagcgc    3420
ctgtacccc gcgacggcgt gctgaagggc gagatccaca aggccctgaa gctgaaggac    3480
ggcggccact acctggtgga gttcaagtcc atctacatgg ccaagaagcc cgtgcagctg    3540
cccggctact actacgtgga ctccaagctg gacatcacct cccacaacga ggactacacc    3600
atcgtggagc agtacgagcg caccgagggc cgccaccacc tgttcctgta gcggccgcga    3660
ctctagatca taatcagcca taccacattt gtagaggttt tacttgcttt aaaaaacctc    3720
ccacacctcc ccctgaacct gaaacataaa atgaatgcaa ttgttgttgt taacttgttt    3780
attgcagctt ataatggtta caaataaagc aatagcatca caaatttcac aaataaagca    3840
ttttttttcac tgcattctag ttgtggtttg tccaaactca tcaatgtatc ttaaggcgta    3900
aattgtaagc gttaatattt tgttaaaatt cgcgttaaat ttttgttaaa tcagctcatt    3960
ttttaaccaa taggccgaaa tcggcaaaat cccttataaa tcaaaagaat agaccgagat    4020
agggttgagt gttgttccag tttggaacaa gagtccacta ttaaagaacg tggactccaa    4080
cgtcaaaggg cgaaaaaccg tctatcaggg cgatggccca ctacgtgaac catcacccta    4140
atcaagtttt ttggggtcga ggtgccgtaa agcactaaat cggaacccta agggagcccc    4200
ccgatttaga gcttgacggg gaaagccggc gaacgtggcg agaaaggaag ggaagaaagc    4260
gaaaggagcg ggcgctaggg cgctggcaag tgtagcggtc acgctgcgcg taaccaccac    4320
acccgccgcg cttaatgcgc cgctacaggg cgcgtcaggt ggcactttc ggggaaatgt    4380
gcgcggaacc cctatttgtt tatttttcta aatacattca aatatgtatc cgctcatgag    4440
acaataaccc tgataaatgc ttcaataata ttgaaaaagg aagagtcctg aggcggaaag    4500
```

```
aaccagctgt ggaatgtgtg tcagttaggg tgtggaaagt ccccaggctc cccagcaggc    4560
agaagtatgc aaagcatgca tctcaattag tcagcaacca ggtgtggaaa gtccccaggc    4620
tccccagcag gcagaagtat gcaaagcatg catctcaatt agtcagcaac catagtcccg    4680
cccctaactc cgcccatccc gcccctaact ccgcccagtt ccgcccattc tccgcccat     4740 ggctgactaa ttttttttat ttatgcagag gccgaggccg cctcggcctc tgagctattc    4800
cagaagtagt gaggaggctt ttttggaggc ctaggctttt gcaaagatcg atcaagagac    4860
aggatgagga tcgtttcgca tgattgaaca agatggattg cacgcaggtt ctccggccgc    4920
ttgggtggag aggctattcg gctatgactg ggcacaacag acaatcggct gctctgatgc    4980
cgccgtgttc cggctgtcag cgcaggggcg cccggttctt tttgtcaaga ccgacctgtc    5040
cggtgccctg aatgaactgc aagacgaggc agcgcggcta tcgtggctgg ccacgacggg    5100
cgttccttgc gcagctgtgc tcgacgttgt cactgaagcg ggaagggact ggctgctatt    5160
gggcgaagtg ccggggcagg atctcctgtc atctcacctt gctcctgccg agaaagtatc    5220
catcatggct gatgcaatgc ggcggctgca tacgcttgat ccggctacct gcccattcga    5280
ccaccaagcg aaacatcgca tcgagcgagc acgtactcgg atggaagccg gtcttgtcga    5340
tcaggatgat ctggacgaag agcatcaggg gctcgcgcca gccgaactgt tcgccaggct    5400
caaggcgagc atgcccgacg gcgaggatct cgtcgtgacc catggcgatg cctgcttgcc    5460
gaatatcatg gtggaaaatg gccgcttttc tggattcatc gactgtggcc ggctgggtgt    5520
ggcggaccgc tatcaggaca tagcgttggc tacccgtgat attgctgaag agcttggcgg    5580
cgaatgggct gaccgcttcc tcgtgcttta cggtatcgcc gctcccgatt cgcagcgcat    5640
cgccttctat cgccttcttg acgagttctt ctgagcggga ctctggggtt cgaaatgacc    5700
gaccaagcga cgcccaacct gccatcacga gatttcgatt ccaccgccgc cttctatgaa    5760
aggttgggct tcggaatcgt tttccgggac gccggctgga tgatcctcca gcgcggggat    5820
ctcatgctgg agttcttcgc ccaccctagg gggaggctaa ctgaaacacg aaggagaca     5880 ataccggaag gaaccgcgc tatgacggca ataaaaagac agaataaaac gcacggtgtt     5940
gggtcgtttg ttcataaacg cggggttcgg tcccagggct ggcactctgt cgatacccca    6000
ccgagacccc attggggcca atacgcccgc gtttcttcct tttccccacc caccccccca    6060
agttcgggtg aaggcccagg gctcgcagcc aacgtcgggg cggcaggccc tgccatagcc    6120
tcaggttact catatatact ttagattgat ttaaaacttc attttttaatt taaaaggatc    6180 taggtgaaga tccttttga taatctcatg accaaaatcc cttaacgtga gttttcgttc     6240
cactgagcgt cagaccccgt agaaaagatc aaaggatctt cttgagatcc ttttttttctg    6300 cgcgtaatct gctgcttgca acaaaaaaa ccaccgctac cagcggtggt ttgtttgccg     6360
gatcaagagc taccaactct ttttccgaag gtaactggct tcagcagagc gcagatacca    6420
aatactgtcc ttctagtgta gccgtagtta ggccaccact tcaagaactc tgtagcaccg    6480
cctacatacc tcgctctgct aatcctgtta ccagtggctg ctgccagtgg cgataagtcg    6540
tgtcttaccg ggttggactc aagacgatag ttaccggata aggcgcagcg gtcgggctga    6600
acggggggtt cctgcacaca gcccagcttg gagcgaacga cctacaccga actgagatac    6660
ctacagcgtg agctatgaga aagcgccacg cttcccgaag ggagaaaggc ggacaggtat    6720
ccggtaagcg gcagggtcgg aacaggagag cgcacgaggg agcttccagg gggaaacgcc    6780
tggtatcttt atagtcctgt cgggtttcgc cacctctgac ttgagcgtcg attttttgtga   6840 tgctcgtcag gggggcggag cctatggaaa aacgccagca acgcggcctt tttacggttc    6900
```

-continued

```
ctggccttttt gctggccttt tgctcacatg ttctttcctg cgttatcccc tgattctgtg    6960
gataaccgta ttaccgccat gcat                                             6984

<210> SEQ ID NO 46
<211> LENGTH: 4613
<212> TYPE: DNA
<213> ORGANISM: Artificial Sequence
<220> FEATURE:
<223> OTHER INFORMATION: Description of Artificial Sequence: pCRII-ITR
      sequence
<220> FEATURE:
<221> NAME/KEY: CDS
<222> LOCATION: (344)..(922)

<400> SEQUENCE: 46
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gccaagcttg    240
gtaccgagct cggatccact agtaacggcc gccagtgtgc tggaattcgg cttggatccc    300
atgcgtcaat tttacgcaga ctatctttct aggttaatc tag ctg cat cag gat        355
                                             Leu His Gln Asp
                                              1 cat atc gtc ggg tct ttt ttc cgg ctc agt cat cgc cca agc tgg cgc       403
His Ile Val Gly Ser Phe Phe Arg Leu Ser His Arg Pro Ser Trp Arg
  5              10                  15                  20 tat ctg ggc atc ggg gag gaa gaa gcc cgt gcc ttt tcc cgc gag gtt       451
Tyr Leu Gly Ile Gly Glu Glu Glu Ala Arg Ala Phe Ser Arg Glu Val
             25                  30                  35 gaa gcg gca tgg aaa gag ttt gcc gag gat gac tgc tgc tgc att gac       499
Glu Ala Ala Trp Lys Glu Phe Ala Glu Asp Asp Cys Cys Cys Ile Asp
         40                  45                  50 gtt gag cga aaa cgc acg ttt acc atg atg att cgg gaa ggt gtg gcc       547
Val Glu Arg Lys Arg Thr Phe Thr Met Met Ile Arg Glu Gly Val Ala
     55                  60                  65 atg cac gcc ttt aac ggt gaa ctg ttc gtt cag gcc acc tgg gat acc       595
Met His Ala Phe Asn Gly Glu Leu Phe Val Gln Ala Thr Trp Asp Thr
 70                  75                  80 agt tcg tcg cgg ctt ttc cgg aca cag ttc cgg atg gtc agc ccg aag       643
Ser Ser Ser Arg Leu Phe Arg Thr Gln Phe Arg Met Val Ser Pro Lys
 85                  90                  95                 100 cgc atc agc aac ccg aac aat acc ggc gac agc cgg aac tgc cgt gcc       691
Arg Ile Ser Asn Pro Asn Asn Thr Gly Asp Ser Arg Asn Cys Arg Ala
                105                 110                 115 ggt gtg cag att aat gac agc ggt gcg gcg ctg gga tat tac gtc agc       739
Gly Val Gln Ile Asn Asp Ser Gly Ala Ala Leu Gly Tyr Tyr Val Ser
            120                 125                 130 gag gac ggg tat cct ggc tgg atg ccg cag aaa tgg aca tgg ata ccc       787
Glu Asp Gly Tyr Pro Gly Trp Met Pro Gln Lys Trp Thr Trp Ile Pro
        135                 140                 145 cgt gag tta ccc ggc ggg cgc gcc tcg ttc att cac gtt ttt gaa ccc       835
Arg Glu Leu Pro Gly Gly Arg Ala Ser Phe Ile His Val Phe Glu Pro
    150                 155                 160 gtg gag gac ggg cag act cgc ggt gca aat gtg ttt tac agc gtg atg       883
Val Glu Asp Gly Gln Thr Arg Gly Ala Asn Val Phe Tyr Ser Val Met
165                 170                 175                 180 gag cag atg aag atg ctc gac acg ctg cag aac acg cag ctagattaac       932
Glu Gln Met Lys Met Leu Asp Thr Leu Gln Asn Thr Gln
```

```
                185            190
cctagaaaga taatcatatt gtgacgtacg ttaaagataa tcatgcgtaa aattgacgca    992
tgggatccaa gccgaattct gcagatatcc atcacactgg cggccgctcg agcatgcatc   1052
tagagggccc aattcgccct atagtgagtc gtattacaat tcactggccg tcgttttaca   1112
acgtcgtgac tgggaaaacc ctggcgttac ccaacttaat cgccttgcag cacatccccc   1172
tttcgccagc tggcgtaata gcgaagaggc ccgcaccgat cgcccttccc aacagttgcg   1232
cagcctgaat ggcgaatggg acgcgccctg tagcggcgca ttaagcgcgg cgggtgtggt   1292
ggttacgcgc agcgtgaccg ctacacttgc cagcgcccta gcgcccgctc ctttcgcttt   1352
cttcccttcc tttctcgcca cgttcgccgg ctttccccgt caagctctaa atcgggggct   1412
ccctttaggg ttccgattta gagctttacg gcacctcgac cgcaaaaaac ttgatttggg   1472
tgatggttca cgtagtgggc catcgccctg atagacggtt tttcgccctt gacgttgga    1532 gtccacgttc tttaatagtg gactcttgtt ccaaactgga acaacactca accctatcgc   1592
ggtctattct tttgatttat aagggatttt gccgatttcg gcctattggt taaaaaatga   1652
gctgatttaa caaattcagg gcgcaagggc tgctaaagga accggaacac gtagaaagcc   1712
agtccgcaga aacggtgctg accccggatg aatgtcagct actgggctat ctggacaagg   1772
gaaaacgcaa gcgcaaagag aaagcaggta gcttgcagtg gcttacatg gcgatagcta    1832 gactgggcgg ttttatggac agcaagcgaa ccggaattgc cagctggggc gccctctggt   1892
aaggttggga agccctgcaa agtaaactgg atggctttct gccgccaag gatctgatgg    1952 cgcaggggat caagatctga tcaagagaca ggatgaggat cgtttcgcat gattgaacaa   2012
gatggattgc acgcaggttc tccggccgct tgggtggaga ggctattcgg ctatgactgg   2072
gcacaacaga caatcggctg ctctgatgcc gccgtgttcc ggctgtcagc gcaggggcgc   2132
ccggttcttt ttgtcaagac cgacctgtcc ggtgccctga atgaactgca ggacgaggca   2192
gcgcggctat cgtggctggc cacgacgggc gttccttgcg cagctgtgct cgacgttgtc   2252
actgaagcgg gaagggactg gctgctattg ggcgaagtgc cggggcagga tctcctgtca   2312
tctcgccttg ctcctgccga gaaagtatcc atcatggctg atgcaatgcg gcggctgcat   2372
acgcttgatc cggctacctg cccattcgac caccaagcga acatcgcat cgagcgagca    2432 cgtactcgga tggaagccgg tcttgtcgat caggatgatc tggacgaaga gcatcagggg   2492
ctcgcgccag ccgaactgtt cgccaggctc aaggcgcgca tgcccgacgg cgaggatctc   2552
gtcgtgatcc atggcgatgc ctgcttgccg aatatcatgg tggaaaatgg ccgcttttct   2612
ggattcaacg actgtggccg gctgggtgtg gcggaccgct atcaggacat agcgttggat   2672
acccgtgata ttgctgaaga gcttggcggc gaatgggctg accgcttcct cgtgctttac   2732
ggtatcgccg ctcccgattc gcagcgcatc gccttctatc gccttcttga cgagttcttc   2792
tgaattgaaa aggaagagt atgagtattc aacatttccg tgtcgccctt attccctttt   2852
ttgcggcatt ttgccttcct gtttttgctc acccagaaac gctggtgaaa gtaaagatg    2912 ctgaagatca gttgggtgca cgagtgggtt acatcgaact ggatctcaac agcggtaaga   2972
tccttgagag ttttcgcccc gaagaacgtt ttccaatgat gagcactttt aaagttctgc   3032
tatgtcatac actattatcc cgtattgacg ccgggcaaga gcaactcggt cgccgggcgc   3092
ggtattctca gaatgacttg gttgagtact caccagtcac agaaaagcat cttacggatg   3152
gcatgacagt aagagaatta tgcagtgctg ccataaccat gagtgataac actgcggcca   3212
acttacttct gacaacgatc ggaggaccga aggagctaac cgcttttttg cacaacatgg   3272
```

| | | | |
|---|---|---|---|
| gggatcatgt | aactcgcctt gatcgttggg aaccggagct gaatgaagcc ataccaaacg | 3332 | |
| acgagagtga | caccacgatg cctgtagcaa tgccaacaac gttgcgcaaa ctattaactg | 3392 | |
| gcgaactact | tactctagct tcccggcaac aattaataga ctggatggag gcggataaag | 3452 | |
| ttgcaggacc | acttctgcgc tcggcccttc cggctggctg gtttattgct gataaatctg | 3512 | |
| gagccggtga | gcgtgggtct cgcggtatca ttgcagcact ggggccagat ggtaagccct | 3572 | |
| cccgtatcgt | agttatctac acgacgggga gtcaggcaac tatggatgaa cgaaatagac | 3632 | |
| agatcgctga | gataggtgcc tcactgatta agcattggta actgtcagac caagtttact | 3692 | |
| catatatact | ttagattgat ttaaaacttc attttaatt taaaaggatc taggtgaaga | 3752 | |
| tcctttttga | taatctcatg accaaaatcc cttaacgtga gttttcgttc cactgagcgt | 3812 | |
| cagacccgt | agaaaagatc aaaggatctt cttgagatcc ttttttctg cgcgtaatct | 3872 | |
| gctgcttgca | aacaaaaaaa ccaccgctac cagcggtggt ttgtttgccg gatcaagagc | 3932 | |
| taccaactct | ttttccgaag gtaactggct tcagcagagc gcagatacca aatactgtcc | 3992 | |
| ttctagtgta | gccgtagtta ggccaccact tcaagaactc tgtagcaccg cctacatacc | 4052 | |
| tcgctctgct | aatcctgtta ccagtggctg ctgccagtgg cgataagtcg tgtcttaccg | 4112 | |
| ggttggactc | aagacgatag ttaccggata aggcgcagcg gtcgggctga acggggggtt | 4172 | |
| cgtgcacaca | gcccagcttg gagcgaacga cctacaccga actgagatac ctacagcgtg | 4232 | |
| agcattgaga | aagcgccacg cttcccgaag ggagaaaggc ggacaggtat ccggtaagcg | 4292 | |
| gcagggtcgg | aacaggagag cgcacgaggg agcttccagg gggaaacgcc tggtatcttt | 4352 | |
| atagtcctgt | cgggtttcgc cacctctgac ttgagcgtcg attttgtga tgctcgtcag | 4412 | |
| gggggcggag | cctatggaaa aacgccagca acgcggcctt tttacggttc ctggccttt | 4472 | |
| gctggccttt | tgctcacatg ttctttcctg cgttatcccc tgattctgtg gataaccgta | 4532 | |
| ttaccgcctt | tgagtgagct gataccgctc gccgcagccg aacgaccgag cgcagcgagt | 4592 | |
| cagtgagcga | ggaagcggaa g | 4613 | |

<210> SEQ ID NO 47
<211> LENGTH: 193
<212> TYPE: PRT
<213> ORGANISM: Artificial Sequence
<220> FEATURE:
<223> OTHER INFORMATION: Description of Artificial Sequence: pCRII-ITR
    amino acid sequence

<400> SEQUENCE: 47

Leu His Gln Asp His Ile Val Gly Ser Phe Phe Arg Leu Ser His Arg
 1               5                  10                  15

Pro Ser Trp Arg Tyr Leu Gly Ile Gly Glu Glu Ala Arg Ala Phe
            20                  25                  30

Ser Arg Glu Val Glu Ala Ala Trp Lys Glu Phe Ala Glu Asp Cys
        35                  40                  45

Cys Cys Ile Asp Val Glu Arg Lys Arg Thr Phe Thr Met Met Ile Arg
    50                  55                  60

Glu Gly Val Ala Met His Ala Phe Asn Gly Glu Leu Phe Val Gln Ala
65                  70                  75                  80

Thr Trp Asp Thr Ser Ser Ser Arg Leu Phe Arg Thr Gln Phe Arg Met
                85                  90                  95

Val Ser Pro Lys Arg Ile Ser Asn Pro Asn Asn Thr Gly Asp Ser Arg
            100                 105                 110

-continued

```
Asn Cys Arg Ala Gly Val Gln Ile Asn Asp Ser Gly Ala Ala Leu Gly
        115                 120                 125
Tyr Tyr Val Ser Glu Asp Gly Tyr Pro Gly Trp Met Pro Gln Lys Trp
    130                 135                 140
Thr Trp Ile Pro Arg Glu Leu Pro Gly Gly Arg Ala Ser Phe Ile His
145                 150                 155                 160
Val Phe Glu Pro Val Glu Asp Gly Gln Thr Arg Gly Ala Asn Val Phe
                165                 170                 175
Tyr Ser Val Met Glu Gln Met Lys Met Leu Asp Thr Leu Gln Asn Thr
            180                 185                 190
Gln
```

<210> SEQ ID NO 48
<211> LENGTH: 8999
<212> TYPE: DNA
<213> ORGANISM: Artificial Sequence
<220> FEATURE:
<223> OTHER INFORMATION: Description of Artificial Sequence:
      p(PZ)-Bac-EYFP sequence

<400> SEQUENCE: 48

| | | |
|---|---|---|
| accgaagtat acacttaaat tcagtgcacg tttgcttgtt gagaggaaag gttgtgtgcg | 60 |
| gacgaatttt tttttgaaaa cattaaccct tacgtggaat aaaaaaaaat gaaatattgc | 120 |
| aaattttgct gcaaagctgt gactggagta aaattaattc acgtgccgaa gtgtgctatt | 180 |
| aagagaaaat tgtgggagca gagccttggg tgcagccttg gtgaaaactc ccaaatttgt | 240 |
| gatacccact ttaatgattc gcagtggaag gctgcacctg caaaggtca gacatttaaa | 300 |
| aggaggcgac tcaacgcaga tgccgtacct agtaaagtga tagagcctga accagaaaag | 360 |
| ataaaagaag gctataccag tgggagtaca caaacagagt aagtttgaat agtaaaaaaa | 420 |
| atcatttatg taaacaataa cgtgactgtg cgttaggtcc tgttcattgt ttaatgaaaa | 480 |
| taagagcttg agggaaaaaa ttcgtacttt ggagtacgaa atgcgtcgtt tagagcagca | 540 |
| gccgaattca ctggccgtcg ttttacaacg tcgtgactgg gaaaaccctg gcgttaccca | 600 |
| acttaatcgc cttgcagcac atccccctt cgccagctgg cgtaatagcg aagaggcccg | 660 |
| caccgatcgc ccttcccaac agttgcgcag cctgaatggc gaatggcgct ttgcctggtt | 720 |
| tccggcacca gaagcggtgc cggaaagctg gctggagtgc gatcttcctg aggccgatac | 780 |
| tgtcgtcgtc ccctcaaact ggcagatgca cggttacgat gcgcccatct acaccaacgt | 840 |
| aacctatccc attacggtca atccgccgtt tgttcccacg gagaatccga cgggttgtta | 900 |
| ctcgctcaca tttaatgttg atgaaagctg gctacaggaa ggccagacgc gaattatttt | 960 |
| tgatggcgtt aactcggcgt tcatctgtg gtgcaacggg cgctgggtcg ttacggcca | 1020 |
| ggacagtcgt ttgccgtctg aatttgacct gagcgcattt ttacgcgccg gagaaaaccg | 1080 |
| cctcgcggtg atggtgctgc gttggagtga cggcagttat ctggaagatc aggatatgtg | 1140 |
| gcggatgagc ggcatttcc gtgacgtctc gttgctgcat aaaccgacta cacaaatcag | 1200 |
| cgatttccat gttgccactc gctttaatga tgatttcagc cgcgctgtac tggaggctga | 1260 |
| agttcagatg tgcggcgagt tgcgtgacta cctacgggta acagtttctt tatggcaggg | 1320 |
| tgaaacgcag gtcgccagcg gcaccgcgcc tttcggcggt gaaattatcg atgagcgtgg | 1380 |
| tggttatgcc gatcgcgtca cactacgtct gaacgtcgaa aacccgaaac tgtggagcgc | 1440 |
| cgaaatcccg aatctctatc gtgcggtggt tgaactgcac accgccgacg gcacgctgat | 1500 |
| tgaagcagaa gcctgcgatg tcggtttccg cgaggtgcgg attgaaaatg gtctgctgct | 1560 |

-continued

```
gctgaacggc aagccgttgc tgattcgagg cgttaaccgt cacgagcatc atcctctgca      1620
tggtcaggtc atggatgagc agacgatggt gcaggatatc ctgctgatga agcagaacaa      1680
ctttaacgcc gtgcgctgtt cgcattatcc gaaccatccg ctgtggtaca cgctgtgcga      1740
ccgctacggc ctgtatgtgg tggatgaagc caatattgaa acccacggca tggtgccaat      1800
gaatcgtctg accgatgatc cgcgctggct accggcgatg agcgaacgcg taacgcgaat      1860
ggtgcagcgc gatcgtaatc acccgagtgt gatcatctgg tcgctgggga atgaatcagg      1920
ccacggcgct aatcacgacg cgctgtatcg ctggatcaaa tctgtcgatc cttcccgccc      1980
ggtgcagtat gaaggcggcg agccgacac cacggccacc gatattattt gcccgatgta      2040
cgcgcgcgtg gatgaagacc agcccttccc ggctgtgccg aaatggtcca tcaaaaaatg      2100
gctttcgcta cctggagaga cgcgcccgct gatcctttgc gaatacgccc acgcgatggg      2160
taacagtctt ggcggtttcg ctaaatactg gcaggcgttt cgtcagtatc cccgtttaca      2220
gggcggcttc gtctgggact gggtggatca gtcgctgatt aaatatgatg aaaacggcaa      2280
cccgtggtcg gcttacggcg gtgattttgg cgatacgccg aacgatcgcc agttctgtat      2340
gaacggtctg gtctttgccg accgcacgcc gcatccagcg ctgacggaag caaaacacca      2400
gcagcagttt ttccagttcc gtttatccgg gcaaaccatc gaagtgacca gcgaataccct      2460 gttccgtcat agcgataacg agctcctgca ctggatggtg gcgctggatg gtaagccgct      2520
ggcaagcggt gaagtgcctc tggatgtcgc tccacaaggt aaacagttga ttgaactgcc      2580
tgaactaccg cagccggaga cgccgggca actctggctc acagtacgcg tagtgcaacc      2640
gaacgcgacc gcatggtcag aagccgggca catcagcgcc tggcagcagt ggcgtctggc      2700
ggaaaacctc agtgtgacgc tccccgccgc gtcccacgcc atcccgcatc tgaccaccag      2760
cgaaatggat ttttgcatcg agctgggtaa taagcgttgg caatttaacc gccagtcagg      2820
cttcctttca cagatgtgga ttggcgataa aaaacaactg ctgacgccgc tgcgcgatca      2880
gttcacccgt gcaccgctgg ataacgacat tggcgtaagt gaagcgaccc gcattgaccc      2940
taacgcctgg gtcgaacgct ggaaggcggc gggccattac caggccgaag cagcgttgtt      3000
gcagtgcacg gcagatacac ttgctgatgc ggtgctgatt acgaccgctc acgcgtggca      3060
gcatcagggg aaaaccttat ttatcagccg gaaaacctac cggattgatg gtagtggtca      3120
aatggcgatt accgttgatg ttgaagtggc gagcgataca ccgcatccgg cgcggattgg      3180
cctgaactgc cagctggcgc aggtagcaga gcgggtaaac tggctcggat tagggccgca      3240
agaaaactat cccgaccgcc ttactgccgc ctgttttgac cgctgggatc tgccattgtc      3300
agacatgtat accccgtacg tcttcccgag cgaaaacggt ctgcgctgcg ggacgcgcga      3360
attgaattat ggcccacacc agtggcgcgg cgacttccag ttcaacatca gccgctacag      3420
tcaacagcaa ctgatggaaa ccagccatcg ccatctgctg cacgcggaag aaggcacatg      3480
gctgaatatc gacggtttcc atatgggat tggtggcgac gactcctgga gcccgtcagt      3540
atcggcggaa ttcagctga gcgccggtcg ctaccattac cagttggtct ggtgtcgggg      3600
atccgtcgac taaggccaaa gagtctaatt tttgttcatc aatgggttat aacatatggg      3660
ttatattata agtttgtttt aagttttga gactgataag aatgtttcga tcgaatattc      3720
catagaacaa caatagtatt acctaattac caagtcttaa tttagcaaaa atgttattgc      3780
ttatagaaaa aataaattat ttatttgaaa tttaaagtca acttgtcatt taatgtcttg      3840
tagacttttg aaagtcttac gatacaatta gtatctaata tacatgggtt cattctacat      3900
```

-continued

```
tctatattag tgatgatttc tttagctagt aatacatttt aattatattc ggctttgatg    3960
attttctgat tttttccgaa cggattttcg tagacccttt cgatctcata atggctcatt    4020
ttattgcgat ggacggtcag gagagctcca cttttgaatt tctgttcgca gacaccgcat    4080
ttgtagcaca tagccgggac atccggtttg gggagatttt ccagtctctg ttgcaattgg    4140
ttttcgggaa tgcgttgcag gcgcatacgc tctatatcct ccgaacggcg ctggttgacc    4200
ctagcattta cataaggatc agcagcaaaa tttgcctctg cttcattgcc cggaatcaca    4260
gcaatcagat gtccctttcg gttacgatgg atattcaggt gcgaaccgca cacaaagctc    4320
tcgccgcaca ctccacactg atatggtcgc tcgccctgtg gcgccgcata tggatcttaa    4380
ggtcgttgga ctgcacaaag ctcttgctgc acattttgca ggagtacggc ctttgacccg    4440
tgtgcaatcg catgtgtcgc gccagcttgt tctgcgaaat aaacttcttg gagcagatgc    4500
ggccgcccgg ggtgggcgaa gaactccagc atgagatccc cgcgctggag gatcatccag    4560
ccggcgtccc ggaaaacgat tccgaagccc aacctttcat agaaggcggc ggtggaatcg    4620
aaatctcgtg atggcaggtt gggcgtcgct tggtcggtca tttcgaaccc cagagtcccg    4680
ctcagaagaa ctcgtcaaga aggcgataga aggcgatgcg ctgcgaatcg ggagcggcga    4740
taccgtaaag cacgaggaag cggtcagccc attcgccgcc aagctcttca gcaatatcac    4800
gggtagccaa cgctatgtcc tgatagcggt ccgccacacc cagccggcca cagtcgatga    4860
atccagaaaa gcggccattt ccaccatga tattcggcaa gcaggcatcg ccatgggtca    4920
cgacgagatc ctcgccgtcg ggcatgcgcg ccttgagcct ggcgaacagt tcggctggcg    4980
cgagcccctg atgctcttcg tccagatcat cctgatcgac aagaccggct tccatccgag    5040
tacgtgctcg ctcgatgcga tgtttcgctt ggtggtcgaa tgggcaggta gccggatcaa    5100
gcgtatgcag ccgccgcatt gcatcagcca tgatggatac tttctcggca ggagcaaggt    5160
gagatgacag gagatcctgc cccggcactt cgcccaatag cagccagtcc cttcccgctt    5220
cagtgacaac gtcgagcaca gctgcgcaag gaacgcccgt cgtggccagc cacgatagcc    5280
gcgctgcctc gtcctgcagt tcattcaggg caccggacag gtcggtcttg acaaaaagaa    5340
ccgggcgccc ctgcgctgac agccggaaca cggcggcatc agagcagccg attgtctgtt    5400
gtgcccagtc atagccgaat agcctctcca cccaagcggc cggagaacct gcgtgcaatc    5460
catcttgttc aatcatgcga aacgatcctc atcctgtctc ttgatcagat cttgatcccc    5520
tgcgccatca gatccttggc ggcaagaaag ccatccagtt tactttgcag ggcttcccaa    5580
ccttaccaga gggcgcccca gctggcaatt ccggttcgct tgctgtccat aaaaccgccc    5640
agtctagcta tcgccatgta agcccactgc aagctacctg cttctctttt gcgcttgcgt    5700
tttcccttgt ccagatagcc cagtagctga cattcatccg gggtcagcac cgtttctgcg    5760
gactggcttt ctacgtgttc cgcttccttt agcagccctt gcgccctgag tgcttgcggc    5820
agcgtgaagc taattcatgg ttataaattt tgttaaatc agctcatttt ttaaccaata    5880
ggccgaaatc ggcaaaatcc cttataaatc aaaagaatag cccgagatag ggttgagtgt    5940
tgttccagtt tggaacaaga gtccactatt aagaacgtg gactccaacg tcaaagggcg    6000
aaaaaccgtc tatcagggcg atggccggat cagcttatgc ggtgtgaaat accgcacaga    6060
tgcgtaagga gaaaataccg catcaggcgc tcttccgctt cctcgctcac tgactcgctg    6120
cgctcggtcg ttcggctgcg gcgagcggta tcagctcact caaaggcggt aatacggtta    6180
tccacagaat caggggataa cgcaggaaag aacatgtgag caaaaggcca gcaaaaggcc    6240
aggaaccgta aaaaggccgc gttgctggcg tttttccata ggctccgccc ccctgacgag    6300
```

```
catcacaaaa atcgacgctc aagtcagagg tggcgaaacc cgacaggact ataaagatac    6360
caggcgtttc ccctggaag ctccctcgtg cgctctcctg ttccgaccct gccgcttacc     6420
```



```
catcacaaaa atcgacgctc aagtcagagg tggcgaaacc cgacaggact ataaagatac    6360
caggcgtttc ccctggaag ctccctcgtg cgctctcctg ttccgaccct gccgcttacc     6420
ggatacctgt ccgcctttct ccttcggga agcgtggcgc tttctcatag ctcacgctgt     6480
aggtatctca gttcggtgta ggtcgttcgc tccaagctgg gctgtgtgca cgaaccccc     6540 gttcagcccg accgctgcgc cttatccggt aactatcgtc ttgagtccaa cccggtaaga    6600
cacgacttat cgccactggc agcagccact ggtaacagga ttagcagagc gaggtatgta    6660
ggcggtgcta cagagttctt gaagtggtgg cctaactacg gctacactag aaggacagta    6720
tttggtatct gcgctctgct gaagccagtt accttcggaa aaagagttgg tagctcttga    6780
tccggcaaac aaaccaccgc tggtagcggc ggtttttgt ttgcaagcag cagattacgc     6840
gcagaaaaaa aggatctcaa aagatcctt tgatcttttc ttactgaacg gtgatcccca    6900
ccggaattgc ggccgcggaa ttctcatgtt tgacagctta tcatcgataa gctggccgct    6960
ctagaactag tgttcccaca atggttaatt cgagctcgcc cggggatcta attcaattag    7020
agactaattc aattgagct aattcaatta ggatccaagc ttatcgattt cgaaccctcg     7080
accgccggag tataaataga ggcgcttcgt ctacggagcg acaattcaat tcaaacaagc    7140
aaagtgaaca cgtcgctaag cgaaagctaa gcaaataaac aagcgcagct gaacaagcta    7200
aacaatcggg gtaccgctag agtcgacggt acgatccacc ggtcgccacc atggtgagca    7260
agggcgagga gctgttcacc ggggtggtgc ccatcctggt cgagctggac ggcgacgtaa    7320
acggccacaa gttcagcgtg tccggcgagg gcgagggcga tgccacctac ggcaagctga    7380 cccctgaagtt catctgcacc accggcaagc tgcccgtgcc ctggcccacc ctcgtgacca    7440
ccttcggcta cggcctgcag tgcttcgccc gctaccccga ccacatgaag cagcacgact    7500
tcttcaagtc cgccatgccc gaaggctacg tccaggagcg caccatcttc ttcaaggacg    7560
acggcaacta caagacccgc gccgaggtga agttcgaggg cgacaccctg gtgaaccgca    7620
tcgagctgaa gggcatcgac ttcaaggagg acggcaacat cctggggcac aagctggagt    7680
acaactacaa cagccacaac gtctatatca tggccgacaa gcagaagaac ggcatcaagg    7740
tgaacttcaa gatccgccac aacatcgagg acggcagcgt gcagctcgcc gaccactacc    7800
agcagaacac ccccatcggc gacggccccg tgctgctgcc cgacaaccac tacctgagct    7860
accagtccgc cctgagcaaa gaccccaacg agaagcgcga tcacatggtc ctgctggagt    7920
tcgtgaccgc cgccgggatc actctcggca tggacgagct gtacaagtaa agcggccgcg    7980
actctagatc ataatcagcc ataccacatt tgtagaggtt ttacttgctt taaaaaacct    8040
cccacacctc cccctgaacc tgaaacataa aatgaatgca attgttgttg ttaacttgtt    8100
tattgcagct tataatggtt acaaataaag caatagcatc acaaatttca caaataaagc    8160
atttttttca ctgcattcta gttgtggttt gtccaaactc atcaatgtat cttaaagctt    8220
atcgatacgc gtacggcact agtggatccc atgcgtcaat tttacgcatg attatcttta    8280
acgtacgtca caatatgatt atctttctag ggttaatcta gctgcgtgtt ctgcagcgtg    8340
tcgagcatct tcatctgctc catcacgctg taaaacacat ttgcaccgcg agtctgcccg    8400
tcctccacgg gttcaaaaac gtgaatgaac gaggcgcgcc cgccgggtaa ctcacggggt    8460
atccatgtcc atttctgcgg catccagcca ggatacccgt cctcgctgac gtaatatccc    8520
agcgccgcac cgctgtcatt aatctgcaca ccggcacggc agttccggct gtcgccggta    8580
ttgttcgggt tgctgatgcg cttcgggctg accatccgga actgtgtccg gaaaagccgc    8640
```

-continued

```
gacgaactgg tatcccaggt ggcctgaacg aacagttcac cgttaaaggc gtgcatggcc    8700
acaccttccc gaatcatcat ggtaaacgtg cgttttcgct caacgtcaat gcagcagcag    8760
tcatcctcgg caaactcttt ccatgccgct tcaacctcgc gggaaaaggc acgggcttct    8820
tcctccccga tgcccagata cgccagcttg ggcgatgac tgagccggaa aaaagacccg     8880
acgatatgat cctgatgcag ctagattaac cctagaaaga tagtctgcgt aaaattgacg    8940
catgggatcc cccgggctgc aggaattcga tatcaagctt atcgataccg tcgaagctt    8999
```

<210> SEQ ID NO 49
<211> LENGTH: 9012
<212> TYPE: DNA
<213> ORGANISM: Artificial Sequence
<220> FEATURE:
<223> OTHER INFORMATION: Description of Artificial Sequence:
      p(PZ)-Bac-ECFP sequence

<400> SEQUENCE: 49

```
accgaagtat acacttaaat tcagtgcacg tttgcttgtt gagaggaaag gttgtgtgcg      60
gacgaatttt tttttgaaaa cattaacccct tacgtggaat aaaaaaaaat gaaatattgc    120
aaattttgct gcaaagctgt gactggagta aaattaattc acgtgccgaa gtgtgctatt    180
aagagaaaat tgtgggagca gagccttggg tgcagccttg gtgaaaactc ccaaatttgt    240
gatacccact ttaatgattc gcagtggaag gctgcacctg caaaaggtca gacatttaaa    300
aggaggcgac tcaacgcaga tgccgtacct agtaaagtga tagagcctga accagaaaag    360
ataaaagaag gctataccag tgggagtaca caaacagagt aagtttgaat agtaaaaaaa    420
atcatttatg taaacaataa cgtgactgtg cgttaggtcc tgttcattgt ttaatgaaaa    480
taagagcttg agggaaaaaa ttcgtacttt ggagtacgaa atgcgtcgtt tagagcagca    540
gccgaattca ctggccgtcg ttttacaacg tcgtgactgg gaaaaccctg gcgttaccca    600
acttaatcgc cttgcagcac atccccccttt cgccagctgg cgtaatagcg aagaggcccg    660
caccgatcgc ccttcccaac agttgcgcag cctgaatggc gaatggcgct ttgcctggtt    720
tccggcacca gaagcggtgc cggaaagctg gctggagtgc gatcttcctg aggccgatac    780
tgtcgtcgtc ccctcaaact ggcagatgca cggttacgat gcgcccatct acaccaacgt    840
aacctatccc attacggtca atccgccgtt tgttcccacg gagaatccga cgggttgtta    900
ctcgctcaca tttaatgttg atgaaagctg gctacaggaa ggccagacgc gaattatttt    960
tgatggcgtt aactcggcgt ttcatctgtg gtgcaacggg cgctgggtcg gttacggcca   1020
ggacagtcgt ttgccgtctg aatttgacct gagcgcattt ttacgcgccg gagaaaaccg   1080
cctcgcggtg atggtgctgc gttggagtga cggcagttat ctggaagatc aggatatgtg   1140
gcggatgagc ggcattttcc gtgacgtctc gttgctgcat aaaccgacta cacaaatcag   1200
cgatttccat gttgccactc gctttaatga tgatttcagc cgcgctgtac tggaggctga   1260
agttcagatg tgcggcgagt tgcgtgacta cctacgggta acagtttctt tatggcaggg   1320
tgaaacgcag gtcgccagcg gcaccgcgcc tttcggcggt gaaattatcg atgagcgtgg   1380
tggttatgcc gatcgcgtca cactacgtct gaacgtcgaa acccgaaac tgtggagcgc    1440 cgaaatcccg aatctctatc gtgcggtggt tgaactgcac accgccgacg gcacgctgat   1500
tgaagcagaa gcctgcgatg tcggtttccg cgaggtgcgg attgaaaatg gtctgctgct   1560
gctgaacggc aagccgttgc tgattcgagg cgttaaccgt cacgagcatc atcctctgca   1620
tggtcaggtc atggatgagc agacgatggt gcaggatatc ctgctgatga agcagaacaa   1680
```

```
ctttaacgcc gtgcgctgtt cgcattatcc gaaccatccg ctgtggtaca cgctgtgcga    1740
ccgctacggc ctgtatgtgg tggatgaagc caatattgaa acccacggca tggtgccaat    1800
gaatcgtctg accgatgatc cgcgctggct accggcgatg agcgaacgcg taacgcgaat    1860
ggtgcagcgc gatcgtaatc acccgagtgt gatcatctgg tcgctgggga atgaatcagg    1920
ccacggcgct aatcacgacg cgctgtatcg ctggatcaaa tctgtcgatc cttcccgccc    1980
ggtgcagtat gaaggcggcg gagccgacac cacggccacc gatattattt gcccgatgta    2040
cgcgcgcgtg gatgaagacc agcccttccc ggctgtgccg aaatggtcca tcaaaaaatg    2100
gctttcgcta cctggagaga cgcgcccgct gatcctttgc gaatacgccc acgcgatggg    2160
taacagtctt ggcggtttcg ctaaatactg gcaggcgttt cgtcagtatc ccgtttaca    2220
gggcggcttc gtctgggact gggtggatca gtcgctgatt aaatatgatg aaaacggcaa    2280
cccgtggtcg gcttacggcg gtgattttgg cgatacgccg aacgatcgcc agttctgtat    2340
gaacggtctg gtctttgccg accgcacgcc gcatccagcg ctgacggaag caaaacacca    2400
gcagcagttt ttccagttcc gtttatccgg gcaaaccatc gaagtgacca gcgaatacct    2460
gttccgtcat agcgataacg agctcctgca ctggatggtg cgctggatg gtaagccgct    2520
ggcaagcggt gaagtgcctc tggatgtcgc tccacaaggt aaacagttga ttgaactgcc    2580
tgaactaccg cagccggaga cgccgggca actctggctc acagtacgcg tagtgcaacc    2640
gaacgcgacc gcatggtcag aagccgggca catcagcgcc tggcagcagt ggcgtctggc    2700
ggaaaacctc agtgtgacgc tccccgccgc gtcccacgcc atcccgcatc tgaccaccag    2760
cgaaatggat ttttgcatcg agctgggtaa taagcgttgg caatttaacc gccagtcagg    2820
ctttctttca cagatgtgga ttggcgataa aaaacaactg ctgacgccgc tgcgcgatca    2880
gttcacccgt gcaccgctgg ataacgacat tggcgtaagt gaagcgaccc gcattgaccc    2940
taacgcctgg gtcgaacgct ggaaggcggc gggccattac caggccgaag cagcgttgtt    3000
gcagtgcacg gcagatacac ttgctgatgc ggtgctgatt acgaccgctc acgcgtggca    3060
gcatcagggg aaaaaccttat ttatcagccg gaaaacctac cggattgatg gtagtggtca    3120
aatggcgatt accgttgatg ttgaagtggc gagcgataca ccgcatccgg cgcggattgg    3180
cctgaactgc cagctggcgc aggtagcaga gcgggtaaac tggctcggat tagggccgca    3240
agaaaactat cccgaccgcc ttactgccgc ctgttttgac cgctgggatc tgccattgtc    3300
agacatgtat accccgtacg tcttcccgag cgaaaacggt ctgcgctgcg ggacgcgcga    3360
attgaattat ggcccacacc agtggcgcgg cgacttccag ttcaacatca gccgctacag    3420
tcaacagcaa ctgatggaaa ccagccatcg ccatctgctg cacgcggaag aaggcacatg    3480
gctgaatatc gacggtttcc atatgggat tggtggcgac gactcctgga gcccgtcagt    3540
atcggcggaa ttccagctga gcgccggtcg ctaccattac cagttggtct ggtgtcgggg    3600
atccgtcgac taaggccaaa gagtctaatt tttgttcatc aatgggttat aacatatggg    3660
ttatattata agtttgtttt aagttttga gactgataag aatgtttcga tcgaatattc    3720
catagaacaa caatagtatt acctaattac caagtcttaa tttagcaaaa atgttattgc    3780
ttatagaaaa aataaattat ttatttgaaa tttaaagtca acttgtcatt taatgtcttg    3840
tagactttg aaagtcttac gatacaatta gtatctaata tacatgggtt cattctacat    3900
tctatattag tgatgatttc tttagctagt aatacatttt aattatattc ggctttgatg    3960
attttctgat tttttccgaa cggatttccg tagacccttt cgatctcata atggctcatt    4020
ttattgcgat ggacggtcag gagagctcca ctttgaatt tctgttcgca gacaccgcat    4080
```

```
ttgtagcaca tagccgggac atccggtttg gggagatttt ccagtctctg ttgcaattgg   4140
ttttcgggaa tgcgttgcag gcgcatacgc tctatatcct ccgaacggcg ctggttgacc   4200
ctagcattta cataaggatc agcagcaaaa tttgcctctg cttcattgcc cggaatcaca   4260
gcaatcagat gtccctttcg gttacgatgg atattcaggt gcgaaccgca cacaaagctc   4320
tcgccgcaca ctccacactg atatggtcgc tcgccctgtg gcgccgcata tggatcttaa   4380
ggtcgttgga ctgcacaaag ctcttgctgc acattttgca ggagtacggc ctttgacccg   4440
tgtgcaatcg catgtgtcgc gccagcttgt tctgcgaaat aaacttcttg gagcagatgc   4500
ggccgcccgg ggtgggcgaa gaactccagc atgagatccc cgcgctggag gatcatccag   4560
ccggcgtccc ggaaaacgat tccgaagccc aacctttcat agaaggcggc ggtggaatcg   4620
aaatctcgtg atggcaggtt gggcgtcgct tggtcggtca tttcgaaccc cagagtcccg   4680
ctcagaagaa ctcgtcaaga aggcgataga aggcgatgcg ctgcgaatcg ggagcggcga   4740
taccgtaaag cacgaggaag cggtcagccc attcgccgcc aagctcttca gcaatatcac   4800
gggtagccaa cgctatgtcc tgatagcggt ccgccacacc cagccggcca cagtcgatga   4860
atcgagaaaa gcggccattt tccaccatga tattcggcaa gcaggcatcg ccatgggtca   4920
cgacgagatc ctcgccgtcg ggcatgcgcg ccttgagcct ggcgaacagt tcggctggcg   4980
cgagcccctg atgctcttcg tccagatcat cctgatcgac aagaccggct tccatccgag   5040
tacgtgctcg ctcgatgcga tgtttcgctt ggtggtcgaa tgggcaggta gccggatcaa   5100
gcgtatgcag ccgccgcatt gcatcagcca tgatggatac tttctcggca ggagcaaggt   5160
gagatgacag gagatcctgc cccggcactt cgcccaatag cagccagtcc cttcccgctt   5220
cagtgacaac gtcgagcaca gctgcgcaag gaacgcccgt cgtggccagc cacgatagcc   5280
gcgctgcctc gtcctgcagt tcattcaggg caccggacag gtcggtcttg acaaaaagaa   5340
ccgggcgccc ctgcgctgac agccggaaca cggcggcatc agagcagccg attgtctgtt   5400
gtgcccagtc atagccgaat agcctctcca cccaagcggc cggagaacct gcgtgcaatc   5460
catcttgttc aatcatgcga aacgatcctc atcctgtctc ttgatcagat cttgatcccc   5520
tgcgccatca gatccttggc ggcaagaaag ccatccagtt tactttgcag ggcttcccaa   5580
ccttaccaga gggcgcccca gctggcaatt ccggttcgct tgctgtccat aaaaccgccc   5640
agtctagcta tcgccatgta agcccactgc aagctacctg ctttctcttt gcgcttgcgt   5700
tttcccttgt ccagatagcc cagtagctga cattcatccg gggtcagcac cgtttctgcg   5760
gactggcttt ctacgtgttc cgcttccttt agcagccctt gcgccctgag tgcttgcggc   5820
agcgtgaagc taattcatgg ttataaattt ttgttaaatc agctcatttt ttaaccaata   5880
ggccgaaatc ggcaaaatcc cttataaatc aaaagaatag cccgagatag ggttgagtgt   5940
tgttccagtt tggaacaaga gtccactatt aaagaacgtg gactccaacg tcaaagggcg   6000
aaaaaccgtc tatcagggcg atggccggat cagcttatgc ggtgtgaaat accgcacaga   6060
tgcgtaagga gaaaataccg catcaggcgc tcttccgctt cctcgctcac tgactcgctg   6120
cgctcggtcg ttcggctgcg gcgagcggta tcagctcact caaaggcggt aatacggtta   6180
tccacagaat caggggataa cgcaggaaag aacatgtgag caaaaggcca gcaaaaggcc   6240
aggaaccgta aaaaggccgc gttgctggcg ttttccata ggctccgccc ccctgacgag   6300
catcacaaaa atcgacgctc aagtcagagg tggcgaaacc cgacaggact ataaagatac   6360
caggcgtttc ccctggaag ctccctcgtg cgctctcctg ttccgaccct gccgcttacc   6420
```

-continued

```
ggatacctgt ccgcctttct cccttcggga agcgtggcgc tttctcatag ctcacgctgt    6480
aggtatctca gttcggtgta ggtcgttcgc tccaagctgg gctgtgtgca cgaacccccc    6540
gttcagcccg accgctgcgc cttatccggt aactatcgtc ttgagtccaa cccggtaaga    6600
cacgacttat cgccactggc agcagccact ggtaacagga ttagcagagc gaggtatgta    6660
ggcggtgcta cagagttctt gaagtggtgg cctaactacg gctacactag aaggacagta    6720
tttggtatct gcgctctgct gaagccagtt accttcggaa aaagagttgg tagctcttga    6780
tccggcaaac aaaccaccgc tggtagcggc ggtttttttgt ttgcaagcag cagattacgc    6840
gcagaaaaaa aggatctcaa gaagatcctt tgatcttttc ttactgaacg gtgatcccca    6900
ccggaattgc ggccgcggaa ttctcatgtt tgacagctta tcatcgataa gctggccgct    6960
ctagaactag tgttcccaca atggttaatt cgagctcgcc cggggatcta attcaattag    7020
agactaattc aattagagct aattcaatta ggatccaagc ttatcgattt cgaaccctcg    7080
accgccggag tataaataga ggcgcttcgt ctacggagcg acaattcaat tcaaacaagc    7140
aaagtgaaca cgtcgctaag cgaaagctaa gcaaataaac aagcgcagct gaacaagcta    7200
aacaatcggg gtaccgctag agtcgacggt acgatccacc ggtcgccacc atggtgagca    7260
agggcgagga gctgttcacc ggggtggtgc ccatcctggt cgagctggac ggcgacgtaa    7320
acggccacaa gttcagcgtg tccggcgagg gcgagggcga tgccacctac ggcaagctga    7380
ccctgaagtt catctgcacc accggcaagc tgcccgtgcc ctggcccacc ctcgtgacca    7440
ccctgacctg gggcgtgcag tgcttcagcc gctaccccga ccacatgaag cagcacgact    7500
tcttcaagtc cgccatgccc gaaggctacg tccaggagcg caccatcttc ttcaaggacg    7560
acggcaacta caagacccgc gccgaggtga agttcgaggg cgacaccctg gtgaaccgca    7620
tcgagctgaa gggcatcgac ttcaaggagg acggcaacat cctggggcac aagctggagt    7680
acaactagat cagccacaac gtctatatca ccgccgacaa gcagaagaac ggcatcaagg    7740
ccaacttcaa gatccgccac aacatcgagg acggcagcgt gcagctcgcc gaccactacc    7800
agcagaacac ccccatcggc gacggccccg tgctgctgcc cgacaaccac tacctgagca    7860
cccagtccgc cctgagcaaa gaccccaacg agaagcgcga tcacatggtc ctgctggagt    7920
tcgtgaccgc cgccgggatc actctcggca tggacgagct gtacaagtaa agcgccgcg    7980
actctagatc ataatcagcc ataccacatt tgtagaggtt ttacttgctt taaaaaacct    8040
cccacacctc cccctgaacc tgaaacataa aatgaatgca attgttgttg ttaacttgtt    8100
tattgcagct tataatggtt acaaataaag caatagcatc acaaatttca caaataaagc    8160
atttttttca ctgcattcta gttgtggttt gtccaaactc atcaatgtat cttaaagctt    8220
atcgatacgc gtacggcgcg cctaggccgg ccgattggat cccatgcgtc aattttacgc    8280
atgattatct ttaacgtacg tcacaatatg attatctttc tagggttaat ctagctgcgt    8340
gttctgcagc gtgtcgagca tcttcatctg ctccatcacg ctgtaaaaca catttgcacc    8400
gcgagtctgc ccgtcctcca cgggttcaaa aacgtgaatg aacgaggcgc gcccgccggg    8460
taactcacgg ggtatccatg tccatttctg cggcatccag ccaggatacc cgtcctcgct    8520
gacgtaatat cccagcgccg caccgctgtc attaatctgc acaccggcac ggcagttccg    8580
gctgtcgccg gtattgttcg ggttgctgat gcgcttcggg ctgaccatcc ggaactgtgt    8640
ccggaaaagc cgcgacgaac tggtatccca ggtggcctga cgaacagtt caccgttaaa    8700
ggcgtgcatg gccacacctt cccgaatcat catggtaaac gtgcgttttc gctcaacgtc    8760
aatgcagcag cagtcatcct cggcaaactc tttccatgcc gcttcaacct cgcgggaaaa    8820
```

-continued

| | |
|---|---|
| ggcacgggct tcttcctccc cgatgcccag atagcgccag cttgggcgat gactgagccg | 8880 |
| gaaaaaagac ccgacgatat gatcctgatg cagctagatt aaccctagaa agatagtctg | 8940 |
| cgtaaaattg acgcatggga tcccccgggc tgcaggaatt cgatatcaag cttatcgata | 9000 |
| ccgtcgaagc tt | 9012 |

<210> SEQ ID NO 50
<211> LENGTH: 9013
<212> TYPE: DNA
<213> ORGANISM: Artificial Sequence
<220> FEATURE:
<223> OTHER INFORMATION: Description of Artificial Sequence:
p(PZ)-Bac-EGFP sequence

<400> SEQUENCE: 50

| | |
|---|---|
| accgaagtat acacttaaat tcagtgcacg tttgcttgtt gagaggaaag gttgtgtgcg | 60 |
| gacgaatttt tttttgaaaa cattaaccct tacgtggaat aaaaaaaaat gaaatattgc | 120 |
| aaattttgct gcaaagctgt gactggagta aaattaattc acgtgccgaa gtgtgctatt | 180 |
| aagagaaaat tgtgggagca gagccttggg tgcagccttg gtgaaaactc ccaaatttgt | 240 |
| gatacccact ttaatgattc gcagtggaag gctgcacctg caaaaggtca gacatttaaa | 300 |
| aggaggcgac tcaacgcaga tgccgtacct agtaaagtga tagagcctga accagaaaag | 360 |
| ataaaagaag gctataccag tgggagtaca caaacagagt aagtttgaat agtaaaaaaa | 420 |
| atcatttatg taaacaataa cgtgactgtg cgttaggtcc tgttcattgt ttaatgaaaa | 480 |
| taagagcttg agggaaaaaa ttcgtacttt ggagtacgaa atgcgtcgtt tagagcagca | 540 |
| gccgaattca ctggccgtcg ttttacaacg tcgtgactgg gaaaaccctg gcgttaccca | 600 |
| acttaatcgc cttgcagcac atcccccttt cgccagctgg cgtaatagcg aagaggcccg | 660 |
| caccgatcgc ccttcccaac agttgcgcag cctgaatggc gaatggcgct ttgcctggtt | 720 |
| tccggcacca gaagcggtgc cggaaagctg gctggagtgc gatcttcctg aggccgatac | 780 |
| tgtcgtcgtc ccctcaaact ggcagatgca cggttacgat gcgcccatct acaccaacgt | 840 |
| aacctatccc attacggtca atccgccgtt tgttcccacg gagaatccga cgggttgtta | 900 |
| ctcgctcaca tttaatgttg atgaaagctg gctacaggaa ggccagacgc gaattatttt | 960 |
| tgatggcgtt aactcggcgt ttcatctgtg gtgcaacggg cgctgggtcg gttacggcca | 1020 |
| ggacagtcgt ttgccgtctg aatttgacct gagcgcattt ttacgcgccg gagaaaaccg | 1080 |
| cctcgcggtg atggtgctgc gttggagtga cggcagttat ctggaagatc aggatatgtg | 1140 |
| gcggatgagc ggcattttcc gtgacgtctc gttgctgcat aaaccgacta cacaaatcag | 1200 |
| cgatttccat gttgccactc gctttaatga tgatttcagc cgcgctgtac tggaggctga | 1260 |
| agttcagatg tgcggcgagt tgcgtgacta cctacgggta acagtttctt tatggcaggg | 1320 |
| tgaaacgcag tcgccagcg gcaccgcgcc tttcggcggt gaaattatcg atgagcgtgg | 1380 |
| tggttatgcc gatcgcgtca cactacgtct gaacgtcgaa aacccgaaac tgtggagcgc | 1440 |
| cgaaatcccg aatctctatc gtgcggtggt tgaactgcac accgccgacg gcacgctgat | 1500 |
| tgaagcagaa gcctgcgatg tcggtttccg cgaggtgcgg attgaaaatg gtctgctgct | 1560 |
| gctgaacggc aagccgttgc tgattcgagg cgttaaccgt cacagcatc atcctctgca | 1620 |
| tggtcaggtc atggatgagc agacgatggt gcaggatatc ctgctgatga agcagaacaa | 1680 |
| ctttaacgcc gtgcgctgtt cgcattatcc gaaccatccg ctgtggtaca cgctgtgcga | 1740 |
| ccgctacggc ctgtatgtgg tggatgaagc caatattgaa acccacggca tggtgccaat | 1800 |

```
gaatcgtctg accgatgatc cgcgctggct accggcgatg agcgaacgcg taacgcgaat    1860
ggtgcagcgc gatcgtaatc acccgagtgt gatcatctgg tcgctgggga atgaatcagg    1920
ccacggcgct aatcacgacg cgctgtatcg ctggatcaaa tctgtcgatc cttcccgccc    1980
ggtgcagtat gaaggcggcg gagccgacac cacggccacc gatattattt gcccgatgta    2040
cgcgcgcgtg gatgaagacc agcccttccc ggctgtgccg aaatggtcca tcaaaaaatg    2100
gctttcgcta cctggagaga cgcgcccgct gatcctttgc gaatacgccc acgcgatggg    2160
taacagtctt ggcggtttcg ctaaatactg gcaggcgttt cgtcagtatc cccgtttaca    2220
gggcggcttc gtctgggact gggtggatca gtcgctgatt aaatatgatg aaaacggcaa    2280
cccgtggtcg gcttacggcg gtgatttttgg cgatacgccg aacgatcgcc agttctgtat    2340
gaacggtctg gtctttgccg accgcacgcc gcatccagcg ctgacggaag caaaacacca    2400
gcagcagttt tccagttcc gtttatccgg gcaaaccatc gaagtgacca gcgaatacct    2460
gttccgtcat agcgataacg agctcctgca ctggatggtg gcgctggatg gtaagccgct    2520
ggcaagcggt gaagtgcctc tggatgtcgc tccacaaggt aaacagttga ttgaactgcc    2580
tgaactaccg cagccggaga gcgccgggca actctggctc acagtacgcg tagtgcaacc    2640
gaacgcgacc gcatggtcag aagcgggca catcagcgcc tggcagcagt ggcgtctggc    2700
ggaaaacctc agtgtgacgc tccccgccgc gtcccacgcc atcccgcatc tgaccaccag    2760
cgaaatggat ttttgcatcg agctgggtaa taagcgttgg caatttaacc gccagtcagg    2820
ctttctttca cagatgtgga ttggcgataa aaaacaactg ctgacgccgc tgcgcgatca    2880
gttcacccgt gcaccgctgg ataacgacat tggcgtaagt gaagcgaccc gcattgaccc    2940
taacgcctgg gtcgaacgct ggaaggcggc gggccattac caggccgaag cagcgttgtt    3000
gcagtgcacg gcagatacac ttgctgatgc ggtgctgatt acgaccgctc acgcgtggca    3060
gcatcagggg aaaaccttat ttatcagccg gaaaacctac cggattgatg gtagtggtca    3120
aatggcgatt accgttgatg ttgaagtggc gagcgataca ccgcatccgg cgcggattgg    3180
cctgaactgc cagctggcgc aggtagcaga gcgggtaaac tggctcggat tagggccgca    3240
agaaaactat cccgaccgcc ttactgccgc ctgttttgac cgctgggatc tgccattgtc    3300
agacatgtat accccgtacg tcttcccgag cgaaaacggt ctgcgctgcg ggacgcgcga    3360
attgaattat ggcccacacc agtggcgcgg cgacttccag ttcaacatca gccgctacag    3420
tcaacagcaa ctgatggaaa ccagccatcg ccatctgctg cacgcggaag aaggcacatg    3480
gctgaatatc gacggtttcc atatggggat tggtggcgac gactcctgga gcccgtcagt    3540
atcggcggaa ttccagctga gcgccggtcg ctaccattac cagttggtct ggtgtcgggg    3600
atccgtcgac taaggccaaa gagtctaatt tttgttcatc aatgggttat aacatatggg    3660
ttatattata agtttgtttt aagtttttga gactgataag aatgtttcga tcgaatattc    3720
catagaacaa caatagtatt acctaattac caagtcttaa tttagcaaaa atgtaattgc    3780
ttatagaaaa aataaattat ttatttgaaa tttaaagtca acttgtcatt taatgtcttg    3840
tagacttttg aaagtcttac gatacaatta gtatctaata tacatgggtt cattctacat    3900
tctatattag tgatgatttc tttagctagt aatacatttt aattatattc ggctttgatg    3960
attttctgat ttttttccgaa cggattttcg tagacccttt cgatctcata atggctcatt    4020
ttattgcgat ggacggtcag gagagctcca cttttgaatt tctgttcgca gacaccgcat    4080
ttgtagcaca tagccgggac atccggtttg gggagatttt ccagtctctg ttgcaattgg    4140
```

-continued

```
ttttcgggaa tgcgttgcag gcgcatacgc tctatatcct ccgaacggcg ctggttgacc    4200
ctagcattta cataaggatc agcagcaaaa tttgcctctg cttcattgcc cggaatcaca    4260
gcaatcagat gtccctttcg gttacgatgg atattcaggt gcgaaccgca cacaaagctc    4320
tcgccgcaca ctccacactg atatggtcgc tcgccctgtg gcgccgcata tggatcttaa    4380
ggtcgttgga ctgcacaaag ctcttgctgc acattttgca ggagtacggc ctttgacccg    4440
tgtgcaatcg catgtgtcgc gccagcttgt tctgcgaaat aaacttcttg gagcagatgc    4500
ggccgcccgg ggtgggcgaa gaactccagc atgagatccc cgcgctggag gatcatccag    4560
ccggcgtccc ggaaaacgat tccgaagccc aacctttcat agaaggcggc ggtggaatcg    4620
aaatctcgtg atggcaggtt gggcgtcgct tggtcggtca tttcgaaccc cagagtcccg    4680
ctcagaagaa ctcgtcaaga aggcgataga aggcgatgcg ctgcgaatcg ggagcggcga    4740
taccgtaaag cacgaggaag cggtcagccc attcgccgcc aagctcttca gcaatatcac    4800
gggtagccaa cgctatgtcc tgatagcggt ccgccacacc cagccggcca cagtcgatga    4860
atccagaaaa gcggccattt tccaccatga tattcggcaa gcaggcatcg ccatgggtca    4920
cgacgagatc ctcgccgtcg ggcatgcgcg ccttgagcct ggcgaacagt tcggctggcg    4980
cgagcccctg atgctcttcg tccagatcat cctgatcgac aagaccggct tccatccgag    5040
tacgtgctcg ctcgatgcga tgtttcgctt ggtggtcgaa tgggcaggta ccggatcaa     5100 gcgtatgcag ccgccgcatt gcatcagcca tgatggatac tttctcggca ggagcaaggt    5160
gagatgacag gagatcctgc cccggcactt cgcccaatag cagccagtcc cttcccgctt    5220
cagtgacaac gtcgagcaca gctgcgcaag gaacgcccgt cgtggccagc cacgatagcc    5280
gcgctgcctc gtcctgcagt tcattcaggg caccggacag gtcggtcttg acaaaaagaa    5340
ccgggcgccc ctgcgctgac agccggaaca cggcggcatc agagcagccg attgtctgtt    5400
gtgcccagtc atagccgaat agcctctcca cccaagcggc cggagaacct gcgtgcaatc    5460
catcttgttc aatcatgcga aacgatcctc atcctgtctc ttgatcagat cttgatcccc    5520
tgcgccatca gatccttggc ggcaagaaag ccatccagtt tactttgcag gcttcccaa     5580 ccttaccaga gggcgcccca gctggcaatt ccggttcgct tgctgtccat aaaaccgccc    5640
agtctagcta tcgccatgta agcccactgc aagctacctg ctttctcttt gcgcttgcgt    5700
tttcccttgt ccagatagcc cagtagctga cattcatccg gggtcagcac cgtttctgcg    5760
gactggcttt ctacgtgttc cgcttccttt agcagccctt gcgccctgag tgcttgcggc    5820
agcgtgaagc taattcatgg ttataaattt ttgttaaatc agctcatttt ttaaccaata    5880
ggccgaaatc ggcaaaatcc cttataaatc aaaagaatag cccgagatag ggttgagtgt    5940
tgttccagtt tggaacaaga gtccactatt aaagaacgtg gactccaacg tcaaagggcg    6000
aaaaaccgtc tatcagggcg atggccggat cagcttatgc ggtgtgaaat accgcacaga    6060
tgcgtaagga gaaaataccg catcaggcgc tcttccgctt cctcgctcac tgactcgctg    6120
cgctcggtcg ttcggctgcg gcgagcggta tcagctcact caaaggcggt aatacggtta    6180
tccacagaat caggggataa cgcaggaaag aacatgtgag caaaaggcca gcaaaggcc     6240 aggaaccgta aaaaggccgc gttgctggcg ttttttccata ggctccgccc cctgacgag    6300 catcacaaaa atcgacgctc aagtcagagg tggcgaaacc cgacaggact ataaagatac    6360
caggcgtttc ccctggaag ctccctcgtg cgctctcctg ttccgaccct gccgcttacc     6420
ggatacctgt ccgcctttct cccttcggga agcgtggcgc tttctcatag ctcacgctgt    6480
aggtatctca gttcggtgta ggtcgttcgc tccaagctgg gctgtgtgca cgaaccccc     6540
```

```
gttcagcccg accgctgcgc cttatccggt aactatcgtc ttgagtccaa cccggtaaga    6600
cacgacttat cgccactggc agcagccact ggtaacagga ttagcagagc gaggtatgta    6660
ggcggtgcta cagagttctt gaagtggtgg cctaactacg gctacactag aaggacagta    6720
tttggtatct gcgctctgct gaagccagtt accttcggaa aaagagttgg tagctcttga    6780
tccggcaaac aaaccaccgc tggtagcggc ggttttttgt ttgcaagcag cagattacgc    6840
gcagaaaaaa aggatctcaa gaagatcctt tgatcttttc ttactgaacg gtgatcccca    6900
ccggaattgc ggccgcggaa ttctcatgtt tgacagctta tcatcgataa gctggccgct    6960
ctagaactag tgttcccaca atggttaatt cgagctcgcc cggggatcta attcaattag    7020
agactaattc aattagagct aattcaatta ggatccaagc ttatcgattt cgaaccctcg    7080
accgccggag tataaataga ggcgcttcgt ctacggagcg acaattcaat tcaaacaagc    7140
aaagtgaaca cgtcgctaag cgaaagctaa gcaaataaac aagcgcagct gaacaagcta    7200
aacaatcggg gtaccgctag agtcgacggt accgcgggcc cgggatccac cggtcgccac    7260
catggtgagc aagggcgagg agctgttcac cggggtggtg cccatcctgg tcgagctgga    7320
cggcgacgta aacggccaca gttcagcgt gtccggcgag ggcgagggcg atgccaccta    7380
cggcaagctg accctgaagt tcatctgcac caccggcaag ctgcccgtgc cctggcccac    7440
cctcgtgacc cccctgacct acggcgtgca gtgcttcagc cgctacccccg accacatgaa    7500
gcagcacgac ttcttcaagt ccgccatgcc cgaaggctac gtccaggagc gcaccatctt    7560
cttcaaggac gacggcaact acaagacccg cgccgaggtg aagttcgagg gcgacaccct    7620
ggtgaaccgc atcgagctga agggcatcga cttcaaggag gacggcaaca tcctggggca    7680
caagctggag tacaactaca acagccacaa cgtctatatc atggccgaca gcagaagaa    7740
cggcatcaag gtgaacttca agatccgcca caacatcgag gacggcagcg tgcagctcgc    7800
cgaccactac cagcagaaca cccccatcgg cgacggcccc gtgctgctgc ccgacaacca    7860
ctacctgagc acccagtccg ccctgagcaa agaccccaac gagaagcgcg atcacatggt    7920
cctgctggag ttcgtgaccg ccgccgggat cactctcggc atggacgagc tgtacaagta    7980
aagcggccgc gactctagat cataatcagc cataccacat ttgtagaggt tttacttgct    8040
ttaaaaaacc tcccacacct cccccctgaac ctgaaacata aaatgaatgc aattgttgtt    8100
gttaacttgt ttattgcagc ttataatggt tacaaataaa gcaatagcat cacaaatttc    8160
acaaataaag catttttttc actgcattct agttgtggtt tgtccaaact catcaatgta    8220
tcttaaagct tatcgatacg cgtacggcgc gcctagtgga tcccatgcgt caattttacg    8280
catgattatc tttaacgtac gtcacaatat gattatcttt ctagggttaa tctagctgcg    8340
tgttctgcag cgtgtcgagc atcttcatct gctccatcac gctgtaaaac acatttgcac    8400
cgcgagtctg cccgtcctcc acgggttcaa aaacgtgaat gaacgaggcg cgcccgccgg    8460
gtaactcacg gggtatccat gtccatttct gcggcatcca gccaggatac ccgtcctcgc    8520
tgacgtaata tccagcgcc gcaccgctgt cattaatctg cacaccggca cggcagttcc    8580
ggctgtcgcc ggtattgttc gggttgctga tgcgcttcgg gctgaccatc cggaactgtg    8640
tccggaaaag ccgcgacgaa ctggtatccc aggtggcctg aacgaacagt tcaccgttaa    8700
aggcgtgcat ggccacacct tcccgaatca tcatggtaaa cgtgcgtttt cgctcaacgt    8760
caatgcagca gcagtcatcc tcggcaaact ctttccatgc cgcttcaacc tcgcgggaaa    8820
aggcacgggc ttcttcctcc ccgatgccca gatagcgcca gcttgggcga tgactgagcc    8880
```

-continued

```
ggaaaaaaga cccgacgata tgatcctgat gcagctagat taaccctaga aagatagtct    8940
gcgtaaaatt gacgcatggg atcccccggg ctgcaggaat tcgatatcaa gcttatcgat    9000
accgtcgaag ctt                                                       9013
```

<210> SEQ ID NO 51
<211> LENGTH: 4951
<212> TYPE: DNA
<213> ORGANISM: Artificial Sequence
<220> FEATURE:
<223> OTHER INFORMATION: Description of Artificial Sequence:
      pXL-Bac-EYFP sequence

<400> SEQUENCE: 51

```
ctaaattgta agcgttaata ttttgttaaa attcgcgtta aattttttgtt aaatcagctc      60 attttttaac caataggccg aaatcggcaa aatcccttat aaatcaaaag aatagaccga     120 gataggttg agtgttgttc cagtttggaa caagagtcca ctattaaaga acgtggactc      180
caacgtcaaa gggcgaaaaa ccgtctatca gggcgatggc ccactacgtg aaccatcacc    240
ctaatcaagt ttttgggt cgaggtgccg taaagcacta aatcggaacc ctaaagggag      300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgccgccg ggtaactcac ggggtatcca tgtccatttc     660
tgcggcatcc agccaggata cccgtcctcg ctgacgtaat atcccagcgc cgcaccgctg    720
tcattaatct gcacaccggc acggcagttc cggctgtcgc cggtattgtt cgggttgctg    780
atgcgcttcg ggctgaccat ccggaactgt gtccggaaaa gccgcgacga actggtatcc    840
caggtggcct gaacgaacag ttcaccgtta aaggcgtgca tggccacacc ttcccgaatc    900
atcatggtaa acgtgcgttt tcgctcaacg tcaatgcagc agcagtcatc ctcggcaaac    960
tctttccatg ccgcttcaac ctcgcgggaa aaggcacggg cttcttcctc cccgatgccc    1020
agatagcgcc agcttgggcg atgactgagc cggaaaaaag acccgacgat atgatcctga    1080
tgcagctaga ttaaccctag aaagatagtc tgcgtaaaat tgacgcatga tctaattaac    1140
cctcactaaa gggaacaaaa gctggagctc caccgcggtg gcggccgctc tagaactagt    1200
gttcccacaa tggttaattc gagctcgccc ggggatctaa ttcaattaga gactaattca    1260
attagagcta attcaattag gatccaagct tatcgatttc gaaccctcga ccgccggagt    1320
ataaatagag gcgcttcgtc tacggagcga caattcaatt caaacaagca aagtgaacac    1380
gtcgctaagc gaaagctaag caaataaaca agcgcagctg aacaagctaa acaatcgggg    1440
taccgctaga gtcgacggta cgatccaccg gtcgccacca tggtgagcaa gggcgaggag    1500
ctgttcaccg gggtggtgcc catcctggtc gagctggacg gcgacgtaaa cggccacaag    1560
ttcagcgtgt ccggcgaggg cgagggcgat gccacctacg gcaagctgac cctgaagttc    1620
atctgcacca ccggcaagct gcccgtgccc tggcccaccc tcgtgaccac cttcggctac    1680
ggcctgcagt gcttcgcccg ctaccccgac cacatgaagc agcacgactt cttcaagtcc    1740
gccatgcccg aaggctacgt ccaggagcgc accatcttct tcaaggacga cggcaactac    1800
aagacccgcg ccgaggtgaa gttcgagggc gacaccctgg tgaaccgcat cgagctgaag    1860
```

```
ggcatcgact tcaaggagga cggcaacatc ctggggcaca agctggagta caactacaac      1920
agccacaacg tctatatcat ggccgacaag cagaagaacg catcaaggt gaacttcaag       1980 atccgccaca acatcgagga cggcagcgtg cagctcgccg accactacca gcagaacacc      2040
cccatcggcg acggccccgt gctgctgccc gacaaccact acctgagcta ccagtccgcc      2100
ctgagcaaag accccaacga gaagcgcgat cacatggtcc tgctggagtt cgtgaccgcc      2160
gccgggatca ctctcggcat ggacgagctg tacaagtaaa gcggccgcga ctctagatca      2220
taatcagcca taccacattt gtagaggttt tacttgcttt aaaaaacctc ccacacctcc      2280
ccctgaacct gaaacataaa atgaatgcaa ttgttgttgt taacttgttt attgcagctt      2340
ataatggtta caaataaagc aatagcatca caaatttcac aaataaagca ttttttttcac    2400 tgcattctag ttgtggtttg tccaaactca tcaatgtatc ttaaagctta tcgatacgcg     2460
tacggcgcgc ctaggcacta gtggatcccc cgggctgcag gaattcgata tcaagcttat     2520
cgataccgtc gacctcgagg gggggcccgg tacccaattc gccctatagt gagtcgtatt     2580
aagatcacgc gtagatccat gcgtcaattt tacgcatgat tatctttaac gtacgtcaca     2640
atatgattat ctttctaggg ttaatctagc tgcgtgttct gcagcgtgtc gagcatcttc     2700
atctgctcca tcacgctgta aaacacattt gcaccgcgag tctgcccgtc ctccacgggt     2760
tcaaaaacgt gaatgaacga ggcgcgcttg gcgtaatcat ggtcatagct gtttcctgtg     2820
tgaaattgtt atccgctcac aattccacac aacatacgag ccggaagcat aaagtgtaaa     2880
gcctggggtg cctaatgagt gagctaactc acattaattg cgttgcgctc actgcccgct     2940
ttccagtcgg gaaacctgtc gtgccagctg cattaatgaa tcggccaacg cgcggggaga     3000
ggcggtttgc gtattgggcg ctcttccgct tcctcgctca ctgactcgct gcgctcggtc     3060
gttcggctgc ggcgagcggt atcagctcac tcaaaggcgg taatacggtt atccacagaa     3120
tcaggggata acgcaggaaa gaacatgtga gcaaaaggcc agcaaaaggc caggaaccgt     3180
aaaaaggccg cgttgctggc gtttttccat aggctccgcc cccctgacga gcatcacaaa     3240
aatcgacgct caagtcagag gtggcgaaac ccgacaggac tataaagata ccaggcgttt     3300
ccccctggaa gctccctcgt gcgctctcct gttccgaccc tgccgcttac cggatacctg     3360 tccgccttc tcccttcggg aagcgtggcg ctttctcata gctcacgctg taggtatctc      3420
agttcggtgt aggtcgttcg ctccaagctg ggctgtgtgc acgaaccccc cgttcagccc     3480
gaccgctgcg ccttatccgg taactatcgt cttgagtcca acccggtaag acacgactta     3540
tcgccactgg cagcagccac tggtaacagg attagcagag cgaggtatgt aggcggtgct     3600
acagagttct tgaagtggtg gcctaactac ggctacacta aaggacagt atttggtatc      3660 tgcgctctgc tgaagccagt taccttcgga aaaagagttg gtagctcttg atccggcaaa     3720
caaaccaccg ctggtagcgg tggttttttt gtttgcaagc agcagattac gcgcagaaaa     3780
aaaggatctc aagaagatcc tttgatcttt tctacggggt ctgacgctca gtggaacgaa     3840
aactcacgtt aagggatttt ggtcatgaga ttatcaaaaa ggatcttcac ctagatcctt     3900
ttaaattaaa aatgaagttt taaatcaatc taaagtatat atgagtaaac ttggtctgac     3960
agttaccaat gcttaatcag tgaggcacct atctcagcga tctgtctatt tcgttcatcc     4020
atagttgcct gactccccgt cgtgtagata actacgatac gggagggctt accatctggc     4080
cccagtgctg caatgatacc gcgagaccca cgctcaccgg ctccagattt atcagcaata     4140
aaccagccag ccggaagggc cgagcgcaga agtggtcctg caactttatc cgcctccatc     4200
cagtctatta attgttgccg ggaagctaga gtaagtagtt cgccagttaa tagtttgcgc     4260
```

-continued

```
aacgttgttg ccattgctac aggcatcgtg gtgtcacgct cgtcgtttgg tatggcttca    4320
ttcagctccg gttcccaacg atcaaggcga gttacatgat cccccatgtt gtgcaaaaaa    4380
gcggttagct ccttcggtcc tccgatcgtt gtcagaagta agttggccgc agtgttatca    4440
ctcatggtta tggcagcact gcataattct cttactgtca tgccatccgt aagatgcttt    4500
tctgtgactg gtgagtactc aaccaagtca ttctgagaat agtgtatgcg gcgaccgagt    4560
tgctcttgcc cggcgtcaat acgggataat accgcgccac atagcagaac tttaaaagtg    4620
ctcatcattg gaaaacgttc ttcggggcga aaactctcaa ggatcttacc gctgttgaga    4680
tccagttcga tgtaacccac tcgtgcaccc aactgatctt cagcatcttt tactttcacc    4740
agcgtttctg ggtgagcaaa aacaggaagg caaaatgccg caaaaaaggg aataagggcg    4800
acacggaaat gttgaatact catactcttc cttttcaat attattgaag catttatcag    4860
ggttattgtc tcatgagcgg atacatattt gaatgtattt agaaaaataa acaaataggg    4920
gttccgcgca catttccccg aaaagtgcca c                                   4951
```

<210> SEQ ID NO 52
<211> LENGTH: 4952
<212> TYPE: DNA
<213> ORGANISM: Artificial Sequence
<220> FEATURE:
<223> OTHER INFORMATION: Description of Artificial Sequence:
       pXL-Bac-EGFP sequence

<400> SEQUENCE: 52

```
ctaaattgta agcgttaata ttttgttaaa attcgcgtta aattttgtt aaatcagctc     60 attttttaac caataggccg aaatcggcaa atcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgccgccg  ggtaactcac ggggtatcca tgtccatttc    660
tgcggcatcc agccaggata cccgtcctcg ctgacgtaat atcccagcgc cgcaccgctg    720
tcattaatct gcacaccggc acggcagttc cggctgtcgc cggtattgtt cgggttgctg    780
atgcgcttcg ggctgaccat ccggaactgt gtccggaaaa ccgcgacga actggtatcc    840 caggtggcct gaacgaacag ttcaccgtta aggcgtgca tggccacacc ttcccgaatc    900
atcatggtaa acgtgcgttt tcgctcaacg tcaatgcagc agcagtcatc ctcggcaaac    960
tctttccatg ccgcttcaac ctcgcgggaa aaggcacggg cttcttcctc cccgatgccc   1020
agatagcgcc agcttgggcg atgactgagc cggaaaaaag acccgacgat atgatcctga   1080
tgcagctaga ttaaccctag aaagatagtc tgcgtaaaat tgacgcatga tctaattaac   1140
cctcactaaa gggaacaaaa gctggagctc caccgcggtg gcggccgctc tagaactagt   1200
gccgtacgcg tatcgataag ctttaagata cattgatgag tttggacaaa ccacaactag   1260
aatgcagtga aaaaaatgct ttatttgtga aatttgtgat gctattgctt tatttgtaac   1320
```

```
cattataagc tgcaataaac aagttaacaa caacaattgc attcatttta tgtttcaggt   1380 tcaggggag gtgtgggagg ttttttaaag caagtaaaac ctctacaaat gtggtatggc    1440
tgattatgat ctagagtcgc ggccgcttta cttgtacagc tcgtccatgc cgagagtgat   1500
cccggcggcg gtcacgaact ccagcaggac catgtgatcg cgcttctcgt tggggtcttt   1560
gctcagggcg gactgggtgc tcaggtagtg gttgtcgggc agcagcacgg ggccgtcgcc   1620 gatggggtg ttctgctggt agtggtcggc gagctgcacg ctgccgtcct cgatgttgtg    1680
gcggatcttg aagttcacct tgatgccgtt cttctgcttg tcggccatga tatagacgtt   1740
gtggctgttg tagttgtact ccagcttgtg ccccaggatg ttgccgtcct ccttgaagtc   1800
gatgcccttc agctcgatgc ggttcaccag ggtgtcgccc tcgaacttca cctcggcgcg   1860
ggtcttgtag ttgccgtcgt ccttgaagaa gatggtgcgc tcctggacgt agccttcggg   1920
catggcggac ttgaagaagt cgtgctgctt catgtggtcg gggtagcggc tgaagcactg   1980
cacgccgtag gtcagggtgg tcacgagggt gggccagggc acgggcagct tgccggtggt   2040
gcagatgaac ttcagggtca gcttgccgta gtggcatcg ccctcgccct cgccggacac    2100
gctgaacttg tggccgttta cgtcgccgtc cagctcgacc aggatgggca ccaccccggt   2160
gaacagctcc tcgcccttgc tcaccatggt ggcgaccggt ggatcccggg ccgcggtac    2220 cgtcgactct agcggtaccc cgattgttta gcttgttcag ctgcgcttgt ttatttgctt   2280
agctttcgct tagcgacgtg ttcactttgc ttgtttgaat tgaattgtcg ctccgtagac   2340
gaagcgcctc tatttatact ccggcggtcg agggttcgaa atcgataagc ttggatccta   2400
attgaattag ctctaattga attagtctct aattgaatta gatccccggg cgagctcgaa   2460
ttaaccattg tgggaacact agtggatccc ccgggctgca ggaattcgat atcaagctta   2520
tcgataccgt cgacctcgag gggggcccg gtacccaatt cgccctatag tgagtcgtat    2580
taagatcacg cgtagatcca tgcgtcaatt ttacgcatga ttatctttaa cgtacgtcac   2640
aatatgatta tctttctagg gttaatctag ctgcgtgttc tgcagcgtgt cgagcatctt   2700
catctgctcc atcacgctgt aaaacacatt gcaccgcga gtctgcccgt cctccacggg    2760
ttcaaaaacg tgaatgaacg aggcgcgctt ggcgtaatca tggtcatagc tgtttcctgt   2820
gtgaaattgt tatccgctca caattccaca acacatacga gccggaagca taaagtgtaa   2880
agcctggggt gcctaatgag tgagctaact cacattaatt gcgttgcgct cactgcccgc   2940
tttccagtcg ggaaacctgt cgtgccagct gcattaatga atcggccaac gcgcggggag   3000
aggcggtttg cgtattgggc gctcttccgc ttcctcgctc actgactcgc tgcgctcggt   3060
cgttcggctg cggcgagcgg tatcagctca ctcaaaggcg gtaatacggt tatccacaga   3120
atcaggggat aacgcaggaa agaacatgtg agcaaaaggc cagcaaaagg ccaggaaccg   3180
taaaaaggcc gcgttgctgg cgttttccca taggctccgc cccctgacg agcatcacaa    3240 aaatcgacgc tcaagtcaga ggtggcgaaa cccgacagga ctataaagat accaggcgtt   3300
tccccctgga agctccctcg tgcgctctcc tgttccgacc ctgccgctta ccggatacct   3360
gtccgccttt ctcccttcgg gaagcgtggc gctttctcat agctcacgct gtaggtatct   3420
cagttcggtg taggtcgttc gctccaagct gggctgtgtg cacgaacccc ccgttcagcc   3480
cgaccgctgc gccttatccg gtaactatcg tcttgagtcc aacccggtaa gacacgactt   3540
atcgccactg gcagcagcca ctggtaacag gattagcaga gcgaggtatg taggcggtgc   3600
tacagagttc ttgaagtggt ggcctaacta cggctacact agaaggacag tatttggtat   3660
```

-continued

```
ctgcgctctg ctgaagccag ttaccttcgg aaaaagagtt ggtagctctt gatccggcaa    3720
acaaaccacc gctggtagcg gtggtttttt tgtttgcaag cagcagatta cgcgcagaaa    3780
aaaaggatct caagaagatc ctttgatctt ttctacgggg tctgacgctc agtggaacga    3840
aaactcacgt taagggattt tggtcatgag attatcaaaa aggatcttca cctagatcct    3900
tttaaattaa aaatgaagtt ttaaatcaat ctaaagtata tatgagtaaa cttggtctga    3960
cagttaccaa tgcttaatca gtgaggcacc tatctcagcg atctgtctat ttcgttcatc    4020
catagttgcc tgactccccg tcgtgtagat aactacgata cgggagggct taccatctgg    4080
ccccagtgct gcaatgatac cgcgagaccc acgctcaccg gctccagatt tatcagcaat    4140
aaaccagcca gccggaaggg ccgagcgcag aagtggtcct gcaactttat ccgcctccat    4200
ccagtctatt aattgttgcc gggaagctag agtaagtagt tcgccagtta atagtttgcg    4260
caacgttgtt gccattgcta caggcatcgt ggtgtcacgc tcgtcgtttg gtatggcttc    4320
attcagctcc ggttcccaac gatcaaggcg agttacatga tcccccatgt tgtgcaaaaa    4380
agcggttagc tccttcggtc ctccgatcgt tgtcagaagt aagttggccg cagtgttatc    4440
actcatggtt atggcagcac tgcataattc tcttactgtc atgccatccg taagatgctt    4500
ttctgtgact ggtgagtact caaccaagtc attctgagaa tagtgtatgc ggcgaccgag    4560
ttgctcttgc ccggcgtcaa tacgggataa taccgcgcca catagcagaa ctttaaaagt    4620
gctcatcatt ggaaaacgtt cttcggggcg aaaactctca aggatcttac cgctgttgag    4680
atccagttcg atgtaaccca ctcgtgcacc caactgatct tcagcatctt ttactttcac    4740
cagcgtttct gggtgagcaa aaacaggaag gcaaaatgcc gcaaaaaagg gaataagggc    4800
gacacggaaa tgttgaatac tcatactctt cctttttcaa tattattgaa gcatttatca    4860
gggttattgt ctcatgagcg gatacatatt tgaatgtatt tagaaaaata aacaaatagg    4920
ggttccgcgc acatttcccc gaaaagtgcc ac                                  4952
```

<210> SEQ ID NO 53
<211> LENGTH: 4941
<212> TYPE: DNA
<213> ORGANISM: Artificial Sequence
<220> FEATURE:
<223> OTHER INFORMATION: Description of Artificial Sequence:
      pXL-Bac-ECFP sequence

<400> SEQUENCE: 53

```
ctaaattgta agcgttaata ttttgttaaa attcgcgtta aatttttgtt aaatcagctc      60
attttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta atcggaacc ctaaagggag     300 cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggt ttttcccagt cacgacgttg     600
taaaacgacg gccagtgagc gcgccgccg gtaactcac gggtatcca tgtccatttc     660 tgcggcatcc agccaggata cccgtcctcg ctgacgtaat atcccagcgc cgcaccgctg     720
```

```
tcattaatct gcacaccggc acggcagttc cggctgtcgc cggtattgtt cgggttgctg      780
atgcgcttcg ggctgaccat ccggaactgt gtccggaaaa gccgcgacga actggtatcc      840
caggtggcct gaacgaacag ttcaccgtta aggcgtgca tggccacacc ttcccgaatc       900
atcatggtaa acgtgcgttt tcgctcaacg tcaatgcagc agcagtcatc ctcggcaaac      960
tctttccatg ccgcttcaac ctcgcggaa aaggcacggg cttcttcctc cccgatgccc      1020
agatagcgcc agcttgggcg atgactgagc cggaaaaaag acccgacgat atgatcctga    1080
tgcagctaga ttaaccctag aaagatagtc tgcgtaaaat tgacgcatga tctaattaac     1140
cctcactaaa gggaacaaaa gctggagctc caccgcggtg gccgccgctc tagaactagt     1200
gttcccacaa tggttaattc gagctcgccc gggatctaa ttcaattaga gactaattca      1260
attagagcta attcaattag gatccaagct tatcgatttc gaaccctcga ccgccggagt     1320
ataaatagag gcgcttcgtc tacggagcga caattcaatt caaacaagca agtgaacac     1380 gtcgctaagc gaaagctaag caaataaaca agcgcagctg aacaagctaa acaatcgggg    1440
taccgctaga gtcgacggta cgatccaccg gtcgccacca tggtgagcaa gggcgaggag     1500
ctgttcaccg gggtggtgcc catcctggtc gagctggacg gcgacgtaaa cggccacaag     1560
ttcagcgtgt ccggcgaggg cgaggcgat gccacctacg gcaagctgac cctgaagttc     1620
atctgcacca ccggcaagct gcccgtgccc tggcccaccc tcgtgaccac cctgacctgg    1680
ggcgtgcagt gcttcagccg ctaccccgac cacatgaagc agcacgactt cttcaagtcc    1740
gccatgcccg aaggctacgt ccaggagcgc accatcttct tcaaggacga cggcaactac    1800
aagacccgcg ccgaggtgaa gttcgagggc gacaccctgg tgaaccgcat cgagctgaag    1860
ggcatcgact tcaaggagga cggcaacatc ctggggcaca gctggagta caactacatc     1920 agccacaacg tctatatcac cgccgacaag cagaagaacg gcatcaaggc caacttcaag    1980
atccgccaca acatcgagga cggcagcgtg cagctcgccg accactacca gcagaacacc    2040
cccatcggcg acggccccgt gctgctgccc gacaaccact acctgagcac ccagtccgcc    2100
ctgagcaaag cccccaacga gaagcgcgat cacatggtcc tgctggagtt cgtgaccgcc    2160
gccgggatca ctctcggcat ggacgagctg tacaagtaaa gcggccgcga ctctagatca    2220
taatcagcca taccacattt gtagaggttt tacttgcttt aaaaaacctc ccacacctcc    2280
ccctgaacct gaaacataaa atgaatgcaa ttgttgttgt taacttgttt attgcagctt    2340
ataatggtta caaataaagc aatagcatca caaatttcac aaataaagca tttttttcac    2400
tgcattctag ttgtggtttg tccaaactca tcaatgtatc ttaaagctta tcgatacgcg    2460
tacggcacta gtggatcccc cgggctgcag gaattcgata tcaagcttat cgataccgtc    2520
gacctcgagg gggggcccgg tacccaattc gccctatagt gagtcgtatt aagatcacgc    2580
gtagatccat gcgtcaattt tacgcatgat tatctttaac gtacgtcaca atatgattat    2640 cttttctaggg ttaatctagc tgcgtgttct gcagcgtgtc gagcatcttc atctgctcca    2700
tcacgctgta aaacacattt gcaccgcgag tctgcccgtc ctccacgggt tcaaaaacgt    2760
gaatgaacga ggcgcgcttg gcgtaatcat ggtcatagct gtttcctgtg tgaaattgtt    2820
atccgctcac aattccacac aacatacgag ccggaagcat aaagtgtaaa gcctggggtg    2880
cctaatgagt gagctaactc acattaattg cgttgcgctc actgcccgct ttccagtcgg    2940
gaaacctgtc gtgccagctg cattaatgaa tcggccaacg cgcgggagag gcggtttgc     3000 gtattgggcg ctcttccgct tcctcgctca ctgactcgct gcgctcggtc gttcggctgc    3060
ggcgagcggt atcagctcac tcaaaggcgg taatacggtt atccacagaa tcaggggata    3120
```

-continued

```
acgcaggaaa gaacatgtga gcaaaaggcc agcaaaaggc caggaaccgt aaaaaggccg      3180
cgttgctggc gtttttccat aggctccgcc cccctgacga gcatcacaaa aatcgacgct      3240
caagtcagag gtggcgaaac ccgacaggac tataaagata ccaggcgttt ccccctggaa      3300
gctccctcgt gcgctctcct gttccgaccc tgccgcttac cggatacctg tccgcctttc      3360
tcccttcggg aagcgtggcg ctttctcata gctcacgctg taggtatctc agttcggtgt      3420
aggtcgttcg ctccaagctg gctgtgtgc acgaaccccc cgttcagccc gaccgctgcg       3480
ccttatccgg taactatcgt cttgagtcca acccggtaag acacgactta tcgccactgg      3540
cagcagccac tggtaacagg attagcagag cgaggtatgt aggcggtgct acagagttct      3600
tgaagtggtg gcctaactac ggctacacta aggacagt atttggtatc tgcgctctgc        3660
tgaagccagt taccttcgga aaaagagttg gtagctcttg atccggcaaa caaaccaccg      3720
ctggtagcgg tggttttttt gtttgcaagc agcagattac gcgcagaaaa aaaggatctc      3780
aagaagatcc tttgatcttt tctacggggt ctgacgctca gtggaacgaa aactcacgtt      3840
aagggatttt ggtcatgaga ttatcaaaaa ggatcttcac ctagatcctt ttaaattaaa      3900
aatgaagttt taaatcaatc taaagtatat atgagtaaac ttggtctgac agttaccaat      3960
gcttaatcag tgaggcacct atctcagcga tctgtctatt tcgttcatcc atagttgcct      4020
gactccccgt cgtgtagata actacgatac gggagggctt accatctggc cccagtgctg      4080
caatgatacc gcgagaccca cgctcaccgg ctccagattt atcagcaata aaccagccag      4140
ccggaagggc cgagcgcaga agtggtcctg caactttatc cgcctccatc cagtctatta      4200
attgttgccg ggaagctaga gtaagtagtt cgccagttaa tagtttgcgc aacgttgttg      4260
ccattgctac aggcatcgtg gtgtcacgct cgtcgtttgg tatggcttca ttcagctccg      4320
gttcccaacg atcaaggcga gttacatgat cccccatgtt gtgcaaaaaa gcggttagct      4380
ccttcggtcc tccgatcgtt gtcagaagta agttggccgc agtgttatca ctcatggtta      4440
tggcagcact gcataattct cttactgtca tgccatccgt aagatgcttt tctgtgactg      4500
gtgagtactc aaccaagtca ttctgagaat agtgtatgcg gcgaccgagt tgctcttgcc      4560
cggcgtcaat acgggataat accgcgccac atagcagaac tttaaaagtg ctcatcattg      4620
gaaaacgttc ttcggggcga aaactctcaa ggatcttacc gctgttgaga tccagttcga      4680
tgtaacccac tcgtgcaccc aactgatctt cagcatcttt tactttcacc agcgtttctg      4740
ggtgagcaaa aacaggaagg caaaatgccg caaaaaaggg aataagggcg acacggaaat      4800
gttgaatact catactcttc ctttttcaat attattgaag catttatcag ggttattgtc      4860
tcatgagcgg atacatattt gaatgtattt agaaaaataa acaaataggg gttccgcgca      4920
catttccccg aaaagtgcca c                                                4941
```

<210> SEQ ID NO 54
<211> LENGTH: 4943
<212> TYPE: DNA
<213> ORGANISM: Artificial Sequence
<220> FEATURE:
<223> OTHER INFORMATION: Description of Artificial Sequence:
      PBS-ITR-ECFP sequence

<400> SEQUENCE: 54

```
cacctgacgc gccctgtagc ggcgcattaa gcgcggcggg tgtggtggtt acgcgcagcg       60
tgaccgctac acttgccagc gccctagcgc ccgctccttt cgctttcttc ccttcctttc      120
tcgccacgtt cgccggcttt ccccgtcaag ctctaaatcg gggctccctt tagggttcc       180
```

-continued

```
gatttagtgc tttacggcac ctcgacccca aaaaacttga ttagggtgat ggttcacgta      240
gtgggccatc gccctgatag acggttttc gcccttgac gttggagtcc acgttcttta       300
atagtggact cttgttccaa actgaacaa cactcaaccc tatctcggtc tattcttttg      360
atttataagg gattttgccg atttcggcct attggttaaa aaatgagctg atttaacaaa    420
aatttaacgc gaattttaac aaaatattaa cgcttacaat ttccattcgc cattcaggct     480
gcgcaactgt tgggaagggc gatcggtgcg ggcctcttcg ctattacgcc agctggcgaa    540 aggggggatgt gctgcaaggc gattaagttg gtaacgcca gggttttccc agtcacgacg     600
ttgtaaaacg acggccagtg aattgtaata cgactcacta tagggcgaat tgggtaccgg    660
gccccccctc gaggtcgacg gtatcgataa gcttgatatc gaattcctgc agcccggggg    720
atcccatgcg tcaattttac gcagactatc tttctagggt taatctagct gcatcaggat    780
catatcgtcg ggtcttttt ccggctcagt catcgcccaa gctggcgcta tctgggcatc    840
ggggaggaag aagcccgtgc cttttcccgc gaggttgaag cggcatggaa agagtttgcc    900
gaggatgact gctgctgcat tgacgttgag cgaaaacgca cgtttaccat gatgattcgg    960
gaaggtgtgg ccatgcacgc ctttaacggt gaactgttcg ttcaggccac ctgggatacc   1020
agttcgtcgc ggcttttccg gacacagttc cggatggtca gcccgaagcg catcagcaac   1080
ccgaacaata ccgcgacag ccggaactgc cgtgccggtg tgcagattaa tgacagcggt    1140
gcggcgctgg gatattacgt cagcgaggac gggtatcctg gctggatgcc gcagaaatgg    1200
acatggatac cccgtgagtt acccggcggc tcgttcattc acgttttga acccgtggag    1260 gacgggcaga ctcgcggtgc aaatgtgttt tacagcgtga tggagcagat gaagatgctc    1320
gacacgctgc agaacacgca gctagattaa ccctagaaag ataatcatat tgtgacgtac   1380
gttaaagata atcatgcgta aaattgacgc atgggatcca ctagtgttcc cacaatggtt    1440
aattcgagct cgcccgggga tctaattcaa ttagagacta attcaattag agctaattca    1500
attaggatcc aagcttatcg atttcgaacc ctcgaccgcc ggagtataaa tagaggcgct    1560
tcgtctacgg agcgacaatt caattcaaac aagcaaagtg aacacgtcgc taagcgaaag    1620
ctaagcaaat aaacaagcgc agctgaacaa gctaaacaat cggggtaccg ctagagtcga    1680
cggtacgatc caccggtcgc caccatggtg agcaagggcg aggagctgtt caccggggtg    1740
gtgcccatcc tggtcgagct ggacggcgac gtaaacggcc acaagttcag cgtgtccggc    1800
gagggcgagg gcgatgccac ctacggcaag ctgaccctga gttcatctg caccaccggc     1860 aagctgcccg tgccctggcc caccctcgtg accaccctga cctgggcgt gcagtgcttc    1920 agccgctacc ccgaccacat gaagcagcac gacttcttca gtccgccat gcccgaaggc     1980 tacgtccagg agcgcaccat cttcttcaag gacgacggca actacaagac ccgcgccgag   2040
gtgaagttcg agggcgacac cctggtgaac cgcatcgagc tgaagggcat cgacttcaag   2100
gaggacggca acatcctggg gcacaagctg gagtacaact acatcagcca caacgtctat    2160
atcaccgccg acaagcagaa gaacggcatc aaggccaact tcaagatccg ccacaacatc    2220
gaggacggca gcgtgcagct cgccgaccac taccagcaga cacccccat cggcgacggc    2280 cccgtgctgc tgcccgacaa ccactacctg agcacccagt ccgccctgag caaagacccc    2340
aacgagaagc gcgatcacat ggtcctgctg gagttcgtga ccgccgccgg gatcactctc   2400
ggcatggacg agctgtacaa gtaaagcggc cgcgactcta gatcataatc agccatacca   2460
catttgtaga ggttttactt gctttaaaaa acctcccaca cctccccctg aacctgaaac    2520
```

-continued

```
ataaaatgaa tgcaattgtt gttgttaact tgtttattgc agcttataat ggttacaaat     2580
aaagcaatag catcacaaat ttcacaaata aagcatttt ttcactgcat tctagttgtg      2640
gtttgtccaa actcatcaat gtatcttaaa gcttatcgat acgcgtacgg cgcgcctagg    2700
ccggccgata ctagttctag agcggccgcc accgcggtgg agctccagct tttgttccct    2760
ttagtgaggg ttaatttcga gcttggcgta atcatggtca tagctgtttc ctgtgtgaaa    2820
ttgttatccg ctcacaattc cacacaacat acgagccgga agcataaagt gtaaagcctg    2880
gggtgcctaa tgagtgagct aactcacatt aattgcgttg cgctcactgc ccgctttcca    2940
gtcgggaaac ctgtcgtgcc agctgcatta atgaatcggc caacgcgcgg ggagaggcgg    3000
tttgcgtatt gggcgctctt ccgcttcctc gctcactgac tcgctgcgct cggtcgttcg    3060
gctgcggcga gcggtatcag ctcactcaaa ggcggtaata cggttatcca cagaatcagg    3120
ggataacgca ggaaagaaca tgtgagcaaa aggccagcaa aaggccagga accgtaaaaa    3180
ggccgcgttg ctggcgtttt tccataggct ccgcccccct gacgagcatc acaaaaatcg    3240
acgctcaagt cagaggtggc gaaacccgac aggactataa agataccagg cgtttccccc    3300
tggaagctcc ctcgtgcgct ctcctgttcc gaccctgccg cttaccggat acctgtccgc    3360 cttctccct tcgggaagcg tggcgctttc tcatagctca cgctgtaggt atctcagttc     3420
ggtgtaggtc gttcgctcca agctgggctg tgtgcacgaa ccccccgttc agcccgaccg    3480
ctgcgcctta tccggtaact atcgtcttga gtccaacccg gtaagacacg acttatcgcc    3540
actggcagca gccactggta acaggattag cagagcgagg tatgtaggcg gtgctacaga    3600
gttcttgaag tggtggccta actacggcta cactagaagg acagtatttg gtatctgcgc    3660
tctgctgaag ccagttacct tcggaaaaag agttggtagc tcttgatccg gcaaacaaac    3720
caccgctggt agcggtggtt tttttgtttg caagcagcag attacgcgca gaaaaaaagg    3780
atctcaagaa gatcctttga tcttttctac ggggtctgac gctcagtgga acgaaaactc    3840
acgttaaggg attttggtca tgagattatc aaaaaggatc ttcacctaga tccttttaaa    3900
ttaaaaatga gtttaaat caatctaaag tatatatgag taaacttggt ctgacagtta     3960
ccaatgctta atcagtgagg cacctatctc agcgatctgt ctatttcgtt catccatagt    4020
tgcctgactc cccgtcgtgt agataactac gatacgggag ggcttaccat ctggccccag    4080
tgctgcaatg ataccgcgag acccacgctc accggctcca gatttatcag caataaacca    4140
gccagccgga agggccgagc gcagaagtgg tcctgcaact ttatccgcct ccatccagtc    4200
tattaattgt tgccgggaag ctagagtaag tagttcgcca gttaatagtt tgcgcaacgt    4260
tgttgccatt gctacaggca tcgtggtgtc acgctcgtcg tttggtatgg cttcattcag    4320
ctccggttcc caacgatcaa ggcgagttac atgatccccc atgttgtgca aaaaagcggt    4380
tagctccttc ggtcctccga tcgttgtcag aagtaagttg gccgcagtgt tatcactcat    4440
ggttatggca gcactgcata attctcttac tgtcatgcca tccgtaagat gcttttctgt    4500
gactggtgag tactcaacca agtcattctg agaatagtgt atgcggcgac cgagttgctc    4560
ttgcccggcg tcaatacggg ataataccgc gccacatagc agaactttaa aagtgctcat    4620
cattggaaaa cgttcttcgg ggcgaaaact ctcaaggatc ttaccgctgt tgagatccag    4680
ttcgatgtaa cccactcgtg cacccaactg atcttcagca tcttttactt tcaccagcgt    4740
ttctgggtga gcaaaaacag gaaggcaaaa tgccgcaaaa aagggaataa gggcgacacg    4800
gaaatgttga atactcatac tcttcctttt tcaatattat tgaagcattt atcagggtta    4860
ttgtctcatg agcggataca tatttgaatg tatttagaaa aataaacaaa tagggggttcc   4920
```

```
gcgcacattt ccccgaaaag tgc                                        4943

<210> SEQ ID NO 55
<211> LENGTH: 4944
<212> TYPE: DNA
<213> ORGANISM: Artificial Sequence
<220> FEATURE:
<223> OTHER INFORMATION: Description of Artificial Sequence:
      PBS-ITR-EGFP sequence

<400> SEQUENCE: 55
cacctgacgc gccctgtagc ggcgcattaa gcgcggcggg tgtggtggtt acgcgcagcg     60
tgaccgctac acttgccagc gccctagcgc ccgctccttt cgctttcttc ccttcctttc    120
tcgccacgtt cgccggcttt ccccgtcaag ctctaaatcg gggctccct ttaggg ttcc    180 gatttagtgc tttacggcac ctcgacccca aaaaacttga ttagggtgat ggttcacgta    240
gtgggccatc gccctgatag acggtttttc gccctttgac gttggagtcc acgttcttta    300
atagtggact cttgttccaa actggaacaa cactcaaccc tatctcggtc tattcttttg    360
atttataagg gattttgccg atttcggcct attggttaaa aaatgagctg atttaacaaa    420
aatttaacgc gaattttaac aaaatattaa cgcttacaat ttccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg aattgtaata cgactcacta tagggcgaat tgggtaccgg    660
gccccccctc gaggtcgacg gtatcgataa gcttgatatc gaattcctgc agcccggggg    720
atcccatgcg tcaattttac gcagactatc tttctagggt taatctagct gcatcaggat    780
catatcgtcg gtctttttt ccggctcagt catcgcccaa gctggcgcta tctgggcatc    840
ggggaggaag aagcccgtgc cttttcccgc gaggttgaag cggcatggaa agagtttgcc    900
gaggatgact gctgctgcat tgacgttgag cgaaaacgca cgtttaccat gatgattcgg    960
gaaggtgtgg ccatgcacgc ctttaacggt gaactgttcg ttcaggccac ctgggatacc   1020
agttcgtcgc ggcttttccg gacacagttc cggatggtca gcccgaagcg catcagcaac   1080
ccgaacaata ccggcgacag ccggaactgc cgtgccggtg tgcagattaa tgacagcggt   1140
gcggcgctgg gatattacgt cagcgaggac gggtatcctg gctggatgcc gcagaaatgg   1200
acatggatac cccgtgagtt acccggcggc tcgttcattc acgttttga acccgtggag   1260 gacgggcaga ctcgcggtgc aaatgtgttt tacagcgtga tggagcagat gaagatgctc   1320
gacacgctgc agaacacgca gctagattaa ccctagaaag ataatcatat tgtgacgtac   1380
gttaaagata atcatgcgta aaattgacgc atgggatcca ctagtgttcc cacaatggtt   1440
aattcgagct cgcccgggga tctaattcaa ttagagacta attcaattag agctaattca   1500
attaggatcc aagcttatcg atttcgaacc ctcgaccgcc ggagtataaa tagaggcgct   1560
tcgtctacgg agcgacaatt caattcaaac aagcaaagtg aacacgtcgc taagcgaaag   1620
ctaagcaaat aaacaagcgc agctgaacaa gctaaacaat cggggtaccg ctagagtcga   1680
cggtaccgcg ggcccgggat ccaccggtcg ccaccatggt gagcaagggc gaggagctgt   1740
tcaccggggt ggtgcccatc ctggtcgagc tggacggcga cgtaaacggc cacaagttca   1800
gcgtgtccgg cgagggcgag ggcgatgcca cctacggcaa gctgaccctg aagttcatct   1860
gcaccaccgg caagctgccc gtgccctggc ccaccctcgt gaccaccctg acctacggcg   1920
tgcagtgctt cagccgctac cccgaccaca tgaagcagca cgacttcttc aagtccgcca   1980
```

-continued

```
tgcccgaagg ctacgtccag gagcgcacca tcttcttcaa ggacgacggc aactacaaga    2040
cccgcgccga ggtgaagttc gagggcgaca ccctggtgaa ccgcatcgag ctgaagggca    2100
tcgacttcaa ggaggacggc aacatcctgg ggcacaagct ggagtacaac tacaacagcc    2160
acaacgtcta tatcatggcc gacaagcaga agaacggcat caaggtgaac ttcaagatcc    2220
gccacaacat cgaggacggc agcgtgcagc tcgccgacca ctaccagcag aacaccccca    2280
tcggcgacgg ccccgtgctg ctgcccgaca ccactacct gagcacccag tccgccctga    2340
gcaaagaccc caacgagaag cgcgatcaca tggtcctgct ggagttcgtg accgccgccg    2400
ggatcactct cggcatggac gagctgtaca gtaaagcgg ccgcgactct agatcataat    2460
cagccatacc acatttgtag aggttttact tgctttaaaa aacctcccac acctccccct    2520
gaacctgaaa cataaaatga atgcaattgt tgttgttaac ttgtttattg cagcttataa    2580
tggttacaaa taaagcaata gcatcacaaa tttcacaaat aaagcatttt tttcactgca    2640
ttctagttgt ggtttgtcca aactcatcaa tgtatcttaa agcttatcga tacgcgtacg    2700
gcgcgcctag actagttcta gagcggccgc caccgcggtg gagctccagc ttttgttccc    2760
tttagtgagg gttaatttcg agcttggcgt aatcatggtc atagctgttt cctgtgtgaa    2820
attgttatcc gctcacaatt ccacacaaca tacgagccgg aagcataaag tgtaaagcct    2880
ggggtgccta atgagtgagc taactcacat taattgcgtt gcgctcactg cccgctttcc    2940
agtcgggaaa cctgtcgtgc cagctgcatt aatgaatcgg ccaacgcgcg gggagaggcg    3000
gtttgcgtat tgggcgctct tccgcttcct cgctcactga ctcgctgcgc tcggtcgttc    3060
ggctgcggcg agcggtatca gctcactcaa aggcggtaat acggttatcc acagaatcag    3120
gggataacgc aggaaagaac atgtgagcaa aaggccagca aaaggccagg aaccgtaaaa    3180
aggccgcgtt gctggcgttt ttccataggc tccgcccccc tgacgagcat cacaaaaatc    3240
gacgctcaag tcagaggtgg cgaaacccga caggactata aagataccag gcgtttcccc    3300
ctggaagctc cctcgtgcgc tctcctgttc cgaccctgcc gcttaccgga tacctgtccg    3360
cctttctccc ttcgggaagc gtggcgcttt ctcatagctc acgctgtagg tatctcagtt    3420
cggtgtaggt cgttcgctcc aagctgggct gtgtgcacga accccccgtt cagcccgacc    3480
gctgcgcctt atccggtaac tatcgtcttg agtccaaccc ggtaagacac gacttatcgc    3540
cactggcagc agccactggt aacaggatta gcagagcgag gtatgtaggc ggtgctacag    3600
agttcttgaa gtggtggcct aactacggct acactagaag gacagtattt ggtatctgcg    3660
ctctgctgaa gccagttacc ttcggaaaaa gagttggtag ctcttgatcc ggcaaacaaa    3720
ccaccgctgg tagcggtggt ttttttgttt gcaagcagca gattacgcgc agaaaaaaag    3780
gatctcaaga agatcctttg atcttttcta cggggtctga cgctcagtgg aacgaaaact    3840
cacgttaagg gattttggtc atgagattat caaaaaggat cttcacctag atccttttaa    3900
attaaaaatg aagttttaaa tcaatctaaa gtatatatga gtaaacttgg tctgacagtt    3960
accaatgctt aatcagtgag gcacctatct cagggatctg tctatttcgt tcatccatag    4020
ttgcctgact ccccgtcgtg tagataacta cgatacggga gggcttacca tctggcccca    4080
gtgctgcaat gataccgcga gacccacgct caccggctcc agatttatca gcaataaacc    4140
agccagccgg aagggccgag cgcagaagtg gtcctgcaac tttatccgcc tccatccagt    4200
ctattaattg ttgccgggaa gctagagtaa gtagttcgcc agttaatagt ttgcgcaacg    4260
ttgttgccat tgctacaggc atcgtggtgt cacgctcgtc gtttggtatg gcttcattca    4320
```

```
gctccggttc ccaacgatca aggcgagtta catgatcccc catgttgtgc aaaaaagcgg    4380
ttagctcctt cggtcctccg atcgttgtca gaagtaagtt ggccgcagtg ttatcactca    4440
tggttatggc agcactgcat aattctctta ctgtcatgcc atccgtaaga tgcttttctg    4500
tgactggtga gtactcaacc aagtcattct gagaatagtg tatgcggcga ccgagttgct    4560
cttgcccggc gtcaatacgg gataataccg cgccacatag cagaacttta aaagtgctca    4620
tcattggaaa acgttcttcg gggcgaaaac tctcaaggat cttaccgctg ttgagatcca    4680
gttcgatgta acccactcgt gcacccaact gatcttcagc atcttttact ttcaccagcg    4740
tttctgggtg agcaaaaaca ggaaggcaaa atgccgcaaa aaagggaata agggcgacac    4800
ggaaatgttg aatactcata ctcttccttt ttcaatatta ttgaagcatt tatcagggtt    4860
attgtctcat gagcggatac atatttgaat gtatttagaa aaataaacaa ataggggttc    4920
cgcgcacatt tccccgaaaa gtgc                                           4944
```

<210> SEQ ID NO 56
<211> LENGTH: 4944
<212> TYPE: DNA
<213> ORGANISM: Artificial Sequence
<220> FEATURE:
<223> OTHER INFORMATION: Description of Artificial Sequence:
    pBS-ITR-EYFP sequence

<400> SEQUENCE: 56

```
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg gggctccct ttagggttcc      180 gatttagtgc tttacggcac ctcgacccca aaaaacttga ttagggtgat ggttcacgta     240
gtgggccatc gccctgatag acggtttttc gccctttgac gttggagtcc acgttcttta     300
atagtggact cttgttccaa actggaacaa cactcaaccc tatctcggtc tattcttttg     360
atttataagg gattttgccg atttcggcct attggttaaa aaatgagctg atttaacaaa     420
aatttaacgc gaattttaac aaaatattaa cgcttacaat ttccattcgc cattcaggct     480
gcgcaactgt tgggaagggc gatcggtgcg ggcctcttcg ctattacgcc agctggcgaa     540
agggggatgt gctgcaaggc gattaagttg gtaacgcca gggttttccc agtcacgacg      600
ttgtaaaacg acggccagtg aattgtaata cgactcacta tagggcgaat gggtaccgg      660 gccccccctc gaggtcgacg gtatcgataa gcttgatatc gaattcctgc agcccggggg     720
atcccatgcg tcaattttac gcagactatc tttctagggt taatctagct gcatcaggat     780
catatcgtcg gtctttttt ccggctcagt catcgcccaa gctggcgcta tctgggcatc      840
ggggaggaag aagcccgtgc cttttcccgc gaggttgaag cggcatggaa agagtttgcc     900
gaggatgact gctgctgcat tgacgttgag cgaaaacgca cgtttaccat gatgattcgg     960
gaaggtgtgg ccatgcacgc ctttaacggt gaactgttcg ttcaggccac ctgggatacc    1020
agttcgtcgc ggcttttccg gacacagttc cggatggtca gcccgaagcg catcagcaac    1080
ccgaacaata ccggcgacag ccggaactgc cgtgccggtg tgcagattaa tgacagcggt    1140
gcggcgctgg gatattacgt cagcgaggac gggtatcctg gctggatgcc gcagaaatgg    1200
acatggatac cccgtgagtt acccggcggc tcgttcattc acgtttttga acccgtggag    1260
gacgggcaga ctcgcggtgc aaatgtgttt tacagcgtga tggagcagat gaagatgctc    1320
gacacgctgc agaacacgca gctagattaa ccctagaaag ataatcatat tgtgacgtac    1380
```

-continued

```
gttaaagata atcatgcgta aaattgacgc atgggatcca ctagtgttcc cacaatggtt    1440
aattcgagct cgcccgggga tctaattcaa ttagagacta attcaattag agctaattca    1500
attaggatcc aagcttatcg atttcgaacc ctcgaccgcc ggagtataaa tagaggcgct    1560
tcgtctacgg agcgacaatt caattcaaac aagcaaagtg aacacgtcgc taagcgaaag    1620
ctaagcaaat aaacaagcgc agctgaacaa gctaaacaat cggggtaccg ctagagtcga    1680
cggtacgatc caccggtcgc caccatggtg agcaagggcg aggagctgtt caccggggtg    1740
gtgcccatcc tggtcgagct ggacggcgac gtaaacggcc acaagttcag cgtgtccggc    1800
gagggcgagg gcgatgccac ctacggcaag ctgaccctga agttcatctg caccaccggc    1860
aagctgcccg tgccctggcc caccctcgtg accaccttcg gctacggcct gcagtgcttc    1920
gcccgctacc ccgaccacat gaagcagcac gacttcttca gtccgccat gcccgaaggc    1980 tacgtccagg agcgcaccat cttcttcaag gacgacggca actacaagac ccgcgccgag    2040
gtgaagttcg agggcgacac cctggtgaac cgcatcgagc tgaagggcat cgacttcaag    2100
gaggacggca acatcctggg gcacaagctg gagtacaact acaacagcca caacgtctat    2160
atcatggccg acaagcagaa gaacggcatc aaggtgaact tcaagatccg ccacaacatc    2220
gaggacggca gcgtgcagct cgccgaccac taccagcaga cacccccat cggcgacggc    2280 cccgtgctgc tgcccgacaa ccactacctg agctaccagt ccgccctgag caaagacccc    2340
aacgagaagc gcgatcacat ggtcctgctg gagttcgtga ccgccgccgg gatcactctc    2400
ggcatggacg agctgtacaa gtaaagcggc cgcgactcta gatcataatc agccatacca    2460
catttgtaga ggttttactt gctttaaaaa acctcccaca cctcccctg aacctgaaac    2520 ataaaatgaa tgcaattgtt gttgttaact tgtttattgc agcttataat ggttacaaat    2580
aaagcaatag catcacaaat ttcacaaata aagcattttt ttcactgcat tctagttgtg    2640
gtttgtccaa actcatcaat gtatcttaaa gcttatcgat acgcgtacgg cgcgcctagg    2700
ccggccgatc actagttcta gagcggccgc caccgcggtg gagctccagc ttttgttccc    2760
tttagtgagg gttaatttcg agcttggcgt aatcatggtc atagctgttt cctgtgtgaa    2820
attgttatcc gctcacaatt ccacacaaca tacgagccgg aagcataaag tgtaaagcct    2880
ggggtgccta atgagtgagc taactcacat taattgcgtt gcgctcactg cccgctttcc    2940
agtcgggaaa cctgtcgtgc cagctgcatt aatgaatcgg ccaacgcgcg gggagaggcg    3000
gtttgcgtat tgggcgctct tccgcttcct cgctcactga ctcgctgcgc tcggtcgttc    3060
ggctgcggcg agcggtatca gctcactcaa aggcggtaat acggttatcc acagaatcag    3120
gggataacgc aggaaagaac atgtgagcaa aaggccagca aaaggccagg aaccgtaaaa    3180
aggccgcgtt gctggcgttt ttccataggc tccgcccccc tgacgagcat cacaaaaatc    3240
gacgctcaag tcagaggtgg cgaaacccga caggactata agataccag gcgtttcccc    3300 ctggaagctc cctcgtgcgc tctcctgttc cgacctgcc gcttaccgga tacctgtccg    3360
cctttctccc ttcgggaagc gtggcgcttt ctcatagctc acgctgtagg tatctcagtt    3420
cggtgtaggt cgttcgctcc aagctgggct gtgtgcacga accccccgtt cagcccgacc    3480
gctgcgcctt atccggtaac tatcgtcttg agtccaaccc ggtaagacac gacttatcgc    3540
cactggcagc agccactggt aacaggatta gcagagcgag gtatgtaggc ggtgctacag    3600
agttcttgaa gtggtggcct aactacggct acactagaag gacagtattt ggtatctgcg    3660
ctctgctgaa gccagttacc ttcggaaaaa gagttggtag ctcttgatcc ggcaaacaaa    3720
ccaccgctgg tagcggtggt ttttttgttt gcaagcagca gattacgcgc agaaaaaaag    3780
```

```
gatctcaaga agatcctttg atcttttcta cggggtctga cgctcagtgg aacgaaaact    3840
cacgttaagg gattttggtc atgagattat caaaaaggat cttcacctag atccttttaa    3900
attaaaaatg aagttttaaa tcaatctaaa gtatatatga gtaaacttgg tctgacagtt    3960
accaatgctt aatcagtgag gcacctatct cagcgatctg tctatttcgt tcatccatag    4020
ttgcctgact ccccgtcgtg tagataacta cgatacggga gggcttacca tctggcccca    4080
gtgctgcaat gataccgcga gacccacgct caccggctcc agatttatca gcaataaacc    4140
agccagccgg aagggccgag cgcagaagtg gtcctgcaac tttatccgcc tccatccagt    4200
ctattaattg ttgccgggaa gctagagtaa gtagttcgcc agttaatagt ttgcgcaacg    4260
ttgttgccat tgctacaggc atcgtggtgt cacgctcgtc gtttggtatg gcttcattca    4320
gctccggttc ccaacgatca aggcgagtta catgatcccc catgttgtgc aaaaaagcgg    4380
ttagctcctt cggtcctccg atcgttgtca agtaagtt ggccgcagtg ttatcactca    4440
tggttatggc agcactgcat aattctctta ctgtcatgcc atccgtaaga tgcttttctg    4500
tgactggtga gtactcaacc aagtcattct gagaatagtg tatgcggcga ccgagttgct    4560
cttgcccggc gtcaatacgg gataataccg cgccacatag cagaacttta aaagtgctca    4620
tcattggaaa acgttcttcg ggcgaaaac tctcaaggat cttaccgctg ttgagatcca    4680
gttcgatgta acccactcgt gcacccaact gatcttcagc atcttttact ttcaccagcg    4740
tttctgggtg agcaaaaaca ggaaggcaaa atgccgcaaa aaagggaata agggcgacac    4800
ggaaatgttg aatactcata ctcttccttt ttcaatatta ttgaagcatt tatcagggtt    4860
attgtctcat gagcggatac atatttgaat gtatttagaa aaataaacaa atagggttc    4920 cgcgcacatt tccccgaaaa gtgc                                          4944

<210> SEQ ID NO 57
<211> LENGTH: 7670
<212> TYPE: DNA
<213> ORGANISM: Artificial Sequence
<220> FEATURE:
<223> OTHER INFORMATION: Description of Artificial Sequence:
      pIAO-pL DNA sequence

<400> SEQUENCE: 57
aacgcgcggg gagaggcggt ttgcgtattg ggcgctcttc cgcttcctcg ctcactgact     60
cgctgcgctc ggtcgttcgg ctgcggcgag cggtatcagc tcactcaaag gcggtaatac    120
ggttatccac agaatcaggg gataacgcag gaaagaacat gtgagcaaaa ggccagcaaa    180
aggccaggaa ccgtaaaaag gccgcgttgc tggcgttttt ccataggctc cgcccccctg    240
acgagcatca caaaaatcga cgctcaagtc agaggtggcg aaacccgaca ggactataaa    300
gataccaggc gtttccccct ggaagctccc tcgtgcgctc tcctgttccg accctgccgc    360
ttaccggata cctgtccgcc tttctccctt cgggaagcgt ggcgctttct caatgctcac    420
gctgtaggta tctcagttcg gtgtaggtcg ttcgctccaa gctgggctgt gtgcacgaac    480
cccccgttca gcccgaccgc tgcgccttat ccggtaacta tcgtcttgag tccaacccgg    540
taagacacga cttatcgcca ctggcagcag ccactggtaa caggattagc agagcgaggt    600
atgtaggcgg tgctacagag ttcttgaagt ggtggcctaa ctacggctac actagaagga    660
cagtatttgg tatctgcgct ctgctgaagc cagttacctt cggaaaaaga gttggtagct    720
cttgatccgg caaacaaacc accgctggta gcggtggttt ttttgtttgc aagcagcaga    780
ttacgcgcag aaaaaaagga tctcaagaag atcctttgat cttttctacg gggtctgacg    840
```

-continued

```
ctcagtggaa cgaaaactca cgttaaggga ttttggtcat gagattatca aaaaggatct      900
tcacctagat cctttttaaat taaaaatgaa gttttaaatc aatctaaagt atatatgagt     960
aaacttggtc tgacagttac caatgcttaa tcagtgaggc acctatctca gcgatctgtc    1020
tatttcgttc atccatagtt gcctgactcc ccgtcgtgta gataactacg atacgggagg    1080
gcttaccatc tggccccagt gctgcaatga taccgcgaga cccacgctca ccggctccag    1140
atttatcagc aataaaccag ccagccggaa gggccgagcg cagaagtggt cctgcaactt    1200
tatccgcctc catccagtct attaattgtt gccgggaagc tagagtaagt agttcgccag    1260
ttaatagttt gcgcaacgtt gttgccattg ctacaggcat cgtggtgtca cgctcgtcgt    1320
ttggtatggc ttcattcagc tccggttccc aacgatcaag gcgagttaca tgatccccca    1380
tgttgtgcaa aaaagcggtt agctccttcg gtcctccgat cgttgtcaga agtaagttgg    1440
ccgcagtgtt atcactcatg gttatggcag cactgcataa ttctcttact gtcatgccat    1500
ccgtaagatg cttttctgtg actggtgagt actcaaccaa gtcattctga aatagtgta    1560
tgcggcgacc gagttgctct tgcccggcgt caatacggga taataccgcg ccacatagca    1620
gaactttaaa agtgctcatc attggaaaac gttcttcggg gcgaaaactc tcaaggatct    1680
taccgctgtt gagatccagt tcgatgtaac ccactcgtgc acccaactga tcttcagcat    1740
cttttacttt caccagcgtt tctgggtgag caaaaacagg aaggcaaaat gccgcaaaaa    1800
agggaataag ggcgacacgg aaatgttgaa tactcatact cttcctttt caatattatt    1860
gaagcattta tcagggttat tgtctcatga gcggatacat atttgaatgt atttagaaaa    1920
ataaacaaat aggggttccg cgcacatttc cccgaaaagt gccacctgac gtctaagaaa    1980
ccattattat catgacatta acctataaaa ataggcgtat cacggggccc tgagtgaac    2040
caattgtcac acgtaatatt acgacaacta ccgtgcacag gctttgataa ctccttcacg    2100
tagtattcac cgagtggtac tccgttggtc tgtgttcctc ttcccaaata aggcattcca    2160
tttatcatat acttcgtacc actgtcacac atcatgagga ttttattcc atacttactt    2220
ggcttgtttg ggatatacat cctaaacgga caccgtcctc taaaaccaag taactgttca    2280
tctatggtca aatgagcccc tggagtgtaa ttttgtatgc actgatggat aaagagatcc    2340
catatttttc taacaggagt aaatacatcg ttttctcgaa gtgtgggccg tatacttttg    2400
tcatccattc taagacatcg tatcaaaaaa tccaaaacga tccacagact cattacagag    2460
acgtacacat tgcaaagat cgatccaaag aggtcatctg tggacatgtg gttatctttt    2520
ctcactgctg tcattaccag aataccaaag aaagcataga tttcatcttc attcgtgtca    2580
cgaaatgtag cacctgtcat agattcccga cgtttcaatg atatctcagc atttgtccat    2640
tttacaattt gcgaaattat ctcatcagta aaaaatagtt tgaagcataa aagtgggtca    2700
tatatattgc ggcacatacg cgtcggacct ctttgagatc tgacaatgtt cagtgcagag    2760
actcggctac cgctcgtgga ctttgaagtt aaattcagat ataaagacgc tgaaaatcat    2820
ttgattttcg ctctaacata ccaccctaaa gattataaat ttaatgaatt attaaaatac    2880
gtacaacaat tgtctgtaaa tcaacaacgc acagaatcta gcgcttaata aatgtactaa    2940
taacaatgta tcgtgtttta atacgccgga ccagtgaaca gaggtgcgtc tggtgcaaac    3000
tcctttactt tgaacaccag ggaaacttca aggagaattt cctcctcttc agcagagtcg    3060
gtaccggtca cccgggatc cccctgccc ggttattatt attttgaca ccagaccaac    3120
tggtaatggt agcgaccggc gctcagctgg aattccgccg atactgacgg gctccaggag    3180
```

-continued

```
tcgtcgccac caatcccat atggaaaccg tcgatattca gccatgtgcc ttcttccgcg    3240
tgcagcagat ggcgatggct ggtttccatc agttgctgtt gactgtagcg gctgatgttg    3300
aactggaagt cgccgcgcca ctggtgtggg ccataattca attcgcgcgt cccgcagcgc    3360
agaccgtttt cgctcgggaa gacgtacggg gtatacatgt ctgacaatgg cagatcccag    3420
cggtcaaaac aggcggcagt aaggcggtcg ggatagtttt cttgcggccc taatccgagc    3480
cagtttaccc gctctgctac ctgcgccagc tggcagttca ggccaatccg cgccggatgc    3540
ggtgtatcgc tcgccacttc aacatcaacg gtaatcgcca tttgaccact accatcaatc    3600
cggtaggttt tccggctgat aaataaggtt ttcccctgat gctgccacgc gtgagcggtc    3660
gtaatcagca ccgcatcagc aagtgtatct gccgtgcact gcaacaacgc tgcttcggcc    3720
tggtaatggc ccgccgcctt ccagcgttcg acccaggcgt tagggtcaat gcgggtcgct    3780
tcacttacgc caatgtcgtt atccagcggt gcacgggtga actgatcgcg cagcggcgtc    3840
agcagttgtt ttttatcgcc aatccacatc tgtgaaagaa agcctgactg gcggttaaat    3900
tgccaacgct tattacccag ctcgatgcaa aaatccattt cgctggtggt cagatgcggg    3960
atggcgtggg acgcggcggg gagcgtcaca ctgaggtttt ccgccagacg ccactgctgc    4020
caggcgctga tgtgcccggc ttctgaccat gcggtcgcgt tcggttgcac tacgcgtact    4080
gtgagccaga gttgcccggc gctctccggc tgcggtagtt caggcagttc aatcaactgt    4140
ttaccttgtg gagcgacatc cagaggcact tcaccgcttg ccagcggctt accatccagc    4200
gccaccatcc agtgcaggag ctcgttatcg ctatgacgga acaggtattc gctggtcact    4260
tcgatggttt gcccggataa acggaactgg aaaaactgct gctggtgttt tgcttccgtc    4320
agcgctggat gcgcgtgcg gtcggcaaag accagaccgt tcatacagaa ctggcgatcg    4380
ttcggcgtat cgccaaaatc accgccgtaa gccgaccacg ggttgccgtt ttcatcatat    4440
ttaatcagcg actgatccac ccagtcccag acgaagccgc cctgtaaacg ggatactga    4500 cgaaacgcct gccagtattt agcgaaaccg ccaagactgt tacccatcgc gtgggcgtat    4560
tcgcaaagga tcagcgggcg cgtctctcca ggtagcgaaa gccatttttt gatgaccat    4620 ttcggcacag ccgggaaggg ctggtcttca tccacgcgcg cgtacatcgg gcaaataata    4680
tcggtggccg tggtgtcggc tccgccgcct tcatactgca ccgggcggga aggatcgaca    4740
gatttgatcc agcgatacag cgcgtcgtga ttagcgccgt ggcctgattc attccccagc    4800
gaccagatga tcacactcgg gtgattacga tcgcgctgca ccattcgcgt tacgcgttcg    4860
ctcatcgccg gtagccagcg cggatcatcg gtcagacgat tcattggcac catgccgtgg    4920
gtttcaatat tggcttcatc caccacatac aggccgtagc ggtcgcacag cgtgtaccac    4980
agcggatggt tcgataatg cgaacagcgc acggcgttaa agttgttctg cttcatcagc    5040
aggatatcct gcaccatcgt ctgctcatcc atgacctgac catgcagagg atgatgctcg    5100
tgacggttaa cgcctcgaat cagcaacggc ttgccgttca gcagcagcag accatttca    5160 atccgcacct cgcggaaacc gacatcgcag gcttctgctt caatcagcgt gccgtcggcg    5220
gtgtgcagtt caaccaccgc acgatagaga ttcgggatt cggcgctcca cagtttcggg    5280
ttttcgacgt tcagacgtag tgtgacgcga tcggcataac caccacgctc atcgataatt    5340
tcaccgccga aaggcgcggt gccgctggcg acctgcgttt caccctgcca taagaaact    5400 gttacccgta ggtagtcacg caactcgccg cacatctgaa cttcagcctc cagtacagcg    5460
cggctgaaat catcattaaa gcgagtggca acatggaaat cgctgatttg tgtagtcggt    5520
ttatgcagca acgagacgtc acggaaaatg ccgctcatcc gccacatatc ctgatcttcc    5580
```

-continued

```
agataactgc cgtcactcca acgcagcacc atcaccgcga ggcggttttc tccggcgcgt    5640
aaaaatgcgc tcaggtcaaa ttcagacggc aaacgactgt cctggccgta accgacccag    5700
cgcccgttgc accacagatg aaacgccgag ttaacgccat caaaaataat tcgcgtctgg    5760
ccttcctgta gccagctttc atcaacatta aatgtgagcg agtaacaacc cgtcggattc    5820
tccgtgggaa caaacggcgg attgaccgta atgggatagg ttacgttggt gtagatgggc    5880
gcatcgtaac cgtgcatctg ccagtttgag gggacgacga cgggatccgt tttttattta    5940
caaaactgtt acgaaaacag taaaatactt atttattcgg accaacaatg tttattctta    6000
cctctaatag tcctctgtgg caaggtcaag attctgttag aagccaatga agaacctggt    6060
tgttcaataa cattttgttc gtctaatatt tcactacgct tgacgttggc tgacacttca    6120
tgtacctcat ctataaacgc ttcttctgta tcgctctgga cgtcttcact tacgtgatct    6180
gatatttcac tgtcagaatc ctcaccaaca agctcgtcat cgccttgcag aagagcagag    6240
aggatatgct catcgtctaa agaacatccc attttattat atattagtca cgatatctat    6300
aacaagaaaa tatatatata ataagttatc acgtaagtag aacatgaaat aacaatatta    6360
attatcgtat gagttaaatc ttaaaagtca cgtaaaagat aatcatgcgt cattttgact    6420
cacgcggtcg ttatagttca aaatcagtga cacttaccgc attgacaagc acgcctcagc    6480
cgagctccaa gcggcgactg agatgtccta aattgcaaac agcgacggat tcgcgctatt    6540
tagaaagaga gagcaatatt tcaagaatgc atgcgtcaat tttacgcaga ctatctttct    6600
agggttaatc tagaggatcc tctagattaa ccctagaaag ataatcatat tgtgacgtac    6660
gttaaagata atcatgcgta aaattgacgc atgtgttttt atcggtctgt atatcgaggt    6720
ttatttatta atttgaatag atattaagtt ttattatatt tacacttaca tactaataat    6780
aaattcaaca acaatttat ttatgtttat ttatttatta aaaaaaaaca aaaactcaaa     6840
atttcttcta aagtaacaaa acttttaaac attctctctt ttacaaaaat aaacttattt    6900
tgtactttaa aaacagtcat gttgtattat aaaataagta attagcttaa cttatacata    6960
atagaaacaa attatactta ttagtcagtc cagaaacaac tttggcacat atcaatatta    7020
tgctctcgac aaataacttt tttgcattt tttgcacgatg catttgcctt tcgccttatt     7080
ttagaggggc agtaagtaca gtaagtacgt tttttcatta ctggctcttc agtactgtca    7140
tctgatgtac caggcacttc atttggcaaa atattagaga tattatcgcg caaatatctc    7200
ttcaaagtag gagcttctaa acggttacgc ataaacgatg acgtcaggct catgtaaagg    7260
tttctcataa attttttgcg actttgaacc ttttctccct tgctactgac attatggctg    7320
tatataataa aagaatttat gcaggcaatg tttatcattc cgtacaataa tgccataggc    7380
cacctattcg tcttcctact gcaggtcatc acagaacaca tttggtctag cgtgtccact    7440
ccgcctttag tttgattata atacataacc atttgcggtt taccggtact ttcgttgata    7500
gaagcatcct catcacaaga tgataataag tataccatct tagctggctt cggtttatat    7560
gagacgagag taagggtcc gtcaaaacaa aacatcgatg ttcccactgg cctggagcga     7620 ctgttttca gtacttccgg tatctcgcgt ttgtttgatc gcacggtacc                7670
```

<210> SEQ ID NO 58
<211> LENGTH: 286
<212> TYPE: PRT
<213> ORGANISM: Artificial Sequence
<220> FEATURE:
<223> OTHER INFORMATION: Description of Artificial Sequence: pIAO-pL
    amino acid sequence

```
<400> SEQUENCE: 58

Trp His Lys Ile Leu Ser Ala Gly Ile Glu Ala Ile Gln Arg Asn Arg
  1               5                  10                  15

Glu Asp Met Thr Ala Gln Ser Gly Thr Thr Tyr Ile Val Val Ile Arg
             20                  25                  30

Ser Pro Lys Gly Asp Pro Gly Leu Ala Ala Ile Ile Gly Arg Ser Gly
         35                  40                  45

Arg Glu Gly Ala Gly Ser Lys Asp Ala Ile Phe Trp Gly Ala Pro Leu
     50                  55                  60

Ala Ser Arg Leu Leu Pro Gly Ala Val Lys Asp Ala Glu Met Trp Asp
 65                  70                  75                  80

Ile Leu Gln Gln Arg Ser Ala Leu Thr Leu Leu Glu Gly Thr Leu Leu
                 85                  90                  95

Lys Arg Leu Thr Thr Ala Met Ala Val Pro Met Thr Thr Asp Arg Glu
             100                 105                 110

Asp Asn Pro Ile Ala Glu Asn Leu Glu Pro Glu Trp Arg Asp Leu Arg
         115                 120                 125

Thr Val His Asp Gly Met Asn His Leu Phe Ala Thr Leu Glu Lys Pro
    130                 135                 140

Gly Gly Ile Thr Thr Leu Leu Leu Asn Ala Ala Thr Asn Asp Ser Met
145                 150                 155                 160

Thr Ile Ala Ala Ser Cys Leu Glu Arg Val Thr Met Gly Asp Thr Leu
                165                 170                 175

His Lys Glu Thr Val Pro Ser Tyr Glu Val Leu Asp Asn Gln Ser Tyr
            180                 185                 190

His Ile Arg Arg Gly Leu Gln Glu Gln Gly Ala Asp Ile Arg Ser Leu
        195                 200                 205

Val Ala Gly Cys Leu Leu Val Lys Phe Thr Ser Met Met Pro Phe Arg
    210                 215                 220

Glu Glu Pro Arg Phe Ser Glu Leu Ile Lys Gly Ser Asn Leu Asp Leu
225                 230                 235                 240

Glu Ile Tyr Gly Val Arg Ala Gly Leu Gln Asp Glu Ala Asp Lys Val
                245                 250                 255

Lys Val Leu Thr Glu Pro His Ala Phe Val Pro Leu Cys Phe Ala Ala
            260                 265                 270

Phe Phe Pro Ile Leu Ala Val Arg Phe His Gln Ile Ser Met
        275                 280                 285

<210> SEQ ID NO 59
<211> LENGTH: 240
<212> TYPE: PRT
<213> ORGANISM: Artificial Sequence
<220> FEATURE:
<223> OTHER INFORMATION: Description of Artificial Sequence: pIAO-pL
      amino acid sequence

<400> SEQUENCE: 59

Arg Tyr Phe Tyr Ala Tyr Pro Ala Arg Leu His Val Leu Gln Val Tyr
  1               5                  10                  15

Tyr Ser Leu Arg Ala Cys Ala Lys Ile Val Gly Glu Arg Leu Ile Arg
             20                  25                  30

Thr Thr Ser Arg Gln Asp Thr Asn Arg Lys Gly Phe Leu Ala Asn Trp
         35                  40                  45

Lys Asp Tyr Val Glu Tyr Trp Gln Val Asp His Pro Asn Lys Asn Trp
     50                  55                  60
```

-continued

Val Lys Ala Gln Lys Pro Tyr Val Asp Val Ser Val Thr Arg Phe Trp
 65                  70                  75                  80

Thr Val Thr Arg His Asp Phe Ser Gly Arg Ser His Leu Lys Thr His
                 85                  90                  95

Val Ser Pro Tyr Leu Ser Gly Met Asn Lys Cys Ser Tyr Ile Cys Arg
            100                 105                 110

Lys Arg Ser Thr His Ala Thr Tyr Lys Gln Gly Asn Ser Met Thr Asp
        115                 120                 125

Phe Phe Gly Phe Arg Asp Val Ser Glu Asn Cys Leu Arg Val Cys Gln
    130                 135                 140

Cys Leu Asp Ile Trp Leu Pro Arg His Val His Pro Arg Lys Glu Ser
145                 150                 155                 160

Ser Asp Asn Gly Ser Tyr Trp Leu Phe Cys Leu Asn Arg Glu His Ser
                165                 170                 175

Ile Tyr Cys Arg Asp Tyr Ile Gly Ser Thr Glu Ile Ile Asp Cys Lys
            180                 185                 190

Asp Met Lys Cys Asn Ala Phe Asn Asp Tyr Phe Ile Thr Gln Leu Met
        195                 200                 205

Phe Thr Pro Ile Tyr Gln Pro Val Tyr Ala Asp Ser Arg Lys Ser Ile
    210                 215                 220

Gln Cys His Glu Thr Cys Leu Ser Pro Arg Glu His Val Lys Phe Asn
225                 230                 235                 240

<210> SEQ ID NO 60
<211> LENGTH: 933
<212> TYPE: PRT
<213> ORGANISM: Artificial Sequence
<220> FEATURE:
<223> OTHER INFORMATION: Description of Artificial Sequence: pIAO-pL
      amino acid sequence

<400> SEQUENCE: 60

Lys Gln Cys Trp Val Leu Gln Tyr His Tyr Arg Gly Ala Ser Leu Gln
  1               5                  10                  15

Phe Glu Ala Ser Val Ser Pro Ser Trp Ser Asp Gly Gly Ile Gly
             20                  25                  30

Met His Phe Gly Asp Ile Asn Leu Trp Thr Gly Glu Glu Ala His Leu
         35                  40                  45

Leu His Arg His Ser Thr Glu Met Leu Gln Gln Ser Tyr Arg Ser
     50                  55                  60

Ile Asn Phe Gln Phe Asp Gly Arg Trp Gln His Pro Gly Tyr Asn Leu
 65                  70                  75                  80

Glu Arg Thr Gly Cys Arg Leu Gly Asn Glu Ser Pro Phe Val Tyr Pro
                 85                  90                  95

Thr Tyr Met Asp Ser Leu Pro Leu Asp Trp Arg Asp Phe Cys Ala Ala
            100                 105                 110

Thr Leu Arg Asp Pro Tyr Asn Glu Gln Pro Gly Leu Gly Leu Trp Asn
        115                 120                 125

Val Arg Glu Ala Val Gln Ala Leu Gln Cys Asn Leu Gly Ile Arg Ala
    130                 135                 140

Pro His Pro Thr Asp Ser Ala Val Glu Val Asp Val Thr Ile Ala Met
145                 150                 155                 160

Gln Gly Ser Gly Asp Ile Arg Tyr Thr Lys Arg Ser Ile Phe Leu Thr
                165                 170                 175

Lys Gly Gln His Gln Trp Ala His Ala Thr Thr Ile Leu Val Ala Asp

```
                180              185              190
Ala Leu Thr Asp Ala Thr Cys Gln Leu Ala Glu Ala Gln Tyr
            195              200              205
His Gly Ala Ala Lys Trp Arg Glu Val Trp Ala Asn Pro Asp Ile Arg
        210              215              220
Thr Ala Glu Ser Val Gly Ile Asp Asn Asp Leu Pro Ala Arg Thr Phe
225              230              235              240
Gln Asp Arg Leu Pro Thr Leu Leu Gln Lys Lys Asp Gly Ile Trp Met
                245              250              255
Gln Ser Leu Phe Gly Ser Gln Arg Asn Phe Gln Trp Arg Lys Asn Gly
            260              265              270
Leu Glu Ile Cys Phe Asp Met Glu Ser Thr Thr Leu His Pro Ile Ala
        275              280              285
His Ser Ala Ala Pro Leu Thr Val Ser Leu Asn Glu Ala Leu Arg Trp
    290              295              300
Gln Gln Trp Ala Ser Ile His Gly Ala Glu Ser Trp Ala Thr Ala Asn
305              310              315              320
Pro Gln Val Val Arg Val Thr Leu Trp Leu Gln Gly Ala Ser Glu Pro
                325              330              335
Gln Pro Leu Glu Pro Leu Glu Ile Leu Gln Lys Gly Gln Pro Ala Val
            340              345              350
Asp Leu Pro Val Glu Gly Ser Ala Leu Pro Lys Gly Asp Leu Ala Val
        355              360              365
Met Trp His Leu Leu Glu Asn Asp Ser His Arg Phe Leu Tyr Glu Ser
    370              375              380
Thr Val Glu Ile Thr Gln Gly Ser Leu Arg Phe Gln Phe Gln Gln
385              390              395              400
Gln His Lys Ala Glu Thr Leu Ala Pro His Pro Thr Arg Asp Ala Phe
                405              410              415
Val Leu Gly Asn Met Cys Phe Gln Arg Asp Asn Pro Thr Asp Gly Phe
            420              425              430
Asp Gly Gly Tyr Ala Ser Trp Pro Asn Gly Asn Glu Asp Tyr Lys Ile
        435              440              445
Leu Ser Gln Asp Val Trp Asp Trp Val Phe Gly Gly Gln Leu Arg Pro
450              455              460
Tyr Gln Arg Phe Ala Gln Trp Tyr Lys Ala Phe Gly Gly Leu Ser Asn
465              470              475              480
Gly Met Ala His Ala Tyr Glu Cys Leu Ile Leu Pro Arg Thr Glu Gly
                485              490              495
Pro Leu Ser Leu Trp Lys Lys Ile Ser Trp Lys Pro Val Ala Pro Phe
            500              505              510
Pro Gln Asp Glu Asp Val Arg Ala Tyr Met Pro Cys Ile Ile Asp Thr
        515              520              525
Ala Thr Thr Asp Ala Gly Gly Glu Tyr Gln Val Pro Arg Ser Pro
    530              535              540
Asp Val Ser Lys Ile Trp Arg Tyr Leu Ala Asp His Asn Ala Gly His
545              550              555              560
Gly Ser Glu Asn Gly Leu Ser Trp Ile Ile Val Ser Pro His Asn Arg
                565              570              575
Asp Arg Gln Val Met Arg Thr Val Arg Glu Ser Met Ala Pro Leu Trp
            580              585              590
Arg Pro Asp Asp Thr Leu Arg Asn Met Pro Val Met Gly His Thr Glu
        595              600              605
```

-continued

```
Ile Asn Ala Glu Asp Val Val Tyr Leu Gly Tyr Arg Asp Cys Leu Thr
    610                 615                 620

Tyr Trp Leu Pro His Asn Pro Tyr His Ser Cys Arg Val Ala Asn Phe
625                 630                 635                 640

Asn Asn Gln Lys Met Leu Leu Ile Asp Gln Val Met Thr Gln Glu Asp
            645                 650                 655

Met Val Gln Gly His Leu Pro His His Glu His Arg Asn Val Gly Arg
        660                 665                 670

Ile Leu Leu Pro Lys Gly Asn Leu Leu Leu Gly Asn Glu Ile Arg
        675                 680                 685

Val Glu Arg Phe Gly Val Asp Cys Ala Glu Ala Glu Ile Leu Thr Gly
690                 695                 700

Asp Ala Thr His Leu Glu Val Val Ala Arg Tyr Leu Asn Pro Ile Glu
705                 710                 715                 720

Ala Ser Trp Leu Lys Pro Asn Glu Val Asn Leu Arg Leu Thr Val Arg
            725                 730                 735

Asp Ala Tyr Gly Gly Arg Glu Asp Ile Ile Glu Gly Gly Phe Pro Ala
        740                 745                 750

Thr Gly Ser Ala Val Gln Thr Glu Gly Gln Trp Leu Ser Val Thr Val
    755                 760                 765

Arg Leu Tyr Asp Arg Leu Glu Gly Cys Met Gln Val Glu Ala Glu Leu
770                 775                 780

Val Ala Arg Ser Phe Asp Asp Asn Phe Arg Thr Ala Val His Phe Asp
785                 790                 795                 800

Ser Ile Gln Thr Thr Pro Lys His Leu Leu Ser Val Asp Arg Phe Ile
            805                 810                 815

Gly Ser Met Arg Trp Met Asp Gln Asp Glu Leu Tyr Ser Gly Asp Ser
        820                 825                 830

Trp Arg Leu Val Met Val Ala Leu Arg Asn Glu Gly Ala Arg Leu Phe
    835                 840                 845

Ala Ser Leu Asp Phe Glu Ser Pro Leu Arg Ser Asp Gln Gly Tyr Gly
850                 855                 860

Val Trp Arg Gly Asn Cys Trp Leu His Phe Ala Ser Asn Val Gly Asp
865                 870                 875                 880

Phe Ile Ile Arg Thr Gln Gly Glu Gln Leu Trp Ser Glu Asp Val Asn
            885                 890                 895

Phe Thr Leu Ser Tyr Cys Gly Thr Pro Asn Glu Thr Pro Val Phe Pro
        900                 905                 910

Pro Asn Val Thr Ile Pro Tyr Thr Val Asn Thr Tyr Ile Pro Ala Asp
    915                 920                 925

Tyr Gly His Met Gln
    930
```

<210> SEQ ID NO 61
<211> LENGTH: 110
<212> TYPE: PRT
<213> ORGANISM: Artificial Sequence
<220> FEATURE:
<223> OTHER INFORMATION: Description of Artificial Sequence: pIAO-pL
    amino acid sequence
<220> FEATURE:
<221> NAME/KEY: MOD_RES
<222> LOCATION: (110)
<223> OTHER INFORMATION: Any amino acid

<400> SEQUENCE: 61

```
Val Leu Leu Thr Glu Trp Asn Ser Pro Val Val Pro Asp Thr Lys
 1               5                  10                  15

Lys Asn Cys Phe Gln Ser Phe Leu Ile Ser Ile Glu Ser Trp Cys
             20                  25                  30

Arg Tyr Asp Glu Thr Ala Leu Asp Leu Asn Gln Phe Gly Ile Phe Phe
         35                  40                  45

Arg Thr Thr Tyr Cys Lys Thr Arg Arg Ile Asn Ala Gln Arg Gln Ser
 50                  55                  60

Val Ser Thr Gly Arg Tyr Val Ser Arg Arg Tyr Arg Glu Pro Arg Arg
 65                  70                  75                  80

Lys Arg Ser Arg Ile Asn Gln Phe Gly Trp Cys Ala Arg Arg Arg Ala
                 85                  90                  95

Ser Ser Cys Leu Pro Tyr Ala Arg Arg Phe Phe Met Gly Xaa
                100                 105                 110

<210> SEQ ID NO 62
<211> LENGTH: 229
<212> TYPE: PRT
<213> ORGANISM: Artificial Sequence
<220> FEATURE:
<223> OTHER INFORMATION: Description of Artificial Sequence: pIAO-pL
      amino acid sequence

<400> SEQUENCE: 62

Asp Thr Trp Phe Cys Ser Gln Cys Met Asp Ile Asn His Glu Arg Cys
 1               5                  10                  15

Ile Val Lys Lys Cys Lys Lys Cys Ser Ala Asn Ala Lys Arg Arg Ile
             20                  25                  30

Lys Ser Pro Cys Tyr Thr Cys Tyr Thr Arg Lys Lys Met Val Pro Glu
         35                  40                  45

Glu Thr Ser Asp Asp Ser Thr Gly Pro Val Glu Asn Pro Leu Ile Asn
 50                  55                  60

Ser Ile Asn Asp Arg Leu Tyr Arg Lys Leu Thr Pro Ala Glu Leu Arg
 65                  70                  75                  80

Asn Arg Met Phe Ser Ser Thr Leu Ser Met Tyr Leu Asn Arg Met Phe
                 85                  90                  95

Lys Lys Arg Ser Gln Val Lys Glu Gly Lys Ser Ser Val Asn His Ser
                100                 105                 110

Tyr Ile Ile Phe Ser Asn Ile Cys Ala Ile Asn Ile Met Gly Tyr Leu
            115                 120                 125

Leu Ala Met Pro Trp Arg Asn Thr Lys Arg Ser Cys Thr Met Val Ser
130                 135                 140

Cys Met Gln Asp Leu Thr Asp Val Gly Gly Lys Thr Gln Asn Tyr Tyr
145                 150                 155                 160

Met Val Met Gln Pro Lys Gly Thr Ser Glu Asn Ile Ser Ala Asp Glu
                165                 170                 175

Asp Cys Ser Ser Leu Leu Tyr Val Met Lys Ala Pro Lys Pro Lys Tyr
                180                 185                 190

Ser Val Leu Thr Leu Pro Gly Asp Phe Cys Phe Met Ser Thr Gly Val
            195                 200                 205

Pro Arg Ser Arg Ser Asn Lys Leu Val Glu Pro Ile Glu Arg Lys Asn
210                 215                 220

Ser Arg Val Thr Gly
225

<210> SEQ ID NO 63
```

-continued

```
<211> LENGTH: 9984
<212> TYPE: DNA
<213> ORGANISM: Artificial Sequence
<220> FEATURE:
<223> OTHER INFORMATION: Description of Artificial Sequence:
      pIAO-p/L-Lambda-2.2kb sequence

<400> SEQUENCE: 63
aacgcgcggg gagaggcggt ttgcgtattg ggcgctcttc cgcttcctcg ctcactgact      60
cgctgcgctc ggtcgttcgg ctgcggcgag cggtatcagc tcactcaaag gcggtaatac     120
ggttatccac agaatcaggg gataacgcag gaaagaacat gtgagcaaaa ggccagcaaa     180
aggccaggaa ccgtaaaaag gccgcgttgc tggcgttttt ccataggctc cgcccccctg     240
acgagcatca caaaaatcga cgctcaagtc agaggtggcg aaacccgaca ggactataaa     300
gataccaggc gtttccccct ggaagctccc tcgtgcgctc tcctgttccg accctgccgc     360
ttaccggata cctgtccgcc tttctccctt cgggaagcgt ggcgctttct caatgctcac     420
gctgtaggta tctcagttcg gtgtaggtcg ttcgctccaa gctgggctgt gtgcacgaac     480
cccccgttca gcccgaccgc tgcgccttat ccggtaacta tcgtcttgag tccaacccgg     540
taagacacga cttatcgcca ctggcagcag ccactggtaa caggattagc agagcgaggt     600
atgtaggcgg tgctacagag ttcttgaagt ggtggcctaa ctacggctac actagaagga     660
cagtatttgg tatctgcgct ctgctgaagc cagttacctt cggaaaaaga gttggtagct     720
cttgatccgg caaacaaacc accgctggta gcggtggttt ttttgtttgc aagcagcaga     780
ttacgcgcag aaaaaaagga tctcaagaag atcctttgat cttttctacg gggtctgacg     840
ctcagtggaa cgaaaactca cgttaaggga ttttggtcat gagattatca aaaaggatct     900
tcacctagat ccttttaaat taaaatgaa gttttaaatc aatctaaagt atatatgagt      960
aaacttggtc tgacagttac caatgcttaa tcagtgaggc acctatctca gcgatctgtc    1020
tatttcgttc atccatagtt gcctgactcc ccgtcgtgta gataactacg atacgggagg    1080
gcttaccatc tggccccagt gctgcaatga taccgcgaga cccacgctca ccggctccag    1140
atttatcagc aataaaccag ccagccggaa gggccgagcg cagaagtggt cctgcaactt    1200
tatccgcctc catccagtct attaattgtt gccgggaagc tagagtaagt agttcgccag    1260
ttaatagttt gcgcaacgtt gttgccattg ctacaggcat cgtggtgtca cgctcgtcgt    1320
ttggtatggc ttcattcagc tccggttccc aacgatcaag gcgagttaca tgatccccca    1380
tgttgtgcaa aaaagcggtt agctccttcg gtcctccgat cgttgtcaga agtaagttgg    1440
ccgcagtgtt atcactcatg gttatggcag cactgcataa ttctcttact gtcatgccat    1500
ccgtaagatg cttttctgtg actggtgagt actcaaccaa gtcattctga atagtgta     1560 tgcggcgacc gagttgctct tgcccggcgt caatacggga taataccgcg ccacatagca    1620
gaactttaaa agtgctcatc attggaaaac gttcttcggg gcgaaaactc tcaaggatct    1680
taccgctgtt gagatccagt tcgatgtaac ccactcgtgc acccaactga tcttcagcat    1740
cttttacttt caccagcgtt tctgggtgag caaaaacagg aaggcaaaat gccgcaaaaa    1800
agggaataag ggcgacacgg aaatgttgaa tactcatact cttcctttt caatattatt    1860 gaagcattta tcaggttat tgtctcatga gcggatacat atttgaatgt atttagaaaa    1920
ataaacaaat aggggttccg cgcacatttc cccgaaaagt gccacctgac gtctaagaaa    1980
ccattattat catgacatta acctataaaa ataggcgtat cacggggccc tgaggtgaac    2040
caattgtcac acgtaatatt acgacaacta ccgtgcacag gctttgataa ctccttcacg    2100
```

```
tagtattcac cgagtggtac tccgttggtc tgtgttcctc ttcccaaata aggcattcca    2160
tttatcatat acttcgtacc actgtcacac atcatgagga tttttattcc atacttactt    2220
ggcttgtttg ggatatacat cctaaacgga caccgtcctc taaaaccaag taactgttca    2280
tctatggtca aatgagcccc tggagtgtaa ttttgtatgc actgatggat aaagagatcc    2340 catattttc taacaggagt aaatacatcg ttttctcgaa gtgtgggccg tatacttttg     2400
tcatccattc taagacatcg tatcaaaaaa tccaaaacga tccacagact cattacagag    2460
acgtacacat tgacaaagat cgatccaaag aggtcatctg tggacatgtg gttatctttt    2520
ctcactgctg tcattaccag aataccaaag aaagcataga tttcatcttc attcgtgtca    2580
cgaaatgtag cacctgtcat agattcccga cgtttcaatg atatctcagc atttgtccat    2640
tttacaattt gcgaaattat ctcatcagta aaaatagtt tgaagcataa aagtgggtca     2700
tatatattgc ggcacatacg cgtcggacct ctttgagatc tgacaatgtt cagtgcagag    2760
actcggctac cgctcgtgga ctttgaagtt aaattcagat ataaagacgc tgaaaatcat    2820
ttgattttcg ctctaacata ccaccctaaa gattataaat ttaatgaatt attaaaatac    2880
gtacaacaat tgtctgtaaa tcaacaacgc acagaatcta gcgcttaata aatgtactaa    2940
taacaatgta tcgtgtttta atacgccgga ccagtgaaca gaggtgcgtc tggtgcaaac    3000
tcctttactt tgaacaccag ggaaacttca aggagaattt cctcctcttc agcagagtcg    3060
gtaccggtca cccggggatc cccctgccc ggttattatt atttttgaca ccagaccaac      3120
tggtaatggt agcgaccggc gctcagctgg aattccgccg atactgacgg gctccaggag    3180
tcgtcgccac caatccccat atggaaaccg tcgatattca gccatgtgcc ttcttccgcg    3240
tgcagcagat ggcgatggct ggtttccatc agttgctgtt gactgtagcg gctgatgttg    3300
aactggaagt cgccgcgcca ctggtgtggg ccataattca attcgcgcgt cccgcagcgc    3360
agaccgtttt cgctcgggaa gacgtacggg gtatacatgt ctgacaatgg cagatcccag    3420
cggtcaaaac aggcggcagt aaggcggtcg ggatagtttt cttgcggccc taatccgagc    3480
cagtttaccc gctctgctac ctgcgccagc tggcagttca ggccaatccg cgccggatgc    3540
ggtgtatcgc tcgccacttc aacatcaacg gtaatcgcca tttgaccact accatcaatc    3600
cggtaggttt tccggctgat aaataaggtt ttcccctgat gctgccacgc gtgagcggtc    3660
gtaatcagca ccgcatcagc aagtgtatct gccgtgcact gcaacaacgc tgcttcggcc    3720
tggtaatggc ccgccgcctt ccagcgttcg acccaggcgt tagggtcaat gcgggtcgct    3780
tcacttacgc caatgtcgtt atccagcggt gcacgggtga actgatcgcg cagcggcgtc    3840
agcagttgtt ttttatcgcc aatccacatc tgtgaaagaa agcctgactg gcggttaaat    3900
tgccaacgct tattacccag ctcgatgcaa aaatccattt cgctggtggt cagatgcggg    3960
atggcgtggg acgcggcggg gagcgtcaca ctgaggtttt ccgccagacg ccactgctgc    4020
caggcgctga tgtgcccggc ttctgaccat gcggtcgcgt tcgttgcac tacgcgtact      4080 gtgagccaga gttgcccggc gctctccggc tgcggtagtt caggcagttc aatcaactgt    4140
ttaccttgtg gagcgacatc cagaggcact tcaccgcttg ccagcggctt accatccagc    4200
gccaccatcc agtgcaggag ctcgttatcg ctatgacgga acaggtattc gctggtcact    4260
tcgatggttt gcccggataa acggaactgg aaaaactgct gctggtgttt tgcttccgtc    4320
agcgctggat gcggcgtgcg gtcggcaaag accagaccgt tcatacagaa ctggcgatcg    4380
ttcggcgtat cgccaaaatc accgccgtaa gccgaccacg ggttgccgtt ttcatcatat    4440
ttaatcagcg actgatccac ccagtcccag acgaagccgc cctgtaaacg gggatactga    4500
```

```
cgaaacgcct gccagtattt agcgaaaccg ccaagactgt tacccatcgc gtgggcgtat      4560
tcgcaaagga tcagcgggcg cgtctctcca ggtagcgaaa gccattttt gatggaccat       4620 ttcggcacag ccgggaaggg ctggtcttca tccacgcgcg cgtacatcgg gcaaataata     4680
tcggtggccg tggtgtcggc tccgccgcct tcatactgca ccgggcggga aggatcgaca     4740
gatttgatcc agcgatacag cgcgtcgtga ttagcgccgt ggcctgattc attccccagc    4800
gaccagatga tcacactcgg gtgattacga tcgcgctgca ccattcgcgt tacgcgttcg    4860
ctcatcgccg gtagccagcg cggatcatcg gtcagacgat tcattggcac catgccgtgg   4920
gtttcaatat tggcttcatc caccacatac aggccgtagc ggtcgcacag cgtgtaccac    4980
agcggatggt tcggataatg cgaacagcgc acggcgttaa agttgttctg cttcatcagc    5040
aggatatcct gcaccatcgt ctgctcatcc atgacctgac catgcagagg atgatgctcg   5100
tgacggttaa cgcctcgaat cagcaacggc ttgccgttca gcagcagcag accattttca   5160
atccgcacct cgcggaaacc gacatcgcag gcttctgctt caatcagcgt gccgtcggcg   5220
gtgtgcagtt caaccaccgc acgatagaga ttcgggattt cggcgctcca cagtttcggg   5280
ttttcgacgt tcagacgtag tgtgacgcga tcggcataac caccacgctc atcgataatt   5340
tcaccgccga aaggcgcggt gccgctggcg acctgcgttt caccctgcca taaagaaact   5400
gttacccgta ggtagtcacg caactcgccg cacatctgaa cttcagcctc cagtacagcg  5460
cggctgaaat catcattaaa gcgagtggca acatggaaat cgctgatttg tgtagtcggt    5520
ttatgcagca acgagacgtc acggaaaatg ccgctcatcc gccacatatc ctgatcttcc   5580
agataactgc cgtcactcca acgcagcacc atcaccgcga ggcggttttc tccggcgcgt    5640
aaaaatgcgc tcaggtcaaa ttcagacggc aaacgactgt cctggccgta accgacccag   5700
cgcccgttgc accacagatg aaacgccgag ttaacgccat caaaaataat tcgcgtctgg    5760
ccttcctgta gccagctttc atcaacatta aatgtgagcg agtaacaacc cgtcggattc    5820
tccgtgggaa caaacggcgg attgaccgta atgggatagg ttacgttggt gtagatgggc   5880
gcatcgtaac cgtgcatctg ccagtttgag gggacgacga cgggatccgt ttttttatta     5940
caaaactgtt acgaaaacag taaaatactt atttattcgg accaacaatg tttattctta     6000
cctctaatag tcctctgtgg caaggtcaag attctgttag aagccaatga agaacctggt    6060
tgttcaataa cattttgttc gtctaatatt tcactacgct tgacgttggc tgacacttca     6120
tgtacctcat ctataaacgc ttcttctgta tcgctctgga cgtcttcact tacgtgatct    6180
gatatttcac tgtcagaatc ctcaccaaca agctcgtcat cgccttgcag aagagcagag    6240
aggatatgct catcgtctaa agaacatccc attttattat atattagtca cgatatctat      6300
aacaagaaaa tatatatata ataagttatc acgtaagtag aacatgaaat aacaatatta     6360
attatcgtat gagttaaatc ttaaaagtca cgtaaaagat aatcatgcgt cattttgact      6420
cacgcggtcg ttatagttca aaatcagtga cacttaccgc attgacaagc acgcctcagc    6480
cgagctccaa gcggcgactg agatgtccta aattgcaaac agcgacggat tcgcgctatt     6540
tagaaagaga gagcaatatt tcaagaatgc atgcgtcaat tttacgcaga ctatctttct      6600
agggttaatc tagcttttct aatttaacct ttgtcaggtt accaactact aaggttgtag     6660
gctcaagagg gtgtgtcctg tcgtaggtaa ataactgacc tgtcgagctt aatattctat     6720
attgttgttc tttctgcaaa aaagtgggga agtgagtaat gaaattattt ctaacattta      6780
tctgcatcat accttccgag catttattaa gcatttcgct ataagttctc gctggaagag     6840
```

```
gtagtttttt cattgtactt taccttcatc tctgttcatt atcatcgctt ttaaaacggt    6900
tcgaccttct aatcctatct gaccattata attttttaga atggtttcat aagaaagctc    6960
tgaatcaacg gactgcgata ataagtggtg gtatccagaa tttgtcactt caagtaaaaa    7020
cacctcacga gttaaaacac ctaagttctc accgaatgtc tcaatatccg gacggataat    7080
atttattgct tctcttgacc gtaggacttt ccacatgcag gattttggaa cctcttgcag    7140
tactactggg gaatgagttg caattattgc tacaccattg cgtgcatcga gtaagtcgct    7200
taatgttcgt aaaaagcag agagcaaagg tggatgcaga tgaacctctg gttcatcgaa      7260
taaaactaat gacttttcgc caacgacatc tactaatctt gtgatagtaa ataaaacaat    7320
tgcatgtcca gagctcattc gaagcagata tttctggata ttgtcataaa acaatttagt    7380
gaatttatca tcgtccactt gaatctgtgg ttcattacgt cttaactctt catatttaga    7440
aatgaggctg atgagttcca tatttgaaaa gttttcatca ctacttagtt ttttgatagc    7500
ttcaagccag agttgtcttt ttctatctac tctcatacaa ccaataaatg ctgaaatgaa    7560
ttctaagcgg agatcgccta gtgattttaa actattgctg gcagcattct tgagtccaat    7620
ataaaagtat tgtgtacctt ttgctgggtc aggttgttct ttaggaggag taaaaggatc    7680
aaatgcacta aacgaaactg aaacaagcga tcgaaaatat cccttggga ttcttgactc      7740 gataagtcta ttattttcag agaaaaaata ttcattgttt tctgggttgg tgattgcacc    7800
aatcattcca ttcaaaattg ttgttttacc acacccattc cgcccgataa aagcatgaat    7860
gttcgtgctg gcatagaat taaccgtcac ctcaaaaggt atagttaaat cactgaatcc      7920
gggagcactt tttctattaa atgaaaagtg gaaatctgac aattctggca aaccatttaa    7980
cacacgtgcg aactgtccat gaatttctga aagagttacc cctctaagta atgaggtgtt    8040
aaggacgctt tcattttcaa tgtcggctaa tcgatttggc catactacta aatcctgaat    8100
agctttaaga aggttatgtt taaaaccatc gcttaatttg ctgagattaa catagtagtc    8160
aatgctttca cctaaggaaa aaaacatttc agggagttga ctgaattttt tatctattaa    8220
tgaataagtg cttacttctt cttttttgacc tacaaaacca atttaacat ttccgatatc     8280 gcattttttca ccatgctcat caaagacagt aagataaaac attgtaacaa aggaatagtc    8340
attccaacca tctgctcgta ggaatgcctt attttttttct actgcaggaa tatacccgcc    8400
tctttcaata acactaaact ccaacatata gtaaccctta attttattaa ataaccgca     8460 atttatttgg cggcaacaca ggatctctct tttaagttac tctctattac atacgttttc    8520
catctaaaaa ttagtagtat tgaacttaac ggggcatcgt attgtagttt tccatattta    8580
gctttctgct tccttttgga taacccactt ttattcatgt tgcatggtgc actgtttata    8640
ccaacgatat agtctattaa tgcatatata gtatcgccga acgattagct cttcaggctt    8700
ctgaagaagc gtttcaagta ctaataagcc gatagatagc cacggacttc gtagccattt    8760
ttcataagtg ttaacttccg ctcctcgctc ataacagaca ttcactacag ttatggcgga    8820
aaggtatgca tgctgggtgt ggggaagtcg tgaagaaaa gaagtcagct gcgtcgtttg      8880
acatcactgc tatcttctta ctggttatgc aggtcgtagt gggtggcaca caaagctaga    8940
ttaaccctag aaagataatc atattgtgac gtacgttaaa gataatcatg cgtaaaattg    9000
acgcatgtgt ttttatcggt ctgtatatcg aggtttattt attaatttga atagatatta    9060
agttttatta tatttacact tacatactaa taataaattc aacaaacaat ttatttatgt    9120
ttatttattt attaaaaaaa aacaaaaact caaaatttct tctaaagtaa caaaactttt    9180
aaacattctc tcttttacaa aaataaactt attttgtact ttaaaaacag tcatgttgta    9240
```

```
ttataaaata agtaattagc ttaacttata cataatagaa acaaattata cttattagtc    9300
agtccagaaa caactttggc acatatcaat attatgctct cgacaaataa cttttttgca    9360
ttttttgcac gatgcatttg cctttcgcct tattttagag gggcagtaag tacagtaagt    9420
acgttttttc attactggct cttcagtact gtcatctgat gtaccaggca cttcatttgg    9480
caaaatatta gagatattat cgcgcaaata tctcttcaaa gtaggagctt ctaaacggtt    9540
acgcataaac gatgacgtca ggctcatgta aaggtttctc ataaatttt tgcgactttg     9600 aacctttct cccttgctac tgacattatg gctgtatata ataaagaat ttatgcaggc       9660 aatgtttatc attccgtaca ataatgccat aggccaccta ttcgtcttcc tactgcaggt    9720
catcacagaa cacatttggt ctagcgtgtc cactccgcct ttagtttgat tataatacat    9780
aaccatttgc ggtttaccgg tactttcgtt gatagaagca tcctcatcac aagatgataa    9840
taagtatacc atcttagctg gcttcggttt atatgagacg agagtaaggg gtccgtcaaa    9900
acaaaacatc gatgttccca ctggcctgga gcgactgttt ttcagtactt ccggtatctc    9960
gcgtttgttt gatcgcacgg tacc                                           9984
```

<210> SEQ ID NO 64
<211> LENGTH: 60
<212> TYPE: PRT
<213> ORGANISM: Artificial Sequence
<220> FEATURE:
<223> OTHER INFORMATION: Description of Artificial Sequence:
      pIAO-p/L-Lambda-2.2kb amino acid sequence

<400> SEQUENCE: 64

Lys Arg Ile Gly Lys Asp Pro Trp Ser Ser Leu Asn Tyr Ala Ser Pro
1               5                   10                  15

Thr Asp Gln Arg Leu Tyr Ile Val Ser Arg Asp Leu Lys Ile Asn Ile
            20                  25                  30

Thr Thr Arg Glu Ala Phe Phe His Pro Leu Ser Tyr His Phe Lys Cys
        35                  40                  45

Lys Asp Ala Asp Tyr Arg Gly Leu Met Ala Asn Arg
    50                  55                  60

<210> SEQ ID NO 65
<211> LENGTH: 470
<212> TYPE: PRT
<213> ORGANISM: Artificial Sequence
<220> FEATURE:
<223> OTHER INFORMATION: Description of Artificial Sequence:
      pIAO-p/L-Lambda-2.2kb amino acid sequence

<400> SEQUENCE: 65

Ser Tyr Thr Arg Ala Pro Leu Pro Leu Lys Lys Met Thr Ser Arg Arg
1               5                   10                  15

Gln Glu Asn Asp Asp Ser Lys Phe Arg Asn Ser Arg Arg Ile Arg Asp
            20                  25                  30

Ser Trp Leu Lys Lys Ser His Asn Leu Phe Ala Arg Phe Arg Val Ala
        35                  40                  45

Ile Ile Leu Pro Pro Ile Trp Phe Lys Asp Ser Thr Phe Val Gly Ser
    50                  55                  60

Asn Phe Cys Arg Leu Glu Arg Ile Asp Tyr Gly Ser Pro Tyr Tyr Lys
65                  70                  75                  80

Asn Ser Arg Lys Val Thr Pro Ser Glu Val His Leu Ile Lys Ser Gly
            85                  90                  95

-continued

```
Arg Ala Thr Ser Ser Pro Phe Ser Asn Cys Asn Asn Ser Cys Trp Gln
            100                 105                 110

Thr Cys Arg Thr Leu Arg Lys Ile Asn Thr Phe Phe Cys Leu Ala Phe
        115                 120                 125

Thr Ser Ala Ser Ser Gly Arg Thr Arg Ile Phe Ser Ile Val Lys Arg
    130                 135                 140

Trp Arg Cys Arg Ser Ile Lys His Tyr Tyr Ile Phe Cys Asn Cys Thr
145                 150                 155                 160

Trp Leu Glu Asn Ser Ala Ser Ile Glu Pro Tyr Gln Leu Val Ile His
                165                 170                 175

Ile Arg Gly Ser Ser Asp Thr Thr Lys Val Arg Ile Phe His Pro
            180                 185                 190

Gln His Thr Gly Tyr Lys Phe Leu Lys Lys Thr Lys Gln Tyr Ser Ala
        195                 200                 205

Leu Thr Thr Lys Lys Arg Ser Glu Tyr Leu Trp Tyr Ile Ser Phe His
    210                 215                 220

Ile Arg Leu Pro Ser Arg Arg Thr Ile Lys Phe Gln Gln Cys Cys Glu
225                 230                 235                 240

Gln Thr Trp Tyr Leu Leu Ile Thr Tyr Arg Lys Ser Pro Thr Thr Arg
                245                 250                 255

Ser Ser Tyr Phe Ser Ile Cys Val Phe Ser Phe Cys Ala Ile Ser Phe
            260                 265                 270

Ile Gly Lys Pro Asn Lys Val Arg Tyr Thr Lys Leu Phe Phe Ile Gln
        275                 280                 285

Lys Arg Pro Gln His Asn Cys Trp Asp Asn Trp Glu Phe Asn Asn Asn
    290                 295                 300

Trp Val Trp Glu Ala Arg Tyr Phe Cys Ser His Glu His Gln Ala Tyr
305                 310                 315                 320

Phe Gly Asp Gly Phe Thr Tyr Asn Phe Gln Ile Arg Ser Cys Lys Lys
                325                 330                 335

Ile Phe Leu Pro Phe Arg Val Ile Arg Ala Phe Trp Lys Val Cys Thr
            340                 345                 350

Arg Val Thr Trp Ser Asn Arg Phe Ser Asn Gly Arg Thr Ile Leu His
        355                 360                 365

Pro Arg Lys Lys His Arg Ser Ile Ser Lys Ala Met Ser Ser Phe Gly
    370                 375                 380

Ser Tyr Ser Ser Pro Thr Phe Trp Arg Lys Ile Gln Gln Ser Cys Leu
385                 390                 395                 400

Leu His Lys Arg Leu Phe Phe Val Asn Pro Thr Ser Gln Ile Lys Arg
                405                 410                 415

Asn Ile Phe Leu His Lys Ser Arg Lys Ser Arg Cys Phe Trp Asn
            420                 425                 430

Cys Lys Arg Tyr Arg Met Lys Trp Ala Leu Cys Tyr Ser Leu Val Asn
        435                 440                 445

Tyr Cys Leu Phe Leu Glu Leu Trp Arg Ser Thr Pro Ile Gly Lys Lys
    450                 455                 460

Arg Ser Cys Ser Tyr Val
465                 470

<210> SEQ ID NO 66
<211> LENGTH: 229
<212> TYPE: PRT
<213> ORGANISM: Artificial Sequence
<220> FEATURE:
<223> OTHER INFORMATION: Description of Artificial Sequence:
``` pIAO-P/L-Lambda-2.2kb amino acid sequence

<400> SEQUENCE: 66

```
Asp Thr Trp Phe Cys Ser Gln Cys Met Asp Ile Asn His Glu Arg Cys
 1               5                  10                  15
Ile Val Lys Lys Cys Lys Lys Cys Ser Ala Asn Ala Lys Arg Arg Ile
                20                  25                  30
Lys Ser Pro Cys Tyr Thr Cys Tyr Thr Arg Lys Lys Met Val Pro Glu
            35                  40                  45
Glu Thr Ser Asp Asp Ser Thr Gly Pro Val Glu Asn Pro Leu Ile Asn
        50                  55                  60
Ser Ile Asn Asp Arg Leu Tyr Arg Lys Leu Thr Pro Ala Glu Leu Arg
 65                 70                  75                  80
Asn Arg Met Phe Ser Ser Thr Leu Ser Met Tyr Leu Asn Arg Met Phe
                85                  90                  95
Lys Lys Arg Ser Gln Val Lys Glu Gly Lys Ser Ser Val Asn His Ser
            100                 105                 110
Tyr Ile Ile Phe Ser Asn Ile Cys Ala Ile Asn Ile Met Gly Tyr Leu
        115                 120                 125
Leu Ala Met Pro Trp Arg Asn Thr Lys Arg Ser Cys Thr Met Val Ser
130                 135                 140
Cys Met Gln Asp Leu Thr Asp Val Gly Gly Lys Thr Gln Asn Tyr Tyr
145                 150                 155                 160
Met Val Met Gln Pro Lys Gly Thr Ser Glu Asn Ile Ser Ala Asp Glu
                165                 170                 175
Asp Cys Ser Ser Leu Leu Tyr Val Met Lys Ala Pro Lys Pro Lys Tyr
            180                 185                 190
Ser Val Leu Thr Leu Pro Gly Asp Phe Cys Phe Met Ser Thr Gly Val
        195                 200                 205
Pro Arg Ser Arg Ser Asn Lys Leu Val Glu Pro Ile Glu Arg Lys Asn
    210                 215                 220
Ser Arg Val Thr Gly
225
```

<210> SEQ ID NO 67
<211> LENGTH: 7411
<212> TYPE: DNA
<213> ORGANISM: Artificial Sequence
<220> FEATURE:
<223> OTHER INFORMATION: Description of Artificial Sequence:
      pBSII-Act5c-orf sequence

<400> SEQUENCE: 67

```
ctaaattgta agcgttaata ttttgttaaa attcgcgtta aatttttgtt aaatcagctc      60
attttttaac caataggccg aaatcggcaa atcccttat aaatcaaaag aatagaccga     120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta atcggaacc ctaaagggag     300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaaggcgat cggtgcgggc ctcttcgcta ttacgccagc tggcgaaagg    540
gggatgtgct gcaaggcgat taagttgggt aacgccaggg ttttcccagt cacgacgttg    600
```

```
taaaacgacg gccagtgagc gcgcgtaata cgactcacta tagggcgaat tgggtaccgg    660
gccccccctc gaggtcgacg gtatcgataa gcttgatatc gaattctaaa aaaaatcatg    720
aatggcatca actctgaatc aaatctttgc agatgcacct acttctcatt tccactgtca    780
catcattttt ccagatctcg ctgcctgtta tgtgcccac  aaaccaagac acgttttatg    840
gccattaaag ctggctgatc gtcgccaaac accaaataca tatcaatatg tacattcgag    900
aaagaagcga tcaaagaagc gtcttcgggc gagtaggaga atgcgagga  gaaggagaac    960 gagctgatct agtatctctc cacaatccaa tgccaactga ccaactgcc  atattcggag   1020 caatttgaag ccaatttcca tcgcctggcg atcgctccat tcttggctat atgttttca   1080 ccgttcccgg ggccattttc aaagactcgt cggtaagata agattgtgtc actcgctgtc   1140
tctcttcatt tgtcgaagaa tgctgaggaa tttcgcgatg acgtcggcga gtattttgaa   1200
gaatgagaat aatttgtatt tatacgaaaa tcagttagtg aattttcta  caaaaacatg   1260 ttatctatag ataattttgt tgcaaaatat gttgactatg acaaagattg tatgtatata   1320
cctttaatgt attctcattt tcttatgtat ttataatggc aatgatgata ctgatgatat   1380
tttaagatga tgccagacca caggctgatt tctgcgtctt ttgccgaacg cagtgcatgt   1440
gcggttgttg ttttttggaa tagtttcaat tttcggactg tccgctttga tttcagtttc   1500
ttggcttatt caaaaagcaa agtaaagcca aaaagcgag  atggcaatac caaatgcggc   1560
aaaacggtag tggaaggaaa ggggtgcggg gcagcggaag gaaggtggg  gcggggcgtg   1620 gcggggtctg tggctgggcg cgacgtcacc gacgttggag ccactccttt gaccatgtgt   1680
gcgtgtgtgt attattcgtg tctcgccact cgccggttgt tttttctttt ttatctcgct   1740
ctctctagcg ccatctcgta cgcatgctca acgcaccgca tgttgccgtg tcctttatgc   1800
gtcattttgg ctcgaaatag gcaattattt aaacaaagat tagtcaacga aaacgctaaa   1860
ataaataagt ctacaatatg gttacttatt gccatgtgtg tgcagccaac gatagcaaca   1920
aaagcaacaa cacagtggct ttccctcttt cacttttgt  ttgcaagcgc gtgcgagcaa   1980
gacggcacga ccggcaaacg caattacgct gacaaagagc agacgaagtt ttggccgaaa   2040
aacatcaagg cgcctgatac gaatgcattt gcaataacaa ttgcgatatt taatattgtt   2100
tatgaagctg tttgacttca aaacacacaa aaaaaaaaat aaaacaaatt atttgaaaga   2160
gaattaggaa tcggacagct tatcgttacg ggctaacagc acaccgagac gaaatagctt   2220
acctgacgtc acagcctctg gaagaactgc cgccaagcag acgatgcaga ggacgacaca   2280
tagagtagcg gagtaggcca gcgtagtacg catgtgcttg tgtgaggc  gtctctctct   2340 tcgtctcctg tttgcgcaaa cgcatagact gcactgagaa aatcgattac ctattttta   2400 tgaatgaata tttgcactat tactattcaa aactattaag atagcaatca cattcaatag   2460
ccaaatacta taccacctga gcgatgcaac gaaatgatca atttgagcaa aaatgctgca   2520
tatttaggac ggcatcatta tagaaatgct tcttgctgtg tacttttctc tcgtctggca   2580
gctgtttcgc cgttattgtt aaaccggct  taagttaggt gtgttttcta cgactagtga   2640
tgcccctact agaagatgtg tgttgcacaa atgtccctga ataccaatt  tgaagtgcag   2700 atagcagtaa acgtaagcta atatgaatat tatttaactg taatgtttta atatcgctgg   2760
acattactaa taaacccact ataaacacat gtacatatgt atgttttggc atacaatgag   2820
tagttgggga aaaatgtgt  aaaagcaccg tgaccatcac agcataaaga taaccagctg   2880
aagtatcgaa tatgagtaac ccccaaattg aatcacatgc cgcaactgat aggacccatg   2940
```

```
gaagtacact cttcatggcg atatacaaga cacacacaag cacgaacacc cagttgcgga    3000
ggaaattctc cgtaaatgaa aacccaatcg gcgaacaatt catacccata tatggtaaaa    3060
gttttgaacg cgacttgaga gcggagagca ttgcggctga taaggtttta gcgctaagcg    3120
ggctttataa aacgggctgc gggaccagtt ttcatatcgg atcctatata ataaaatggg    3180
tagttcttta gacgatgagc atatcctctc tgctcttctg caaagcgatg acgagcttgt    3240
tggtgaggat tctgacagtg aaatatcaga tcacgtaagt gaagatgacg tccagagcga    3300
tacagaagaa gcgtttatag atgaggtaca tgaagtgcag ccaacgtcaa gcggtagtga    3360
aatattagac gaacaaaatg ttattgaaca accaggttct tcattggctt ctaacagaat    3420
cttgaccttg ccacagagga ctattagagg taagaataaa cattgttggt caacttcaaa    3480
gtccacgagg cgtagccgag tctctgcact gaacattgtc agatctcaaa gaggtccgac    3540
gcgtatgtgc cgcaatatat atgacccact tttatgcttc aaactatttt ttactgatga    3600
gataatttcg gaaattgtaa aatggacaaa tgctgagata tcattgaaac gtcgggaatc    3660
tatgacaggt gctacatttc gtgacacgaa tgaagatgaa atctatgctt tctttggtat    3720
tctggtaatg acagcagtga gaaaagataa ccacatgtcc acagatgacc tctttgatcg    3780
atctttgtca atggtgtacg tctctgtaat gagtcgtgat cgttttgatt ttttgatacg    3840
atgtcttaga atggatgaca aaagtatacg gcccacactt cgagaaaacg atgtatttac    3900
tcctgttaga aaaatatggg atctctttat ccatcagtgc atacaaaatt acactccagg    3960
ggctcatttg accatagatg aacagttact tggttttaga ggacggtgtc cgtttaggat    4020
gtatatccca aacaagccaa gtaagtatgg aataaaaatc ctcatgatgt gtgacagtgg    4080
tacgaagtat atgataaatg gaatgcctta tttgggaaga ggaacacaga ccaacggagt    4140
accactcggt gaatactacg tgaaggagtt atcaaagcct gtgcacggta gttgtcgtaa    4200
tattacgtgt gacaattggt tcacctcaat ccctttggca aaaaacttac tacaagaacc    4260
gtataagtta accattgtgg gaaccgtgcg atcaaacaaa cgcgagatac cggaagtact    4320
gaaaaacagt cgctccaggc cagtgggaac atcgatgttt tgttttgacg gaccccttac    4380
tctcgtctca tataaaccga agccagctaa gatggtatac ttattatcat cttgtgatga    4440
ggatgcttct atcaacgaaa gtaccggtaa accgcaaatg gttatgtatt ataatcaaac    4500
taaaggcgga gtggacacgc tagaccaaat gtgttctgtg atgacctgca gtaggaagac    4560
gaataggtgg cctatggcat tattgtacgg aatgataaac attgcctgca taaattcttt    4620
tattatatac agccataatg tcagtagcaa gggagaaaag gttcaaagtc gcaaaaaatt    4680
tatgagaaac ctttacatga gcctgacgtc atcgtttatg cgtaagcgtt tagaagctcc    4740
tactttgaag agatatttgc gcgataatat ctctaatatt ttgccaaatg aagtgcctgg    4800
tacatcagat gacagtactg aagagccagt aatgaaaaaa cgtacttact gtacttactg    4860
cccctctaaa ataaggcgaa aggcaaatgc atcgtgcaaa aaatgcaaaa aagttatttg    4920
tcgagagcat aatattgata tgtgccaaag ttgtttctga ctgactaata agtataattt    4980
gtttctatta tgtataagtt aagctaatta cttattttat aatacaacat gactgttttt    5040
aaagtacaaa ataagtttat ttttgtaaaa gagagaatgt ttaaagtttt tgttacttta    5100
gaagaaattt tgagtttttg ttttttttta ataaataaat aaacataaat aaattgtttg    5160
ttgaatttgg atccactagt tctagagcgg ccgccaccgc ggtggagctc cagcttttgt    5220
tccctttagt gagggttaat tgcgcgcttg gcgtaatcat ggtcatagct gtttcctgtg    5280
tgaaattgtt atccgctcac aattccacac aacatacgag ccggaagcat aaagtgtaaa    5340
```

```
gcctggggtg cctaatgagt gagctaactc acattaattg cgttgcgctc actgcccgct      5400
ttccagtcgg gaaacctgtc gtgccagctg cattaatgaa tcggccaacg cgcggggaga      5460
ggcggtttgc gtattgggcg ctcttccgct tcctcgctca ctgactcgct gcgctcggtc      5520
gttcggctgc ggcgagcggt atcagctcac tcaaaggcgg taatacggtt atccacagaa      5580
tcaggggata acgcaggaaa gaacatgtga gcaaaaggcc agcaaaaggc caggaaccgt      5640
aaaaaggccg cgttgctggc gtttttccat aggctccgcc ccctgacga gcatcacaaa       5700
aatcgacgct caagtcagag gtggcgaaac ccgacaggac tataaagata ccaggcgttt      5760
ccccctggaa gctccctcgt gcgctctcct gttccgaccc tgccgcttac cggatacctg      5820
tccgcctttc tcccttcggg aagcgtggcg ctttctcata gctcacgctg taggtatctc      5880
agttcggtgt aggtcgttcg ctccaagctg ggctgtgtgc acgaaccccc cgttcagccc      5940
gaccgctgcg ccttatccgg taactatcgt cttgagtcca acccggtaag acacgactta      6000
tcgccactgg cagcagccac tggtaacagg attagcagag cgaggtatgt aggcggtgct      6060
acagagttct tgaagtggtg gcctaactac ggctacacta aggacagt atttggtatc        6120
tgcgctctgc tgaagccagt taccttcgga aaaagagttg gtagctcttg atccggcaaa      6180
caaaccaccg ctggtagcgg tggttttttt gtttgcaagc agcagattac gcgcagaaaa      6240
aaaggatctc aagaagatcc tttgatcttt tctacggggt ctgacgctca gtggaacgaa      6300
aactcacgtt aagggatttt ggtcatgaga ttatcaaaaa ggatcttcac ctagatcctt      6360
ttaaattaaa aatgaagttt taaatcaatc taaagtatat atgagtaaac ttggtctgac      6420
agttaccaat gcttaatcag tgaggcacct atctcagcga tctgtctatt tcgttcatcc      6480
atagttgcct gactccccgt cgtgtagata actacgatac gggagggctt accatctggc      6540
cccagtgctg caatgatacc gcgagaccca cgctcaccgg ctccagattt atcagcaata      6600
aaccagccag ccggaagggc cgagcgcaga agtggtcctg caactttatc cgcctccatc      6660
cagtctatta attgttgccg ggaagctaga gtaagtagtt cgccagttaa tagtttgcgc      6720
aacgttgttg ccattgctac aggcatcgtg gtgtcacgct cgtcgtttgg tatggcttca      6780
ttcagctccg gttcccaacg atcaaggcga gttacatgat ccccccatgtt gtgcaaaaaa    6840
gcggttagct ccttcggtcc tccgatcgtt gtcagaagta agttggccgc agtgttatca      6900
ctcatggtta tggcagcact gcataattct cttactgtca tgccatccgt aagatgcttt      6960
tctgtgactg gtgagtactc aaccaagtca ttctgagaat agtgtatgcg gcgaccgagt      7020
tgctcttgcc cggcgtcaat acgggataat accgcgccac atagcagaac tttaaaagtg      7080
ctcatcattg gaaaacgttc ttcggggcga aaactctcaa ggatcttacc gctgttgaga      7140
tccagttcga tgtaacccac tcgtgcaccc aactgatctt cagcatcttt tactttcacc      7200
agcgtttctg ggtgagcaaa aacaggaagg caaaatgccg caaaaaaggg aataagggcg      7260
acacggaaat gttgaatact catactcttc cttttcaat attattgaag catttatcag       7320
ggttattgtc tcatgagcgg atacatattt gaatgtattt agaaaaataa acaaataggg      7380
gttccgcgca catttccccg aaaagtgcca c                                     7411
```

<210> SEQ ID NO 68
<211> LENGTH: 10330
<212> TYPE: DNA
<213> ORGANISM: Artificial Sequence
<220> FEATURE:
<223> OTHER INFORMATION: Description of Artificial Sequence:
      pCaSpeR-hs-pBac sequence

<400> SEQUENCE: 68

```
aagcttgggc tgcaggtcga cggatccaaa ttcaacaaac aatttattta tgtttattta      60
tttattaaaa aaaacaaaa actcaaaatt tcttctaaag taacaaaact tttaaacatt      120
ctctctttta caaaataaa cttattttgt actttaaaaa cagtcatgtt gtattataaa      180
ataagtaatt agcttaactt atacataata gaaacaaatt atacttatta gtcagtcaga      240
aacaactttg gcacatatca atattatgct ctcgacaaat aactttttg catttttgc       300
acgatgcatt tgcctttcgc cttattttag aggggcagta agtacagtaa gtacgttttt      360
tcattactgg ctcttcagta ctgtcatctg atgtaccagg cacttcattt ggcaaaatat      420
tagagatatt atcgcgcaaa tatctcttca agtaggagc ttctaaacgc ttacgcataa      480
acgatgacgt caggctcatg taaaggtttc tcataaattt tttgcgactt tgaaccttt      540
ctcccttgct actgacatta tggctgtata aataaaaga atttatgcag gcaatgttta      600
tcattccgta caataatgcc ataggccacc tattcgtctt cctactgcag gtcatcacag      660
aacacatttg gtctagcgtg tccactccgc ctttagtttg attataatac ataaccattt      720
gcggtttacc ggtactttcg ttgatagaag catcctcatc acaagatgat aataagtata      780
ccatcttagc tggcttcggt ttatatgaga cgagagtaag gggtccgtca aaacaaaaca      840
tcgatgttcc cactggcctg gagcgactgt ttttcagtac ttccggtatc tcgcgtttgt      900
ttgatcgcac ggttcccaca atggttaact tatacggttc ttgtagtaag ttttttgcca      960
aagggattga ggtgaaccaa ttgtcacacg taatattacg acaactaccg tgcacaggct     1020
ttgataactc cttcacgtag tattcaccga gtggtactcc gttggtctgt gttcctcttc     1080
ccaaataagg cattccattt atcatatact tcgtaccact gtcacacatc atgaggattt     1140
ttattccata cttacttggc ttgtttggga tatacatcct aaacggacac cgtcctctaa     1200
aaccaagtaa ctgttcatct atggtcaaat gagcccctgg agtgtaattt tgtatgcact     1260
gatggataaa gagatcccat attttttcta caggagtaaa tacatcgttt tctcgaagtg     1320
tgggccgtat acttttgtca tccattctaa gacatcgtat caaaaaatca aaacgatcac     1380
gactcattac agagacgtac accattgaca aagatcgatc aaagaggtca tctgtggaca     1440
tgtggttatc ttttctcact gctgtcatta ccagaatacc aaagaaagca tagatttcat     1500
cttcattcgt gtcacgaaat gtagcacctg tcatagattc ccgacgtttc aatgatatct     1560
cagcatttgt ccatttaca atttccgaaa ttatctcatc agtaaaaaat agtttgaagc     1620
ataaaagtgg gtcatatata ttgcggcaca tacgcgtcgg acctctttga gatctgacaa     1680
tgttcagtgc agagactcgg ctacgcctcg tggactttga agttgaccaa caatgtttat     1740
tcttacctct aatagtcctc tgtggcaagg tcaagattct gttagaagcc aatgaagaac     1800
ctggttgttc aataacattt tgttcgtcta atatttcact accgcttgac gttggctgca     1860
cttcatgtac ctcatctata aacgcttctt ctgtatcgct ctggacgtca tcttcactta     1920
cgtgatctga tatttcactg tcagaatcct caccaacaag ctcgtcatcg ctttgcagaa     1980
gagcagagag gatatgctca tcgtctaaag aactacccat tttattatat aggatccccg     2040
acaccagacc aactggtaat ggtagcgacc ggcgctcagc tggaattagg ccttctagac     2100
cgcggccgca gatctgttaa cgaattccca attccctatt cagagttctc ttcttgtatt     2160
caataattac ttccttggcag atttcagtag ttgcagttga tttacttggt tgctggttac     2220
ttttaattga ttcactttaa cttgcacttt actgcagatt gtttagcttg ttcagctgcg     2280
```

-continued

```
cttgtttatt tgcttagctt tcgcttagcg acgtgttcac ttgcttgttt gaattgaatt    2340
gtcgctccgt agacgaagcg ctctatttat actccggcgc tcttttcgcg aacattcgag    2400
gcgcgctctc tcgaaccaac gagagcagta tgccgtttac tgtgtgacag agtgagagag    2460
cattagtgca gagagggaga cccaaaaaga aaagagagaa taacgaataa cggccagaga    2520
aatttctcga gttttcttct gccaaacaaa tgacctacca caataaccag tttgttttgg    2580
gattctaggg ggatcgggga tcaattctag tatgtatgta agttaataaa acccttttt    2640
ggagaatgta gatttaaaaa aacatatttt ttttttattt tttactgcac tggatatcat    2700
tgaacttatc tgatcagttt taaatttact tcgatccaag ggtatttgaa gtaccaggtt    2760
ctttcgatta cctctcactc aaaatgacat tccactcaaa gtcagcgctg tttgcctcct    2820
tctctgtcca cagaaatatc gccgtctctt tcgccgctgc gtccgctatc tctttcgcca    2880
ccgtttgtag cgttacctag cgtcaatgtc cgccttcagt tgcactttgt cagcggtttc    2940
gtgacgaagc tccaagcggt ttacgccatc aattaaacac aaagtgctgt gccaaaactc    3000
ctctcgcttc ttattttgt ttgttttttg agtgattggg gtggtgattg gttttgggtg    3060
ggtaagcagg ggaaagtgtg aaaaatcccg gcaatgggcc aagaggatca ggagctatta    3120
attcgcggag gcagcaaaca cccatctgcc gagcatctga acaatgtgag tagtacatgt    3180
gcatacatct taagttcact tgatctatag gaactgcgat tgcaacatca aattgtctgc    3240
ggcgtgagaa ctgcgaccca caaaaatccc aaaccgcaat cgcacaaaca aatagtgaca    3300
cgaaacagat tattctggta gctgtgctcg ctatataaga caatttttaa gatcatatca    3360
tgatcaagac atctaaaggc attcattttc gactacattc ttttttacaa aaaatataac    3420
aaccagatat tttaagctga tcctagatgc acaaaaaata aataaaagta taaacctact    3480
tcgtaggata cttcgttttg ttcggggtta gatgagcata acgcttgtag ttgatatttg    3540
agatccccta tcattgcagg gtgacagcgg agcggcttcg cagagctgca ttaaccaggg    3600
cttcgggcag gccaaaaact acggcacgct cctgccaccc agtccgccgg aggactccgg    3660
ttcagggagc ggccaactag ccgagaacct cacctatgcc tggcacaata tggacatctt    3720
tggggcggtc aatcagccgg gctccggatg gcggcagctg gtcaaccgga cacgcggact    3780
attctgcaac gagcgacaca taccggcgcc caggaaacat ttgctcaaga acggtgagtt    3840
tctattcgca gtcggctgat ctgtgtgaaa tcttaataaa gggtccaatt accaatttga    3900
aactcagttt gcggcgtggc ctatccgggc gaacttttgg ccgtgatggg cagttccggt    3960
gccggaaaga cgaccctgct gaatgcccct gcctttcgat cgccgcaggg catccaagta    4020
tcgccatccg ggatgcgact gctcaatggc caacctgtgg acgccaagga gatgcaggcc    4080
aggtgcgcct atgtccagca ggatgacctc tttatcggct ccctaacggc cagggaacac    4140
ctgatttttcc aggccatggt gcggatgcca cgacatctga cctatcggca gcgagtggcc    4200
cgcgtggatc aggtgatcca ggagctttcg ctcagcaaat gtcagcacac gatcatcggt    4260
gtgcccggca gggtgaaagg tctgtccggc ggagaaagga agcgtctggc attcgcctcc    4320
gaggcactaa ccgatccgcc gcttctgatc tgcgatgagc ccacctccgg actggactca    4380
tttaccgccc acagcgtcgt ccaggtgctg aagaagctgt cgcagaaggg caagaccgtc    4440
atcctgacca ttcatcagcc gtcttccgag ctgtttgagc tctttgacaa gatccttctg    4500
atggccgagg gcagggtagc tttcttgggc actcccagcg aagccgtcga cttctttttcc    4560
tagtgagttc gatgtgtta ttaagggtat ctagcattac attacatctc aactcctatc    4620
cagcgtgggt gcccagtgtc ctaccaacta caatccggcg gactttacg tacaggtgtt    4680
```

-continued

```
ggccgttgtg cccggacggg agatcgagtc ccgtgatcgg atcgccaaga tatgcgacaa    4740
ttttgctatt agcaaagtag cccgggatat ggagcagttg ttggccacca aaaatttgga    4800
gaagccactg gagcagccgg agaatgggta cacctacaag gccacctggt tcatgcagtt    4860
ccgggcggtc ctgtggcgat cctggctgtc ggtgctcaag gaaccactcc tcgtaaaagt    4920
gcgacttatt cagacaacgg tgagtggttc cagtggaaac aaatgatata acgcttacaa    4980
ttcttggaaa caaattcgct agattttagt tagaattgcc tgattccaca cccttcttag    5040 ttttttttcaa tgagatgtat agtttatagt tttgcagaaa ataaataaat ttcatttaac    5100
tcgcgaacat gttgaagata tgaatattaa tgagatgcga gtaacatttt aatttgcaga    5160
tggttgccat cttgattggc ctcatctttt tgggccaaca actcacgcaa gtgggcgtga    5220
tgaatatcaa cggagccatc ttcctcttcc tgaccaacat gacctttcaa aacgtctttg    5280
ccacgataaa tgtaagtctt gtttagaata catttgcata ttaataattt actaactttc    5340
taatgaatcg attcgattta ggtgttcacc tcagagctgc cagtttttat gagggaggcc    5400
cgaagtcgac tttatcgctg tgacacatac tttctgggca aaacgattgc cgaattaccg    5460
ctttttctca cagtgccact ggtcttcacg gcgattgcct atccgatgat cggactgcgg    5520
gccggagtgc tgcacttctt caactgcctg gcgctggtca ctctggtggc caatgtgtca    5580
acgtccttcg gatatctaat atcctgcgcc agctcctcga cctcgatggc gctgtctgtg    5640
ggtccgccgg ttatcatacc attcctgctc tttgcggct tcttcttgaa ctcgggctcg    5700
gtgccagtat acctcaaatg gttgtcgtac ctctcatggt tccgttacgc caacgagggt    5760
ctgctgatta ccaatgggc ggacgtggag ccgggcgaaa ttagctgcac atcgtcgaac    5820
accacgtgcc ccagttcggg caaggtcatc ctggagacgc ttaacttctc cgccgccgat    5880
ctgccgctgg actacgtggg tctggccatt ctcatcgtga gcttccgggt gctcgcatat    5940
ctggctctaa gacttcgggc ccgacgcaag gagtagccga catatatccg aaataactgc    6000
ttgttttttt tttaccatt attaccatcg tgtttactgt ttattgcccc ctcaaaaagc    6060
taatgtaatt atatttgtgc caataaaaac aagatatgac ctatagaata caagtatttc    6120
cccttcgaac atccccacaa gtagactttg datttgtctt ctaaccaaaa gacttacaca    6180
cctgcatacc ttacatcaaa aactcgttta tcgctacata aaacaccggg atatattttt    6240
tatatacata cttttcaaat cgcgcgccct cttcataatt cacctccacc acaccacgtt    6300
tcgtagttgc tctttcgctg tctcccaccc gctctccgca acacattcac cttttgttcg    6360
acgaccttgg agcgactgtc gttagttccg cgcgattcgg ttcgctcaaa tggttccgag    6420
tggttcattt cgtctcaata gaaattagta ataaatattt gtatgtacaa tttatttgct    6480
ccaatatatt tgtatatatt tccctcacag ctatatttat tctaatttaa tattatgact    6540
ttttaaggta attttttgtg acctgttcgg agtgattagc gttacaattt gaactgaaag    6600
tgacatccag tgtttgttcc ttgtgtagat gcatctcaaa aaaatggtgg gcataatagt    6660
gttgtttata tatatcaaaa ataagaacta taataataag aatacattta atttagaaaa    6720
tgcttggatt tcactggaac tagaattaat tcggctgctg ctctaaacga cgcatttcgt    6780
actccaaagt acgaattttt tccctcaagc tcttattttc attaaacaat gaacaggacc    6840
taacgcacag tcacgttatt gtttacataa atgatttttt ttactattca aacttactct    6900
gtttgtgtac tcccactggt atagccttct tttatctttt ctggttcagg ctctatcact    6960
ttactaggta cggcatctgc gttgagtcgc ctcctttta atgtctgacc ttttgcaggt    7020
```

-continued

```
gcagccttcc actgcgaatc tttaaagtgg gtatcacaaa tttgggagtt ttcaccaagg    7080
ctgcacccaa ggctctgctc ccacaatttt ctcttaatag cacacttcgg cacgtgaatt    7140
aattttactc cagtcacagc ttgcagcaaa atttgcaata tttcattttt ttttattcca    7200
cgtaagggtt aatgttttca aaaaaaaatt cgtccgcaca caacctttcc tctcaacaag    7260
caaacgtgca ctgaatttaa gtgtatactt cggtaagctt cggctatcga cgggaccacc    7320
ttatgttatt tcatcatggg ccagacccac gtagtccagc ggcagatcgg cggcggagaa    7380
gttaagcgtc tccaggatga ccttgcccga actgggcac gtggtgttcg acgatgtgca     7440
gctaatttcg cccggctcca cgtccgccca ttggttaatc agcagaccct cgttggcgta    7500
acggaaccat gagaggtacg acaaccattt gaggtatact ggcaccgagc ccgagttcaa    7560
gaagaaggcg ttttttccata ggctccgccc ccctgacgag catcacaaaa atcgacgctc   7620
aagtcagagg tggcgaaacc cgacaggact ataaagatac caggcgtttc ccctggaag    7680 ctccctcgtg cgctctcctg ttccgaccct gccgcttacc ggatacctgt ccgcctttct   7740
cccttcggga agcgtggcgc tttctcaatg ctcacgctgt aggtatctca gttcggtgta    7800
ggtcgttcgc tccaagctgg gctgtgtgca cgaaccccc gttcagcccg accgctgcgc     7860
cttatccggt aactatcgtc ttgagtccaa cccggtaaga cacgacttat cgccactggc    7920
agcagccact ggtaacagga ttagcagagc gaggtatgta ggcggtgcta cagagttctt    7980
gaagtggtgg cctaactacg gctacactag aaggacagta tttggtatct gcgctctgct    8040
gaagccagtt accttcggaa aaagagttgg tagctcttga tccggcaaac aaaccaccgc    8100
tggtagcggt ggttttttg tttgcaagca gcagattacg cgcagaaaaa aaggatctca    8160
agaagatcct ttgatctttt ctacggggtc tgacgctcag tggaacgaaa actcacgtta    8220
agggattttg gtcatgagat tatcaaaaag gatcttcacc tagatccttt taaattaaaa    8280
atgaagtttt aaatcaatct aaagtatata tgagtaaact tggtctgaca gttaccaatg    8340
cttaatcagt gaggcaccta tctcagcgat ctgtctattt cgttcatcca tagttgcctg    8400
actccccgtc gtgtagataa ctacgatacg ggagggctta ccatctggcc ccagtgctgc    8460
aatgataccg cgagacccac gctcaccggc tccagattta tcagcaataa accagccagc    8520
cggaagggcc gagcgcagaa gtggtcctgc aactttatcc gcctccatcc agtctattaa    8580
ttgttgccgg gaagctgagt aagtagttcg ccagttaata gtttgcgcaa cgttgttgcc    8640
attgctacag gcatcgtggt gtcacgctcg tcgtttggta tggcttcatt cagctccggt    8700
tcccaacgat caaggcgagt tacatgatcc cccatgttgt gcaaaaaagc ggttagctcc    8760
ttcggtcctc cgatcgttgt cagaagtaag ttggccgcag tgttatcact catggttatg    8820
gcagcactgc ataattctct tactgtcatg ccatccgtaa gatgcttttc tgtgactggt    8880
gagtactcaa ccaagtcatt ctgagaatag tgtatgcggc gaccgagttg ctcttgcccg    8940
gcgtcaatac gggataatac cgcgccacat agcagaactt taaaagtgct catcattgga    9000
aaacgttctt cggggcgaaa actctcaagg atcttaccgc tgttgagatc cagttcgatg    9060
taacccactc gtgcacccaa ctgatcttca gcatctttta ctttcaccag cgtttctggg    9120
tgagcaaaaa caggaaggca aaatgccgca aaaagggaa taagggcgac acggaaatgt    9180
tgaatactca tactcttcct ttttcaatat tattgaagca tttatcaggg ttattgtctc    9240
atgagcggat acatatttga atgtatttag aaaaataaac aaatagggt tccgcgcaca    9300 tttccccgaa aagtgccacc tgacgtctaa gaaaccatta ttatcatgac attaacctat    9360
aaaaataggc gtatcacgag gccctttcgt ctcgcgcgtt tcggtgatga cggtgaaaac    9420
```

```
ctctgacaca tgcagctccc ggagacggtc acagcttgtc tgtaagcgga tgccgggagc   9480
agacaagccc gtcagggcgc gtcagcgggt gttggcgggt gtcgggctg gcttaactat    9540 gcggcatcag agcagattgt actgagagtg caccatatgc ggtgtgaaat accgcaccga   9600
atcgcgcgga actaacgaca gtcgctccaa ggtcgtcgaa caaaggtga atgtgttgcg    9660 gagagcgggt gggagacagc gaaagagcaa ctacgaaacg tggtgtggtg gaggtgaatt   9720
atgaagaggg cgcgcgattt gaaaagtatg tatataaaaa atatatcccg gtgttttatg   9780
tagcgataaa cgagttttg atgtaaggta tgcaggtgtg taagtctttt ggttagaaga    9840
caaatccaaa gtctacttgt ggggatgttc gaaggggaaa tacttgtatt ctataggtca   9900
tatcttgttt ttattggcac aaatataatt acattagctt tttgagggg caataaacag    9960 taaacacgat ggtaataatg gtaaaaaaaa aaacaagcag ttatttcgga tatatgtcgg   10020
ctactccttg cgtcgggccc gaagtcttag agccagatat gcgagcaccc ggaagctcac   10080
gatgagaatg gccagaccat gatgaaataa cataaggtgg tcccgtcggc aagagacatc   10140
cacttaacgt atgcttgcaa taagtgcgag tgaaaggaat agtattctga gtgtcgtatt   10200
gagtctgagt gagacagcga tatgattgtt gattaaccct tagcatgtcc gtggggtttg   10260
aattaactca taatattaat tagacgaaat tattttttaaa gttttatttt taataatttg   10320
cgagtacgca                                                          10330
```

<210> SEQ ID NO 69
<211> LENGTH: 1785
<212> TYPE: DNA
<213> ORGANISM: Unknown Organism
<220> FEATURE:
<223> OTHER INFORMATION: Description of Unknown Organism: Natural piggyBac orf sequence

<400> SEQUENCE: 69

```
atgggtagtt cttagacga tgagcatatc ctctctgctc ttctgcaaag cgatgacgag    60
cttgttggtg aggattctga cagtgaaata tcagatcacg taagtgaaga tgacgtccag   120
agcgatacag aagaagcgtt tatagatgag gtacatgaag tgcagccaac gtcaagcggt   180
agtgaaatat tagacgaaca aaatgttatt gaacaaccag gttcttcatt ggcttctaac   240
agaatcttga ccttgccaca gaggactatt agaggtaaga ataaacattg ttggtcaact   300
tcaaagtcca cgaggcgtag ccgagtctct gcactgaaca ttgtcagatc tcaaagaggt   360
ccgacgcgta tgtgccgcaa tatatatgac ccactttat gcttcaaact atttttact    420 gatgagataa tttcggaaat tgtaaaatgg acaaatgctg agatatcatt gaaacgtcgg   480
gaatctatga caggtgctac atttcgtgac acgaatgaag atgaaatcta tgctttcttt   540
ggtattctgg taatgacagc agtgagaaaa gataaccaca tgtccacaga tgacctcttt   600
gatcgatctt tgtcaatggt gtacgtctct gtaatgagtc gtgatcgttt tgattttttg   660
atacgatgtc ttagaatgga tgacaaaagt atacggccca cacttcgaga aaacgatgta   720
tttactcctg ttagaaaaat atgggatctc tttatccatc agtgcataca aaattacact   780 ccagggctc attttgaccat agatgaacag ttacttggtt ttagaggacg gtgtccgttt   840
aggatgtata tcccaaacaa gccaagtaag tatggaataa aaatcctcat gatgtgtgac   900
agtggtacga gtatatgat aaatggaatg ccttatttgg gaagaggaac acagaccaac   960
ggagtaccac tcggtgaata ctacgtgaag gagttatcaa agcctgtgca cggtagttgt   1020
cgtaatatta cgtgtgacaa ttggttcacc tcaatccctt ggcaaaaaaa cttactacaa   1080
```

-continued

```
gaaccgtata agttaaccat tgtgggaacc gtgcgatcaa acaaacgcga gataccggaa    1140
gtactgaaaa acagtcgctc caggccagtg ggaacatcga tgttttgttt tgacggaccc    1200
cttactctcg tctcatataa accgaagcca gctaagatgg tatacttatt atcatcttgt    1260
gatgaggatg cttctatcaa cgaaagtacc ggtaaaccgc aaatggttat gtattataat    1320
caaactaaag gcggagtgga cacgctagac caaatgtgtt ctgtgatgac ctgcagtagg    1380
aagacgaata ggtggcctat ggcattattg tacggaatga taaacattgc ctgcataaat    1440
tcttttatta tatacagcca taatgtcagt agcaagggag aaaaggttca aagtcgcaaa    1500
aaatttatga gaaaccttta catgagcctg acgtcatcgt ttatgcgtaa gcgtttagaa    1560
gctcctactt tgaagagata tttgcgcgat aatatctcta atattttgcc aaatgaagtg    1620
cctggtacat cagatgacag tactgaagag ccagtaatga aaaaacgtac ttactgtact    1680
tactgcccct ctaaaataag gcgaaaggca aatgcatcgt gcaaaaaatg caaaaaagtt    1740
atttgtcgag agcataatat tgatatgtgc caaagttgtt tctga                   1785
```

<210> SEQ ID NO 70
<211> LENGTH: 1785
<212> TYPE: DNA
<213> ORGANISM: Unknown Organism
<220> FEATURE:
<223> OTHER INFORMATION: Description of Unknown Organism: Optimized piggyBac orf sequence

<400> SEQUENCE: 70

```
atgggtagca gcctggatga tgaacatatc ctgagcgcgc tgctgcagag cgacgacgaa     60
ctggttggtg aagatagcga cagcgaaatc agcgatcacg tgagcgaaga cgacgttcag    120
agcgataccg aagaagcgtt catcgacgaa gttcacgaag tgcagccgac cagcagcggt    180
agcgaaatcc tggatgaaca gaacgttatc gaacagccgg gtagcagcct ggcgagcaac    240
cgtatcctga ccctgccgca gcgcaccatc cgtggtaaaa acaaacactg ttggagcacc    300
agcaaaagca cccgccgtag ccgtgttagc gcgctgaaca ttgttcgtag ccagcgtggt    360
ccgacccgta tgtgccgcaa catctacgat ccgctgctgt gcttcaaact gttcttcacc    420
gatgaaatca tcagcgaaat cgtgaaatgg accaacgccg aaatcagcct gaaacgtcgc    480
gaaagcatga ccggcgcgac cttccgcgat accaacgaag atgaaatcta cgccttcttc    540
ggtatcctgg tgatgaccgc ggtgcgtaaa gataaccaca tgagcaccga tgatctgttt    600
gatcgtagcc tgagcatggt ttacgttagc gttatgagcc gtgaccgttt cgattttctg    660
atccgttgtc tgcgtatgga tgataaaagc atccgcccga ccctgcgcga aaacgatgtg    720 ttcacccccgg ttcgcaaaat ctgggatctg ttcatccacc agtgcatcca gaactacacc    780
ccgggcgcgc acctgaccat cgatgaacag ctgctgggtt ttcgtggtcg ctgtccgttt    840
cgtatgtaca tcccgaacaa accgagcaaa tacggtatca aatcctgat gatgtgtgac    900 agcggtacca gtacatgat caacggtatg ccgtatctgg tcgtggtac ccagaccaac    960 ggtgtgccgc tgggtgaata ctacgtgaaa gaactgagca aaccggtgca cggtagctgt    1020
cgtaacatca cctgtgacaa ctggttcacc agcatcccgc tggcgaaaaa cctgctgcag    1080
gaaccgtata aactgaccat cgtgggtacc gttcgtagca caaacgtga atcccggaa    1140 gtgctgaaaa acagccgtag ccgtccggtg gcaccagca tgttctgttt cgatggtccg    1200
ctgaccctgg ttagctacaa accgaaaccg gcgaaatgg tgtacctgct gagcagctgc    1260
gacgaagacg cgagcatcaa cgaaagcacc ggtaaaccgc agatggttat gtactacaac    1320
```

```
cagaccaaag gcggtgtgga caccctggat cagatgtgca gcgttatgac ctgcagccgc    1380
aaaaccaacc gctggccgat ggcgctgctg tacggtatga tcaacatcgc ctgcatcaac    1440
agctttatca tctacagcca taacgttagc agcaaaggtg aaaaagttca gagccgcaaa    1500
aaatttatgc gtaacctgta catgagcctg accagcagct tcatgcgtaa acgtctggaa    1560
gccccgaccc tgaaacgtta tctgcgcgat aacatcagca acatcctgcc gaacgaagtg    1620
ccgggtacca gcgatgatag caccgaagaa ccggtgatga aaaacgtac ctactgtacc     1680 tactgcccga gcaaaatccg ccgtaaagcg aacgcgagct gcaaaaaatg caaaaaagtt    1740
atctgtcgtg aacataacat cgatatgtgc cagagctgtt tctga                   1785
```

METHODS AND COMPOSITIONS FOR TRANSPOSITION USING MINIMAL SEGMENTS OF THE EUKARYOTIC TRANSFORMATION VECTOR PIGGYBAC

CROSS-REFERENCE TO RELATED APPLICATIONS

This application makes reference to and claims priority to the following U.S. patent applications. The first application is U.S. patent application Ser. No. 10/001,189, entitled "Methods and Compositions for Transposition Using Minimal Segments of the Eukaryotic Transformation Vector PiggyBac," filed Oct. 30, 2001, now U.S. Pat. No. 6,962,810, which claims priority to U.S. Provisional Patent Application No. 60/244,984, filed Nov. 1, 2000, and U.S. Provisional Patent Application No. 60/244,667, filed on Oct. 31, 2000. The second application is U.S. Provisional Patent Application No. 60/562,324, entitled "Methods and Compositions for Transposition Using Minimal Segments of the Eukaryotic Transformation Vector PiggyBac," filed Apr. 15, 2004. The entire disclosure and contents of the four above-identified applications are hereby incorporated by reference.

GOVERNMENT INTEREST STATEMENT

The United States Government has rights in this invention pursuant to USDA/NRI Grant 96-35302-3796, NIH-NIAID 1RO1AI40960, NIH/NIAID 1RO1AI48561, and NIH AI48561.

BACKGROUND

1. Field of the Invention

The present invention relates generally to transposable elements, and more particularly to the transposon piggyBac.

2. Related Art

Transposable elements (transposons) can move around a genome of a cell and are useful for inserting genes for the production of transgenic organisms. The Lepidopteran transposon piggyBac is capable of moving within the genomes of a wide variety of species, and is gaining prominence as a useful gene transduction vector. The transposon structure includes a complex repeat configuration consisting of an internal repeat (IR), a spacer, and a terminal repeat (TR) at both ends, and a single open reading frame encoding a transposase.

The Lepidopteran transposable element piggyBac was originally isolated from the TN-368 *Trichoplusia ni* cell culture as a gene disrupting insertion within spontaneous baculovirus plaque morphology mutants. PiggyBac is a 2475 bp short inverted repeat element that has an asymmetric terminal repeat structure with a 3-bp spacer between the 5' 13-bp TR (terminal repeat) and the 19-bp IR (internal repeat), and a 31-bp spacer between the 3' TR and IR. The single 2.1 kb open reading frame encodes a functional transposase (Cary et al., 1989; Fraser et al., 1983, 1995; Elick et al., 1996a; Lobo et al., 1999; Handler et al., 1998).

PiggyBac transposes via a unique cut-and-paste mechanism, inserting exclusively at 5' TTAA 3' target sites that are duplicated upon insertion, and excising precisely, leaving no footprint (Elick et al., 1996b; Fraser et al., 1996; Wang and Fraser 1993).

Transient excision and interplasmid transposition assays have verified movement of this element in the SF21 AE *Spodoptera frugiperda* cell line, and embryos of the Lepidopteran *Pectinophora glossypiella, Bombyx mori*, and *T. ni*, as well as the Dipteran species *Drosophila melanogaster, Aedes aegypti, Aedes triseriatus, Aedes albopictus, Anopheles stephensi* and *Anopheles gambiae*. There is also evidence of transposition in the Cos-7 primate cell line, and embryos of the zebra fish, *Danio rerio* (Fraser et al., 1995; Buck et al., 1996b; Fraser et al., 1996; Elick et al., 1997; Thibault et al., 1999; Tamura et al., 2000; Lobo et al., 1999).

The piggyBac element has been used successfully as a helper-dependent gene transfer vector in a wide variety of insect species, including the Mediterranean fruit fly, *C. capitata, D. melanogaster, Bombyx mori, P. glossypiella, Tribollium casteneum*, and *Ae. aegypti* (Handler et al., 1998, 1999; Tamura et al., 2000; Berghammer et al., 1999).

Excision assays using both wildtype and mutagenized piggyBac terminal sequences demonstrated that the element does not discriminate between proximal or distal duplicated ends, and suggest that the transposase does not first recognize an internal binding site and then scan towards the ends. In addition, mutagenesis of the terminal trinucleotides or the terminal-proximate three bases of the TTAA target sequence eliminates excision at the altered terminus (Elick et al., 1996b).

Although the reported piggyBac vector is useful, length of genes that could be transferred is limited by the size of the other components of the vector. Minimizing the length of the vector to allow more room for the genetic material to be transferred would improve the versatility of the system and reduce costs of preparing synthetic vectors. Previously, the gene to be expressed or transduced was inserted into the middle of the piggyBac transposon in the plasmid p3E1.2. The final construct included the entire length of the piggyBac transposon (2475 bases) and flanking sequences derived from the baculovirus 25K gene region of approximately 813 bases, as well as the plasmid pUC backbone of 2686 bp, and an overall size of approximately 5962 bp. (In cloning sequences into the pUC vector, 12 bp of multiple cloning site DNA was lost). This size limited the effective size of genes that may be inserted, because plasmids larger than 10 KB are generally more difficult to construct, maintain, and transduce into host genomes.

Another problem was that previous cloning regimens involved the excision of a gene, the promoter controlling the gene, and polyadenylation signals, from one plasmid followed by insertion into the piggyBac transfer vector. This procedure was often complicated by the lack of suitable restriction enzyme sites for these manipulations.

SUMMARY

The present invention identifies the specific sequences in a mobile genetic element, the transposon piggyBac, and sequence configurations outside of piggyBac, that are minimally required for full functionality of the sequence as a transposon. Inserting DNA molecules into cells is enhanced using the methods and compositions of the present invention.

The present invention solves problems in use of the piggyBac vector for gene transfer caused by lack of suitable restriction sites to cut the components needed for gene transfer, and limitations on the sizes (lengths) of genes transferred by use of this vector. Methods and compositions of the present invention enlarge the size of the gene that may be transferred in two ways. First, a minimal sequence cartridge may be easily amplified using primers containing desired restriction endonuclease sites, and the cartridge may then be inserted into any plasmid containing the gene with its attendant promoter and polyadenylation signals intact, converting that plasmid into a piggyBac transposon. Second, a multiple cloning site may be inserted into a minimal plasmid vector, facilitating the insertion of genes in this more traditional plasmid vector. The vectors may both be used for applications including producing transgenic organisms, both plants and animals. The present invention has been successful in exemplary transpositions using the primate Cos-7 vertebrate cell line and embryos of the zebra fish, Danio rerio, among others.

Methods and compositions are disclosed herein for transferring genes using the minimum internal and external sequences of the transformation vector piggyBac. In an embodiment of the invention, all non-essential sequences are removed, including the bulk of the piggyBac internal domain and the flanking baculovirus sequences. By means of the minimal piggyBac cartridge, a DNA molecule may be transferred from a plasmid into a host cell.

According to a first broad aspect of the present invention, there is provided a DNA molecule comprising at least 163 consecutive nucleotide base pairs of the 3' terminal region beginning at the 3' terminal base pair, and at least 125 consecutive nucleotide base pairs of the 5' terminal region beginning at the 5' terminal base pair of the piggyBac molecule, the region extending from the restriction site SacI to the end of the piggyBac molecule.

According to a second broad aspect of the present invention, there is provided a genetic cartridge designated ITR.

According to a third broad aspect of the present invention, there is provided a genetic cartridge designated ITR1.1k.

According to a fourth broad aspect of the present invention, there is provided a vector designated pXL-Bac as shown in FIG. 3.

According to a fifth broad aspect of the present invention, there is provided a vector designated pXL-BacII-ECFP as shown in FIG. 24.

According to a sixth broad aspect of the present invention, there is provided a vector designated pBSII-ITR1.1k-ECFP as shown in FIG. 24.

A Biological Patent Deposit in compliance with the Budapest Treaty has been made to the following International Depository Authority (IDA) on Jan. 12, 2006:
American Type Culture Collection Depository
P.O. Box 1549
Manassas, Va. 20108

The Biological Materials that have been deposited are:

pXL-BACII-ECFP—Accession Number PTA-7310; and pBSII-ITR1.1k-ECFP—Accession Number PTA-7311.

BRIEF DESCRIPTION OF THE DRAWINGS

The invention will be described in conjunction with the accompanying drawings, in which:

FIG. 22 is the nucleotide sequence (SEQ ID NO: 68) of pCaSpeR-hs-pBac;

FIG. 23 is a comparison of natural and optimized piggyBac nucleotide sequences (SEQ ID NOS: 69 and 70) wherein "optimizing" means using codons specific for insects;

FIG. 24(A) shows a plasmid construction map of pCaSpeR-hs-orf. The piggyBac ORF BamHI cassette was cloned as a PCR product into the BamHI site of the pCaSpeR-hs vector for expression using the hsp70 promoter. (B) shows a plasmid construction map of p(PZ)-Bac-EYFP. The 7 kb p(PZ) Hind III fragment containing LacZ, hsp70 and Kan/ori sequences was recircularized to form the p(PZ)-7 kb plasmid. The ITR cartridge (Li et al., 2001) was digested with Not I and Sal I, blunt ended, and inserted into the blunt ended Hind III site of the p(PZ)-7 kb plasmid. A 3xP3-EYFP (Horn and Wimmer, 2000) Spe I fragment was then inserted into the Xba I site to form p(PZ)-Bac-EYFP. (C) is an illustration of the pBSII-ITR1.1k-ECFP minimal piggyBac vector, which contains a minimal piggyBac cartridge with the terminal and subterminal inverted repeats facing each other, and tagged with a 3xP3-ECFP marker. (D) is an illustration of the more traditional piggyBac minimal vector pXL-BacII-ECFP plasmid;

FIG. 26(A) shows direct PCR analysis of transformed flies. A total of three sets of PCRs were used to verify the piggyBac insertion. The first set (IFP2_R1+MF34 primers) detects the 5' terminal region (115 bp), the second set (IFP2_L+MF34 primers) detects the 3' terminal region (240 bp), and the third set (IFP2_R1+IFP2_L primers) detects the presence of the external spacer sequence (945 bp). (B) shows the PCR results in which (a) all transformed strains have the correct sized fragment confirming the 5' terminal region, and there is also a weak band evident in the w$^{1118}$ strain, (b) all transformed strains have the correct sized fragment confirming the 3' terminal region, and this fragment is absent in the w$^{1118}$ strain, and (c) no external spacer sequence fragment is evident in any of the transformed strains;

DETAILED DESCRIPTION

Figure 1:
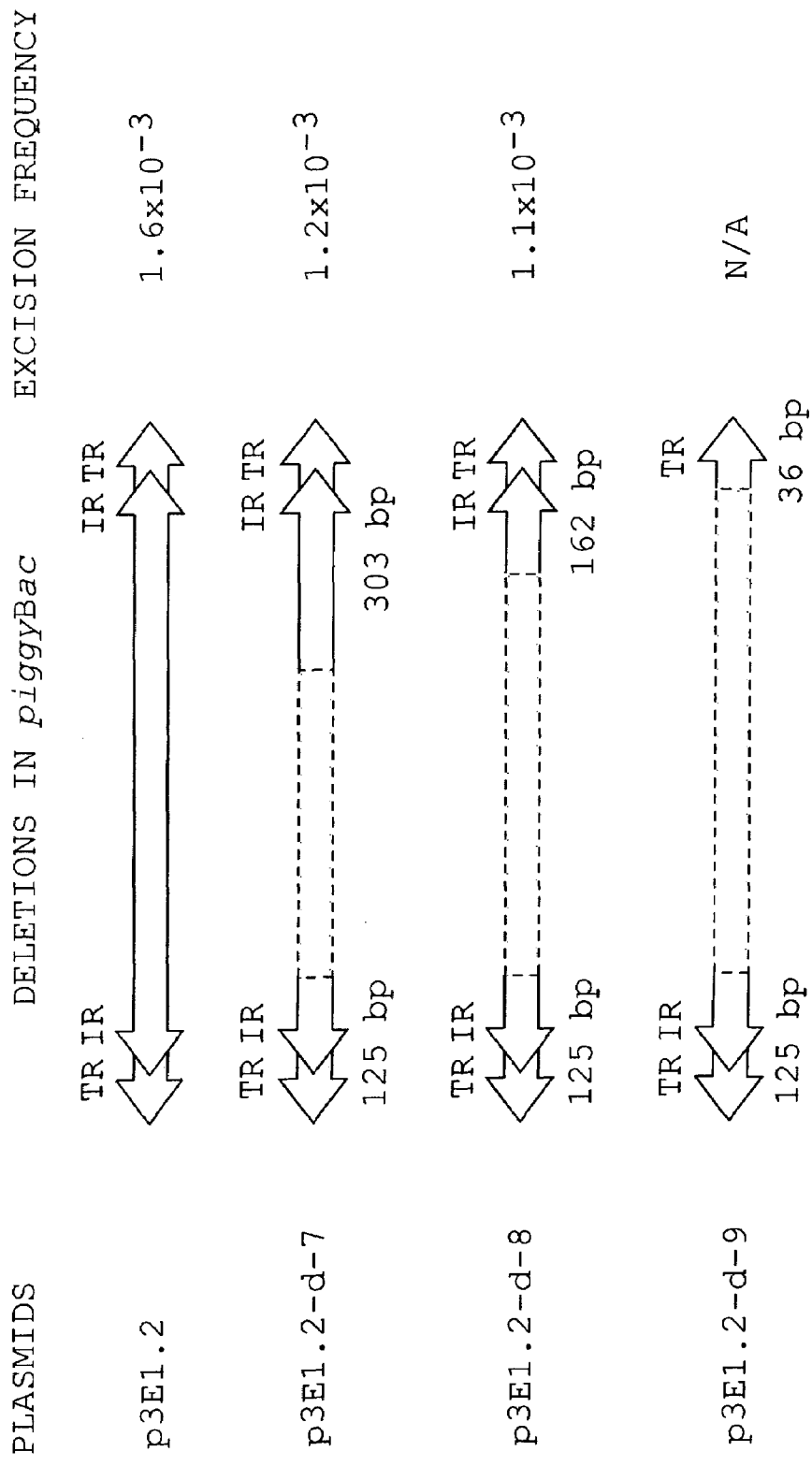
FIG. 1 shows a p3E1.2 deletion series of plasmids and excision assay results; the p3E1.2 plasmid was used to make progressive deletions using the restriction endonuclease ExoIII; three of the maximum deletion plasmids, p3E1.2-d-7, p3E1.2-d-8 and p3E1.2-d-9, were used to perform excision assays in T. ni embryos; p3E1.2-d-7 and p3E1.2-d-8 plasmids retained the complete 3' terminal repeat configurations and were characterized by a similar excision frequency as the intact p3E1.2 plasmid; however, p3E1.2-d-9 did not yield any excision events, and sequencing results show that its 3' IR and part of the 31 bp spacer sequence are deleted.

It is advantageous to define several terms before describing the invention It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "spacer" refers to sequences, for example from about 3 bp to about 31 bp or more in length, separating the 5' and 3' (respectively) terminal repeat and internal repeat sequences of the piggyBac transposon.

For the purposes of the present invention, the term "vector" refers to any plasmid containing piggyBac ends that is capable of moving foreign sequences into the genomes of a target organism or cell.

For the purposes of the present invention, the term "plasmid" refers to any self-replicating extrachromosomal circular DNA molecule capable of maintaining itself in bacteria.

For the purposes of the present invention, the term "transgenic organism" refers to an organism that has been altered by the addition of foreign DNA sequences to its genome.

For the purposes of the present invention, the term "genetic construct" refers to any artificially assembled combination of DNA sequences.

For the purposes of the present invention, the term "helper construct" refers to any plasmid construction that generates the piggyBac transposase gene product upon transfection of cells or injection of embryos.

DESCRIPTION

The minimal sequence cartridges of the present invention facilitate transposition of DNA molecules of interest into cells, and production of transgenic organisms that include the transferred DNA molecule in some or all of their cells. A DNA molecule(s) is excised from a genetic (transformation) construct, and is transferred to a cell where it is inserted into the cell's genome. The DNA molecule is accompanied by regulatory elements sufficient to allow its expression in the host cell. "Cell" as used herein includes eukaryotic and prokaryotic cells. The genetic transposition construct includes a DNA molecule to be transferred flanked by a pair of transposon terminal inverted repeat nucleotide sequences from the piggyBac transposon. The DNA molecule to be transferred may be any molecule capable of being expressed in a host cell and/or transgenic organism. The method would also transfer cells not able to be expressed.

In the present invention, excision (Elick et al., 1996b) and interplasmid transposition assays (Lobo et al., 1999) were used to determine the relative importance of sequences internal to, or external to, the terminal repeat (TR) and internal repeat (IR) sequence configurations for movement of the piggyBac element.

It was found that progressive deletions within the internal sequence of the element have no noticeable effect on either excision or transposition capabilities. In contrast, deletion of the 3' IR eliminated excision of the element. Construction of vectors having only intact 5' and 3' repeat domains regenerates mobility of the plasmids when supplied with a helper vector expressing a transposase. These features permitted construction of a set of minimal vectors for use in transformation experiments.

The length of the intervening sequence between piggyBac termini in the donor plasmid also affects the piggyBac transposition frequency. In an embodiment of the present invention, a minimal distance of 55 nucleotide base pairs (bp) may be used between target sites and termini to provide for movement of the element This suggests that the piggyBac transposase binds the termini simultaneously before any cleavage may occur, and/or that the formation of the transposition complex requires DNA bending between the two termini.

An aspect of this invention is that it allows the design of minimally sized genetic vectors that are functional for efficient insertion of genes into host genomes, in particular animal, plant, and insect genomes.

Useful plasmids created are:

A) A Transposition PiggyBac ITR Cartridge Plasmid: PCR amplifications and restriction endonuclease cleavage and ligation allowed insertion of a 702 bp fragment containing sequences for piggyBac mobility into any given plasmid of choice, converting the recipient plasmid into an operational transposable sequence capable of being mobilized into an animal genome using the piggyBac transposase gene or purified protein. The pCRII (Invitrogen) plasmid re-amplification using specified primers allows this ITR cartridge to be inserted into any plasmid.

B) Operational Transposable Vectors (pXO and pXL-Bac): Standard restriction endonuclease cleavage and ligation allows insertion of any gene of choice between the minimal sequences of the piggyBac transposon necessary for transposition into the genome of an animal. The total size of the resulting plasmid is preferably not larger than 10 kb.

According to an embodiment of the present invention, the inverted repeat configuration indicated as [TTAA/TR/IR . . . IR/31 bp/TR/TTAA] may be utilized to obtain a piggyBac transposon. This observation was arrived at through structured deletion mutagenesis within the piggyBac transposon sequence and examining the properties of both excision and interplasmid transposition of the deleted product.

Additionally, according to an embodiment of the present invention, an insertion sequence between the target site on a plasmid having the terminal repeat configuration [IR/31 bp/TR/TTAA . . . insertion sequence . . . TTAA/TR/IR] may be approximately 55 bp to achieve mobility.

For ease of manipulation, a cartridge having the configuration [IR/31 bp/TR/TTAA. . . 589 . . . TTAA/TR/IR] which may be inserted within a plasmid, converting that plasmid into a functional piggyBac transposon, was constructed. The cartridge was cloned into the plasmid pCRII (Invitrogen). A cartridge is defined herein as a nucleic acid molecule of a specified construction (plasmid) that may be inserted into a vector.

A cartridge was derived from circularization of the construct A and cutting the construct A with BssHII to cleave at a unique BssHII site within the 589 bp spacer. This yielded a fragment BssHII . . . TTAA/TR/31b/IR/BamHI/IR/TR/TTAA . . . . BssHII. Construct B was derived from a pBSII (Stratagene) plasmid by BssHII deletion of the multiple cloning site (MCS). The linearized fragment was then inserted into the pBSII$^a$BssHII backbone. An MCS primer was synthesized and inserted in the BamHI site.

Construct A allows ease of construction of genetic vectors through use of a simple 702 bp cartridge that may be inserted into any existing plasmid to convert it immediately into a functional transposon.

Construct B allows ease of insertion of any genetic sequence into a plasmid having the minimal terminal sequence requirement for piggyBac mobility. The advantage of this construct is it provides a minimal backbone cloning vector for piggyBac transposon construction.

A kit is contemplated that would contain the two vector constructs along with the original p3E1.2, and/or a helper construct allowing constitutive production of piggyBac transposase in virtually any animal system. Promoter driven expression of the piggyBac transposase using either RSV LTR sequences CMV early promoter, AcMNPV/IE-1 promoter of poly-ubiquitin promoter, among others, is also contemplated.

Excision assays of plasmids containing progressive deletions of the piggyBac internal sequence revealed that the 5', and 3' IR, spacer, and TR configurations are sufficient for piggyBac movement when provided with a transposase in the trans position. Interplasmid transposition assays of plasmids having different sequence lengths between the target sites demonstrated a minimal 55 bp intervening sequence provides for satisfactory piggyBac transposition, whereas lengths less than 40 bp result in dramatic decreases in frequency of transpositions. These results suggest that the piggyBac transposase binds the termini simultaneously before cleavage, and/or that the formation of the transposition complex requires DNA bending between the two termini. Based on these results, a 702 bp cartridge having a minimum piggyBac 5' and 3' terminal region configuration and intervening sequence was constructed The ability of this region to convert any existing plasmid into a non-autonomous piggyBac transposon was verified. A minimal piggyBac vector, pXL-Bac, that contains an internal multiple cloning site sequence between the terminal regions, was also constructed. These vectors facilitate manipulations of the piggyBac transposon for use in a wide variety of hosts.

The excision assay provides a rapid way to characterize essential sequences involved in piggyBac transposition. The p3E1.2-d-7 and p3E1.2-d-8 plasmids, which retain the entire 3' and 5' IR, spacer and TR sequences, exhibit precise excision. In contrast, the p3E1.2-d-9 plasmid that retains the entire 5' terminal region and only 36 bp of the 3' terminal domain, including the TR and a portion of the 31 bp spacer, does not excise at a detectable frequency. The requirement for an internal 3' IR sequence in the excision process suggests that the IR region might play an essential role in transposase recognition or cleavage of the target site.

An alternative explanation is that simply shortening the internal sequence may hinder the formation of a transposition complex, or the binding of transposase to two termini simultaneously. A similar result is observed with the IS5O elements for which the lengthening of Tn5 internal sequences increases the transposition frequency (Goryshin et al., 1994). However, insertion of a KOα fragment into the p3E1.2-d-9 at the SphI site did not improve the frequency of precise excision events recovered in the excision assay, suggesting that the length of the internal domain is less important than the presence of an intact IR sequence in excision of the piggyBac element.

The interplasmid transposition assays of pIAO-P/L series plasmids demonstrate that when the external sequence separating the terminal repeats is at least 55 bp, the transposition frequency is over $10^{-4}$, while reducing the length to less than 40 bp depresses the frequency of transposition. The inhibition of piggyBac transposition as terminal sequences are brought closer together, suggests that formation of a transposition complex likely precedes DNA cleavage or nicking, and the shorter distances between these termini do not allow proper bending of the sequences to permit formation of the complex, or result in steric hindrance of transposase binding at the termini.

These results also imply a necessity for transposase binding of both termini simultaneously before any cleavage (or nicking) may occur. If the simultaneous binding were not necessary, then the transposase could bind one terminal repeat, cleave it, and then bind the second to cleave, and transposition should occur with equivalent frequencies even with smaller intervening sequences.

Figure 10A:
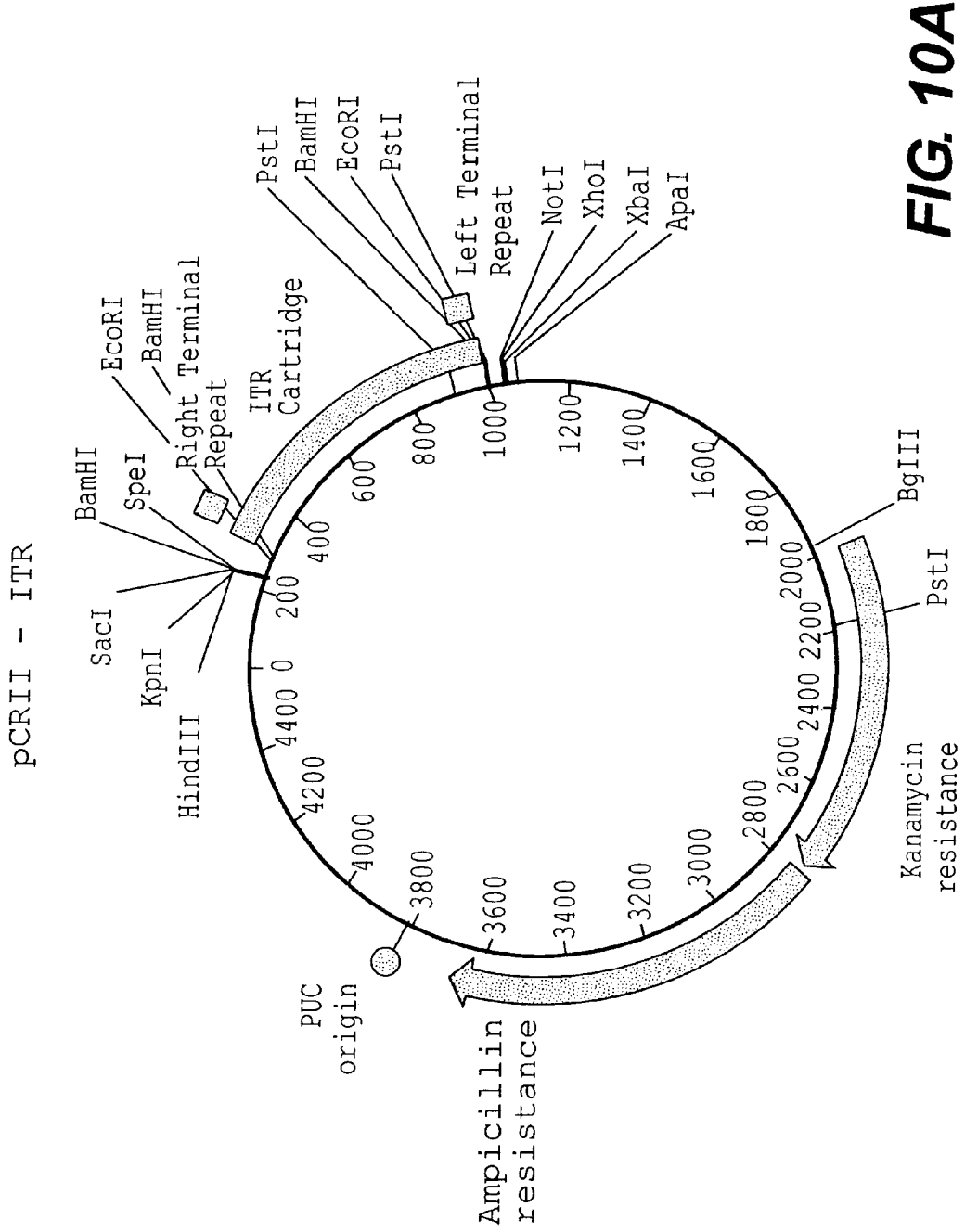
FIG. 10(A) is a plasmid map showing that the ITR cartridge was PCR amplified as a BamHI fragment using a piggyBac internal repeat specific primer (5'-GGATCCCAT-GCGTCAATTTTACGCA-3') (SEQ ID NO: 1) and pIAO-P/L-589 bp plasmid as a template, and cloned into the pCRII plasmid (Invitrogen) to form the pCRII-ITR plasmid; (B) is the nucleotide sequence of pCRII-ITR (SEQ ID NO: 46) and the amino acid sequence (SEQ ID NO: 47)

Interplasmid transposition assays using pCRII-ITR (FIG. 10) verify that the terminal configuration IR, spacer, TR are the minimum sequence requirements for efficient piggyBac transposition. The rest of the piggyBac internal sequence is not required if transposase is provided in trans configuration. With the ITR fragment, a minimum piggyBac vector may easily be constructed from any plasmid which reduces vector size and leaves maximum space for desired foreign genes.

Figure 11:
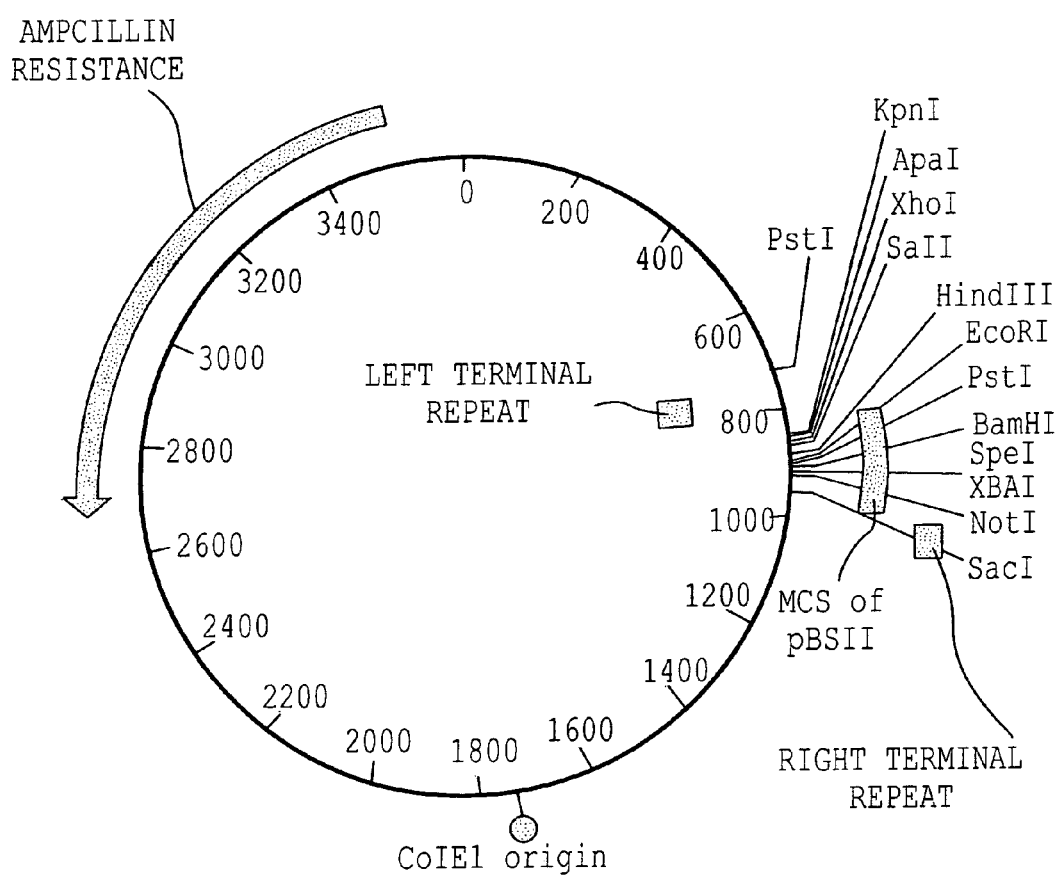
FIG. 11 is a plasmid map showing that the ITR BamHI cartridge was recovered from the pCRII-ITR plasmid and religated, then cut with BssHII and cloned into the BssHII sites of the pBSII plasmid (Stratagene) to form pBS-ITR (rev) plasmid. The Multiple Cloning Sites were PCR amplified as a BglII fragment from the pBSII plasmid and were cloned into the BamHI site to the pXL-Bac plasmid.

Inserting the ITR fragment into pBlueScript II (Stratagene), converts the plasmid into a transposable element that moves with a frequency similar to the intact piggyBac element. This ITR cartridge facilitates the construction of piggyBac transformation vectors from existing plasmids. In addition, the co-integration of the Amp/ori sequences from the donor plasmid into the genome provides an easy way to locate the insertion site because these insertions may be recovered by restriction enzyme digestion, religation, and transformation. The pXL-Bac (FIG. 11) minimum piggyBac vector replaces the internal sequence of the piggyBac transposon with a multiple cloning site. This plasmid allows any desired foreign genes or sequences to be easily inserted between piggyBac termini for movement in the presence of a helper plasmid. These constructs provide useful tools for the examination and use of piggyBac as a gene transfer vector in a wide variety of organisms.

EXAMPLES

Example 1

Excision Assay of p3E1.2 Internal Deletion Series in *T. ni*

The analysis was begun using three plasmids having the most extensive internal deletions, p3E1.2-d-9, p3E1.2-d-8 and p3E1.2-d-7. Sequencing of these three plasmids revealed that p3E1.2-d-8 and p3E1.2-d-7 retained 163 bp and 303 bp of the 3' terminal region, respectively, including the IR, 31 bp spacer, and TR sequence. The p3E1.2-d-9 deletion plasmid retained only 36 bp of the 3' terminal domain, including the 3' TTAA target site, 3' TR and a portion of the 31 bp spacer, but lacked the 3' IR sequence.

Embryos of *T. ni* were injected with combinations of each of the p3E1.2 deletion plasmids and the phspBac helper plasmid. Loss of piggyBac sequences from the deletion series plasmids renders the plasmids resistant to BsiWI and SphI digestion. Transformation of Hirt extract DNAs digested with BsiWI and SphI were compared with transformations employing equal amounts of uncut DNA as a control to determine the frequency of excision. Precise excision events were initially identified by a quick size screen for the characteristic 3.5 kb plasmid in recovered colonies, and these plasmids were then sequenced to confirm the precise excision events.

A quick size screen method is used to quickly identify the plasmids with changed size directly from colonies (Sekar, 1987). Colonies at least 1 mm in diameter are picked up with pipette tips and resuspended in 10 ml protoplasting buffer (30 mM Tris-HCl pH 8.0, 50 mM NaCl, 20% Sucrose 5 mM EDTA, 100 mg/ml RNase, 100 mg/ml Lysozyme) in the Lux 60 well mini culture plate. A 0.9% agarose gel containing ethidium bromide is preloaded with 4.5 ml lysis solution (80 mM Tris, 0.5% Sucrose, 0.04% Bromophenol Blue, 2% SDS, 2.5 mM EDTA) per well. The bacterial suspension is then loaded into the wells and the gel electrophoresed. Two kinds of markers are needed to distinguish the plasmids with changed size. One is the colony from the control plate or the original plasmid, another is a molecular weight marker. The plasmids with a difference of 500 bp or greater in size are easily distinguished. Both the p3E1.2-d-8 and p3E1.2-d-7 yielded precise excision events at about the same relative frequency, while no excision events were recovered with the maximum deletion plasmid p3E1.2-d-9 (FIG. 1).

Example 2

Figure 4A:
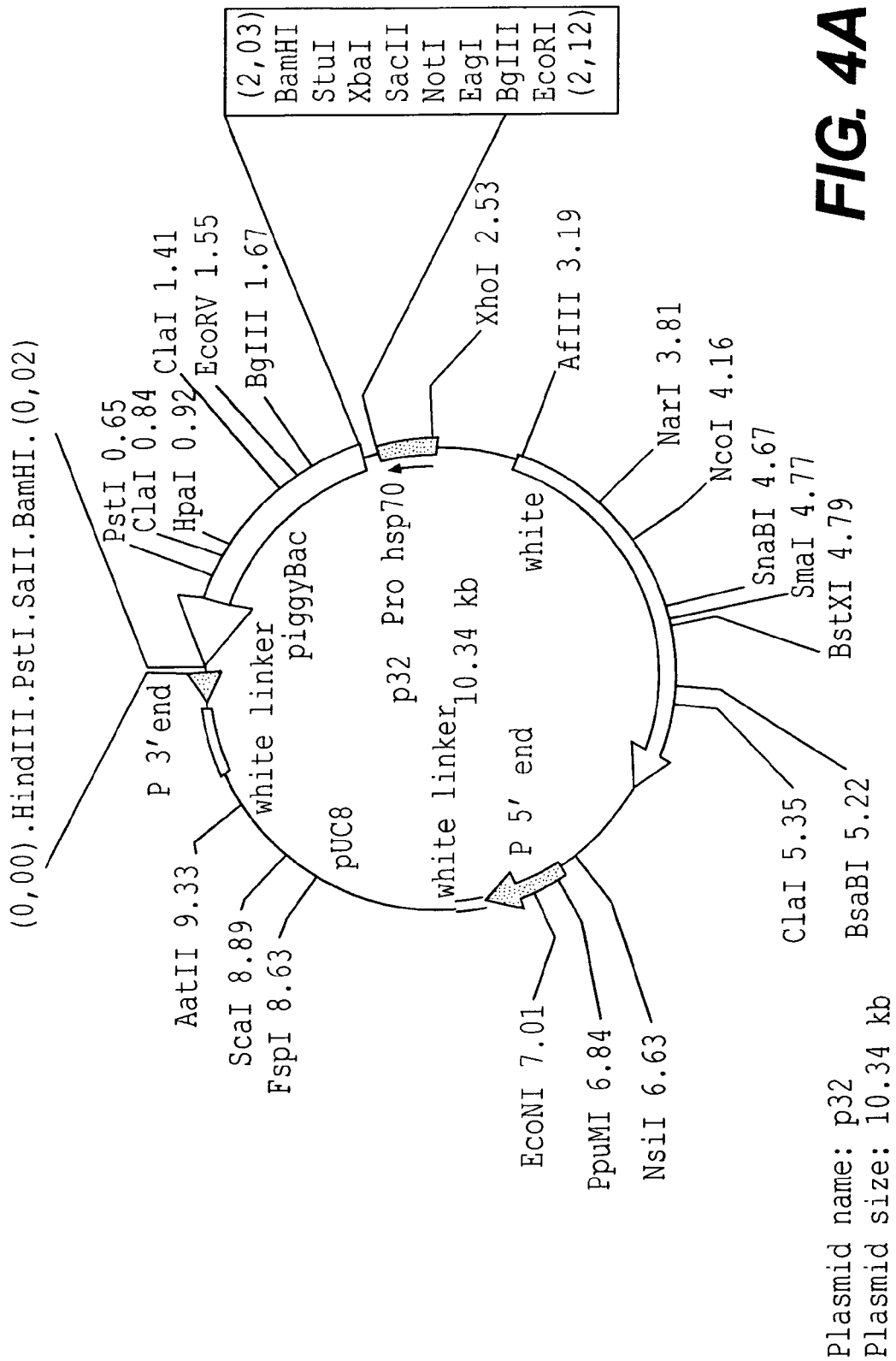
FIG. 4 is a restriction map of plasmid pCaSpeR-hs-orf (p32), containing a 2016 bp PCR BamHI fragment containing piggyBac transposase and its terminator, cloned into BamHI sites of pCaSpeR-hs.
Figure 5A:
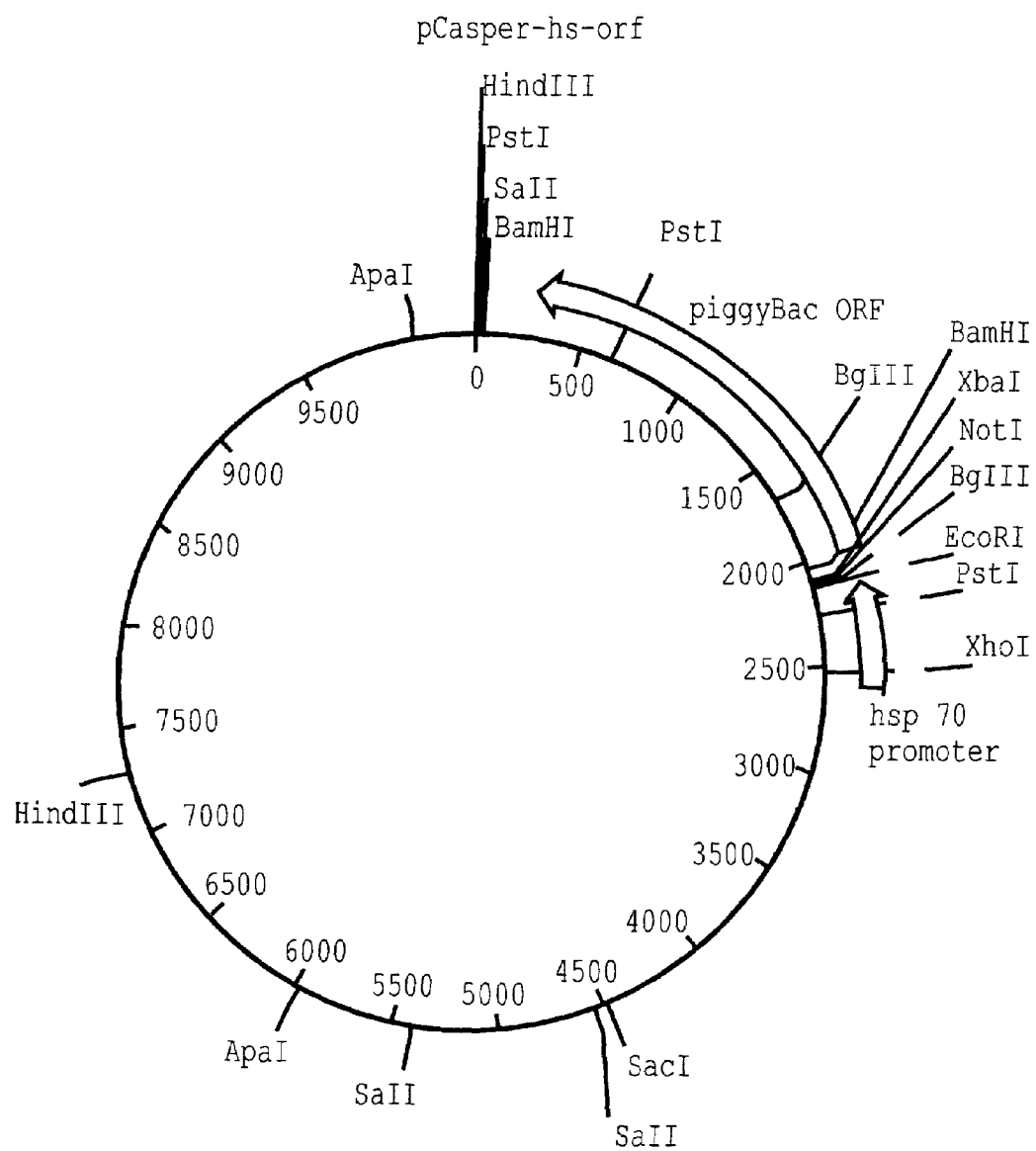
FIG. 5(A) is a plasmid map showing the piggyBac ORF was amplified as a BamHI cartridge from the p3E1.2 plasmid and cloned into pCaSpeR-hs plasmid, positioning it for transcriptional control by the hsp70 promoter; (B) is the nucleotide sequence (SEQ ID NO: 42) of pCaSpeR-hs-orf.

Minimal Distance Required between Termini for Movement of a PiggyBac Transposon Construct The interplasmid transposition assay was carried out essentially as previously described by Lobo et al. (1999), Thibault et al. (1999) and Sarkar et al. (1997a). Embryos were injected with a combination of 3 plasmids. The donor plasmid, pB(KOα), carried a piggyBac element marked with the kanamycin resistance gene, ColE1 origin of replication, and the lacZ gene. The transposase providing helper plasmid, pCaSpeR-pB-orf, expressed the full length of the piggyBac ORF under the control of the *D. melanogaster* hsp70 promoter. The target *B. subtilis* plasmid, pGDV1, is incapable of replication in *E. coli*, and contains the chloramphenicol resistance gene. Upon transposition of the genetically tagged piggyBac element from pB(KOα) into the target plasmid pGDV1 with the help of the transposase provided by the helper pCaSpeR-pB-orf that expresses the piggyBac transposase protein from a minimal hsp70 promoter (see FIG. 4), only the interplasmid transposition product would be able to replicate in *E. coli* and produce blue colonies on LB/kan/cam/X-gal plates. Embryos were injected with a mixture of the transposase-providing helper plasmid, phspBac, one of the pIAO-P/L series plasmids as the donor, and the pGDV1 target plasmid. Transposition of the tagged piggyBac element from any of the pIAO-P/L plasmids into the target plasmid pGDV1 allows the recipient pGDV1 to replicate in *E. coli* and produces blue colonies on LB/Amp/Cam/X-gal plates.

A total of 10 blue colonies were randomly picked from each transformation and prepared for sequencing analysis. Initial sequence analysis of the terminal repeat junction showed that all of the sequenced clones had the distinctive duplication of a TTAA tetranucleotide target site, a characteristic feature of piggyBac transposition. A random set of those clones for which the 5' terminus had been sequenced were also examined at their 3' terminus to confirm the duplication of the TTAA site at both ends. The accumulated results confirmed transposon insertion at 12 of the 21 possible TTAA target sites in the pGDV1 plasmid, all of which were previously identified as insertion sites in Lepidopteran assays by Lobo et al. (1999) and Thibault et al. (1999).

Figure 2B:
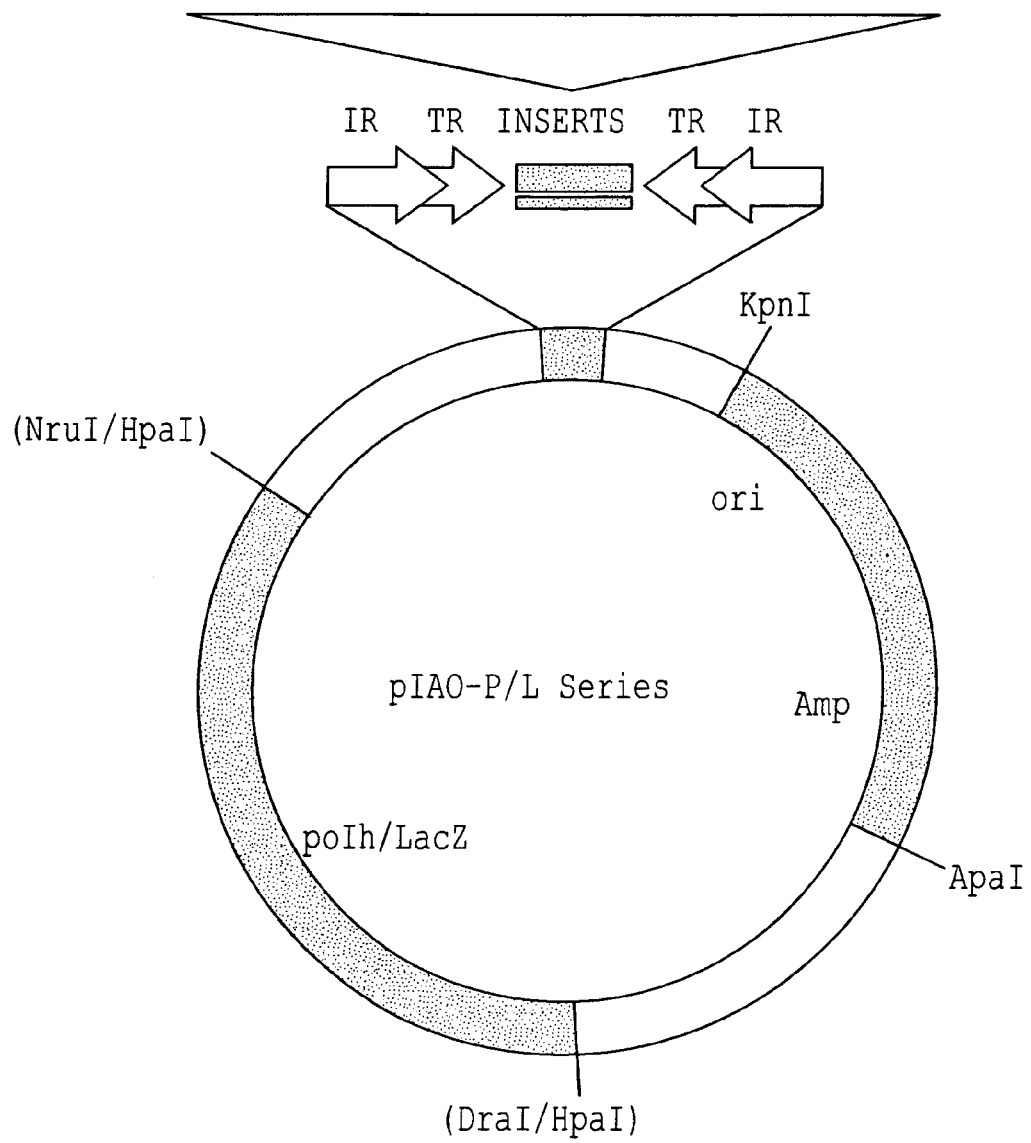
FIG. 2 shows the pIAO-P/L insertion series of plasmids and presents interplasmid transposition assay results: (A) lists the pIAO-P/L series of plasmids' insertion sequences (SEQ ID NOS: 35–39) and their interplasmid transposition assay (IPTA) frequencies are shown; all the pIAO-P/L insertion plasmids were co-injected with the piggyBac helper plasmid, phspBac, and the target plasmid, pGDV1, into T. ni embryos to perform an interplasmid transposition assay; the results show that when the insertion sequence is less than 40 bp, the transposition frequency drops dramatically; (B) is a schematic representation of the pIAO-P/L series plasmids; the piggyBac sequence was PCR amplified from a p3E1.2B/X plasmid, polhlacZ is from a pD2/-gal DraI/NruI fragment and AMP/ori was PCR amplified from a pUC18 plasmid; and (C1) is the nucleotide sequence of pIAO-P/L (SEQ ID NO: 57) and the amino acid sequences (SEQ ID NOS: 58–62) (C2) is the nucleotide sequence of pIAO-P/L-Lambda (2.2 kb) (SEQ ID NO: 63) and the amino acid sequences (SEQ ID NOS: 58–61 and 64–66)
Figure 2(C1):
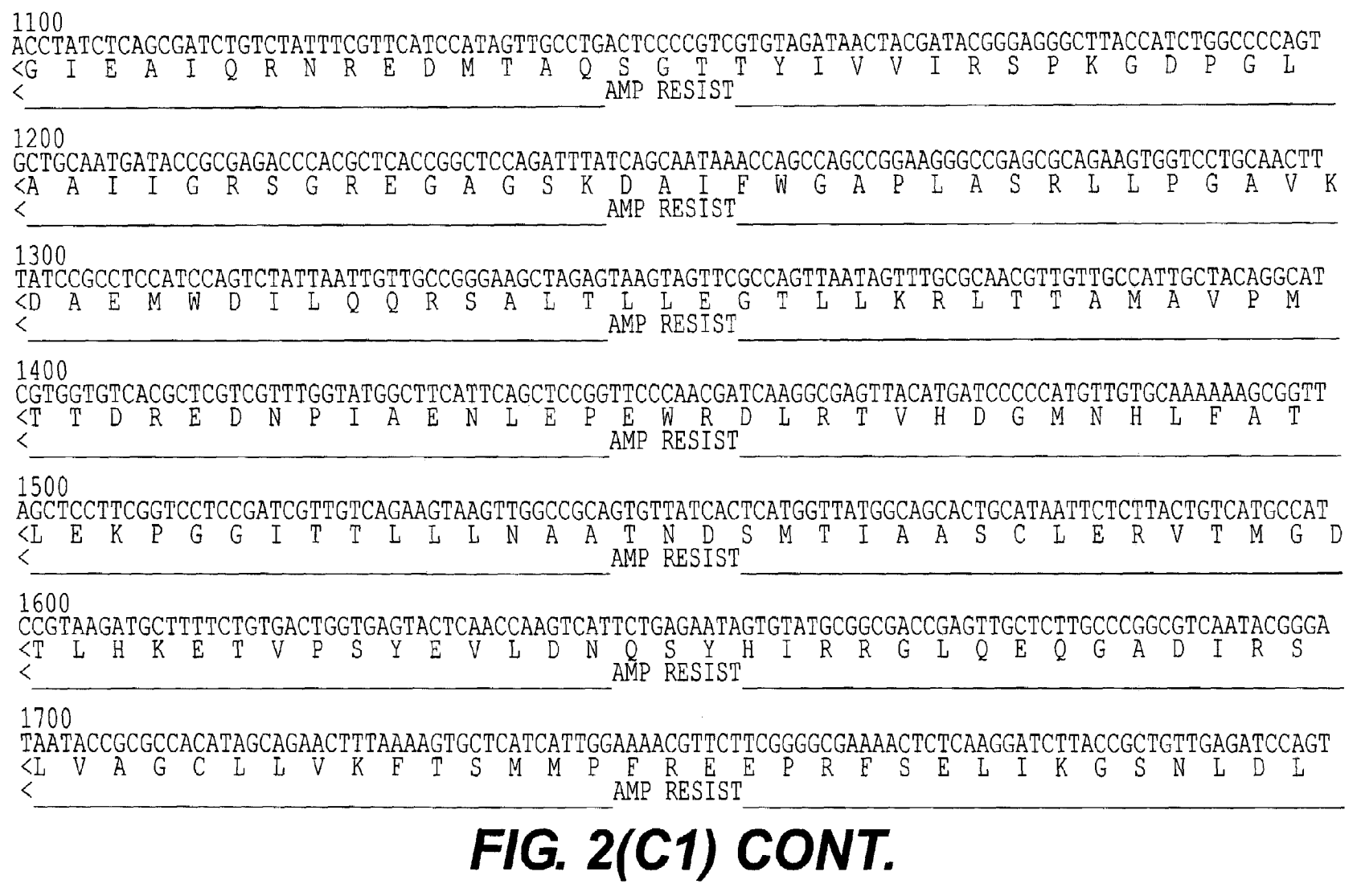
Figure 2(C2):
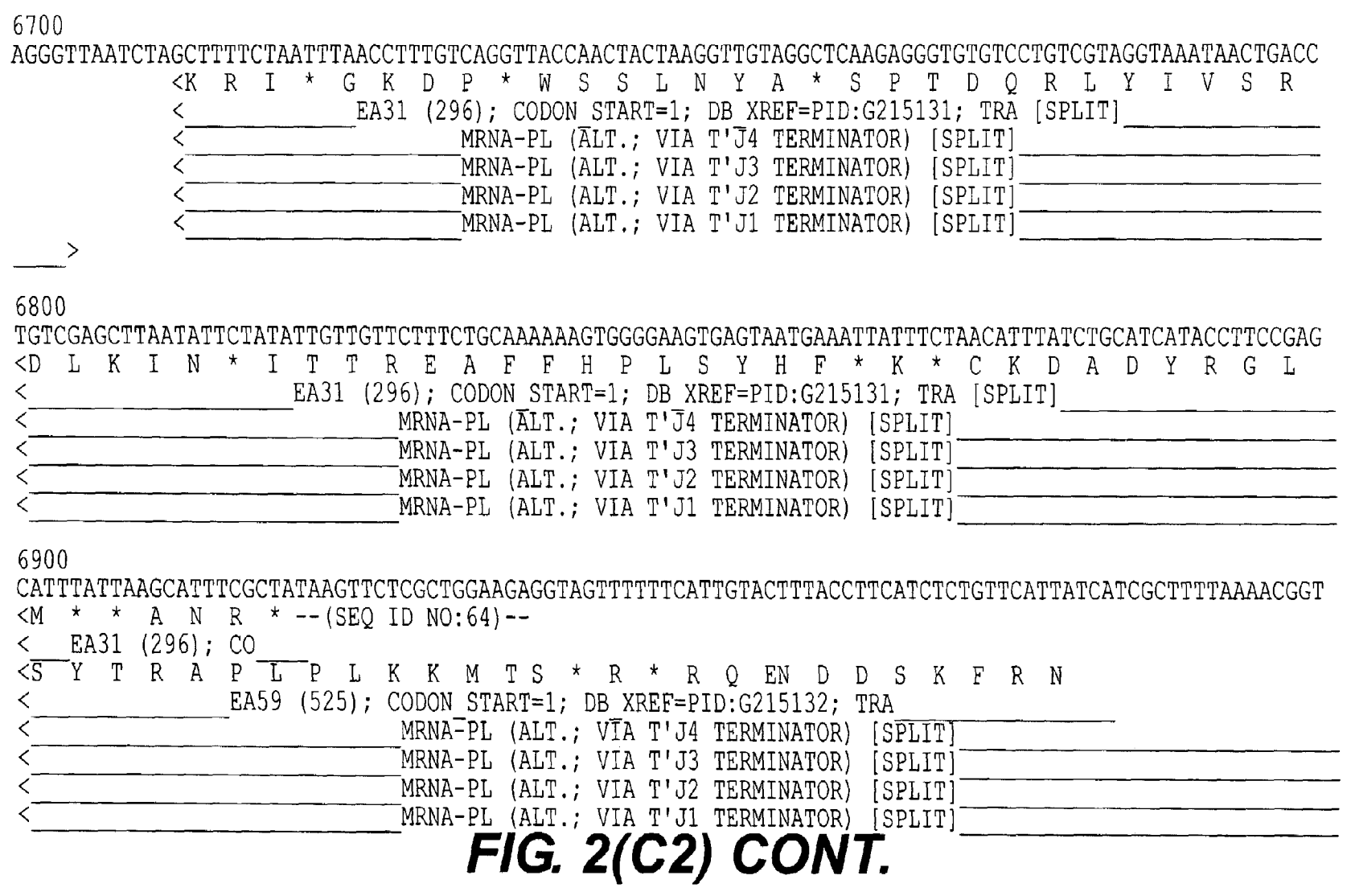
Figure 2(C2):
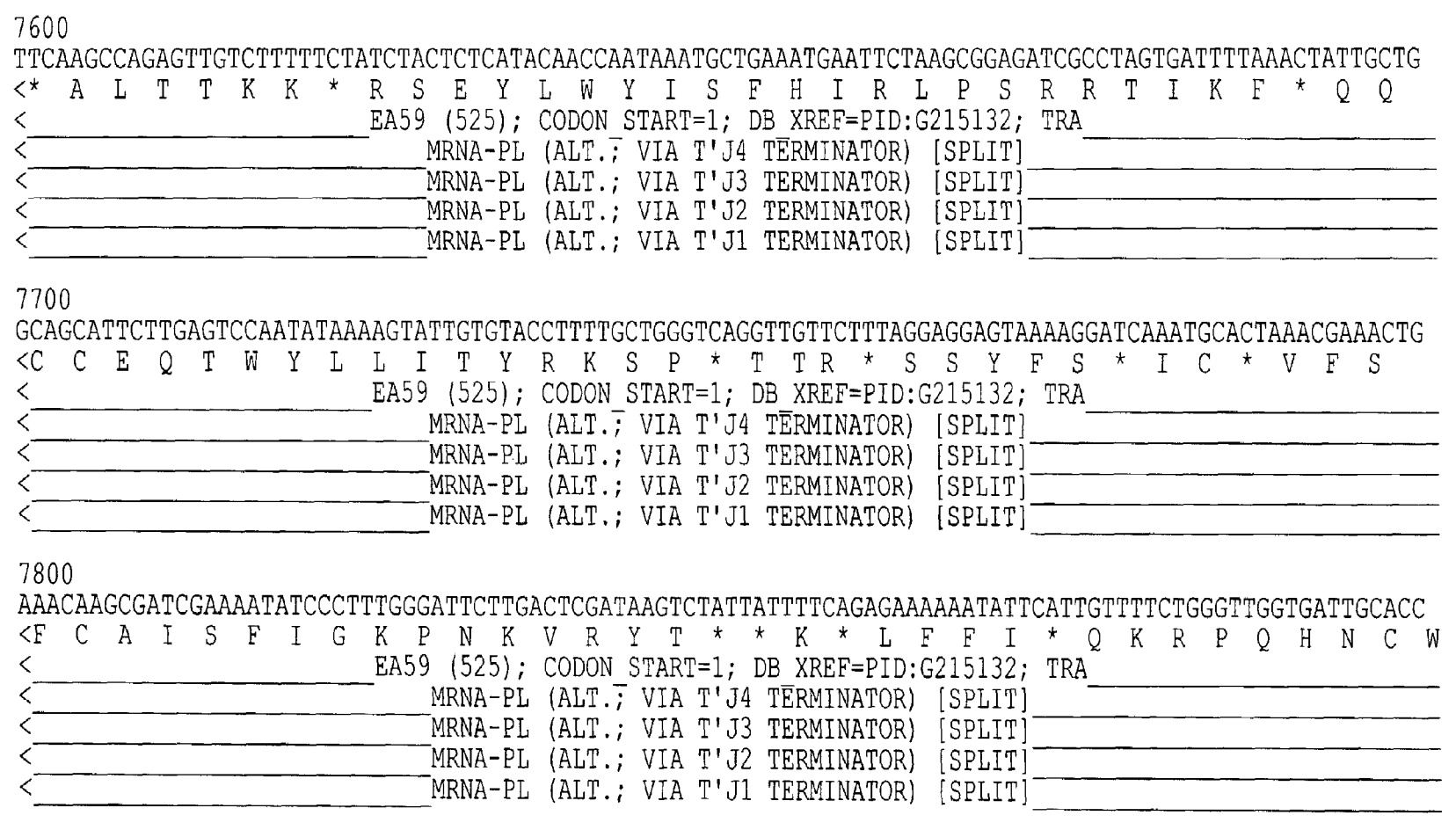

The relative frequency at which a given pIAO-P/L series plasmid was able to undergo transposition into the target plasmid correlated with the sizes of the intervening sequence between the termini. With intervening sequences greater than 55 bp, the transposition frequency was over $1.2 \times 10^{-4}$, which is consistent with the frequency obtained in previous assays with the p3E1.2 derived vectors by Lobo et al. (1999). If the length of the intervening sequence was reduced to 40 bp or less, the frequency of transposition began to decrease dramatically (FIG. 2).

Example 3

Interplasmid Transposition Assay of pCRII-ITR and pBSII-ITR Plasmids

According to an embodiment of the present invention, the excision assay described herein shows that a minimum of 163 bp of the 3' terminal region and 125 bp of the 5' terminal region (from the restriction site SacI to the end of the element) may be used for excision, while the pIAO-P/L constructs showed that a minimal distance of 55 bp between termini may be utilized to effect movement. These data suggested that the inclusion of intact left and right terminal and internal repeats and spacer domains would be sufficient for transposition.

The pCRII-ITR plasmid was constructed following PCR of the terminal domains from pIAO-P/L-589 using a single IR specific primer. A second construct pCRII-JFO3/04 was also prepared using two primers that annealed to the piggyBac 5' and 3' internal domains respectively, in case repeat proximate sequences were required.

The interplasmid transposition assay was performed in *T. ni* embryos and the plasmids were recovered using LB/Kan/Cam plates (Sambrook et al., 1989) with the controls plated on LB/Amp plates. A total of 10 randomly picked colonies were sequenced, and all were confirmed as resulting from transposition events, having the characteristic tetranucleotide TTAA duplication at the insertion sites. These insertion sites in pGDV1 were among the same previously described (Lobo et al., 1999 and Thibault et al., 1999). The sequencing results also confirmed that all 10 transposition events retained the expected terminal domain configurations. The frequency of transposition events was estimated at $2 \times 10^{-4}$, a similar frequency to that obtained with non-mutagenized constructs for this species (Lobo et al., 1999).

Figure 3A:
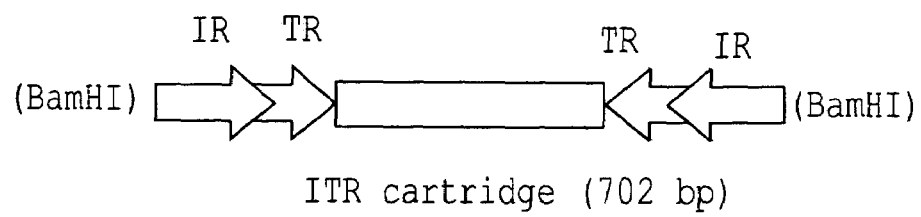
FIG. 3 is a schematic representation of an ITR cartridge and pXL-Bac minimum piggyBac vectors; (A) the ITR cartridge may be amplified from the pIAO-P/L-589 bp plasmid using an IR-specific primer; the amplified ITR may convert any existing plasmid into a piggyBac transposon, which may be mobilized if provided with the piggyBac transposase; (B) is a map of the pXL-Bac plasmid (MCS=multiple cloning site, BamHI or BssHII are restriction sites); (C1) the ITR cartridge nucleotide sequence (SEQ ID NO: 40); and (C2) is the nucleotide sequence (SEQ ID NO: 41) of pXL-Bac.
Figure 3B:
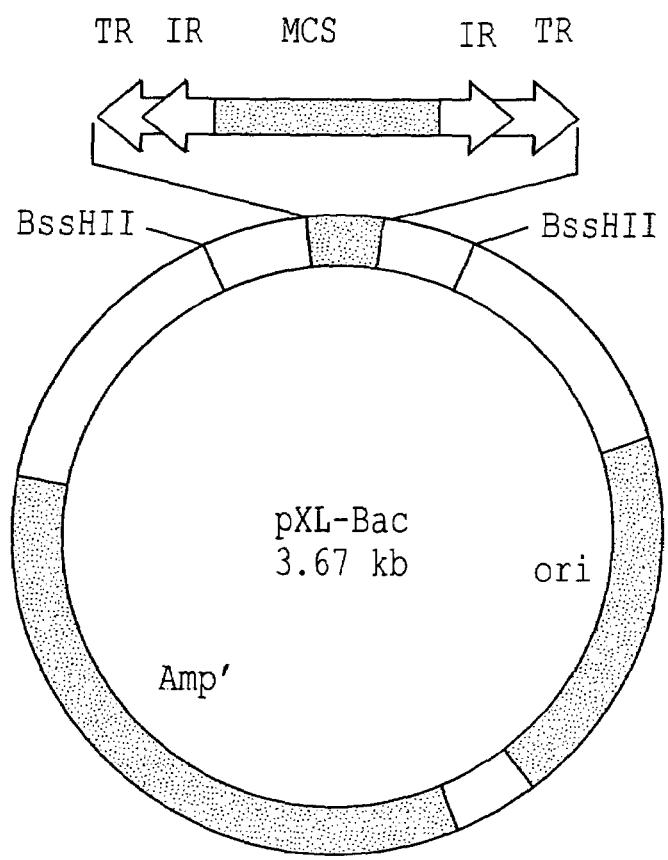

Independent verification that the 702 bp PCR cloned fragment (ITR cartridge, FIG. 3(C1)) may be used as a cartridge to generate transpositionally competent plasmids was obtained by excising the BamHI fragment from pCRII-ITR, and ligating it into the pBlueScript II (Stratagene) plasmid to construct pBSII-ITR. Frequencies similar to those for the pCRII-ITR construct in the interplasmid transposition assay, were obtained.

Example 4

Construction of Minimum PiggyBac Vector pXL-Bac

A new piggyBac minimum vector pXL-Bac (FIG. 3(C2)) was also constructed by combining the 702 bp BamHI ITR fragment with the pBlueScript II BamHI fragment and inserting a PCR amplified pBSII multiple cloning site (MCS) between the terminal repeats. The pXL-Bac vector was tested by inserting an XbaI fragment from πKOα (obtained from A, Sarkar, University of Notre Dame), containing the Kanamycin resistance gene, E. coli replication origin, and Lac a-peptide, into the MCS of pXL-Bac to form pXL-Bac-KOa. Interplasmid transposition assays yielded a frequency of over $10^4$ for transposition of the modified ITR sequence, a similar level as observed for the intact piggyBac element.

Example 5

Derivative Vectors of pXL-Bac

Figure 15A:
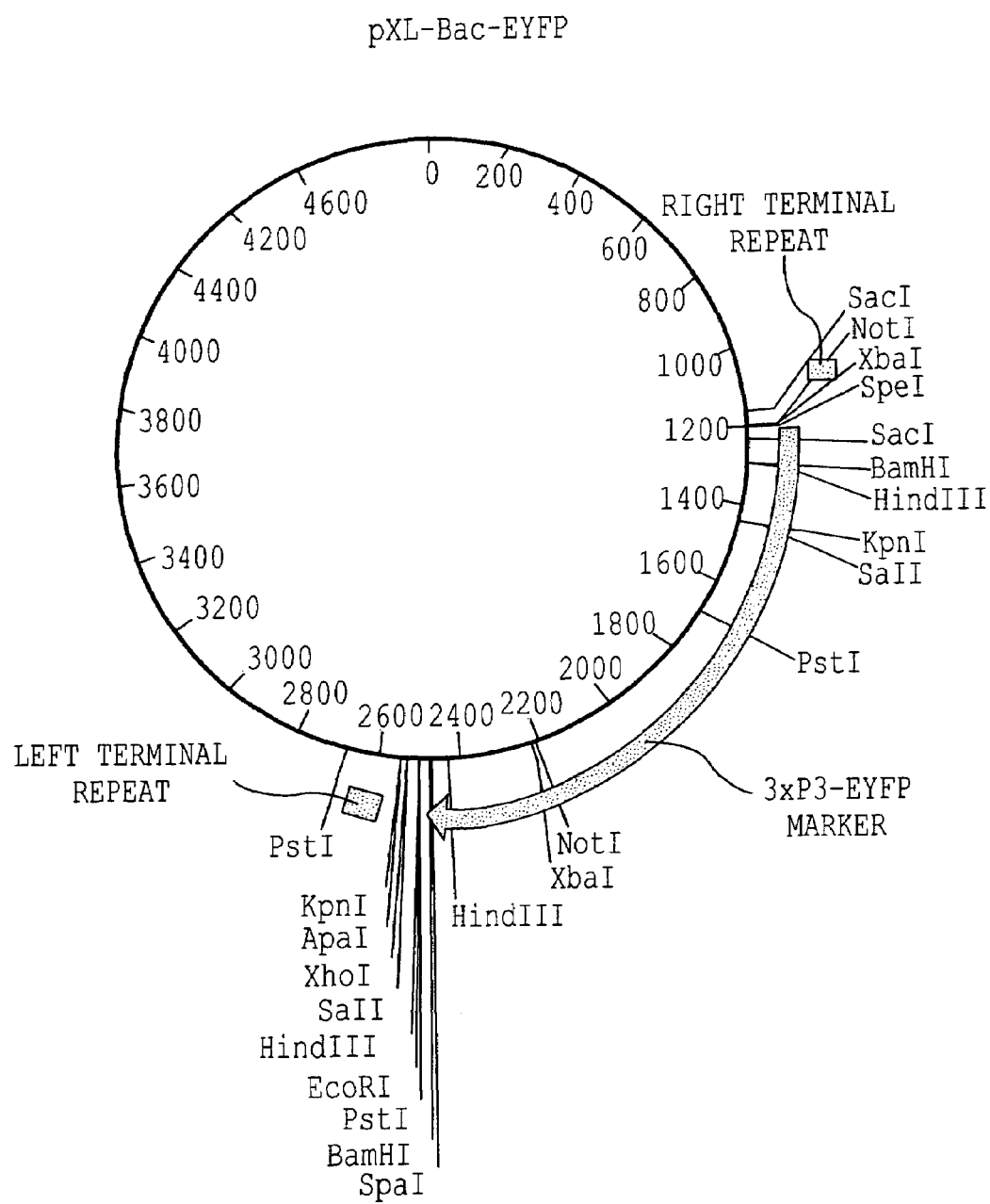
FIG. 15(A) is a plasmid map showing that the 3xP3-EYFP gene was PCR amplified as an Spe I fragment from pBac [3xP3-EYFPafm] (Horn and Wimmer, 2000) and cloned into the Spe I site of the pXL-Bac plasmid to form the pXL-Bac-EYFP plasmid; (B) is the nucleotide sequence (SEQ ID NO: 51) of pXL-Bac-EYFP.
Figure 16A:
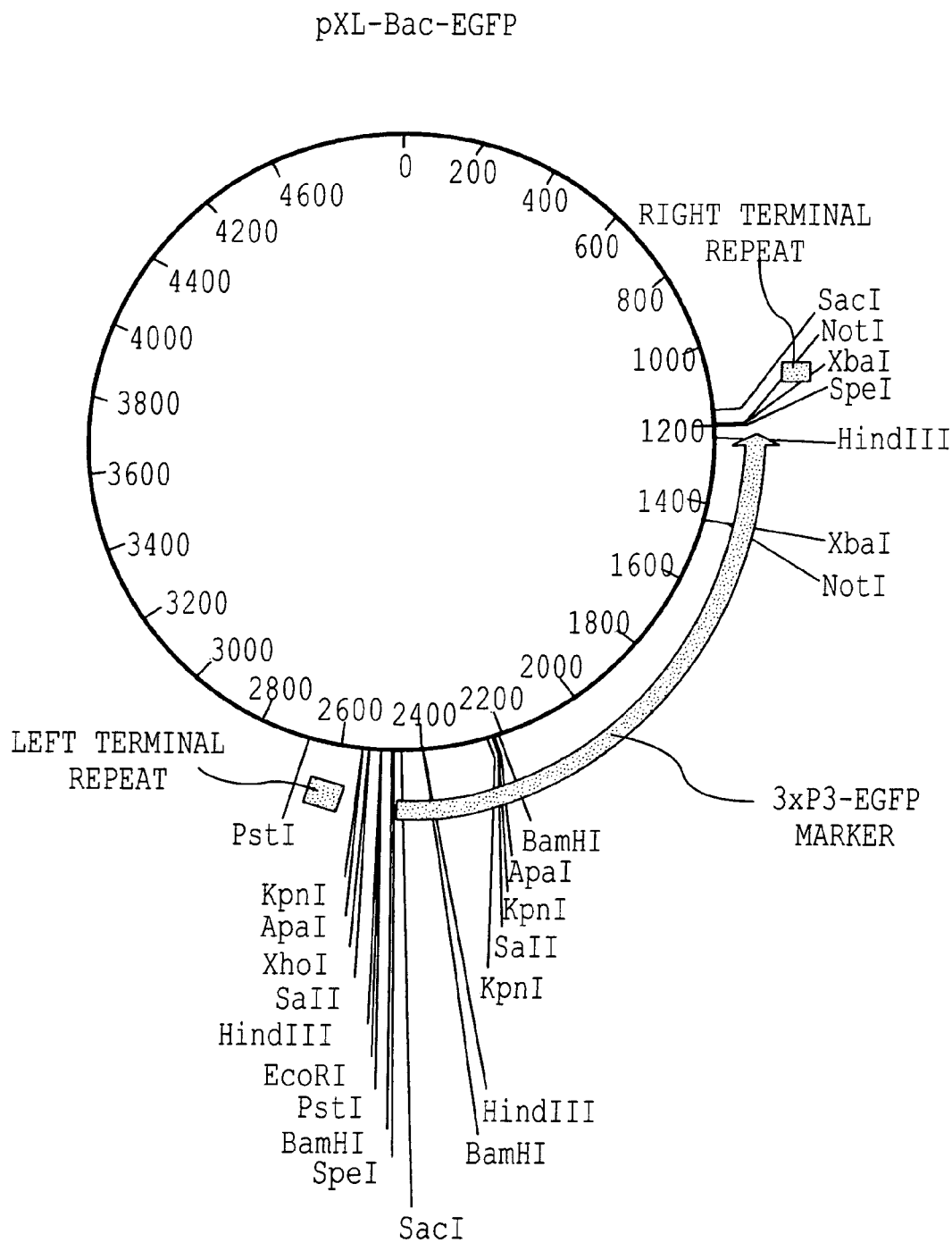
FIG. 16(A) is a plasmid map showing that the 3xP3-EGFP gene was PCR amplified as an Spe I fragment from pBac [3xP3-EGFPafm] (Horn and Wimmer, 2000) and cloned into the Spe I site of the pXL-Bac plasmid to form the pXL-Bac-EGFP plasmid; (B) is the nucleotide sequence (SEQ ID NO: 52) of pXL-Bac-FGFP.
Figure 17A:
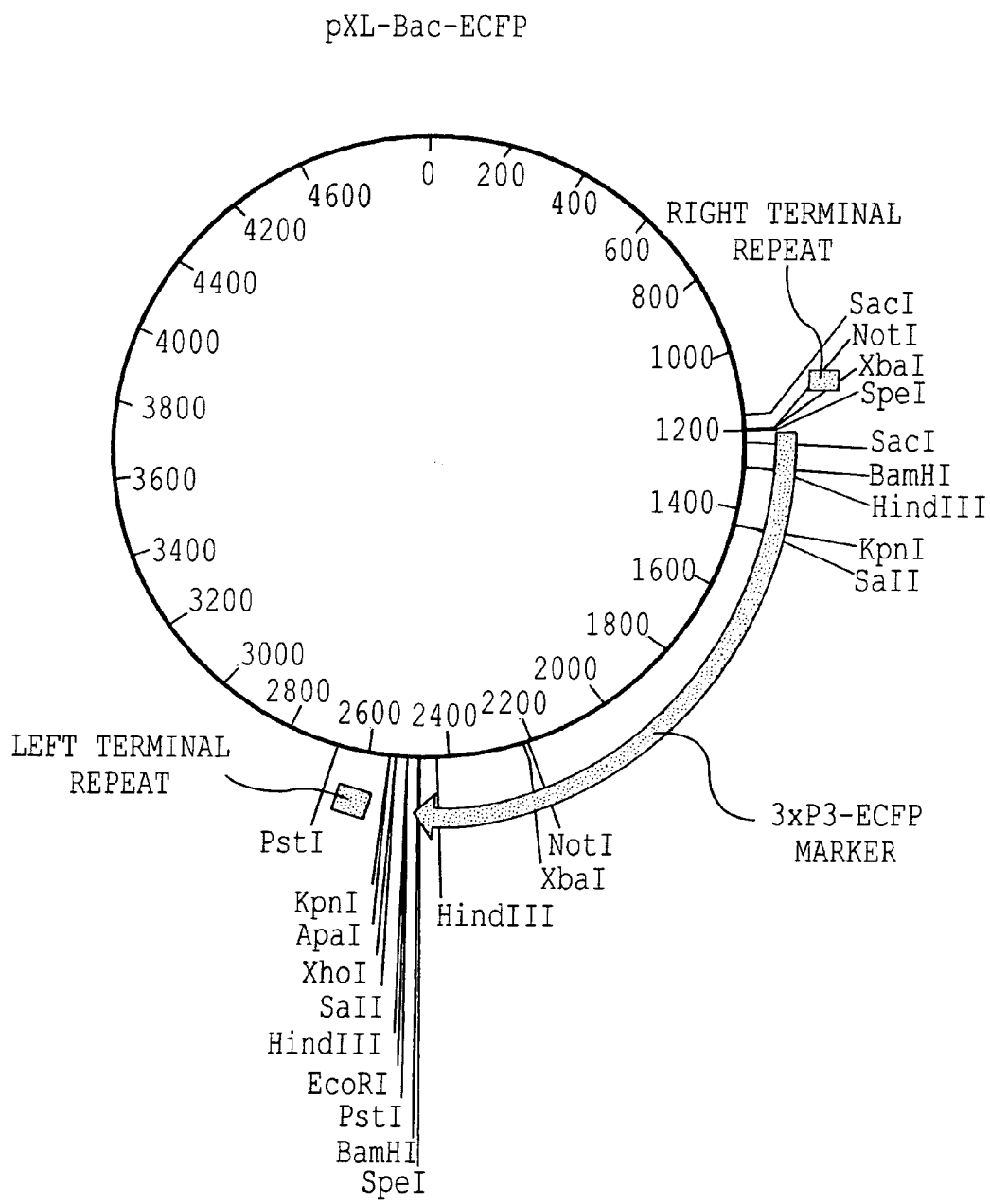
FIG. 17(A) is a plasmid map showing that the 3xP3-ECFP gene was PCR amplified as an Spe I fragment from pBac [3xP3-ECFPafm] (Horn and Wimmer, 2000) and cloned into the Spe I site of the pXL-Bac plasmid to form the pXL-Bac-ECFP plasmid; (B) is the nucleotide sequence (SEQ ID NO: 53) of pXL-Bac-ECFP.

Using the pXL-Bac minimal vector, several derivative vectors may be constructed containing marker genes for detection of successful transformations. In one example, the vectors pXL-Bac-EYFP, pXL-Bac-EGFP, and pXL-Bac-ECFP (FIGS. 15–17) were assembled to contain the 3xP3 promoter driven flourescent protein genes of Horn and Wimmer (2000) by PCR amplifying these sequences from their respective piggyBac vectors using the primers E*FP-for (5' ACGACTAGTGTTCCCACAATGGTTAATTCG 3') (SEQ ID NO: 2) and E*FP-rev (5' ACGACTAGTGCCG-TACGCGTATCGATAAGC 3') (SEQ ID NO: 3) each terminating in an SpeI restriction endonuclease site, and inserting these fragments into the SpeI digested pXL-Bac vector at the unique SpeI site of the multiple cloning site. Vectors constructed in this fashion allow detection of successful transformation by the pXL-Bac vector and may be further modified to include a separate gene of choice and suitable promoter adjacent to the marker gene in the multiple cloning site.

Example 6

Derivative Vectors of pCRII-ITR or pBSII-ITR

Figure 18A:
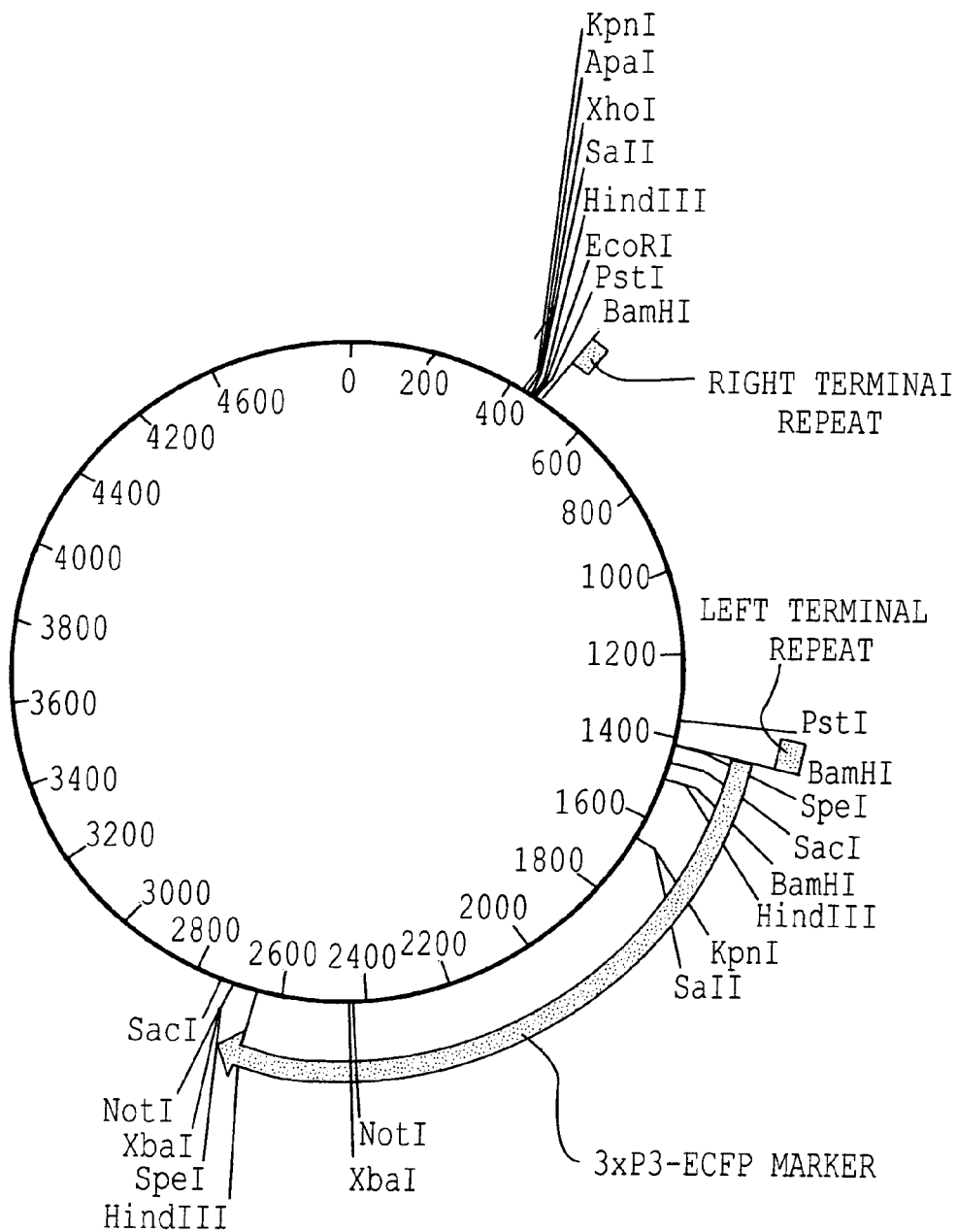
FIG. 18(A) is a plasmid map showing that the 3xP3-ECFP was PCR amplified as an Spe I fragment from pBac[3xP3-ECFPafm] (Horn and Wimmer, 2000) and cloned into the Spe I site of the pBS-ITR plasmid to form the pBS-ITR-ECFP plasmid; (B) is the nucleotide sequence (SEQ ID NO: 54) of pBS-ITR-ECFP.
Figure 19A:
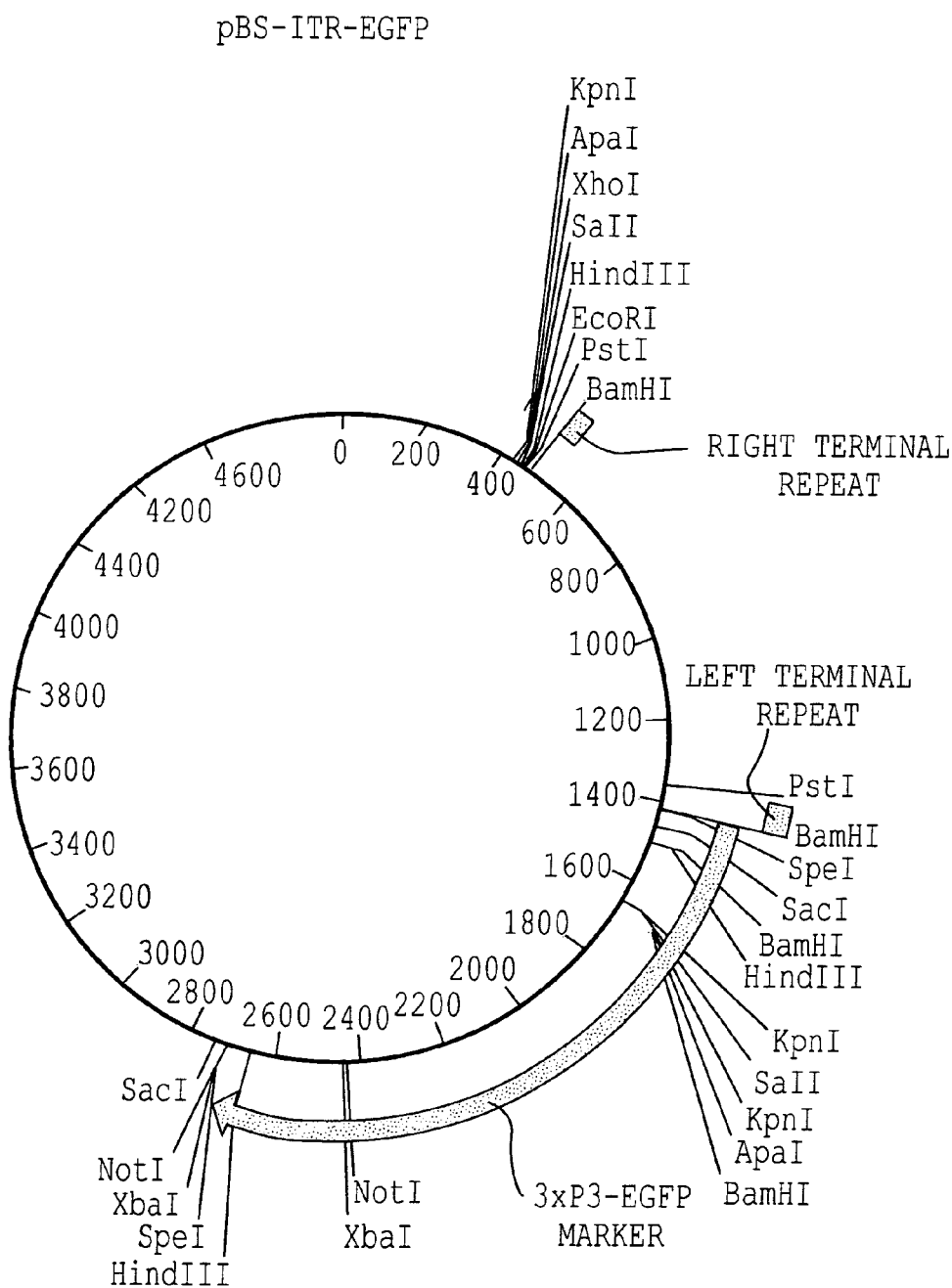
FIG. 19(A) is a plasmid map showing that the 3xP3-EGFP was PCR amplified as an Spe I fragment from pBac[3xP3-EGFPafm] (Horn and Wimmer, 2000) and cloned into the Spe I site of the pBS-ITR plasmid to form the pBS-ITR-EGFP plasmid; (B) is the nucleotide sequence (SEQ ID NO: 55) of pBS-ITR-EGFP.
Figure 20A:
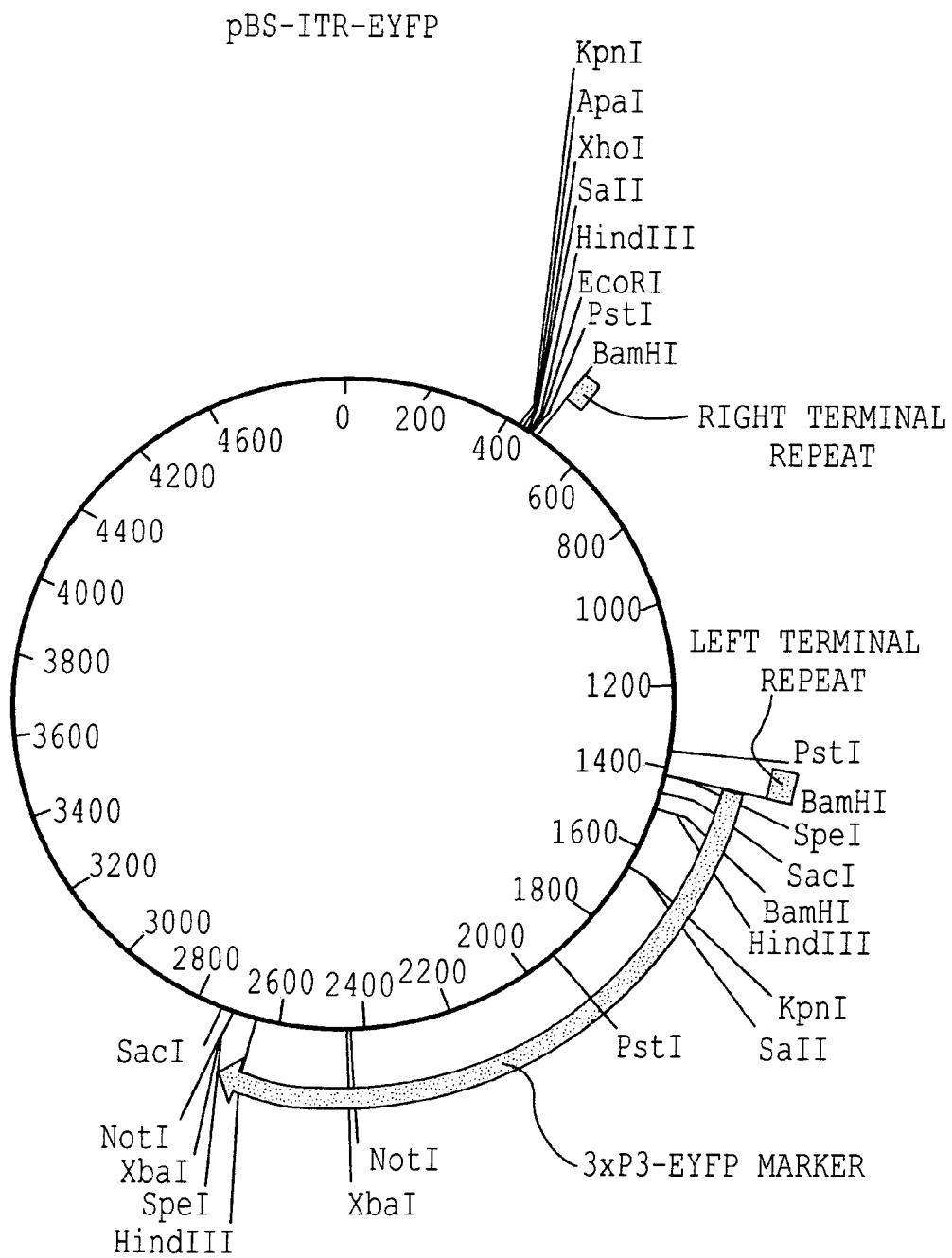
FIG. 20(A) is a plasmid map showing that the 3xP3-EYFP was PCR amplified as an Spe I fragment from pBac[3xP3-EYFPafm] (Horn and Wimmer, 2000) and cloned into the Spe I site of the pBS-ITR plasmid to form the pBS-ITR-EYFP plasmid; (B) is the nucleotide sequence (SEQ ID NO: 56) of pBS-ITR-EYFP.

Similar modifications may be made to either the pCRII-ITR or the companion vector, pBSII-ITR, by inserting a marker gene into the plasmid adjacent to the ITR cartridge of these plasmids. In one example, the plasmids pBSII-ITR-ECFP, pBSII-ITR-EGFP, and pBSII-ITR-EYFP (FIGS. 18–20) were constructed using the strategy described in Example 5 to PRC amplify an SpeI fragment containing the marker genes from the Horn and Wimmer (2000) piggyBac vectors and insert them into the unique SpeI site of the pBSII-ITR plasmid.

Example 7

Facilitating Expression of the Transposase

Expression of the transposase is important in gaining movement of any of the vectors described herein. To facilitate expression of the transposase, a BamHI cartridge containing only the piggyBac open reading frame sequences was PCR amplified from the piggyBac transposon clone p3E1.2 using the primers BamH1E-for1 (5' GCTTGATAA-GAAGAG 3') (SEQ ID NO: 4) and BamH1E-rev1 (5' GCATGTTGCTTGCTATT 3') (SEQ ID NO: 5). This cartridge was then cloned into the pCaSpeR-hs vector at a unique BamH1 site downstream of the Drosophila heat shock promoter (pCaSpeR-hs-orf) to effect heat shock induced expression of the piggyBac transposase following co-injection with any piggyBac vector.

Example 8

In Vitro Expression of mRNA of PiggyBac Transposase

Figure 6A:
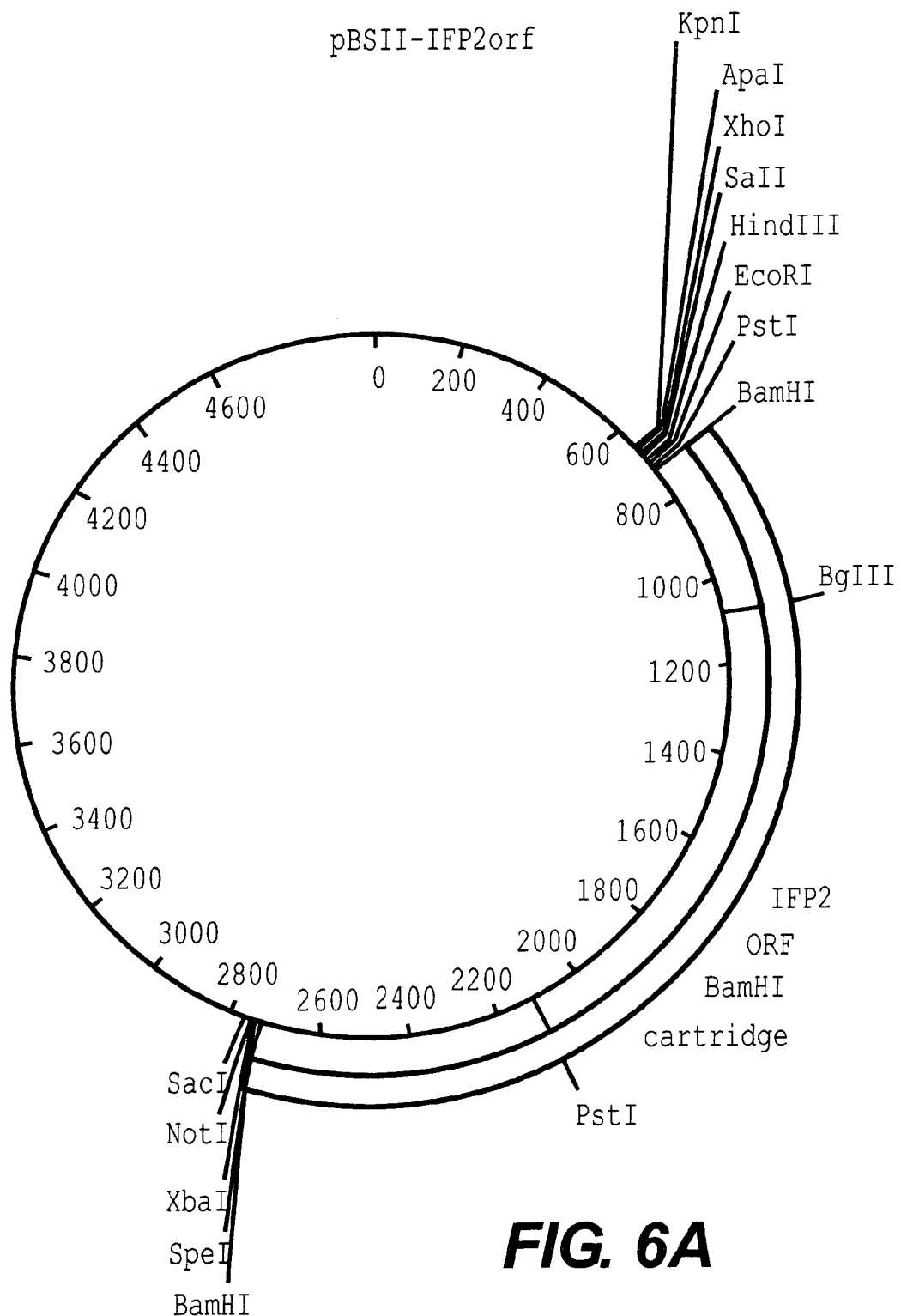
FIG. 6(A) is a plasmid map showing that the piggyBac ORF BamHI cartridge from pCaSpeR-hs-orf was cloned into the pBSII (Stratagene) positioning it for transcription under control of the T7 promoter to form pBSII-IFP2orf; (B) is the nucleotide sequence (SEQ ID NO: 43) of pBSII-IFP2-orf.

In some eukaryotic systems, the heat shock promoter may not function to express the transposase protein. An additional plasmid was constructed to allow in vitro expression of the messenger RNA sequence of the piggyBac transposase. Co-injection of this mRNA into embryos along with the piggyBac vectors would allow translation of the piggyBac transposase without having to rely on the expression of the mRNA from a promoter which may or may not be active in the desired system. In addition, this strategy provides much more transposase protein in the embryos, leading to a greater mobility of the piggyBac vectors. The BamHI cartridge was excised from the plasmid pCaSpeR-hs-orf by restriction digestion with BamHI and ligated into a BamHI digested commercially available vector; pBSII (Stratagene) to make pBSII-IFP2orf (FIG. 6), allowing in vitro transcription of the piggyBac transposase mRNA under control of the bacteriophage T7 promoter.

Example 9

Alternative Promoters for the PiggyBac Transposase Gene

Figure 7:
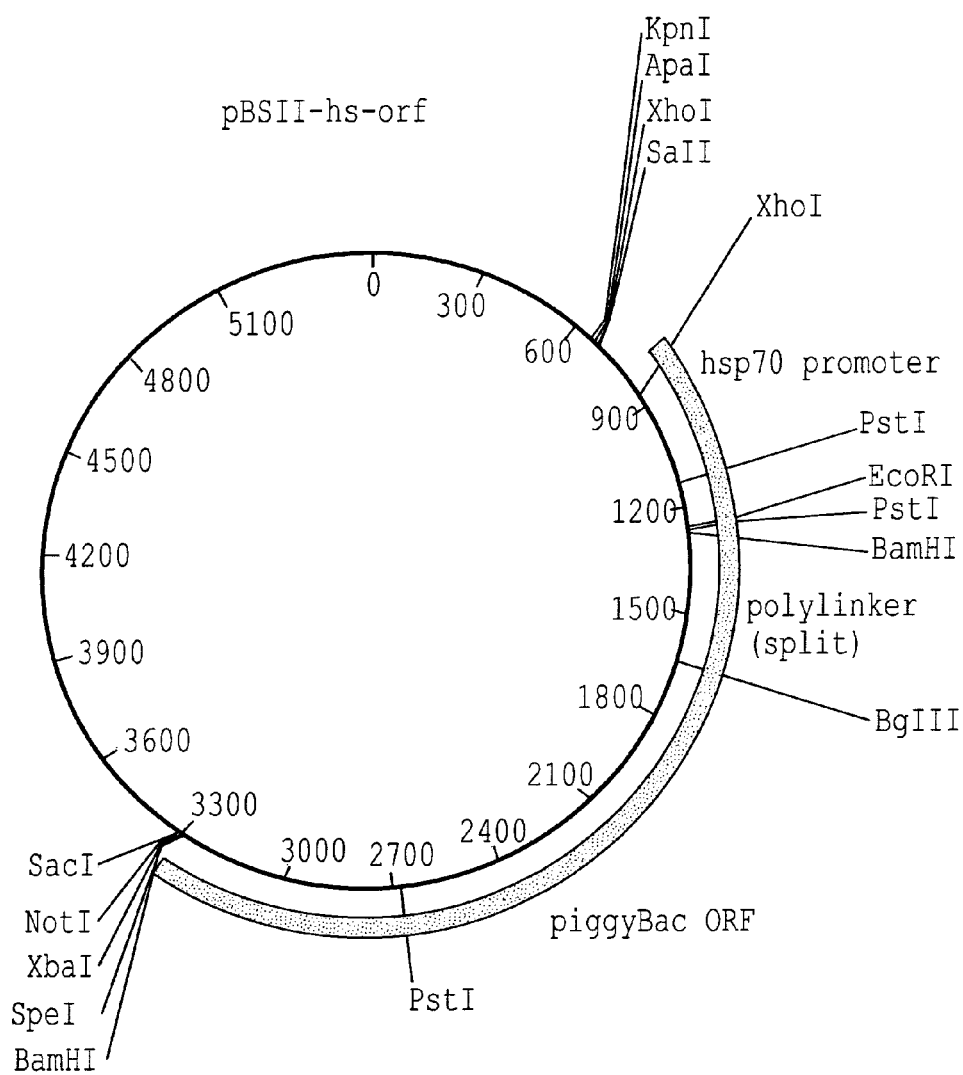
FIG. 7(A) is a plasmid map showing that the hsp70 promoter was excised from the pCaSpeR-hs plasmid by EcoR I and EcoR V digestion, followed by blunt ending, and cloned into pBSII-IFP2orf at the EcoR I and Hind III (blunt ended) sites to form pBSII-hs-orf; (B) is a nucleotide sequence from pBSII-hs-orf.
Figure 8A:
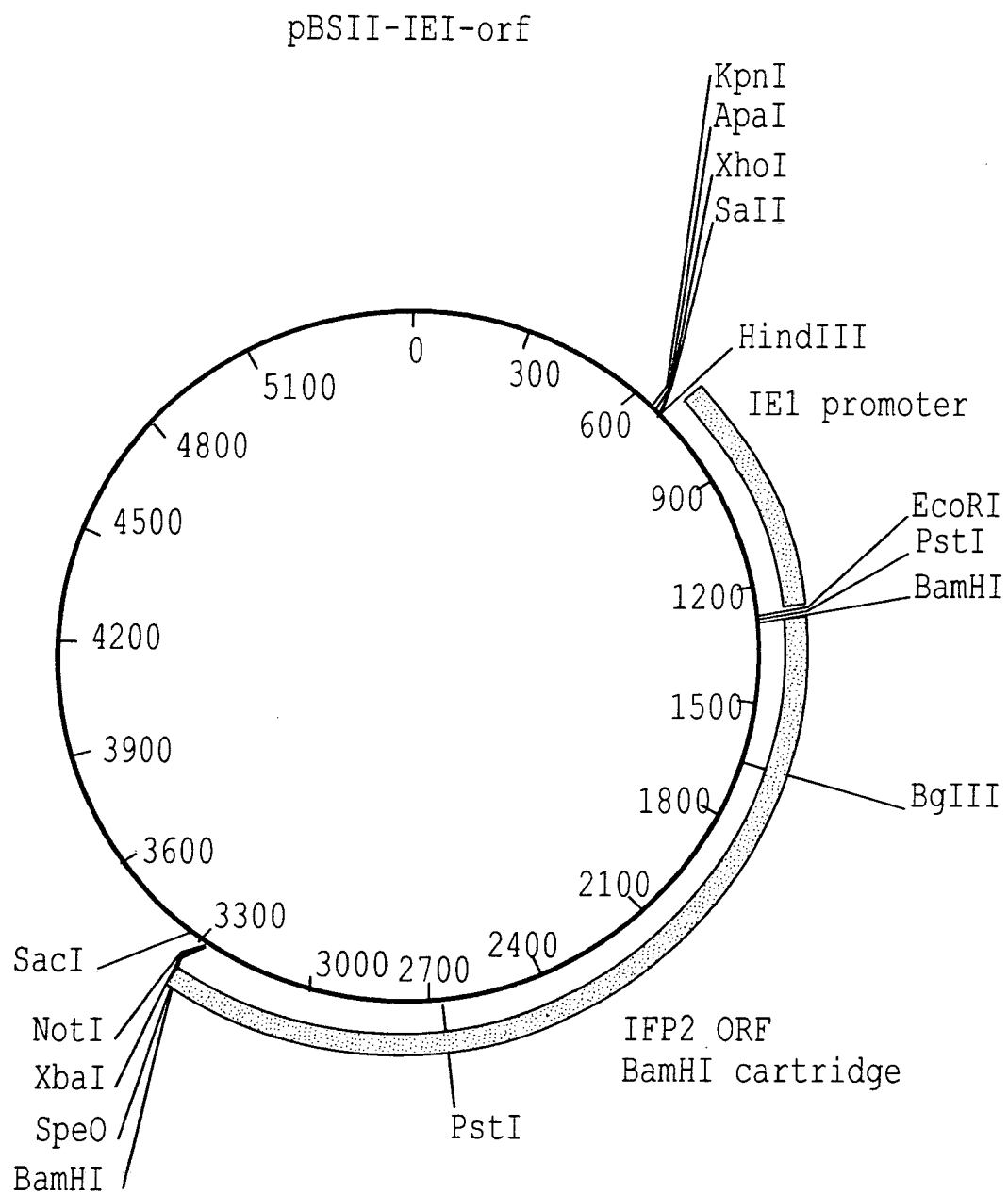
FIG. 8(A) is a plasmid map showing that the IE1 promoter was PCR amplified from the pIE1FB plasmid (Jarvis et al., 1990) and cloned into the pBSII-IFP2orf plasmid to form pBSII-IE1-orf; (B) is the nucleotide sequence (SEQ ID NO: 44) of pBSII-E1-orf.
Figure 21A:
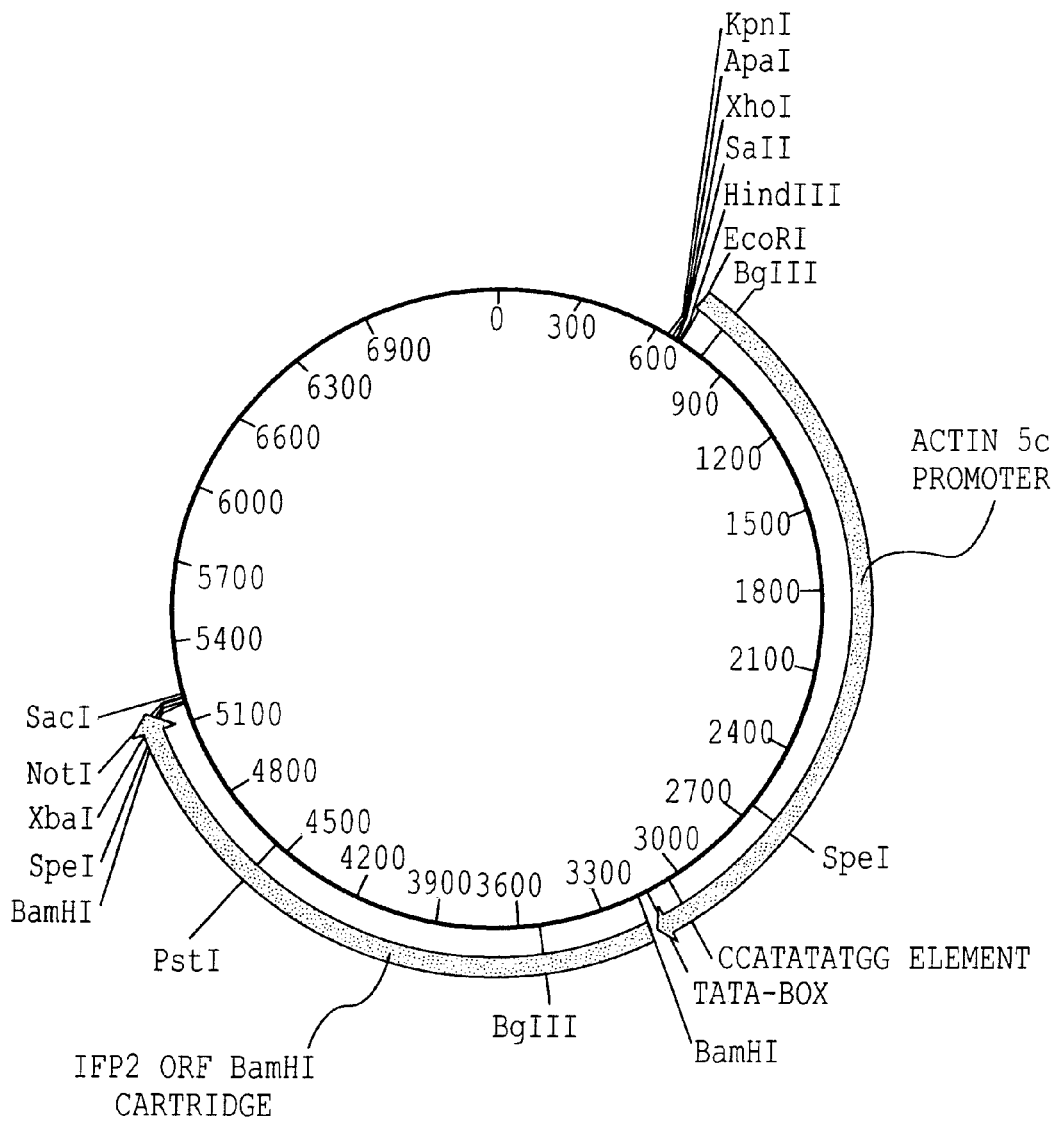
FIG. 21(A) is a plasmid map showing that the Actin 5c promoter was cloned as a BamHI and Eco I fragment (bases 3046 to 3055 of SEQ ID NO: 67) from the pHAct5cEFGP plasmid (from Dr. Atkinson, UC Riverside) into the BamHI and EcoRI sites of the pBSII plasmid (Stratagene) to form the pBSII-Act5c plasmid The piggyBac ORF BamHI cartridge from pCaSpeR-hs-orf was then cloned into pBSII-Act5c plasmid under control of the Act5c promoter; (B) is the nucleotide sequence (SEQ ID NO: 67) of pBSII-Act5c-orf.

Further modification of pBSII-IFP2orf may be effected to introduce alternative promoters that would drive expression of the piggyBac transposase gene. Three examples are provided. pBSII-hs-orf (FIG. 7) was constructed by excising the heat shock promoter region from pCaSpeR-hs using EcoR I and EcoR V digestion followed by blunt end polishing of the EcoRI terminus, and ligating the fragment to the blunt end polished EcoRI/HindIII digested pBSII-IFP2orf plasmid. The plasmid pBSII-IE1-orf was prepared by PCR amplification of the IE1 promoter from the plasmid pIE1FB using the primers IE1-Ac-for (5' ACGTAAGCT-TCGATGTCTTTGTGATGCGCC 3') (SEQ ID NO: 6) and IE1-Ac-rev (5' ACGGAATTCACTTGCAACTGAAA-CAATATCC 3') (SEQ ID NO: 7) to generate an EcoRI/HindIII tailed fragment that was then inserted into EcoRI and HindIII digested pBSII-IFP2orf. This plasmid allows constitutive expression of the piggyBac transposase in a diversity of eukaryotic systems. A final demonstration was prepared by digesting the plasmid pHAct5cEGFP (Pinkerton et al., 2000) with BamHI and EcoRI to recover the *Drosophila* Actin 5c promoter which was then inserted into pBSII digested with EcoRI and BamHI. The BamHI cartridge from pCaSpeR-hs-orf was excised by digestion with BamHI and cloned downstream of the Actin 5c promoter at the unique BamHI to form the plasmid pBSII-Act5c-orf (FIG. 21). This allows high level expression of the piggyBac transposase in embryos of insects.

Example 10

Transposase Expression in Vertebrate Systems

Figure 9A:
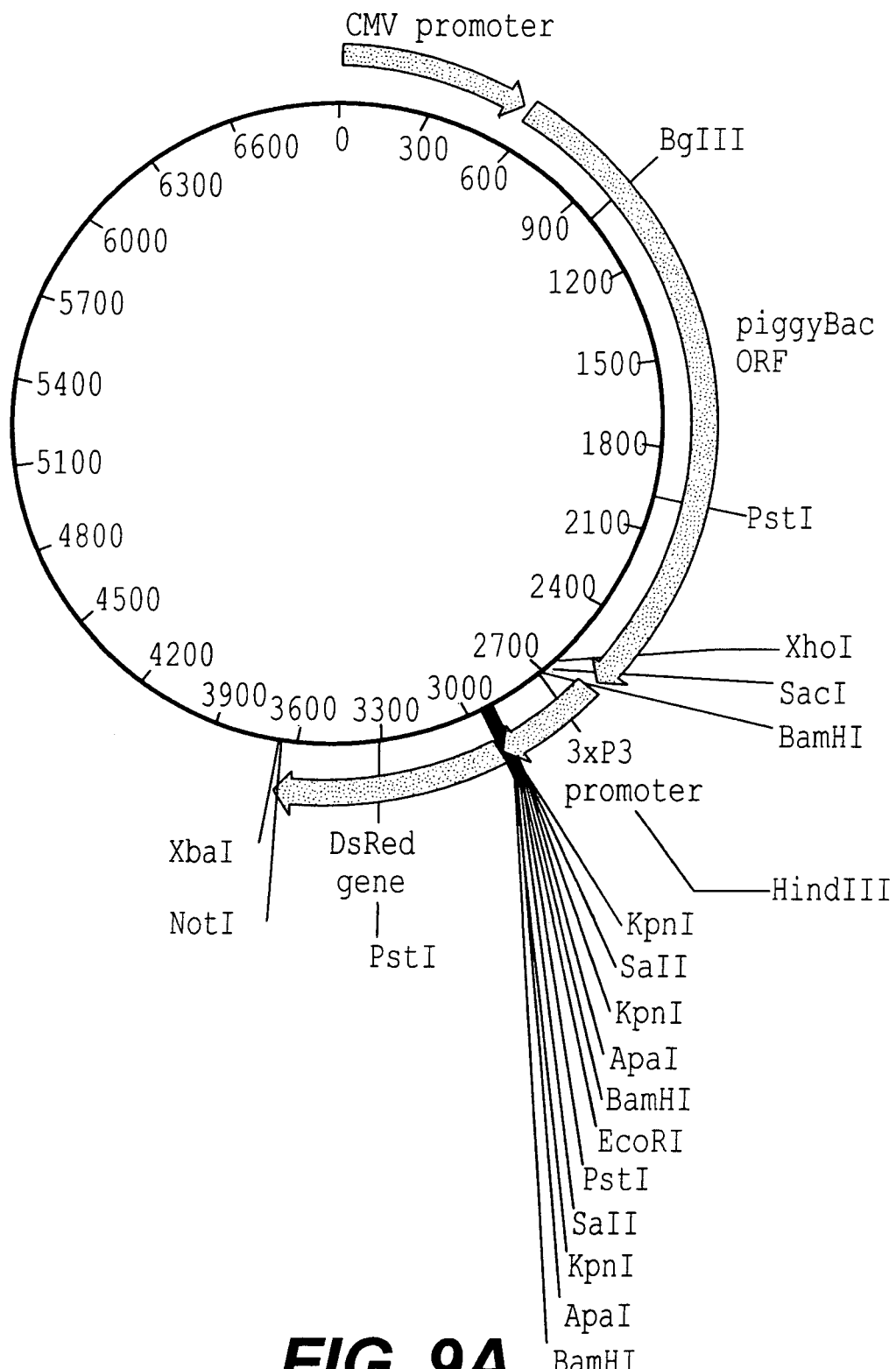
FIG. 9(A) is a plasmid map showing that the base plasmid is pDsRed1-N1 (Clontech). The 3xP3 promoter was PCR amplified from pBac [3xP3-EYFPafm] (Horn and Wimmer, 2000) and cloned into the Xho I and EcoR I sites of pDsRed1-N1 to form the p3xP3-DsRed plasmid. The piggyBac ORF BamHI cartridge from pCaSpeR-hs-orf was then cloned into the BglII site of p3xP3 DsRed positioning it under control of the CMV (cytomegalovirus) promoter to form p3xP3-DsRed-orf; (B) is the nucleotide sequence (SEQ ID NO: 45) of p3xP3-DsRed-orf DsRed is a marker from Invitrogen and 3xP3 is a promoter specific for eyes of insects.

While all of the constructs in Example 9 permit expression of the transposase in insect systems, they may not permit optimal expression of the transposase in vertebrate systems. Using the commercially available pDsRed1-N1 plasmid (Clonetech) the BamHI cartridge was cloned from pBSII-IFP2orf into the BamHI site adjacent to the CMV promoter to effect efficient expression of the piggyBac transposase in vertebrate systems. This plasmid was further modified by adding the 3xP3 promoter through PCR amplification of this promoter from the plasmid pBacl[3xP3-EYFPafm] (Horn and Wimmer, 2000) using the primers 3xP3-for (5' ACTCTCGAGGTTCCCACAATGGTTAAT-TCG 3') (SEQ ID NO: 8) and 3xP3-rev (5' ACTGAAT-TCATGGTGGCGACCGGTGGATCG 3') (SEQ ID NO: 9) to generate a XhoI/EcoRI tailed cartridge that was then cloned into the XhoI and EcoRI digested pDsRed1-N1 backbone to generate the plasmid p3XP3-DsRed-orf (FIG. 9).

Example 11

Optimizing PiggyBac

In some cases it may be preferable to inject transposase protein to permit movement of the piggyBac transposon. The natural piggyBac transposase sequence is not efficiently expressed in prokaryotic systems due to a preponderance of eukaryotic codons. To achieve better expression of the piggyBac transposase in bacterial systems for purification and functional utility a sequence called optimized piggyBac orf (FIG. 23) was created, substituting prokaryotic codon biases wherever possible. This sequence generated the same protein sequence, but represents an artificial gene expressing the piggyBac transposase.

Materials and Methods for Examples 1–11

Plasmids p3E1.2 deletion series: The p3E1.2 plasmid (Fraser et al., 1995) was first linearized using the restriction sites BamHI and EcoRI, blunt ended with the klenow fragment, then religated to construct the p3E1.2(DMCS) eliminating the MCS of the pUC18 sequence. Internal deletions were made using the Erase-A-Base System (Promega). p3E1.2(DMCS) was cut at the unique SacI site within the piggyBac element, generating an ExoIII resistant end, and then cut at the BglII site to generate an ExoIII sensitive end. Fractions of the ExoIII deletion reaction from the BglII site toward the 3' terminus were stopped every 30 seconds, and were blunt ended by S1 nuclease, recircularized, and transformed into DH5a cells. Recovered plasmids were size analyzed using a quick screen method (Sekar, 1987). The presence of intact 3' termini was confirmed using a BsiWI digestion, and then sequenced. Nine consecutive plasmids in the size range of approximately 100~200 bp deletions were recovered and named p3E1.2-d-1 to p3E1.2-d-9, with p3E1.2-d-9 having the maximum deletion (FIG. 1).

pIAO-P/L series: The p3E1.2 B/X plasmid was constructed as a pCRII TA clone (Invitrogen) of the entire piggyBac transposon and flanking TTAA targets sites following PCR from the plasmid p3E1.2 using the BamHI/XbaI-tailed primer M1F34 (5'-GGATCCTCTAGATTAACCCTAGAAAGATA-3') (SEQ ID NO: 10). The element and flanking TTAA sites were then excised using the enzyme BamHI and ligated to form a circular molecule. Two outward facing internal piggyBac primers, one with a terminal ApaI site (5'-GAAA GGGCCCGTGATACGCCTATTTTTATAGGTT-3') (SEQ ID NO: 11) and the other with a terminal KpnI site (5'-AATC GGTACCAACGCGCGGGGAGAGGCGGTTTGCG-3') (SEQ ID NO: 12), were used to generate a linear ApaI/KpnI-tailed fragment. This fragment was ligated to a PCR fragment containing the beta-1 actamase gene and *E. coli* replication origin amplified from pUC18 using an ApaI-tailed primer (5'-CCAA GGGCCCTGACGTGAACCATTGTCACACGT-3') (SEQ ID NO: 13) and a KpnI tailed (5'-TGT GGGTACCGTCGATCAAACAAACGCGAGATAC CG-3') (SEQ ID NO: 14) primer pair. The resulting pIAO plasmid contains the circularized piggyBac transposon with ends separated by an 18 bp fragment of DNA having the restriction sites configuration xbaI/BamHI/xbaI, with a beta-lactamase gene and the *E. coli* origin of replication. The lacZ gene under the control of the polyhedron promoter was excised from pD-2/B-gal (Fraser et al., 1996) using restriction enzymes NruI and DraI, and cloned into the unique HpaI site within the piggyBac element of pIAO to form pIAO-polh/lacZ (pIAO-P/L) plasmid.

The pIAO-P/L-TTAA1 plasmid was constructed by digesting pIAO-polh/lacZ with SphI and BsiWI, and the fragment containing the internal-piggyBac sequence was isolated. Two complementing oligonucleotides, SphI (5'-CGTCAATTTTACGCAGACTATCTTTCTAGGG-3') (SEQ ID NO: 15) and TTAA-SphI (5'-TTAACCCTA-GAAAGATAGTCTGCGTAAAATTGACGCATG-3') (SEQ ID NO: 16), were annealed to form a SphI site on one end and a TTAA overhang on the other end. A second pair of oligonucleotides, BsiWI (5'-GTACGTCACAATATGAT-TATCTTTCTAGGG-3') (SEQ ID NO: 17) and TTAA-BsiWI (5'-TTAACCCTAGAAAGATAATCATATTGT-GAC-3') (SEQ ID NO: 18) were annealed to form a BsiWI site on one end and a TTAA overhang on the other. These two primer pairs were joined using the TTAA overlaps and inserted into the SphI and BsiWI sites of the digested pIAO-polh/lacZ plasmid to form the circular pIAO-P/L-TTAA1 plasmid.

The pIAO-P/L-TTAA2 plasmid was constructed in a similar manner by combining the SphI-terminal primer with TTAATTAA-SphI (5'-TTAATTAACCCTAGAAAGAT-AGTCTGCGTAAAATTGACGCATG-3') (SEQ ID NO:

19), and the BsiWI primer with TTAATTAA-BsiWI (5'-TTAATTAACCCTAGAAAGATAATCATATTGTGAC-3') (SEQ ID NO: 20).

The plasmids pIAO-P/L-2.2 kb, pIAO-P/L-589 bp, pIAO-P/L-354 bp, pIAO-P/L-212 bp and pIAO-P/L-73 bp were constructed by insertion of HindIII or PvuII fragments from the bacteriaphage lambda into the blunt ended XbaI site between the adjacent TTAA target sites of pIAO-polh/lacZ.

Plasmids pIAO-P/L-55 bp, pIAO-P/L-40 bp and pIAO-P/L-22 bp were constructed by annealing oligonucleotide pIAO-4501 (5'-CTAGTACTAGTGCGCCGCGTACG TCTAGAGACGCGCAGTCTAGAAD-3') (SEQ ID NO: 21) and pIAO-4502 (5'-TTCTAGACTGCGCGTC TCTAGACGTACGCGGCGCACTAGTACTAGD-3') (SEQ ID NO: 22), forming two XbaI sites and one SpeI site, and ligating them into the blunt ended pIAO-P/L XbaI fragment to generate pIAO-P/L-55 bp. The pIAO-P/L-40 bp plasmid was constructed by cutting pIAO-P/L-55 bp plasmid at the XbaI sites of the inserted fragment and then religating. Cutting pIAO-P/L-40 bp at the XbaI and SpeI sites, and religating formed the pIAO-P/L-22 bp plasmid.

The pIAO-P/L-18 bp plasmid was constructed by PCR amplification of the pIAO-P/L plasmid using the pIAO— 18 bp primer (5'-GATGACCTGCAGTAGGAAGACGD3') (SEQ ID NO: 23) and the TR-18 bp primer (5'-GAC TCTAGACGTACGCGGAGCTTAACCCTAGAAAGATAD3') (SEQ ID NO: 24). The amplified fragment was cut with XbaI and PstI, and ligated to the pIAO-P/L XbaI and PstI cut fragment.

pCRII-ITR, pCRII-JF03/04 and pBS-ITR plasmids: The oligonucleotide ITR (5'-GGATTCCATGCGTCAATTTTACGCAD-3') (SEQ ID NO: 25), having the piggyBac IR and a terminal BamHI site, was used to PCR amplify the piggyBac 3' and 5' IRs and TRs along with their spacer regions from the pIAO-P/L-589 bp plasmid. The PCR fragment was TA cloned into pCRII (Invitrogen). The resulting plasmid, pCRII-ITR, replaces the entire internal sequence of piggyBac with the pCRII plasmid sequences. A second plasmid, pCRII-JF03/04, was constructed using the same strategy with the primers JFO3 (5'-GGATCCTCGATATACAGACCGATAAAAACACATGD-3') (SEQ ID NO: 26) and JFO4 (5'-GGTACCATTGCAAACAGCGACGGATTCGCGCTATD-3') (SEQ ID NO: 27). JFO3 is 83 bp internal to the 5' terminus, JFO4 is 90 bp internal to the 3' terminus. To construct the pBS-ITR plasmid, the 702 bp BamHI fragment was excised from the pCRII-ITR plasmid and inserted into the BamHI site of the pBlueScript (Stratagene) plasmid.

pXL-Bac plasmid: The 702 bp fragment containing the piggyBac terminal repeats isolated from pCRII-ITR plasmid BamHI digestion was religated to form a circular molecule, followed by BssHII digestion. The pBlueScript II plasmid was also digested by BssHII and the large fragment was band isolated. These two fragments were ligated together to form the pBSII-ITR (Rev) plasmid. The Multiple Cloning Site (MCS) was PCR amplified from the pBSII plasmid using the MCS for (5'-ACGCGT AGATCTTAATACGACTCACTATAGGG-3') (SEQ ID NO: 28) and MCS-rev (5'-ACGCGT AGATCTAATTAACCCTCACTAAAGGG-3') (SEQ ID NO: 29) primers, and cloned into BamHI site of pBSII-ITR(Rev) to construct the pXL-Bac plasmid.

The pXL-Bac minimum piggyBac vector was constructed by circularizing an ITR BamHI fragment, followed by BssHII digestion. The resulting BssHII fragment was then ligated to the pBlueScript II BssHII AMP/ori containing fragment. The multiple cloning site was PCR amplified from pBSII plasmid and inserted into BamHI site to form the pXL-Bac vector. Any desired gene may be inserted into the MCS [the BssHII fragment taken from pBSII (Stratagene)] to construct a piggyBac transposon.

Helper plasmid: phspBac (formerly pBhsDSac, Handler et al., 1998) is a transposase-providing helper plasmid that expresses the piggyBac ORF under the control of the *D. melanogaster* hsp 70 promoter.

Target plasmid: pGDV1 is a *Bacillus subtilis* plasmid (Sarkar et al., 1997a) containing a chloramphenicol resistance gene, and is incapable of replication in *E. coli* unless provided with an *E. coli* origin of replication.

Microinjection: *T. ni* embryos were collected approximately 2 hours post oviposition and microinjected as described by Lobo et al., (1999). After injection, the embryos were allowed to develop for one hour at room temperature, heat shocked at 37° C. for one hour, and allowed to recover at room temperature overnight. Plasmids were recovered using a modified Hirt (1967) extraction procedure.

Excision Assay: The excision assay was performed as described by Thibault et al., (1999). Precise excision events were confirmed by sequencing using a fluorescent labeled M13 reverse primer (Integrated DNA Technologies, Inc.).

Interplasmid Transposition Assay: The interplasmid transposition assay was performed as described by Lobo et al. (1999) and Sarkar et al. (1997a). Plasmids isolated from the injected and heat-shocked embryos, as well as those passaged through *E. coli* only, were resuspended in 20 µl of sterile distilled water and 3 µl of the DNAs were then electropotated into 10 µl of competent *E. coli* DH 10B cells (Gibco-BRL) (Elick et al., 1996a). A 1.0-ml aliquot of SOC (2% w/v Bactotryptone, 0.5% w/v Bacto yeast extract, 8.5 mM NaCl, 2.5 mM Kcl, 10 mM $MgC_2$ 20 mM glucose) was added to the electroporated cells, and the cells were allowed to recover at 37° C. for 15 minutes. An aliquot (1%) of the transformed bacteria was plated on LB plates containing ampicilin (100 µg/ml) and X-Gal (5-bromo-4-chloro-3-indolyl-β3-D-galactosidase; 0.025 µg/ml), and the rest were plated on LB plates containing kanamycin (10 µg/ml), chloramphenicol (10 µg/ml) and X-Gal (0.025 µg/ml). Restriction analysis using HindIII and EcoRV and PCR using outward facing primers specific to piggyBac (JF01: 5'-CCTCGATATACAGACCGATAAAACACATG-3' (SEQ ID NO: 30) and JF02: 5'-GCACGCCTCAGCCGAGCTC-CAAGGGCGAC-3' (SEQ ID NO: 31)) enabled the preliminary identification of clones with putative interplasmid transposition events. The right insertion site of the clones was sequenced, with the Thermo Sequenase fluorescence-labeled primer sequencing kit (Amersham) and an ALF Express Automated Sequencer (Pharmacia Biotech), using the fluorescence-labeled JF02 primer, while the left insertion site was sequenced with the MF 11 reverse primer (5'-GGATCCCTCAAAATTTCTTCTAAAGTA-3') (SEQ ID NO: 32).

To check for plasmid replication in the embryos, Hirt-extracted plasmid DNAs recovered from injected *D. melanogaster* embryos were digested with the restriction enzyme DpnI (Geier and Modrich, 1979). *E. coli* cells were transformed with equal volumes of the digested and undigested plasmid DNAs and plated on LB plates containing kanamycin, chloramphenicol and X-Gal as above.

The pIAO-P/L series transposition events were sequenced using the fluorescent labeled MF 11-reverse primer (5'-GGATCCCTCAAAATTTCTTCTAAAGTA-3') (SEQ ID NO: 33) and JF02 primer (5'-GCACGCCTCAGC- CGAGCTCCAAGCGGCGAC-3') (SEQ ID NO: 34), and the pCRII-ITR and pBSII-ITR transposition events were sequenced using fluorescent labeled M13 reverse primer.

Automatic Thermocycle Sequencing: Sequencing was performed using the Thermo Sequenase Fluorescent Labeled Primer Sequencing Kit (Amersham) and the ALF Express Automated Sequencer (Pharmacia Biotech), following standard protocols provided by the manufacturers.

Figure 12A:
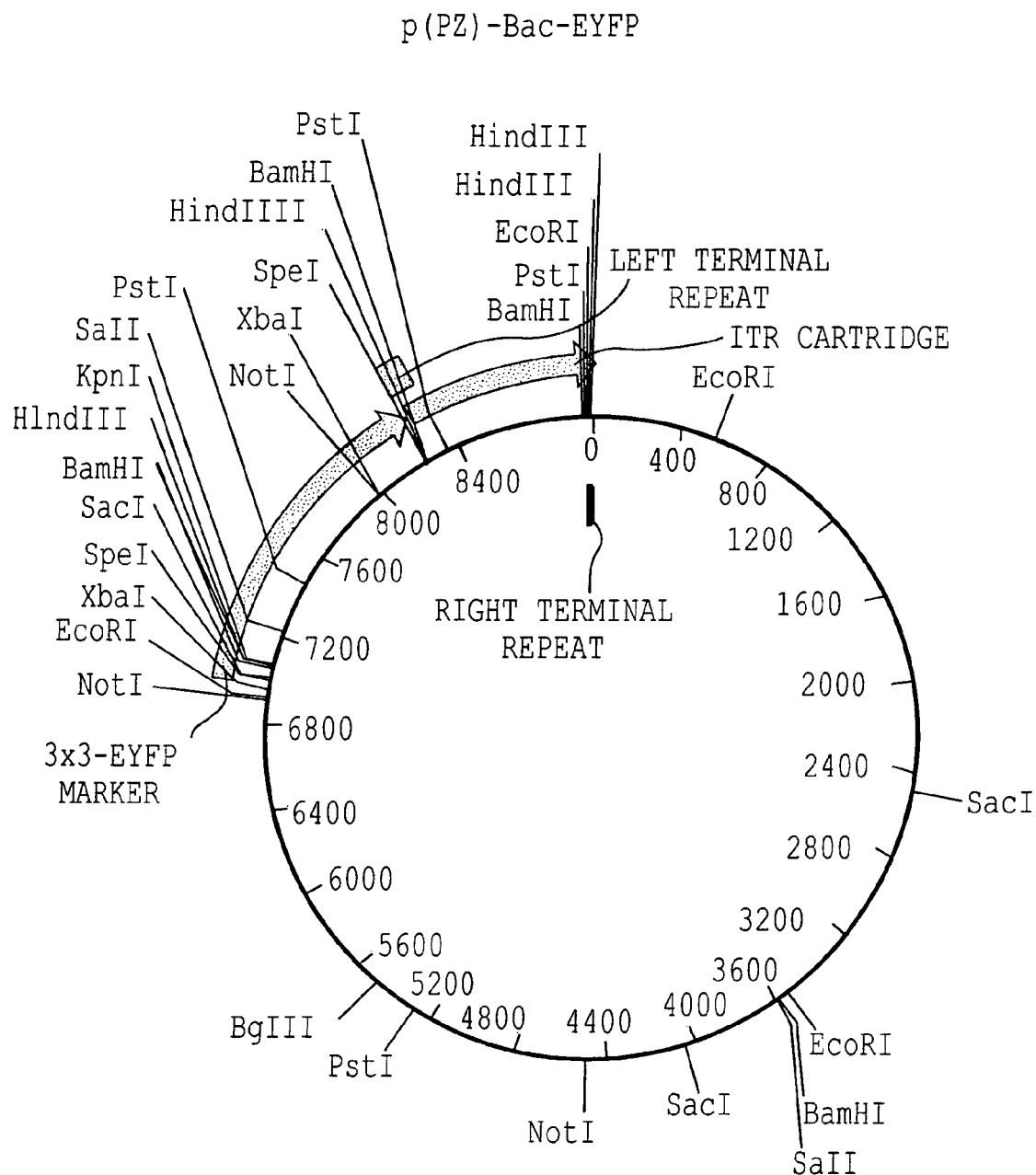
FIG. 12(A) is a plasmid map showing that the P element enhancer trap plasmid pP{PZ} (from Dr. O'Tousa, Univ. of Notre Dame) was digested with Hind III then self-ligated to produce the p(PZ)-HindIII plasmid. The ITR cartridge was excised using Sal I and Not I (blunt-ended) from pCRII-ITR and then cloned into the blunt ended Hind III site to form p(PZ)-Bac. The 3xP3-EYFP was PCR amplified as an Spe I fragment from pBac[3xP3-EYFPafm] (Horn and Wimmer, 2000) and cloned into the Spe I site of p(PZ)-Bac plasmid to form the p(PZ)-Bac-EYFP plasmid; (B) is the nucleotide sequence (SEQ ID NO: 48) of p(PZ)-Bac-EYFP.
Figure 13A:
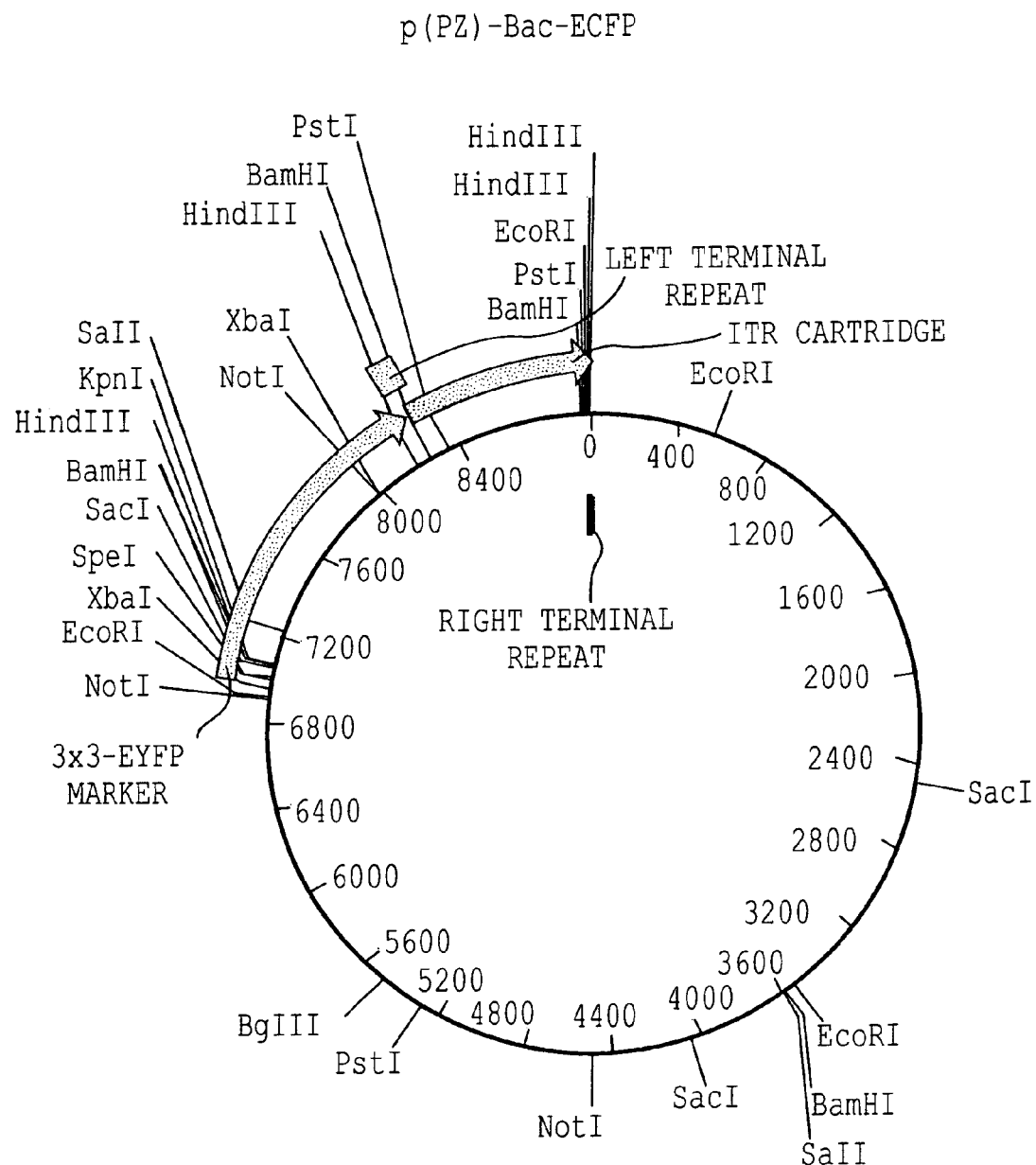
FIG. 13(A) is a plasmid map showing that the P element enhancer trap plasmid pP{PZ} (from Dr. O'Tousa, Univ. of Notre Dame) was digested with HindIII then self-ligated to produce the p(PZ-)-HindIII plasmid. The ITR cartridge was excised using Sal I and Not I (blunt ended) from pCRII-ITR and then cloned into the blunt ended Hind III site to form p(PZ)-Bac. The 3xP3-ECFP was PCR amplified as an Spe I fragment from pBac[3xP3-ECFPafm] (Horn and Wimmer, 2000) and cloned into the Spe I site of the p(PZ)-Bac plasmid to form the p(PZ)-Bac-ECFP plasmid; (B) is the nucleotide sequence (SEQ ID NO: 49) of p(PZ)-Bac-ECFP.
Figure 14A:
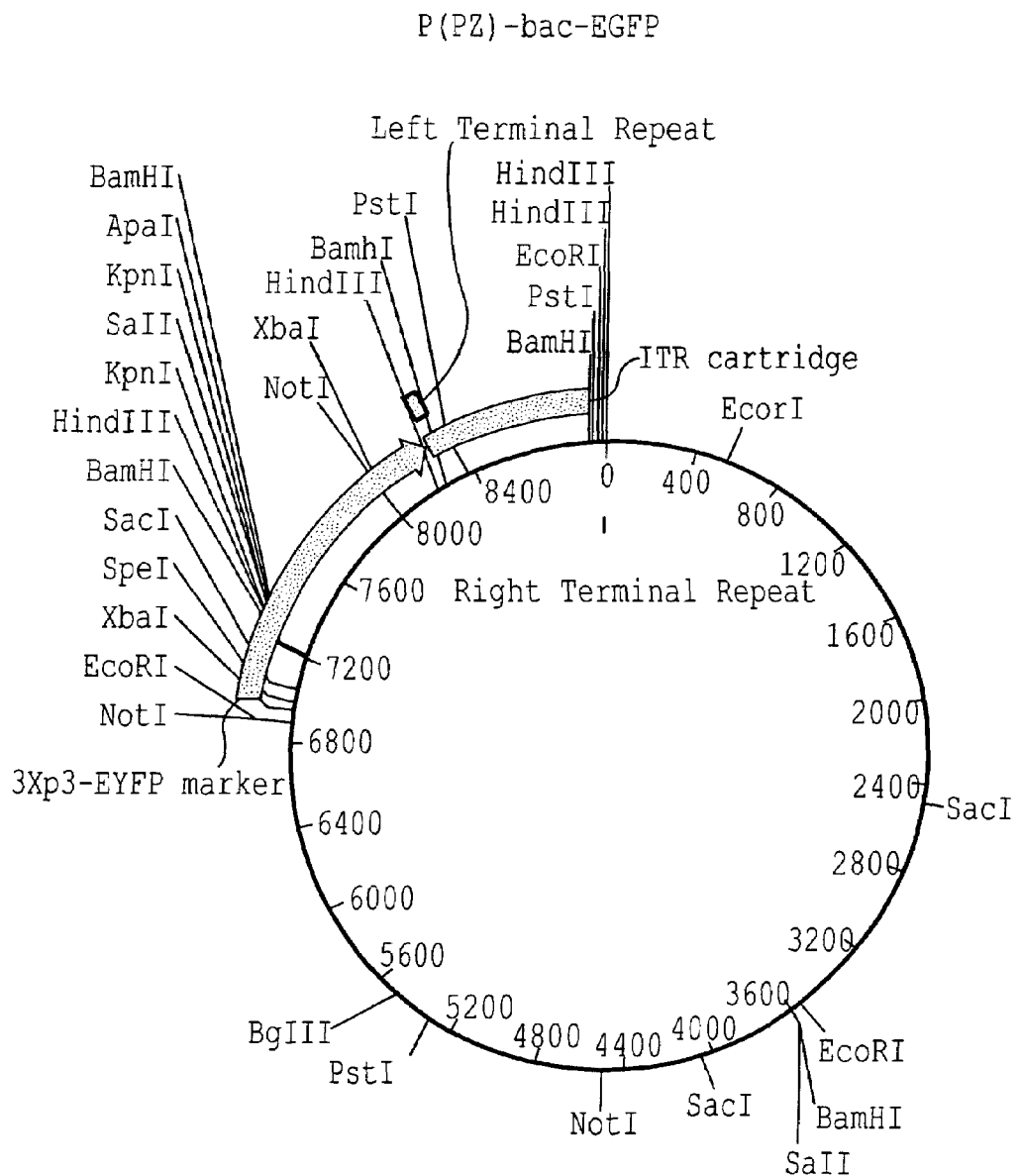
FIG. 14(A) is a plasmid map showing that the P element enhancer trap plasmid pP{PZ} (from Dr. O'Tousa, Univ. of Notre Dame) was digested with Hind III then self-ligated to produce the p(PZ)-HindIII plasmid. The ITR cartridge was excised using Sal I and Not I (blunt ended) from pCRII-ITR and then cloned into the blunt ended HindIII site to form p(PZ)-Bac. The 3xP3-EGFP was PCR amplified as an Spe I fragment from pBac[3xP3-EGFPafm] (Horn and Wimmer, 2000) and cloned into the Spe I site of the p(PZ)-Bac plasmid to form the p(PZ)-Bac-EGFP plasmid; (B) is the nucleotide sequence (SEQ ID NO: 50) of p(PZ)-Bac-EGFP.

Other Plasmids: FIGS. 12, 13 and 14 present alternative plasmids that may be useful for gene transfer.

Example 12

The present invention also provides ID sequences adjacent to the TRD of the piggyBac transposon that contribute to a high frequency of germline transformation in D. melanogaster. The present invention provides an analysis of a series of PCR synthesized deletion vectors constructed with the 3xP3-ECFP gene as a transformation marker (Horn and Wimmer, 2000). These vectors define ID sequences immediately adjacent to the 5' TRD and 3' TRD adjacent ID sequences that effect efficient germline transformation of D. melanogaster. Using this information, the present invention provides a new ITR cartridge, called ITR1.1K, and verifies its utility in converting an existing plasmid into a mobilizable piggyBac vector that enables efficient germline transformation. The present invention also provides a transposon-based cloning vector, pXL-BacII, for insertion of sequences within a minimal piggyBac transposon and verifies its capabilities in germline transformations.

Materials and Methods for Example 12

Plasmids

The pCaSpeR-hs-orf helper plasmid was constructed by PCR amplifying the piggyBac open reading frame using IFP2orf_For and IFP2orf_Rev primers, cloning into the pCRII vector (Invitrogen), excising using BamH I, and inserting into the BamH I site of the P element vector, pCaSpeR-hs (Thummel, et al., 1992). A single clone with the correct orientation and sequence was identified and named pCaSpeR-hs-orf (FIG. 24).

The p(PZ)-Bac-EYFP plasmid was constructed from the p(PZ) plasmid (Rubin and Spradling, 1983) by digesting with Hind III and recircularizing the 7 kb fragment containing LacZ, hsp70 and Kan/ori sequences to form the p(PZ)-7 kb plasmid. The ITR cartridge was excised from pBSII-ITR (L1 et al., 2001b) using Not I and Sal I and blunt end cloned into the Hind III site of the p(PZ)-7 kb plasmid. A 3xP3-EYFP marker gene was PCR amplified from pBac{3xP3-EYFPafm} (Horn and Wimmer, 2000), digested with Spe I, and inserted into the Xba I site to form p(PZ)-Bac-EYFP. It contains the LacZ gene, Drosophila hsp70 promoter, Kanamycin resistance gene, ColE1 replication origin, 3xP3-EYFP marker and the piggyBac terminal repeats-only ITR cartridge (FIG. 24).

The pBSII-3xP3-ECFP plasmid was constructed by PCR amplifying the 3xP3-ECFP marker gene from pBac{3xP3-ECFPafm} (Horn and Wimmer, 2000) using the primer pair ExFP_For and ExFP_Rev, then digesting the amplified fragment with Spe I, and cloning it into the Xba I site of pBlueScript II plasmid (Stratagene).

Figure 25:
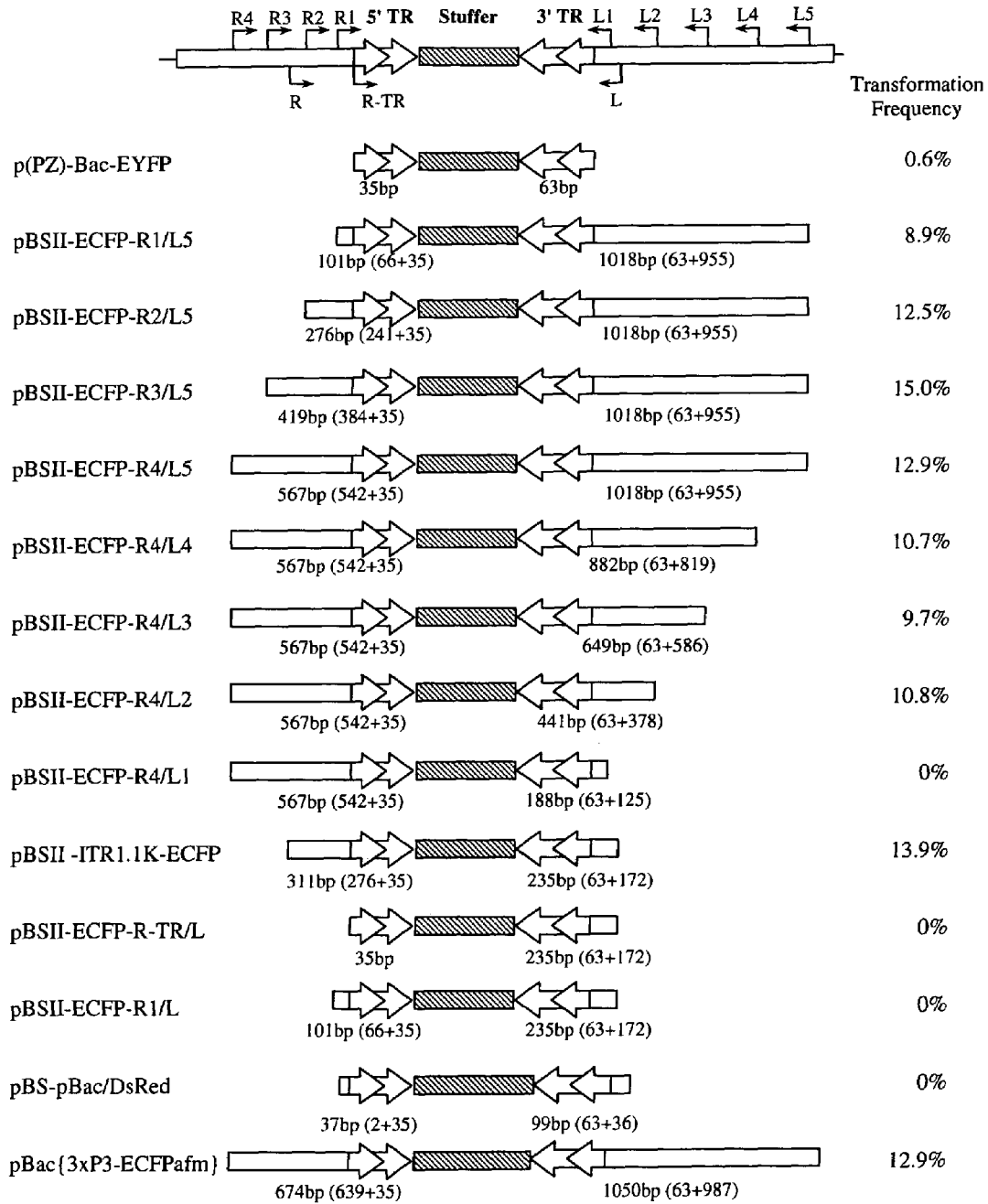
FIG. 25 is a schematic illustration of piggyBac internal deletion series plasmids based on the pIAO-P/L-589 bp. The 5' Terminal Repeat is 35 bp in length and the 3' Terminal Repeat is 63 bp in length. The p(PZ)-Bac-EYFP plasmid contains only the piggyBac terminal repeat regions using the ITR cartridge of Li et al., 2001.

The piggyBac synthetic internal deletion plasmids were constructed by PCR amplification from the pIAO-P/L-589 bp plasmid (L1 et al., 2001b) using a series of primers. A total of 9 PCR products were generated using the combination of IFP2_R4 against all five IFP2_L primers and IFP2_L5 against all four IFP2_R primers. Two additional PCR products were also obtained using the IPF2_R-TR+ IFP2_L and IFP2_R1+IFP2_L primer pairs. These PCR products were then cloned into the pCR II vector using the TOPO TA cloning kit (Invitrogen), excised using Spe I digestion, and cloned into the Spe I site of the pBSII-3xP3-ECFP plasmid to form the piggyBac internal deletion series (FIG. 25). The pBSII-ITR1.1K-ECFP plasmid (FIG. 24) was constructed by cloning the EcoR V/Dra I fragment from pIAO-P/L-589 bp, which contained both piggyBac terminal repeats, into the EcoR V site of pBSII-3xP3-ECFP. The pXL-BacII-ECFP plasmid (FIG. 24) was constructed by PCR amplifying the ITR1.1k cartridge from pBSII-ITR1.1k-ECFP plasmid using MCS_For and MCS_Rev primers flanking by Bgl II site, cutting with Bgl II, religating and cutting again with BssH II, then inserting into the BssH II sites of the pBSII plasmid.

A separate cloning strategy was used to construct pBS-pBac/DsRed. The 731 bp Ase I-blunted fragment from p3E1.2, including 99 bp of 3' piggyBac terminal sequence and adjacent NPV insertion site sequence, was ligated into a unique Kpn I-blunted site in pBS-KS (Stratagene). The resulting plasmid was digested with Sac I and blunted, then digested with Pst I, and ligated to a 173 bp Hinc II-Nsi I fragment from p3E1.2, including 38 bp of 5' piggyBac terminal sequence. The pBS-pBac minimal vector was marked with polyubiquitin-regulated DsRed1 digested from pB[PUbDsRed1] (Handler and Harrell, 2001a) and inserted into an EcoR I-Hind III deletion in the internal cloning site within the terminal sequences.

Transformation of Drosophila melanogaster

The D. melanogaster w[1118] white eye strain was used for all microinjections employing a modification of the standard procedure described by Rubin and Spradling (1982), in which the dechorionation step was eliminated. Equal concentrations (0.5 ug/ul) of each of the internal deletion plasmids, or the control plasmid pBac{3xP3-ECFPafm}, were injected along with an equal amount of the pCaSpeR-hs-orf helper plasmid into fresh fly embryos followed by a one hour heat shock at 37° C. and recovery overnight at room temperature. Emerging adults were individually mated with w[1118] flies, and progeny larvae were screened using an Olympus SZX12 fluorescent dissecting microscope equipped with GFP (480 nm excitation/510 nm barrier), CFP (436 nm excitation/480 nm barrier), and YFP (500 nm excitation/530 barrier) filter sets. Two positive adults from each of the vials were crossed with w[1118] to establish germline transformed strains. The pBS-pBac/DsRed1 minimal vector was also injected and screened under HQ Texas Red® set no. 41004 (Handler and Harrell, 2001 a).

Direct PCR Analysis

Genomic DNAs from each of the transformed stains, the w[1118] wild type strain, and a piggyBac positive strain M23.1 (Handler and Harrell, 1999) were prepared using a modified DNAzol procedure. About 60 flies from each strain were combined with 150 ul of DNAzol (Molecular Research Center, Inc.) in a 1.5 ml eppendorf tube. The flies were homogenized, an additional 450 ul of DNAzol was added, and the homogenates were incubated at room temperature for one hour. The DNAs were extracted twice with phenol: chloroform (1:1 ratio), and the aqueous fractions were transferred to new tubes for precipitation of the DNA with an equal volume of 2-propanol. The DNA pellets were washed with 70% ethanol, air dried, and 150 ul of dH$_2$O containing 10 ug of RNase A was added and resuspended.

Two sets of direct PCRs were performed to identify the presence of piggyBac sequences in transformed fly genomes. Primers MF34 and IFP2_L were used to identify the presence of the piggyBac 3' terminal repeat, while MF34 and IFP2_R1 were used for identifying the piggyBac 5' terminal repeat. To exclude the possibility of recombination, a second PCR was also performed using the IFP2_R1 and IFP2_L primers to amplify the external stuffer fragment (L1 et al., 2001) between the terminal repeat regions.

Southern Hybridization Analysis

Southern hybridization analysis was performed using a standard procedure with minor modifications (Ausubel et al. 1994). Approximately 8 ug of genomic DNA (isolated as above) from each of the transformed fly strains was digested with 40 units of Hind III for four hours, followed by agarose gel electrophoresis at 60 Volts for 4 to 5 hours. The gel was then denatured, neutralized and transferred to nylon membranes, and baked at 80° C. for four hours. The membranes were pre-hybridized in the hybridization buffer overnight. A synthetic probe was prepared by nick translation (Invitrogen kit) using $^{32}P$ labeled dGTP against the pBSII-ITR1.1K-ECFP plasmid template. The purified probe was hybridized at 65° C. overnight followed by several washes, and the membranes were first exposed on phosphor screens (Kodak) overnight for scanning with a Storm phosphor Scanner (Molecular Dynamics System), and then exposed on X-ray film (Kodak).

Universal PCR and Inverse PCR Analysis

The piggyBac insertion sites in the transformed fly strains were identified using either universal PCR (Beeman et al., 1997) or inverse PCR techniques (Ochman et al., 1988). For the universal PCR, the IFP2_L (3' TR) or IPR2_R1 (5' TR) primer was combined with one of 7 universal primers during the first round of PCR (94° C. 1 minute, 40° C. 1 minute, 72° C. 2 minutes, 35 cycles). 2 ul of the reaction mixture from the first round of PCR was then used for a second round of PCR (94° C. 1 minute, 50° C. 1 minute, 72° C. 2 minutes, 35 cycles) using IFP2_L1 (3' TR) or iPCR_R1 (5' TR) together with a T7 primer (nested on the universal primer).

Inverse PCRs were performed by digesting 5 ug of the genomic DNAs from each of the transformed strains completely with HinP1 I for the 3' end or Taq I for the 5' end, followed by purification using the Geneclean kit (Q-Bio-gene) and self-ligation in a 100 ul volume overnight. The self-ligated DNAs were precipitated and resuspended in 30 ul ddH$_2$O. A portion of them were then used for first round PCR (94° C. 1 minute, 40° C. 1 minute, 72° C. 2 minutes, 35 cycles) with primer pairs IFP2_R1+MF14 for the 5' end and JF3+IFP2_Lb for the 3' end. 2 ul of the first round PCR products were used as templates for the second round PCR (94° C. 1 minute, 50° C. 1 minute, 72° C. 2 minutes, 35 cycles) using primer pairs iPCR_R1+iPCR_6 for the 5' end and iPCR_L1+MF04 for the 3' end. The pBSII-ITR1.1k-ECFP strains were slightly different, the primer pair iPCR_L1+ IFP2_L-R were used for the 3' end in the second round PCR. All the PCR products were cloned into the pCRII vector (Invitrogen) and sequenced. The sequences were used to BLAST search the NCBI database to identify the locations of the insertions. MacVector 6.5.3 (Oxford Molecular Group) and ClustalX (Jeanmougin et al., 1998) were used for sequence alignments.

Results

Transformation Experiments with Synthetic Deletion Constructs:

Each of the piggyBac synthetic internal deletion plasmids was formed by PCR amplifying from the pIAO-P/L-589 plasmid (L1 et al., 2001) by PCR amplifying across the facing terminal repeats and spacer with primers that recognize 5' or 3' sequences adjacent to the respective TRDs (FIG. 24). The fragments generated were cloned into a pBSII-3xP3-ECFP plasmid and sequenced.

Each of the synthetic deletion series plasmids and the control plasmid, pBac{3xP3-ECFPafm}, were co-injected with the hsp70-regulated transposase helper into w$^{1118}$ embryos, with surviving adults backcrossed, and G1 adult progeny screened for fluorescence. Positive transformants exhibited fluorescent eyes with CFP and GFP filter sets but not with the YFP filter set. Transformation frequencies from all injections are listed in Table 1, below.

TABLE 1

Transformation of *Drosophila melanogaster*

| Plasmid | Embryos Injected | Embryos Hatched | Adults Mated | Adults Survived | Transformants Lines (G$_0$) | Transformation Frequency |
|---|---|---|---|---|---|---|
| p(PZ)-Bac-EYFP | 2730 | 376 | 217 | 83 | 1 | 0.6% |
| pBSII-ECFP-R1/L5 | 990 | 240 | 83 | 70 | 6 | 8.9% |
| pBSII-ECFP-R2/L5 | 620 | 75 | 21 | 16 | 2 | 12.5% |
| pBSII-ECFP-R3/L5 | 650 | 127 | 29 | 20 | 3 | 15.0% |
| pBSII-ECFP-R4/L5 | 730 | 182 | 39 | 31 | 4 | 12.9% |
| pBSII-ECFP-R4/L4 | 670 | 169 | 44 | 28 | 3 | 10.7% |
| pBSII-ECFP-R4/L3 | 710 | 147 | 44 | 31 | 3 | 9.7% |
| pBSII-ECFP-R4/L2 | 850 | 191 | 55 | 46 | 5 | 10.8% |
| pBSII-ECFP-R4/L1 | 990 | 231 | 75 | 86 | 0 | 0% |
| pBSII-ITR1.1K-ECFP | 530 | 128 | 43 | 84 | 5 | 13.9% |
| pBSII-ECFP-R-TR/L | 610 | 169 | 62 | 71 | 0 | 0% |
| pBSII-ECFP-R1/L | 840 | 247 | 81 | 69 | 0 | 0% |
| pBac{3xP3-ECFPafm} | 650 | 104 | 45 | 69 | 4 | 12.9% |
| pXL-BacII-ECFP | 1020 | 181 | 42 | 36 | 8 | 22.2% |
| pBSII-ITR1.1k-ECFP* | 515 | 120 | 48 | 22 | 8 | 36.4% |
| pXL-BacII-ECFP* | 533 | 199 | 115 | 88 | 22 | 25.0% |

*The injections were done independently (Handler lab) using a 0.4:0.2 ug/ul vector/helper concentration ratio of DNA. The p(PZ)-Bac-EYFP plasmid yielded a low transformation frequency of 0.6% compared to the control plasmid, pBac{3xP3-ECFPafm} frequency of 12.9% (Table 1).

Eight of the eleven synthetic ID deletion plasmids yielded positive transformants at an acceptable (not significantly different from control, P<0.05) frequency. The 5' ID deletion constructs pBSII-ECFP-R1/L5, pBSII-ECFP-R2/L5, pBSII- ECFP-R3/L5 and pBSII-ECFP-R4/L5 had variable deletions of the piggyBac 5' ID, retaining sequences from 66 bp (nucleotides 36~101 of the piggyBac sequence, GenBank Accession Number: AR307779) to 542 bp (36~567 of the piggyBac sequence). Each of these 5' ID deletions yielded ECFP positive germ line transformants at frequencies from 8.9% to 15.0% (Table 1) when paired with 1 kb of the 3' ID sequence (nucleotides 1454~2409 of the piggyBac sequence). These results suggested that a minimal sequence of no more than 66 bp of the 5' ID may be necessary for efficient germline transposition.

The R4 minimum 5' ID sequence primer was then used in combination with a series of 3' ID deletion primers to generate the constructs pBSII-ECFP-R4/L4, pBSII-ECFP-R4/L3, pBSII-ECFP-R4/L2 and pBSII-ECFP-R4/L1. Of these four constructs, only pBSII-ECFP-R4/L1, which represented the greatest deletion of 3' ID sequence (2284~2409 of the piggyBac sequence), failed to yield transformants. Once again, frequencies for the positive transformant constructs were similar to the control (Table 1). It was therefore deduced that the minimal 3' ID sequence requirement for efficient germline transformation was between 125 bp (L1) and 378 bp (L2) of the 3' TRD adjacent ID sequence.

Construction of the ITR1.1k Minimal Sequence piggyBac Cartridge:

To construct a minimal sequence cartridge using the information gained from the synthetic deletion analysis, combinations of 5' and 3' minimal sequences were assembled and their transformation capabilities were tested. The pBSII-ECFP-R-TR/L construct is composed of a 35 bp 5' TRD lacking any 5' ID sequence, coupled to a fragment containing the 65 bp 3' TRD and 172 bp of the adjacent 3' ID sequence. This combination did not yield any transformants, confirming the necessity for having 5' ID sequences in combination with 3' ID sequences for efficient transformation. Unexpectedly, addition of 101 bp of the 5' ID sequences to the 5' TRD sequences in the construct pBSII-ECFP-R1/L was not sufficient to recover transformation capacity when paired with the 172 bp 3' ID sequences, even though the lower limit of essential 5' ID sequences had been suggested to be 66 bp using pBSII-ECFP—R1/L5 (Table 1). Increasing the 5' ID sequences to 276 bp in the pBSII-ITR1.1k-ECFP plasmid recovered the full transformation capability when paired with the 172 bp 3' ID sequence (Table 2). The minimal operational requirement for 5' ID sequences is therefore between 276 and 101 bp when coupled to a minimal 3' ID sequence of 172 bp.

Two independent verifications of the pBSII-ITR1.1k-ECFP plasmid transforming capabilities were conducted for transformation of *D. melanogaster*. These transformation experiments resulted in calculated frequencies of 13.9% (FIG. 24) and 36% (Table 1). The discrepancy in frequencies may be attributed to differences in injection protocols between labs. Unless otherwise indicated, the transformation frequencies presented in Table 1 and FIG. 24 were obtained with injections of 0.6:0.6 ug/ul vector:helper concentration ratios. The increased efficiency of transformation for pBSII-ITR1.1k-ECFP observed in the second independent trial seems to be related to a decreased vector:helper concentration in *D. melanogaster*.

Five recovered pBSII-ITR1.1k-ECFP transformed strains were used to perform genetic mapping to identify their chromosome locations. Several of the strains had insertions on the second and third chromosomes (including strain 1) while strain 3 had an insertion on the X chromosome. Strain 1 and strain 3 were chosen for further analyses.

Direct PCR Analysis of Integrations:

Genomic DNAs from each of the transformed strains obtained with the synthetic deletion constructs in FIG. 24, as well as the piggyBac positive strain M23.1 and the negative white eye strain $w^{1118}$, were used to perform two sets of PCRs to verify the presence of the piggyBac 5' and 3' terminal repeat regions. An additional negative control PCR was performed on all transformants to show the absence of the external lambda phage DNA stuffer sequence (FIG. 26).

The first set of PCRs utilized the IFP2_R1 and MF34 primers to amplify the 5' terminal repeat regions, and the second set of PCRs used the IFP2_L and MF34 primers to amplify the 3' terminal repeat regions. All of the synthetic deletion transformed strains, the M23.1 control strain, and the plasmid control yielded a strong PCR product of the correct size for each of the primer sets, confirming the presence of both of the piggyBac terminal repeat regions in all of the transformed strains. Interestingly, the white eye strain $w^{1118}$ yielded a very weak product of the correct size with the 5' terminal repeat PCR amplification, but failed to generate a product with the 3' terminal specific primer set.

A third set of PCRs was performed using the IFP2_R1 and IFP2_L primers in an attempt to amplify the external lambda phage DNA stuffer sequence which would be present if an insertion resulted from recombination of the entire plasmid sequence rather than transposition. The control product from this PCR reaction is a 925 bp fragment, and no such corresponding fragments were generated with any of the transformed strain genomic DNAs.

Figure 27:
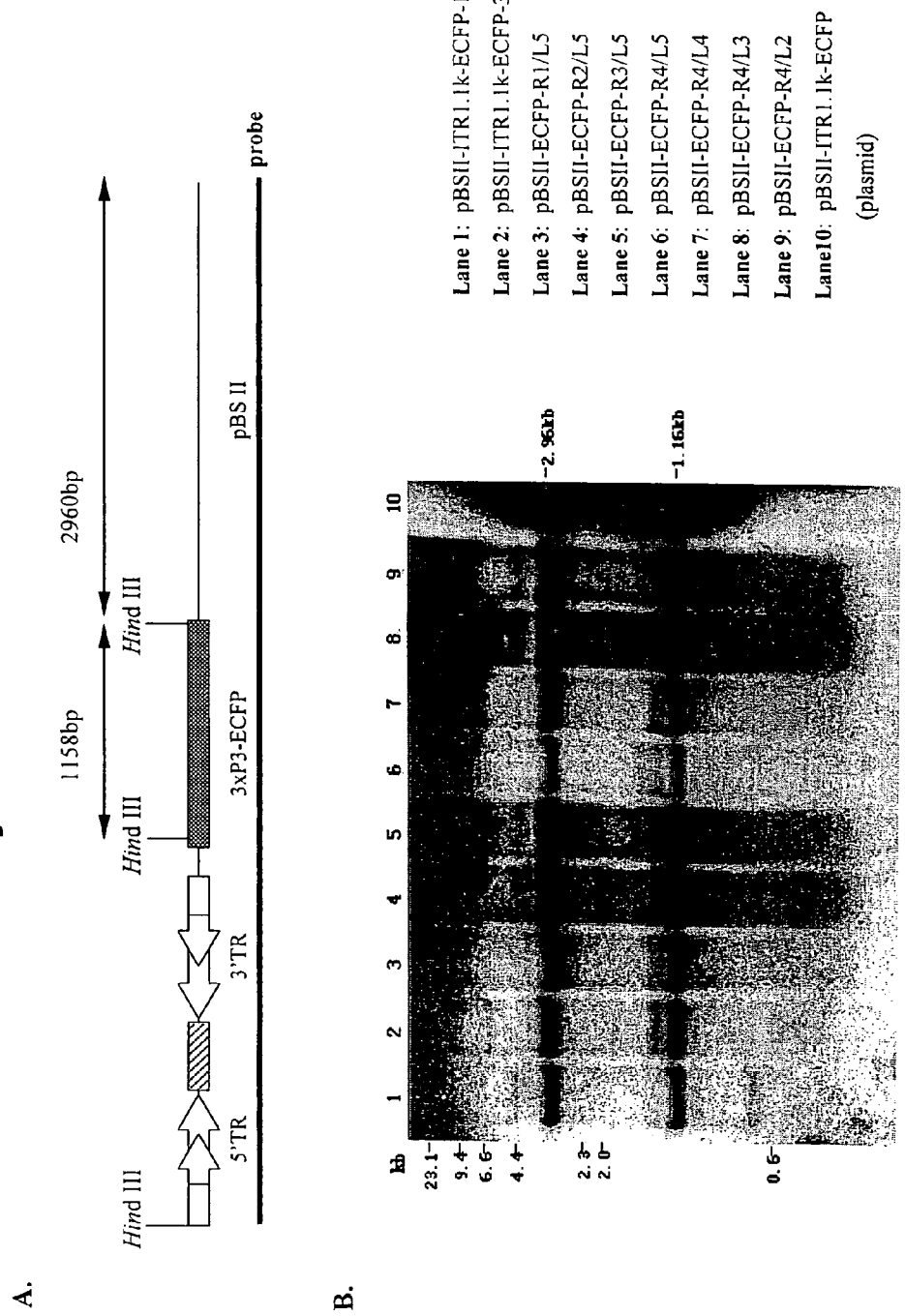
FIG. 27 shows southern hybridization analysis of internal deletion plasmid transformed strains. Genomic DNAs from selected strains and the pBSII-ITR1.1k-ECFP plasmid control were digested with Hind III and hybridized to the pBSII-ITR1.1k-ECFP plasmid probe. The 2.96 kb pBSII and 1.16 kb ECFP marker should be present in all strains. (A) shows a map of the pBSII-ITR1.1k-ECFP plasmid showing the size of expected fragments. (B) shows that all transformed strains exhibit the two diagnostic bands (2.96 kb and 1.16 kb) and at least two additional bands reflecting the piggyBac terminal adjacent sequences at the site of integration. A weak 1.3 kb band is also observed in all strains. The reason that the two additional bands are much weaker than the diagnostic bands may be that these two additional bands represent the piggyBac termini containing bands, which contain only 200~300 bp of AT rich sequences that will be hybridized by the probe. The normal 60° C. washes may wash away these weak hybridizations, thus causing the weak band on the blot.

Southern Hybridization Analysis:

Southern hybridization analysis was performed to verify the copy number and further confirm transposition of the piggyBac deletion plasmids into the *Drosophila* genome (FIG. 27). Genomic DNAs from two of the pBSII-ITR1.1 k-ECFP strains (strain 1 and strain 3) and one of each of the other strains were digested with Hind III, with the pBSII-ITR1.1k-ECFP plasmid Hind III digest as a plasmid control. The Hind III digestion of all transformed strains will generate four fragments if transpositional insertion has occurred: the pBSII plasmid backbone fragment (2960 bp), the 3xP3-ECFP marker fragment (1158 bp), the piggyBac 5' terminus fragment and the piggyBac 3' terminus fragment. Using the pBSII-ITR1.1k-ECFP plasmid as probe, all four fragments generated by the Hind III digestion may be detected.

The diagnostic 2960 bp pBSII backbone and 1158 bp ECFP marker fragments were present in all of the transformed strains examined. All of these strains also exhibited at least two additional bands corresponding to the piggyBac termini and adjacent sequences at the integration site (FIG. 27). These results confirmed that the observed frequencies were the result of transpositional integrations.

Analysis of Insertion Site Sequences:

To further verify that piggyBac-mediated transposition of the synthetic deletion constructs occurred in these transformants, individual insertion sites were examined by isolating joining regions between the transposon and genomic sequences using either universal PCR or inverse PCR. Subsequent sequencing analysis of these joining regions demonstrated that all of the insertions occurred exclusively at single TTAA target sites that were duplicated upon insertion, and all insertion sites had adjacent sequences that were unrelated to the vector. The two pBSII-ITR1.1k-ECFP strains 1 and 3 have a single insertion on the third and X chromosome respectively.

Discussion

Transformation results from synthetic unidirectional deletion plasmids suggest that no more than 66 bp (nt 36~101 of the piggyBac sequence) of the piggyBac 5' ID sequence and 378 bp (nt 2031~2409 of the piggyBac sequence) of the piggyBac 3' ID sequence are necessary for efficient transformation when these deletions are paired with long (378 or 311 bp, respectively, or longer) ID sequences from the opposite end of the transposon. The transformation data from the pBSII-ITR1.1k-ECFP plasmid further defines the 3' ID essential sequence as 172 bp (nt 2237~2409 of the piggyBac sequence). Combining this same 172 bp 3' ID sequence with only the 5' TRD in the pBSII-ECFP-R-TR/L plasmid yielded no transformants, demonstrating that the 3' ID sequence alone was insufficient for full mobility. Unexpectedly, adding the 66 bp 5' ID sequence in pBSII-ECFP-R1/L also does not allow recovery of full transformation capability in spite of the fact that the same 66 bp does allow full transformation capability when coupled to the larger (378 bp) 3' ID sequence in the pBSII-ECFP-R1/L2. This result cannot be explained by size alone, since the ITR cartridge strategy used to test this deletion sequence construct effectively replaces the rest of the piggyBac ID with the 2961 bp pBSII plasmid sequence.

Figure 28:
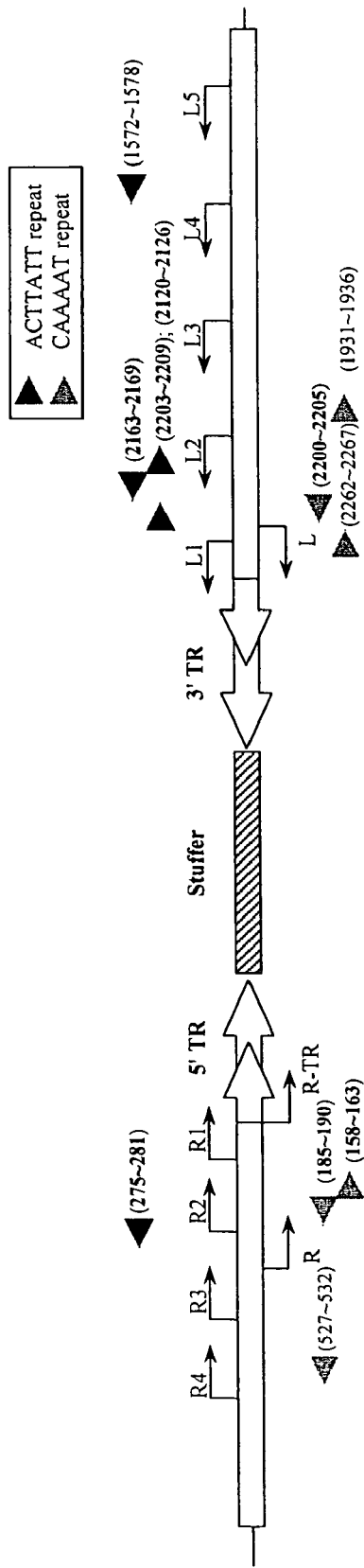
FIG. 28 shows a schematic illustration of the locations of the two short repeat sequences in piggyBac. The repeats with the locations in bold are within the region between R and R1, or L and L2, which appear to be the important regions based on the transformation results discussed in the present invention. These repeats may also be found in some other position of the piggyBac sequence. From the present invention, it appears that a minimum of one set of these repeats on either side of the internal domains are useful for the transposon to permit full transforming capability.

There appears to be an important sequence in the additional 206 bp of the L2 3' ID sequence that compensates for the smaller 5' ID sequence of R1. The data infer that an analogous sequence at the 5' end should be located within the 210 bp added to the 5' ID sequence in construction of the pBSII-ITR1.1k-ECFP, since this construct exhibits full transforming capability using the L 3' ID sequence. Aligning these two sequences using MacVector 6.5.3 identified two small segments of repeat sequences common between these approximately 200 bp sequences. These repeats, ACTTATT (nt 275~281, 2120~2126 and 2163~2169 of the piggyBac sequence) and CAAAAT (nt 185~190, 158~163 and 2200~2205 of the piggyBac sequence), occur in direct and opposite orientations, and are also found in several other locations of the piggyBac ID (FIG. 28). It seems that a minimum of one set of these repeats on either side of the internal domains are required for the transposon to permit full transforming capability.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art Such changes and modifications are to be understood as included within the scope of the present invention as defined by the appended claims, unless they depart therefrom.

DOCUMENTS CITED

Sections of the following that are relevant to the invention are incorporated by reference.

Ausubel F M, Brent R, Kingston R E, Moore D D, Seidman J G, Smith J A and Struhl K (1994) Current protocols in molecular biology, John Wiley & Sons, Inc.

Becker H A, Kunze R (1997) Maize Activator transposase has a bipartite DNA binding domain that recognizes subterminal sequences and the terminal inverted repeats, Mol. Gen. Genet., 254(3): pp. 219–30.

Beeman R W, Stauth D M (1997) Rapid cloning of insect transposon insertion junctions using 'universal' PCR, Insect Mol. Biol., 6(1): pp. 83–8.

Berghammer A J, Klingler M, Wimmer E A (1999) A universal marker for transgenic insects, Nature, 402: pp. 370–1.

Buck T A, Lobo N, Fraser M J Jr (1997) Analysis of the cis-acting DNA elements required for piggyBac transposable element excision, Mol. Gen. Genet., 255: pp, 605–610.

Cary L C, Goebel M., Corsaro B G, Wang H G, Rosen E, Fraser M J Jr (1989) Transposon mutagenesis of baculoviruses: analysis of *Trichoplusia ni* transposon IFP2 insertions within the FP-locus of nuclear polyhedrosis viruses, Virology, 172: pp. 156–69.

Elick T A, Bauser C A, Principe N M, Fraser M J Jr (1996a) PCR analysis of insertion site specificity, transcription, and structural uniformity of the Lepidopteran transposable element IFP2 in the TN-368 cell genome, Genetica., 97(2): pp. 127–39.

Elick T A, Bauser C A, Fraser M J Jr (1996b) Excision of the piggyBac transposable element in vitro is a precise event that is enhanced by the expression of its encoded transposase, Genetica., 98(1): pp. 33–41.

Elick T A, Lobo N, Fraser M J Jr (1997) Analysis of the cis-acting DNA elements required for piggyBac transposable element excision, Mol. Gen. Genet., 255(6): pp. 605–10.

Fraser M J Jr, Smith G B and Summers M D (1983) Acquisition of host cell DNA sequences by baculoviruses: Relationship between host DNA insertions and FP mutants of *Autographa californica* and *Galleria mellonella* nuclear polyhedrosis viruses, J. Virol., 47: pp. 287–300.

Fraser M J Jr, Brusca J S, Smith G E, Summers M D (1985) Transposon-mediated mutagenesis of a baculovirus, Virology, 145(2): pp. 356–61.

Fraser M J Jr, Cary L, Boonvisudhi K, Wang H G (1995) Assay for movement of Lepidopteran transposon IFP2 in insect cells using a baculovirus genome as a target DNA, Virology, 211(2): pp. 397–407.

Fraser M J Jr, Ciszczon T, Elick T, Bauser C (1996) Precise excision of TTAA-specific Lepidopteran transposons piggyBac (IFP2) and tagalong (TFP3) from the baculovirus genome in cell lines from two species of Lepidoptera, Insect Mol. Biol., 5(2): pp. 141–51.

Geier and Modrich (1979).

Gierl A, Lutticke S, Saedler H (1988) TnpA product encoded by the transposable element En-1 of *Zea mays* is a DNA binding protein, EMBO J., 7(13): pp. 4045–53.

Goryshin I Y, Kil Y V, Reznikoff W S (1994) DNA length, binding, and twisting constraints on IS5O transposition, Proc. Natl. Acad. USA, 91: pp. 10834–10838.

Grossman G L, Rafferty C S, Fraser M J Jr, Benedict M Q (2000) The piggyBac element is capable of precise excision and transposition in cells and embryos of the mosquito, *Anopheles gambiae*, Insect Biochem. Mol. Biol., 30(10): pp. 909–14.

Grossman G L, Rafferty C S, Clayton J R, Stevens T K, Mukabayire O, Benedict M (2001) Germline transformation of the malaria vector, *Anopheles gambiae*, with the piggyBac transposable element, Insect Mol. Biol., 10(6): pp. 597–604.

Grossniklaus U, Pearson R K, Gehring W J (1992) The *Drosophila* sloppy paired locus encodes two proteins involved in segmentation that show homology to mammalian transcription factors, Genes Dev., 6(6): pp. 1030–51.

Handler A M, McCombs S D, Fraser M J Jr, Saul S H (1998) The Lepidopteran transposon vector, piggyBac, mediates germ-line transformation in the Mediterranean fruit fly, Proc. Natl. Acad. Sci. USA, 95(13): pp. 7520–5.

Handler A M, Harrell R A 2$^{nd}$ (1999) Germline transformation of *Drosophila melanogaster* with the piggyBac transposon vector, Insect Mol. Biol., 8(4): pp. 449–57.

Handler A M, McCombs S D (2000) The piggyBac transposon mediates germ-line transformation in the Oriental fruit fly and closely related elements exist in its genome, Insect Mol. Biol., 9(6): pp. 605–12.

Handler A M, Harrell R A 2$^{nd}$ (2001a) Polyubiquitin-regulated DsRed marker for transgenic insects, Biotechniques, 31(4): pp. 824–8.

Handler A M, Harrell R A 2$^{nd}$ (2001b) Transformation of the Caribbean fruit fly, *Anastrepha suspensa*, with a piggyBac vector marked with polyubiquitin-regulated GFP, Insect Biochem. Mol. Biol., 31(2): pp. 199–205.

Handler A M (2002) Use of the piggyBac transposon for germ-line transformation of insects, Insect Biochem. Mol. Biol., 32(10): pp. 1211–20.

Hediger M, Niessen M, Wimmer EA, Dubendorfer A, Bopp D (2001) Genetic transformation of the housefly *Musca domestica* with the Lepidopteran derived transposon piggyBac, Insect Mol. Biol., 10(2): pp. 113–9.

Heinrich J C, Li X, Henry R A, Haack N, Stringfellow L, Heath A C, Scott M J (2002) Germ-line transformation of the Australian sheep blowfly *Lucilia cuprina*, Insect Mol. Biol., 11 (1): pp. 1–10.

Hirt B (1967) Selective extraction of polyoma DNA from infected mouse cell cultures, J. Mol. Bio., 26: pp. 367–369.

Horn C, Wimmer E A (2000) A versatile vector set for animal transgenesis, Dev. Genes Evol., 210(12): pp. 630–7.

Ivics Z, Hackett P B, Plasterk R H, Izsvak Z (1997) Molecular reconstruction of Sleeping Beauty, a Tc1-like transposon from fish, and its transposition in human cells, Cell, 91(4): pp. 501–10.

Jarvis et al. (1990).

Jasinskiene N, Coates C J, James A A (2000) Structure of hermes integrations in the germline of the yellow fever mosquito, *Aedes aegypti*, Insect Mol. Biol., 9(1): pp. 11–8.

Kaufman P D, Doll R F, Rio DC (1989) *Drosophila* P element transposase recognizes internal P element DNA sequences, Cell, 59(2): pp. 359–71.

Kokoza V, Ahmed A, Wimmer E A, Raikhel A S (2001) Efficient transformation of the yellow fever mosquito *Aedes aegypti* using the piggyBac transposable element vector pBac[3xP3-EGFP afm], Insect Biochem. Mol. Biol., 31(12): pp. 1137–43.

Kunze R, Starlinger P (1989) The putative transposase of transposable element Ac from *Zea mays* L. interacts with subterminal sequences of Ac, EMBO J., 8(11): pp. 3177–85.

Li X, Heinrich J C, Scott M J (2001a) piggyBac-mediated transposition in *Drosophila melanogaster*: an evaluation of the use of constitutive promoters to control transposase gene expression, Insect Mol. Biol., 10(5): pp. 447–55.

Li X, Lobo N, Bauser C A, Fraser M J Jr (2001b) The minimum internal and external sequence requirements for transposition of the eukaryotic transformation vector piggyBac, Mol. Genet. Gen., 266(2): pp. 190–8.

Liu D, Mack A, Wang R, Galli M, Belk J, Ketpura N I, Crawford N M (2000) Functional dissection of the cis-acting sequences of the *Arabidopsis* transposable element Tag1 reveals dissimilar subterminal sequence and minimal spacing requirements for transposition, Genetics, 157(2): pp. 817–30.

Lobo N, Li X, Fraser M J Jr (1999) Transposition of the piggyBac element in embryos of *Drosophila melanogaster, Aedes aegypti* and *Trichoplusia ni*, Mol. Gen. Genet., 261 (4–5): pp. 803–10.

Lobo N, Li X, Hua-Van A, Fraser M J Jr (2001) Mobility of the piggyBac transposon in embryos of the vectors of Dengue fever (*Aedes albopictus*) and La Crosse encephalitis (*Ae. triseriatus*), Mol. Genet. Gen., 265(1): pp. 66–71.

Lobo N F, Hua-Van A, Li X, Nolen B M, Fraser M J Jr (2002) Germ line transformation of the yellow fever mosquito, *Aedes aegypti*, mediated by transpositional insertion of a piggyBac vector, Insect Mol. Biol., 11(2): pp. 133–9.

Lohe A R, Hartl D L (2001) Efficient mobilization of mariner in vivo requires multiple internal sequences, Genetics, 160(2): pp. 519–26.

Lozovsky E R, Nurminsky D, Wimmer E A, Hartl D L (2002) Unexpected stability of mariner transgenes in *Drosophila*, Genetics, 160(2): pp. 527–35.

Mandrioli M, Wimmer EA (2002) Stable transformation of a *Mamestra brassicae* (Lepidoptera) cell line with the Lepidopteran-derived transposon piggyBac, Insect Biochem. Mol. Biol., 33(1): pp. 1–5.

Mullins M C, Rio D C, Rubin G M (1989) cis-acting DNA sequence requirements for P-element transposition, Genes Dev., 3(5): pp. 729–38.

Nolan T, Bower T M, Brown A E, Crisanti A, Catteruccia F (2002) piggyBac-mediated germline transformation of the malaria mosquito *Anopheles stephensi* using the red fluorescent protein dsRED as a selectable marker, J. Biol. Chem., 277(11): pp. 8759–62.

Ochman H, Gerber A S, Hartl D L (1988) Genetic applications of an inverse polymerase chain reaction, Genetics, 120(3): pp. 621–3.

Peloquin J J, Thibault S T, Staten R, Miller T A (2000) Germ-line transformation of pink bollworm (Lepidoptera: gelechiidae) mediated by the piggyBac transposable element, Insect Mol. Biol., 9(3): pp. 323–33.

Perera O P, Harrell II R A, Handler A M (2002) Germ-line transformation of the South American malaria vector, *Anopheles albimanus*, with a piggyBac/EGFP transposon vector is routine and highly efficient, Insect Mol. Biol., 11(4): pp. 291–7.

Pfaffle P, Jackson V (1990) Studies on rates of nucleosome formation with DNA under stress, J. Biol. Chem., 265(28): pp. 16821–9.

Rio D C, Rubin G M (1988) Identification and purification of a *Drosophila* protein that binds to the terminal 31-base-pair inverted repeats of P transposable element, Proc. Natl. Acad. Sci. USA, 85: pp. 8929–33.

Rubin G M, Spradling A C (1982) Genetic transformation of *Drosophila* with transposable element vectors, Science, 218(4570): pp. 348–53.

Rubin G M, Spradling A C (1983) Vectors for P element-mediated gene transfer in *Drosophila*, Nucleic Acids Res., 11 (18): pp. 6341–51.

Saedler H, Gierl A (Editors) (1996) Transposable Elements, Soringer-Verlag, Berlin.

Sambrook J, Fritsch E F, and Maniatis T (1989) Molecular Cloning: A Laboratory Manual (New York: Cold Spring Harbor Press).

Sarkar A, Yardley K, Atkinson P W, James A A, O'Brochta D A (1997a) Transposition of the Hermes element in embryos of the vector mosquito, *Aedes aegypti*, Insect Biochem. Mol. Biol., 27(5): pp. 359–63.

Sarkar A, Coates C J, Whyard S, Willhoeft U, Atkinson P W, O'Brochta D A (1997b) The Hermes element from

*Musca domestica* can transpose in four families of cyclorrhaphan flies, Genetica., 99(1): pp. 15–29.

Sarkar A, Sim C, Hong Y S, Hogan J R, Fraser M J Jr, Robertson H M, Collins F H (2003) Molecular evolutionary analysis of the widespread piggyBac transposon family and related "domesticated" sequences, Mol. Genet. Genomics, 270(2): pp. 173–80.

Sekar V (1987) A rapid screening procedure for the identification of recombinant bacterial clones, BioTechniques, 5: pp. 11–13.

Sumitani M, Yamamoto D S, Oishi K, Lee J M, Hatakeyama M (2003) Germline transformation of the sawfly, *Athalia rosae* (Hymenoptera: Symphyta), mediated by a piggyBac-derived vector, Insect Biochem. Mol. Biol., 33(4): pp. 449–58.

Tamura T, Thibert C, Royer C, Kanda T, Abraham E, Kamba M, Komoto N, Thomas J L, Mauchamp B, Chavancy G, Shirk P, Fraser M, Prudhomme J C, Couble P, Toshiki T, Chantal T, Corinne R, Toshio K, Eappen A, Mari K, Natuo K, Jean-Luc T, Bernard M, Gerard C, Paul S, Malcolm F, Jean-Claude P, Pierre C (2000) Germline transformation of the silkworm *Bombyx mori* L. using a piggyBac transposon-derived vector, Nat. Biotechnol. 18(1): pp. 81–4.

Thibault S T, Luu H T, Vann N, Miller T A (1999) Precise excision and transposition of piggyBac in pink bollworm embryos, Insect Mol. Biol., 8(1): pp. 119–23.

Thomas J L, Da Rocha M, Besse A, Mauchamp B, Chavancy G (2002) 3xP3-EGFP marker facilitates screening for transgenic silkworm *Bombyx mori* L. from the embryonic stage onwards, Insect Biochem. Mol. Biol., 32(3): pp. 247–53.

Thummel, C S and Pirrotta, V (1992) New pCaSpeR P element vectors, Dros. Info. Service, 71: pp. 150—150.

Tosi L R, Beverley S M (2000) cis and trans factors affecting Mos1 mariner evolution and transposition in vitro, and its potential for functional genomics, Nucleic Acids Res., 28(3): pp. 784–90.

Trentmann S M, Saedler H, Gierl A (1993) The transposable element En/Spm-encoded TNPA protein contains a DNA binding and a dimerization domain, Mol. Gen. Genet., 238(1–2): pp. 201–8.

Wang H H, Fraser M J Jr (1993) TTAA serves as the target site for TFP3 Lepidopteran insertions in both nuclear polyhedrosis virus and *Trichoplusia ni* genomes, Insect Mol. Biol., 1:pp. 109–116.

Zayed H, Izsvak Z, Khare D, Heinemann U, Ivics Z (2003) The DNA-bending protein HMGB1 is a cellular cofactor of Sleeping Beauty transposition, Nucleic Acids Res., 31(9): pp. 2313–22.

What is claimed is:

1. A genetic cartridge designated ITR.
2. A genetic cartridge designated ITR1.1k, wherein ITR1.1k is an insert of pBSII-ITR1.1K-ECFP as shown in FIG. 25.
3. A vector designated pXL-Bac as shown in FIG. 3.
4. A vector designated pXL-BacII-ECFP as shown in FIG. 24.
5. A vector designated pBSII-ITR1.1k-ECFP as shown in FIGS. 24 and 25.
6. A method of converting a plasmid into a functional piggyBac transposon, said method comprising:
    (a) obtaining the cartridge of claim 1; and
    (b) inserting said cartridge into the plasmid.
7. A method of converting a plasmid into a functional piggyBac transposon, said method comprising:
    (a) obtaining the cartridge of claim 2; and
    (b) inserting said cartridge into the plasmid.
8. A DNA construct for transforming a cell, said construct comprising the vector of claim 3.
9. A DNA construct for transforming a cell, said construct comprising the DNA construct of claim 8 and further comprising a DNA molecule to be transferred to the cell.

* * * * *